US012606635B2

(12) United States Patent
Zhang et al.

(10) Patent No.: US 12,606,635 B2
(45) Date of Patent: Apr. 21, 2026

(54) GLYPICAN-2-BINDING MOIETIES, CHIMERIC ANTIGEN RECEPTORS AND USES THEREOF

(71) Applicant: Nanjing Legend Biotech Co., Ltd., Nanjing (CN)

(72) Inventors: Wang Zhang, Nanjing (CN); Jintao Guo, Nanjing (CN); Fengyuan Tang, Nanjing (CN); Shuai Yang, Nanjing (CN); Yuanyuan Peng, Nanjing (CN); An Tang, Nanjing (CN); Xiaojie Tu, Nanjing (CN); Yunlei Liu, Nanjing (CN); Shu Wu, Nanjing (CN)

(73) Assignee: Nanjing Legend Biotech Co., Ltd., Nanjing (CN)

( * ) Notice: Subject to any disclaimer, the term of this patent is extended or adjusted under 35 U.S.C. 154(b) by 811 days.

(21) Appl. No.: 17/910,608

(22) PCT Filed: Mar. 12, 2021

(86) PCT No.: PCT/CN2021/080528
§ 371 (c)(1),
(2) Date: Sep. 9, 2022

(87) PCT Pub. No.: WO2021/180215
PCT Pub. Date: Sep. 16, 2021

(65) Prior Publication Data

US 2023/0136252 A1 May 4, 2023

(30) Foreign Application Priority Data

Mar. 12, 2020 (WO) ................ PCT/CN2020/078972
Feb. 9, 2021 (WO) ................ PCT/CN2021/076367

(51) Int. Cl.
*C07K 16/30* (2006.01)
*A61K 31/454* (2006.01)
(Continued)

(52) U.S. Cl.
CPC ........ *C07K 16/3053* (2013.01); *A61K 31/454* (2013.01); *A61K 35/17* (2013.01); *A61K 38/177* (2013.01); *A61K 38/1774* (2013.01); *A61K 38/2046* (2013.01); *A61K 38/2086* (2013.01); *A61K 39/3955* (2013.01); *A61K 39/39558* (2013.01); *A61K 40/11* (2025.01); *A61K 40/31* (2025.01); *A61K 40/4261* (2025.01); *A61P 11/00* (2018.01); *A61P 25/00* (2018.01); *A61P 35/00* (2018.01); *C07K 14/5418* (2013.01); *C07K 14/5443* (2013.01); *C07K 14/70507* (2013.01); *C07K 14/7051* (2013.01); *C07K 14/70521* (2013.01); *C07K 14/70578* (2013.01); *C07K 16/18* (2013.01); *C07K 16/3084* (2013.01); *C12N 5/0636* (2013.01); *A61K 2039/505* (2013.01); *A61K 2239/31* (2023.05); *A61K 2239/38* (2023.05); *A61K 2239/47* (2023.05); *A61K 2239/55* (2023.05); *C07K 2317/24* (2013.01); *C07K 2317/31* (2013.01); *C07K 2317/35* (2013.01); *C07K 2317/52* (2013.01); *C07K 2317/565* (2013.01);
(Continued)

(58) Field of Classification Search
CPC ............ C07K 16/3053; C07K 14/5418; C07K 14/5443; C07K 14/70507; C07K 14/7051; C07K 14/70521; C07K 14/70578; C07K 16/18; C07K 16/3084; C07K 2317/24; C07K 2317/31; C07K 2317/35; C07K 2317/52; C07K 2317/565; C07K 2317/569; C07K 2317/92; C07K 2319/02; C07K 2319/03; C07K 2319/33; C07K 14/47; C07K 2317/22; C07K 2317/30; C07K 2317/33; C07K 2317/56; C07K 2317/73; C07K 2317/76; C07K 16/30; A61K 31/454; A61K 35/17; A61K 38/177; A61K 38/1774; A61K 38/2046; A61K 38/2086; A61K 39/3955; A61K 39/39558; A61K 40/11; A61K 40/31; A61K 40/4261; A61K 2039/505; A61K 2239/31; A61K 2239/38; A61K 2239/47; A61K 2239/55; A61K 2039/54; A61K 2039/55; A61P 11/00; A61P 25/00; A61P 35/00; C12N 5/0636; C12N 2501/2302; C12N 2502/30
See application file for complete search history.

(56) References Cited

U.S. PATENT DOCUMENTS

2024/0150456 A1 5/2024 Xu et al.

FOREIGN PATENT DOCUMENTS

CN 102775500 A 11/2012
CN 107405362 A 11/2017
(Continued)

OTHER PUBLICATIONS

Rudikoff et al Proc Natl Acad Sci USA 1982 vol. 79 p. 1979-1983 (Year: 1982).*
(Continued)

*Primary Examiner* — Gregory S Emch
*Assistant Examiner* — Kathleen Cunningchen
(74) *Attorney, Agent, or Firm* — Fish & Richardson P.C.

(57) ABSTRACT

The present application provides GPC2-specific antibodies and antigen binding fragments thereof. A chimeric antigen receptor (CAR) that specifically binds glypican-2 (GPC2) comprising a GPC2-specific antibody, a transmembrane domain, and an intracellular signaling domain. T cells comprising the disclosed CAR constructs can be used for cancer immunotherapy.

19 Claims, 58 Drawing Sheets

Specification includes a Sequence Listing.

(51) Int. Cl.

| | |
|---|---|
| ***A61K 35/17*** | (2025.01) |
| ***A61K 38/17*** | (2006.01) |
| ***A61K 38/20*** | (2006.01) |
| ***A61K 39/00*** | (2006.01) |
| ***A61K 39/395*** | (2006.01) |
| ***A61K 40/11*** | (2025.01) |
| ***A61K 40/31*** | (2025.01) |
| ***A61K 40/42*** | (2025.01) |
| ***A61P 11/00*** | (2006.01) |
| ***A61P 25/00*** | (2006.01) |
| ***A61P 35/00*** | (2006.01) |
| ***C07K 14/54*** | (2006.01) |
| ***C07K 14/705*** | (2006.01) |
| ***C07K 14/725*** | (2006.01) |
| ***C07K 16/18*** | (2006.01) |
| ***C12N 5/0783*** | (2010.01) |

(52) U.S. Cl.

CPC .... *C07K 2317/569* (2013.01); *C07K 2317/92* (2013.01); *C07K 2319/02* (2013.01); *C07K 2319/03* (2013.01); *C07K 2319/33* (2013.01); *C12N 2501/2302* (2013.01); *C12N 2502/30* (2013.01)

(56) References Cited

FOREIGN PATENT DOCUMENTS

| | | | | | |
|---|---|---|---|---|---|
| CN | 109715207 | A | | 5/2019 | |
| CN | 112125976 | A | | 12/2020 | |
| CN | 112334193 | A | | 2/2021 | |
| WO | WO-2017019848 | A1 | * | 2/2017 | .............. A61P 35/00 |
| WO | WO 2018/026533 | | | 2/2018 | |
| WO | WO 2019/094482 | | | 5/2019 | |
| WO | WO 2020/033430 | | | 2/2020 | |
| WO | WO 2020183158 | A1 | | 9/2020 | |
| WO | WO-2021000886 | A1 | * | 1/2021 | ......... C07K 16/1225 |
| WO | WO 2021008610 | A1 | | 1/2021 | |
| WO | WO-2024238656 | A1 | * | 11/2024 | ......... A61K 40/4211 |

OTHER PUBLICATIONS

Chen G, Luo D, Zhong N, Li D, Zheng J, Liao H, Li Z, Lin X, Chen Q, Zhang C, Lu Y, Chan YT, Ren Q, Wang N, Feng Y. GPC2 Is a Potential Diagnostic, Immunological, and Prognostic Biomarker in Pan-Cancer. Front Immunol. Mar. 8, 2022;13:857308. doi: 10.3389/fimmu.2022.857308. PMID: 35345673 (Year: 2022).*

Lugert, S., Kremer, T., Jagasia, R. et al. Glypican-2 levels in cerebrospinal fluid predict the status of adult hippocampal neurogenesis. Sci Rep 7, 46543 (2017). https://doi.org/10.1038/srep46543 (Year: 2017).*

Sadelain M, Brentjens R, Rivière I. The basic principles of chimeric antigen receptor design. Cancer Discov. Apr. 2013;3(4):388-98. doi: 10.1158/2159-8290.CD-12-0548. Epub Apr. 2, 2013. PMID: 23550147; PMCID: PMC3667586 (Year: 2013).*

Themeli, M., et al. Generation of tumor-targeted human T lymphocytes from induced pluripotent stem cells for cancer therapy. Nature biotechnology, 31(10), pp. 928-933 (Year: 2013).*

Liu et al., "Expression of C-GPC3 protein and screening of human GPC3 antibody," Chinese Journal of Bioproducts, 2016, 29(1):13-17 (Abstract with English machine translation, 2 pages).

Bosse et al., "Identification of GPC2 as an Oncoprotein and Candidate Immunotherapeutic Target in High-Risk Neuroblastoma," Cancer Cell, Sep. 11, 2017, 32(3):295-309 and e1-e12.

Extended European Search Report in European Appln. No. 21767858.0, mailed on Apr. 23, 2024, 27 pages.

Li et al., "Therapeutically targeting glypican-2 via single domain antibody-based chimeric antigen receptors and immunotoxins in neuroblastoma," Proceedings of the National Academy of Sciences, Jul. 24, 2017, 114(32):E6623-E6631.

Partial Supplementary European Search Report in European Appln. No. 21767858.0, dated Jan. 30, 2024, 31 pages.

PCT International Search Report and Written Opinion in International Appln. No. PCT/CN2021/080528, mailed on Jun. 15, 2021, 11 pages.

PCT International Preliminary Report on Patentability in International Appln. No. PCT/CN2021/080528, mailed on Sep. 6, 2022, 6 pages.

Tahmasebi et al., "Solid Tumors Challenges and New Insights of CAR T Cell Engineering," Stem Cell Reviews and Reports, Jun. 4, 2019, 15(5):619-636.

Cherkassky et al., "Human CART cells with cell-intrinsic PD-1 checkpoint blockade resist tumor-mediated inhibition," J Clin Invest., Aug. 31, 2016, 126(8):3130-3144.

GenBank Accession No. XP 003809003.1, "T-cell antigen CD7 [Pan paniscus]," dated Jun. 5, 2020, 2 pages.

Hou et al., "TGF-β-responsive CAR-T cells promote anti-tumor immune function," Bioengineering & Translational Medicine, Dec. 31, 2018, 3:75-86.

Larson et al. "Recent advances and discoveries in the mechanisms and functions of CART cells," Nature Reviews Cancer, Jan. 22, 2021, 21(3):145-161.

Legler et al., "The [alpha] v[beta] 3 integrin as a tumor homing ligand for lymphocytes", Eur J Immunol, Apr. 23, 2004, 34(6):1608-1616.

Liu et al., "Enhancing CAR-T cell efficacy in solid tumors by targeting the tumor microenvironment," Cellular & Molecular Immunology., Mar. 30, 2021, 18:1085-1095.

Marofi et al., "CART cells in solid tumors: challenges and opportunities," Stem Cell Research & Therapy, Jan. 25, 2021, 12:81, pp. 1-16.

Richards et al., "CAR T-cell therapy for neuroblastoma," frontiers in immunology, Oct. 16, 2018, 9(2380):1-15.

Zhang et al., "Accurate control of dual-receptor-engineered T cell activity through a bifunctional anti-angiogenic peptide," J Hematol Oncol, Mar. 20, 2018, vol. 11, Article 44, 14 pages.

Zhang et al., "The anti tumor capacity of mesothelin-CAR-T cells in targeting solid tumors in mice," Molecular Therapy: Oncolytics, Mar. 31, 2021, 20:556-568.

* cited by examiner

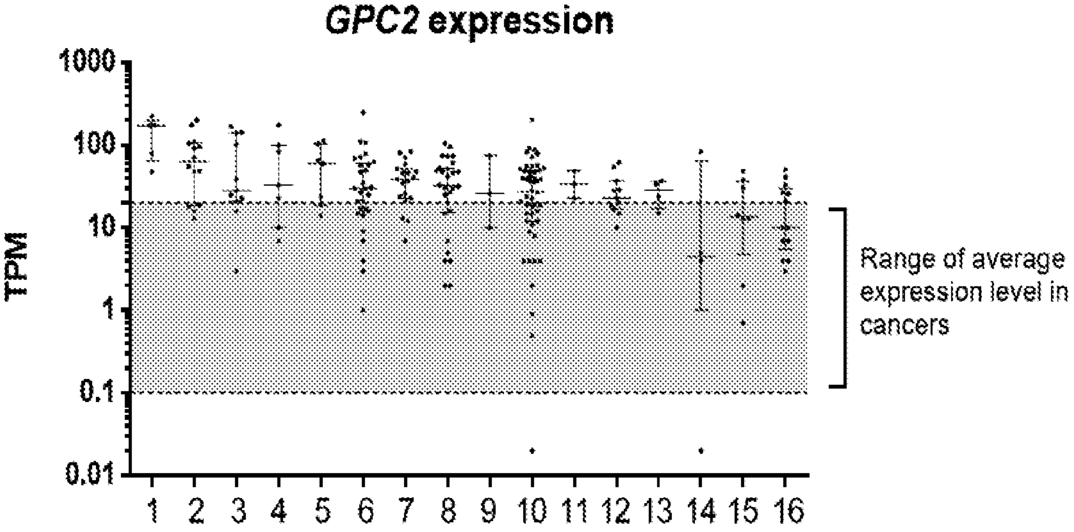

| | |
|---|---|
| 1 | CGP - peripheral nervous system, adrenal gland neuroblastoma |
| 2 | Cell lines - CCLE - neuroblastoma |
| 3 | CGP - peripheral nervous system, neuroblastoma |
| 4 | CGP - brain, neuroblastoma |
| 5 | 675 Genentech - brain, neuroblastoma |
| 6 | 675 Genentech - lung, small cell lung carcinoma |
| 7 | CGP - bone, Ewing sarcoma |
| 8 | CGP - lung, small cell lung carcinoma |
| 9 | CGP - musculature, rhabdomyosarcoma |
| 10 | Cell lines - CCLE - small cell lung carcinoma |
| 11 | CGP - testis, testicular germ cell tumor |
| 12 | Cell lines - CCLE - childhood T acute lymphoblastic leukemia |
| 13 | Cell lines - CCLE - adult T acute lymphoblastic leukemia |
| 14 | 675 Genentech - kidney, renal cell carcinoma |
| 15 | Cell lines - CCLE - Ewing sarcoma |
| 16 | CGP - hematopoietic system, acute lymphoblastic leukemia |

FIG. 1

GLYPICAN-2-BINDING MOIETIES, CHIMERIC ANTIGEN RECEPTORS AND USES THEREOF

BACKGROUND

1. Field

The present disclosure relates to antibodies and chimeric antigen receptors specific for tumor antigens, and their use for cancer immunotherapy. In particular, the present disclosure relates to antibodies and chimeric antigen receptors (CARs) specific for glypican-2 (GPC2) and uses thereof.

2. Description of Related Art

Neuroblastoma (NBL), an extra-cranial cancer arising from neural crest cells, is the third most common childhood cancer after leukemia and brain tumors [1, 2]. NBL accounts for 8-10% of pediatric cancers and 90% of NBL patients are diagnosed at age below five years. Approximately 700 cases of NBL are reported in North America and 1500 cases in Europe per annum. The Asia-Pacific region has approximately 8-12 NBL incidences per million population [3]. Because of rapid invasion and metastasis, the prognosis of NBL patients with high-risk NBL is poor under current treatment schemes. The 5-years survival rate of Stage IV patients is 40%, compared to 90% survival in Stage I-II patients. From the first time of diagnosis, approximately 45% of patients receiving standard therapy have relapses within 14 months, and the mortality rate is above 80% [1, 2]. Therefore there is an unmet and urgent need for a safe and effective treatment of neuroblastoma.

It has been shown that glypican-2 (GPC2) mRNA and protein is highly expressed in neuroblastoma [4, 5]. High level of GPC2 expression was also observed in small cell lung cancer, Ewing sarcoma, rhabdomyosarcoma, testicular germ cell tumor and acute lymphoblastic leukemia (FIG. 1). GPC2 is an extracellular glycosylphosphatidylinositol (GPI)-anchored, proteoglycan signaling co-receptor. It belongs to the six-member human glypican family of proteins that play diverse roles in growth factor signaling and cancer cell growth, and it is required for neuroblastoma cell proliferation [5]. Membrane expression of GPC2 is restricted in pediatric skin and esophagus, and low levels are found in adult testes and developing fetal brain [5, 6]. Recent data suggest that GPC2 can also regulate proliferation of neuron progenitor cells by inhibiting fibroblast growth factor 2-induced progenitor proliferation [7]. Depletion of GPC2 protein abrogates NBL tumor cell growth [4, 5], suggesting that it is essential for NBL tumor cell survival.

Chimeric antigen receptors (CARs) are composed of an extracellular binding domain specific to an antigen such as a tumor antigen, fused to a transmembrane domain and a T-cell-signaling moiety. These receptors, when expressed on the surfaces of T cells, mediate binding of the target and activate T cells, ultimately inducing target cell lysis. CAR T cells are T cells that have been genetically engineered to produce an artificial T-cell receptor, e.g., a CAR, for use in immunotherapy. CAR T cells are emerging as a promising approach to treat multiple leukemia, but their potential for treatment of solid tumors is not fully explored.

BRIEF SUMMARY

The present application provides an antibody or antigen binding fragment that specifically binds to GPC2, such as an anti-GPC2 single domain antibody (sdAb) or antigen binding fragments thereof, chimeric antigen receptors (CARs) including one or more anti-GPC2 sdAbs or antigen binding fragments thereof (such as $V_HH$ fragments), engineered immune effector cells, and methods of use thereof in cancer immunotherapy.

The present disclosure provides a binding moiety, e.g., an antibody or antigen binding fragment thereof, that binds glypican-2 (GPC2), comprising a first variable domain comprising a complementarity determining region (CDR) 1 region having an amino acid sequence selected from the group consisting of SEQ ID NOs:1-30, a CDR2 region having an amino acid sequence selected from the group consisting of SEQ ID NOs: 31-61, and a CDR3 region having an amino acid sequence selected from the group consisting of SEQ ID NOs: 62-92, or one or more variants of said SEQ ID NOs comprising, independently, up to three amino acid substitutions (e.g., one, two or three amino acid substitutions) in each of CDR1, CDR2, and CDR3.

In one aspect, the antibody or antigen binding fragment thereof of the present disclosure may include the CDR1 selected from the group consisting of SEQ ID NOs: 1-30, the CDR2 selected from the group consisting of SEQ ID NOs: 31-61, and the CDR3 selected from the group consisting of SEQ ID NOs: 62-92.

In some embodiments, the antibody or antigen binding fragment thereof of the present disclosure may include the CDR1 comprising SEQ ID NO: 1, the CDR2 comprising SEQ ID NO: 31, and the CDR3 comprising SEQ ID NO: 62, or the CDR1 comprising SEQ ID NO: 2, the CDR2 comprising SEQ ID NO: 32, and the CDR3 comprising SEQ ID NO: 63, or the CDR1 comprising SEQ ID NO: 3, the CDR2 comprising SEQ ID NO: 33, and the CDR3 comprising SEQ ID NO: 64, or the CDR1 comprising SEQ ID NO: 4, the CDR2 comprising SEQ ID NO: 34, and the CDR3 comprising SEQ ID NO: 65, or the CDR1 comprising SEQ ID NO: 5, the CDR2 comprising SEQ ID NO: 35, and the CDR3 comprising SEQ ID NO: 66, or the CDR1 comprising SEQ ID NO: 6, the CDR2 comprising SEQ ID NO: 36, and the CDR3 comprising SEQ ID NO: 67, or the CDR1 comprising SEQ ID NO: 7, the CDR2 comprising SEQ ID NO: 37, and the CDR3 comprising SEQ ID NO: 68, or the CDR1 comprising SEQ ID NO: 8, the CDR2 comprising SEQ ID NO: 38, and the CDR3 comprising SEQ ID NO: 69, or the CDR1 comprising SEQ ID NO: 9, the CDR2 comprising SEQ ID NO: 39, and the CDR3 comprising SEQ ID NO: 70, or the CDR1 comprising SEQ ID NO: 10, the CDR2 comprising SEQ ID NO: 40, and the CDR3 comprising SEQ ID NO: 71, or the CDR1 comprising SEQ ID NO: 11, the CDR2 comprising SEQ ID NO: 41, and the CDR3 comprising SEQ ID NO: 72, or the CDR1 comprising SEQ ID NO: 12, the CDR2 comprising SEQ ID NO: 42, and the CDR3 comprising SEQ ID NO: 73, or the CDR1 comprising SEQ ID NO: 11, the CDR2 comprising SEQ ID NO: 43, and the CDR3 comprising SEQ ID NO: 74, or the CDR1 comprising SEQ ID NO: 13, the CDR2 comprising SEQ ID NO: 44, and the CDR3 comprising SEQ ID NO: 75, or the CDR1 comprising SEQ ID NO: 14, the CDR2 comprising SEQ ID NO: 45, and the CDR3 comprising SEQ ID NO: 76, or the CDR1 comprising SEQ ID NO: 15, the CDR2 comprising SEQ ID NO: 46, and the CDR3 comprising SEQ ID NO: 77, or the CDR1 comprising SEQ ID NO: 16, the CDR2 comprising SEQ ID NO: 47, and the CDR3 comprising SEQ ID NO: 78, or the CDR1 comprising SEQ ID NO: 17, the CDR2 comprising SEQ ID NO: 48, and the CDR3 comprising SEQ ID NO: 79, or the CDR1 comprising SEQ ID NO: 18, the CDR2 comprising SEQ ID NO: 49, and the CDR3 comprising SEQ ID NO: 80, or the CDR1 comprising SEQ ID NO: 19, the CDR2 comprising SEQ ID NO: 50, and the CDR3 comprising SEQ ID NO: 81, or the CDR1 comprising SEQ ID NO: 20, the CDR2 comprising SEQ ID NO: 51, and the CDR3 comprising SEQ ID NO: 82, or the CDR1 comprising SEQ ID NO: 21, the CDR2 comprising SEQ ID NO: 52, and the CDR3 comprising SEQ ID NO: 83, or the CDR1 comprising SEQ ID NO: 22, the CDR2 comprising SEQ ID NO: 53, and the CDR3 comprising SEQ ID NO: 84, or the CDR1 comprising SEQ ID NO: 23, the CDR2 comprising SEQ ID NO: 54, and the CDR3 comprising SEQ ID NO: 85, or the CDR1 comprising SEQ ID NO: 24, the CDR2 comprising SEQ ID NO: 55, and the CDR3 comprising SEQ ID NO: 86, or the CDR1 comprising SEQ ID NO: 25, the CDR2 comprising SEQ ID NO: 56, and the CDR3 comprising SEQ ID NO: 87, or the CDR1 comprising SEQ ID NO: 26, the CDR2 comprising SEQ ID NO: 57, and the CDR3 comprising SEQ ID NO: 88, or the CDR1 comprising SEQ ID NO: 27, the CDR2 comprising SEQ ID NO: 58, and the CDR3 comprising SEQ ID NO: 89, or the CDR1 comprising SEQ ID NO: 28, the CDR2 comprising SEQ ID NO: 59, and the CDR3 comprising SEQ ID NO: 90, or the CDR1 comprising SEQ ID NO: 29, the CDR2 comprising SEQ ID NO: 60, and the CDR3 comprising SEQ ID NO: 91, or the CDR1 comprising SEQ ID NO: 30, the CDR2 comprising SEQ ID NO: 61, and the CDR3 comprising SEQ ID NO: 92, or a variant thereof comprising, independently, one, two, or three conservative amino acid substitutions in the CDR1, the CDR2, and/or the CDR3.

In some embodiments, the antibody or antigen binding fragment thereof of the present disclosure may include the CDR1 comprising SEQ ID NO: 1, the CDR2 comprising SEQ ID NO: 31, and the CDR3 comprising SEQ ID NO: 62, or the CDR1 comprising SEQ ID NO: 2, the CDR2 comprising SEQ ID NO: 32, and the CDR3 comprising SEQ ID NO: 63, or the CDR1 comprising SEQ ID NO: 3, the CDR2 comprising SEQ ID NO: 33, and the CDR3 comprising SEQ ID NO: 64, or the CDR1 comprising SEQ ID NO: 4, the CDR2 comprising SEQ ID NO: 34, and the CDR3 comprising SEQ ID NO: 65, or the CDR1 comprising SEQ ID NO: 5, the CDR2 comprising SEQ ID NO: 35, and the CDR3 comprising SEQ ID NO: 66, or the CDR1 comprising SEQ ID NO: 6, the CDR2 comprising SEQ ID NO: 36, and the CDR3 comprising SEQ ID NO: 67, or the CDR1 comprising SEQ ID NO: 7, the CDR2 comprising SEQ ID NO: 37, and the CDR3 comprising SEQ ID NO: 68, or the CDR1 comprising SEQ ID NO: 8, the CDR2 comprising SEQ ID NO: 38, and the CDR3 comprising SEQ ID NO: 69, or the CDR1 comprising SEQ ID NO: 9, the CDR2 comprising SEQ ID NO: 39, and the CDR3 comprising SEQ ID NO: 70, or the CDR1 comprising SEQ ID NO: 10, the CDR2 comprising SEQ ID NO: 40, and the CDR3 comprising SEQ ID NO: 71, or the CDR1 comprising SEQ ID NO: 11, the CDR2 comprising SEQ ID NO: 41, and the CDR3 comprising SEQ ID NO: 72, or the CDR1 comprising SEQ ID NO: 12, the CDR2 comprising SEQ ID NO: 42, and the CDR3 comprising SEQ ID NO: 73, or the CDR1 comprising SEQ ID NO: 11, the CDR2 comprising SEQ ID NO: 43, and the CDR3 comprising SEQ ID NO: 74, or the CDR1 comprising SEQ ID NO: 13, the CDR2 comprising SEQ ID NO: 44, and the CDR3 comprising SEQ ID NO: 75, or the CDR1 comprising SEQ ID NO: 14, the CDR2 comprising SEQ ID NO: 45, and the CDR3 comprising SEQ ID NO: 76, or the CDR1 comprising SEQ ID NO: 15, the CDR2 comprising SEQ ID NO: 46, and the CDR3 comprising SEQ ID NO: 77, or the CDR1 comprising SEQ ID NO: 16, the CDR2 comprising SEQ ID NO: 47, and the CDR3 comprising SEQ ID NO: 78, or the CDR1 comprising SEQ ID NO: 17, the CDR2 comprising SEQ ID NO: 48, and the CDR3 comprising SEQ ID NO: 79, or the CDR1 comprising SEQ ID NO: 18, the CDR2 comprising SEQ ID NO: 49, and the CDR3 comprising SEQ ID NO: 80, or the CDR1 comprising SEQ ID NO: 19, the CDR2 comprising SEQ ID NO: 50, and the CDR3 comprising SEQ ID NO: 81, or the CDR1 comprising SEQ ID NO: 20, the CDR2 comprising SEQ ID NO: 51, and the CDR3 comprising SEQ ID NO: 82, or the CDR1 comprising SEQ ID NO: 21, the CDR2 comprising SEQ ID NO: 52, and the CDR3 comprising SEQ ID NO: 83, or the CDR1 comprising SEQ ID NO: 22, the CDR2 comprising SEQ ID NO: 53, and the CDR3 comprising SEQ ID NO: 84, or the CDR1 comprising SEQ ID NO: 23, the CDR2 comprising SEQ ID NO: 54, and the CDR3 comprising SEQ ID NO: 85, or the CDR1 comprising SEQ ID NO: 24, the CDR2 comprising SEQ ID NO: 55, and the CDR3 comprising SEQ ID NO: 86, or the CDR1 comprising SEQ ID NO: 25, the CDR2 comprising SEQ ID NO: 56, and the CDR3 comprising SEQ ID NO: 87, or the CDR1 comprising SEQ ID NO: 26, the CDR2 comprising SEQ ID NO: 57, and the CDR3 comprising SEQ ID NO: 88, or the CDR1 comprising SEQ ID NO: 27, the CDR2 comprising SEQ ID NO: 58, and the CDR3 comprising SEQ ID NO: 89, or the CDR1 comprising SEQ ID NO: 28, the CDR2 comprising SEQ ID NO: 59, and the CDR3 comprising SEQ ID NO: 90, or the CDR1 comprising SEQ ID NO: 29, the CDR2 comprising SEQ ID NO: 60, and the CDR3 comprising SEQ ID NO: 91, or the CDR1 comprising SEQ ID NO: 30, the CDR2 comprising SEQ ID NO: 61, and the CDR3 comprising SEQ ID NO: 92.

In some embodiments, the antibody or antigen binding fragment thereof of the present disclosure may include the first variable domain having at least 70%, at least 75%, at least 80%, at least 85%, at least 90%, at least 95%, at least 96%, at least 97%, at least 98%, or at least 99% sequence identity to an amino acid sequence selected from the group consisting of SEQ ID NOs: 93-142.

In some embodiments, the antibody or antigen binding fragment thereof of the present disclosure may include the first variable domain having an amino acid sequence selected from the group consisting of SEQ ID NOs: 93-142.

In another aspect, the antibody or antigen binding fragment thereof described above further comprises a second variable domain comprising an amino acid sequence selected from the group consisting of SEQ ID NOs: 93-142.

In some embodiments, the antibody or antigen binding fragment thereof of the present disclosure may include a tandem antibody comprising a first variable domain comprising an amino acid sequence selected from the group consisting of SEQ ID NOs: 93-142 and a second variable domain comprising an amino acid sequence selected from the group consisting of SEQ ID NOs: 93-142.

In some embodiments, the tandem antibody of the present disclosure may have the first variable domain identical to the second variable domain so that they bind to the same antigen, e.g., a mono-valent tandem antibody.

In some embodiments, the tandem antibody of the present disclosure may have the first variable domain different from the second variable domain so that they bind to different antigens, e.g., a multi-valent tandem antibody.

In some embodiments, the tandem antibody of the present disclosure may include, from N-terminus to C-terminus, the first variable domain comprising SEQ ID NO: 126 and the second variable domain comprising SEQ ID NO: 128, or the first variable domain comprising SEQ ID NO: 128 and the second variable domain comprising SEQ ID NO: 126, or the first variable domain comprising SEQ ID NO: 124 and the second variable domain comprising SEQ ID NO: 127, or the first variable domain comprising SEQ ID NO: 127 and the second variable domain comprising SEQ ID NO: 124, or the first variable domain comprising SEQ ID NO: 124 and the second variable domain comprising SEQ ID NO: 124.

In some embodiments, the tandem antibody of the present disclosure may have the first variable domain linked to the second variable domain optionally via a linker. In some embodiments, the linker comprises a peptide linker, and optionally the peptide linker is a GS linker.

In some embodiments, the tandem antibody of the present disclosure may have at least 70%, at least 75%, at least 80%, at least 85%, at least 90%, at least 95%, at least 96%, at least 97%, at least 98%, or at least 99% sequence identity to an amino acid sequence selected from the group consisting of SEQ ID NOs: 143-147, and 244-245.

In some embodiments, the tandem antibody of the present disclosure may have an amino acid sequence selected from the group consisting of SEQ ID NOs: 143-147, and 244-245.

In some embodiments, the antibody or antigen binding fragment thereof of the present disclosure may have a first variable domain or a second variable domain selected from the group consisting of a single-domain antibody (sdAb), heavy chain only antibody (HCAb), an antigen-binding fragment (Fab), a Fab', a $F(ab')_2$, an antigen-binding variable region fragment (Fv), a single chain Fv (scFv), a $(scFv)_2$, an immunoglobulin (Ig)G1 antibody, an IgG2 antibody, an IgG3 antibody, and an IgG4 antibody.

In some embodiments, the antibody or antigen binding fragment thereof of the present disclosure may have the single-domain antibody (sdAb) comprising a $V_HH$ domain.

In some embodiments, the antibodies or antigen binding fragment thereof of the present disclosure may have the first variable domain and/or the second variable domain of a camelid, chimeric, humanized, or human variable domain.

In another aspect, embodiments of the present disclosure may include a chimeric antigen receptor (CAR) that specifically binds to GPC2, comprising: (a) an extracellular antigen binding domain comprising a first binding domain comprising the antibody or antigen binding fragment thereof described above; b) a transmembrane domain; and (c) an intracellular signaling domain.

In another aspect, embodiments of the present disclosure may include a chimeric antigen receptor (CAR) that specifically binds to GPC2, comprising, from N-terminus to C-terminus: (a) an extracellular antigen binding domain comprising a first binding domain comprising a CDR1 selected from the group consisting of SEQ ID NOs: 1-30, a CDR2 selected from the group consisting of SEQ ID NOs: 31-61, and a CDR3 selected from the group consisting of SEQ ID NOs: 62-92, or a variant thereof comprising, independently, one, two, or three amino acid substitutions in the CDR1, the CDR2, and/or the CDR3, (b) a transmembrane domain; and (c) an intracellular signaling domain.

In some embodiments, the CAR of the present disclosure comprises, from N-terminus to C-terminus: (a) an extracellular antigen binding domain comprising a first binding domain comprising a CDR1 selected from the group consisting of SEQ ID NOs: 1-30, a CDR2 selected from the group consisting of SEQ ID NOs: 31-61, and a CDR3 selected from the group consisting of SEQ ID NOs: 62-92, (b) a transmembrane domain; and (c) an intracellular signaling domain.

In some embodiments, the CAR of the present disclosure may have at least 70%, at least 75%, at least 80%, at least 85%, at least 90%, at least 95%, at least 96%, at least 97%, at least 98%, or at least 99% sequence identity to an amino acid sequence selected from the group consisting of SEQ ID NOs: 189-238, and 248-252.

In some embodiments, the CAR of the present disclosure may have an amino acid sequence selected from the group consisting of SEQ ID NOs: 189-238, and 248-252.

In another aspect, the CAR of the present disclosure may include a tandem CAR having an extracellular antigen binding domain including a first binding domain of CARs of the present disclosure and a second binding domain comprising a CDR1 selected from the group consisting of SEQ ID NOs: 1-30, a CDR2 selected from the group consisting of SEQ ID NOs: 31-61, and a CDR3 selected from the group consisting of SEQ ID NOs: 62-92, or a variant thereof comprising, independently, one, two, or three conservative amino acid substitutions in the CDR1, the CDR2, and/or the CDR3, wherein the first binding domain fuses to the second binding domain optionally via a linker.

In some embodiments, the CAR of the present disclosure further comprises a second binding domain comprising a CDR1 selected from the group consisting of SEQ ID NOs: 1-30, a CDR2 selected from the group consisting of SEQ ID NOs: 31-61, and a CDR3 selected from the group consisting of SEQ ID NOs: 62-92. In some embodiments, the first binding domain fuses to the second binding domain optionally via a linker. In some embodiments, the linker comprises a peptide linker, and optionally the linker is a GS linker.

In some embodiments, the tandem CAR of the present disclosure may have at least 70%, at least 75%, at least 80%, at least 85%, at least 90%, at least 95%, at least 96%, at least 97%, at least 98%, or at least 99% sequence identity to an amino acid sequence selected from the group consisting of SEQ ID NOs: 239-243, and 246-247.

In some embodiments, the tandem CAR of the present disclosure may have an amino acid sequence selected from the group consisting of SEQ ID NOs: 239-243, and 246-247.

In some embodiments, the tandem CAR of the present disclosure may include an extracellular antigen binding domain further comprising a second binding domain that binds to a second antigen, and the second antigen is different from the GPC2. In other words, provided that the first binding domain does not bind to the second antigen.

In some embodiments, the tandem CAR of the present disclosure may include a second antigen of disialoganglioside (GD2) or delta-like protein 3 (DLL3).

In some embodiments, the CAR and the tandem CAR of the present disclosure may further include a signal peptide located at the N-terminus of the polypeptide.

In some embodiments, the CAR and the tandem CAR of the present disclosure may include a signal peptide derived from a molecule selected from the group consisting of cluster of differentiation (CD) 8 alpha chain (CD8α), granulocyte-macrophage colony-stimulating factor (GM-CSF) receptor α, and IgG1 heavy chain.

In some embodiments, the CAR and the tandem CAR of the present disclosure may further include a hinge domain located between the C-terminus of the extracellular antigen binding domain and the N-terminus of the transmembrane domain.

In some embodiments, the CAR and the tandem CAR of the present disclosure may include a hinge domain derived from CD8α, CD28, or IgG4 fragment crystallizable region (Fc).

In some embodiments, the CAR and the tandem CAR of the present disclosure may include a transmembrane domain derived from a molecule selected from the group consisting of CD8α, CD4, CD2, CD27, CD28, CD137, CD80, CD86, CTLA-4 (CD152), ICOS, OX40 and programmed cell death protein 1 (PD-1).

In some embodiments, the CAR and the tandem CAR of the present disclosure may include a intracellular signaling domain comprising a co-stimulatory signaling domain.

In some embodiments, the CAR and the tandem CAR of the present disclosure may include a intracellular signaling domain comprising a primary intracellular signaling domain of an immune effector cell.

In some embodiments, the CAR and the tandem CAR of the present disclosure may include a primary intracellular signaling domain derived from CD3ζ.

In some embodiments, the CAR and the tandem CAR of the present disclosure may include a co-stimulatory signaling domain derived from a co-stimulatory molecule selected from the group consisting of CD27, CD28, 4-1BB (CD137), TNF receptor superfamily member 4 (OX40), CD30, CD40, CD3, TNF receptor superfamily member 14 (HVEM), inducible T cell costimulator (ICOS), MYD88 innate immune signal transduction adaptor (Myd88), integrin subunit alpha L (LFA-1), CD2, CD7, TNF superfamily member 14 (LIGHT), NKG2-C type II integral membrane protein (NKG2C), CD276 molecule (B7-H3), Ligands of CD83, and a combination thereof.

In another aspect, embodiments of the present disclosure may include a dual CAR system, comprising a first CAR as described above, and a second CAR as described above.

In another aspect, embodiments of the present disclosure may include a dual CAR system, including a first CAR that specifically binds to GPC2, comprising, from N-terminus to C-terminus: (a) a first extracellular antigen binding domain comprising a first binding domain comprising a CDR1 selected from the group consisting of SEQ ID NOs: 1-30, a CDR2 selected from the group consisting of SEQ ID NOs: 31-61, and a CDR3 selected from the group consisting of SEQ ID NOs: 62-92, or a variant thereof comprising, independently, one, two, or three conservative amino acid substitutions in the CDR1, the CDR2, and/or the CDR3, (b) a first transmembrane domain; and (c) a first intracellular signaling domain, and a second CAR that specifically binds to GPC2, comprising, from N-terminus to C-terminus: (a) a second extracellular antigen binding domain comprising a second binding domain comprising a CDR1 selected from the group consisting of SEQ ID NOs: 1-30, a CDR2 selected from the group consisting of SEQ ID NOs: 31-61, and a CDR3 selected from the group consisting of SEQ ID NOs: 62-92, or a variant thereof comprising, independently, one, two, or three conservative amino acid substitutions in the CDR1, the CDR2, and/or the CDR3, (b) a second transmembrane domain; and (c) a second intracellular signaling domain, or a second CAR that binds to a second antigen, comprising, from N-terminus to C-terminus: (a) a second extracellular antigen binding domain comprising a second binding domain that binds to the second antigen, provided that the first binding domain does not bind to the second antigen, (b) a second transmembrane domain; and (c) a second intracellular signaling domain.

In some embodiments, the dual CAR system of the present invention may include a first CAR and/or a second CAR having at least 70%, at least 75%, at least 80%, at least 85%, at least 90%, at least 95%, at least 96%, at least 97%, at least 98%, or at least 99% sequence identity to an amino acid sequence selected from the group consisting of SEQ ID NOs: 189-238, and 248-252.

In some embodiments, the dual CAR system of the present invention may include a first CAR and/or a second CAR having an amino acid sequence selected from the group consisting of SEQ ID NOs: 189-238, and 248-252.

In some embodiments, the dual CAR system of the present invention may include a first CAR and/or a second CAR further comprising a signal peptide located at the N-terminus of the polypeptide.

In some embodiments, the dual CAR system of the present invention may include a signal peptide derived from a molecule selected from the group consisting of CD8α, GM-CSF receptor α, and IgG1 heavy chain.

In some embodiments, the dual CAR system of the present invention may include a first CAR and/or a second CAR further comprising a hinge domain located between the C-terminus of the extracellular antigen binding domain and the N-terminus of the transmembrane domain.

In some embodiments, the dual CAR system of the present invention may include a hinge domain derived from CD8α, CD28, or IgG4 Fc.

In some embodiments, the dual CAR system of the present invention may include a first and a second transmembrane domain which are, independently, derived from a molecule selected from the group consisting of CD8α, CD4, CD2, CD27, CD28, CD137, CD80, CD86, CTLA-4 (CD152), ICOS, OX40 and programmed cell death protein 1 (PD-1).

In another aspect, the dual CAR system of the present invention may include a first and/or a second intracellular signaling domain which each, independently, comprise a co-stimulatory signaling domain.

In some embodiments, the dual CAR system of the present invention may include a co-stimulatory signaling domain derived from a co-stimulatory molecule selected from the group consisting of CD27, CD28, CD137, OX40, CD30, CD40, CD3, HVEM, ICOS, Myd88, LFA-1, ICOS, CD2, CD7, LIGHT, NKG2C, B7-H3, ligands of CD83, and a combination thereof.

In some embodiments, the dual CAR system of the present invention may include a first and/or a second intracellular signaling domain, each independently further comprising a primary intracellular signaling domain of an immune effector cell.

In some embodiments, the dual CAR system of the present invention may include a primary intracellular signaling domain derived from CD3ζ.

In some embodiments, the dual CAR system of the present invention may include a intracellular signaling domain of a second CAR which comprises a co-stimulatory signaling domain. In some embodiments, the co-stimulatory signaling domain is derived from a co-stimulatory molecule selected from the group consisting of CD27, CD28, CD137, OX40, CD30, CD40, CD3, HVEM, ICOS, Myd88, LFA-1, ICOS, CD2, CD7, LIGHT, NKG2C, B7-H3, ligands of CD83, and a combination thereof.

In another aspect, embodiments of the present disclosure may include a split CAR system, including the dual CAR system of the present disclosure, in which the first intracellular signaling domain may be structurally different from the second intracellular signaling domain.

In some embodiments, the split CAR system of the present invention may include a first intracellular signaling domain comprising a primary intracellular signaling domain of an immune effector cell and a second intracellular signaling domain comprising a co-stimulatory signaling domain.

In some embodiments, the split CAR system of the present invention may include a first intracellular signaling domain consisting of a primary intracellular signaling domain of an immune effector cell and a second intracellular signaling domain consisting of a co-stimulatory signaling domain.

In some embodiments, the split CAR system of the present invention may include a primary intracellular signaling domain derived from CD3ζ.

In some embodiments, the split CAR system of the present invention may include a co-stimulatory signaling domain derived from a co-stimulatory molecule selected from the group consisting of CD27, CD28, CD137, OX40, CD30, CD40, CD3, HVEM, ICOS, Myd88, LFA-1, ICOS, CD2, CD7, LIGHT, NKG2C, B7-H3, Ligands of CD83, and a combination thereof.

In another aspect, embodiments of the present disclosure may include nucleic acid molecules encoding antibodies including mono-valent antibody and tandem antibody and antigen binding fragment thereof, single CARs, tandem CARs, dual CAR system, and split CAR system of the present disclosure.

In some embodiments, the nucleic acid molecule may be selected from the group consisting of SEQ ID NOs: 148-178.

In an aspect, embodiments of the present disclosure may include an expression vector comprising a nucleic acid molecule of the present disclosure.

In another aspect, the vector may be a viral vector or a non-viral vector. In some embodiments, the viral vector is a lentiviral vector.

In an aspect, embodiments of the present disclosure may include an engineered immune effector cell comprising the vector of the present disclosure, or comprising a nucleic acid of the present disclosure.

In some embodiments, the engineered immune effector cell may include an immune effector cell selected from a group consisting of T cell, NK cell, peripheral blood mononuclear cell (PBMC), hematopoietic stem cell, pluripotent stem cell, embryonic stem cell, and a combination thereof.

In some embodiments, the engineered immune effector cell may include a T cell selected from the group consisting of a cytotoxic T cell, a helper T cell, a natural killer T cell, and a γδ T cell.

In another aspect, the engineered immune effector cell may further comprises a membrane-bound interleukin (IL)-15 or a membrane-bound IL-7.

In an aspect, embodiments of the present disclosure may include a composition comprising a therapeutically effective amount of a engineered immune effector cell of the present disclosure and a pharmaceutically acceptable carrier.

In another aspect, the composition of the present disclosure may further include an immunomodulatory agent.

In another aspect, the immunomodulatory agent may be selected from the group consisting of 3-(4-amino-1-oxo-1,3 dihydro-2H-isoindol-2-yl)piperidine-2,6-dione, pomalidomide, avadomide, pomalidomide, avadomide, and a combination thereof.

In some embodiments, the immunomodulatory agent may include 3-(4-amino-1-oxo-1,3 dihydro-2H-isoindol-2-yl)piperidine-2,6-dione.

In an aspect, embodiments of the present disclosure may include a method of treating a patient who has cancer that expresses GPC2, including administering to the patient a composition of the present disclosure.

In some embodiments, the engineered immune effector cell may be obtained from the patient.

In some embodiments, the engineered immune effector cell may be obtained from a healthy donor.

In another aspect, the cancer may be selected from the group consisting of acute lymphoblastic leukemia cell, Ewing's sarcoma cell, neuroblastoma, Embryonal rhabdomyosarcoma, alveolar rhabdomyosarcoma, lung cancer, brain cancer, uterine cancer, cervical cancer, colorectal cancer, stomach cancer, head and neck cancer, breast cancer, pancreatic cancer, ovarian cancer, kidney cancer, esophageal cancer, testicular cancer, and skin cancer.

Another embodiment includes a chimeric antigen receptor (CAR) comprising (i) an ectodomain comprising at least one single domain antibody that binds selectively to GPC2; (ii) a transmembrane domain; and (iii) an endodomain comprising one or more immunoreceptor tyrosine-based activation motif (ITAM) domains. In some embodiments, the ectodomain may be multimeric. The multimers can be formed by pairing two single domain antibodies into what may be referred to as a multi-valent antibody using a glycine-serine linker. In some embodiments of the present disclosure, the glycine-serine linker, e.g., $(GGGGS)_n$, wherein n is an integer between 0 and 8. In some embodiments, n is 3, i.e., GGGGSGGGGSGGGGS (SEQ ID NO: 181). The dual-specific antibody can also be formed by pairing one single domain antibody (e.g., $V_HH$) with another single domain antibody (e.g., $V_HH$) or a single chain antibody (scFv) specific for a different antigen using a glycine-serine linker. The hinge portion of the CAR may in some embodiments comprise or consist of a proportion of CD8α, a proportion of CD28, or a proportion of IgG4 Fc. The transmembrane portion of CAR may be derived from the same molecule as the flexible hinge. The endodomain may comprise a zeta chain of the T-cell receptor or any of its homologs (e.g., eta, delta, gamma, or epsilon), MB1 chain, B29, common FcR gamma (FCER1G), Fc gamma RIM, FcR beta (Fc Epsilon R1b), and combinations of one, two or more intracellular signaling domain, such as CD27, CD28, CD137 (4-1BB or TNF receptor superfamily member 9), CD40, DAP-10, DAP-12, CD2, ICOS, OX40/CD134, FcεRIγ, IL-2Rbeta/CD122, IL 2Ralpha/CD132, and CD40 to enhance CAR T cell persistence and therapeutic efficacy.

Examples of tumor associated antigens that may be targeted in addition to GPC2 with CARs described herein include, e.g., disialoganglioside (GD2), cancer antigen 125 (CA-125), Mucin 1 (MUC-1), Delta-like 3 (DLL3), carcinoembryonic antigen, alphafetoprotein, epidermal growth factor receptor (EGFR), EGFR VIII, erb-b2 receptor tyrosine kinase (Her)2, Her3, epithelial tumor antigen, C-type lectin domain comprising 7A (Dectin-1), and so forth.

In some embodiments, a CAR may be co-expressed with a membrane-bound cytokine, e.g., to improve persistence when there is a low amount of tumor-associated antigen. For example, a CAR can be co-expressed with membrane-bound IL-15 or membrane-bound IL-7.

In some embodiments, a CAR may be co-expressed with a chemokine receptor, e.g., to improve T cell trafficking and tumor infiltration. For example, a CAR can be co-expressed with C-X-C motif chemokine receptor (CXCR)1/2, CXCR3, CXCR4, CXCR5, C-C motif chemokine receptor (CCR)2 or CCR7.

In some embodiments, a CAR may be co-expressed with a dominant-negative PD-1 receptor or a dominant-negative transforming growth factor (TGF)β receptor that comprises an intact ectodomain but lacks an intracellular signaling domain to improve T cell persistence and anti-tumor efficacy.

In some embodiments, GPC2 CAR T cells may be used in combination with 3-(4-amino-1-oxo-1,3 dihydro-2H-isoindol-2-yl)piperidine-2,6-dione (shown as Compound A) to improve CAR T expansion and anti-tumor functions.

(Compound A)

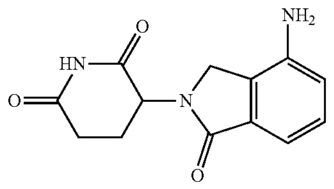

BRIEF DESCRIPTION OF THE DRAWINGS

FIG. 1 shows GPC2 mRNA expression level across different tumor databases.

DETAILED DESCRIPTION

Figure 2A:
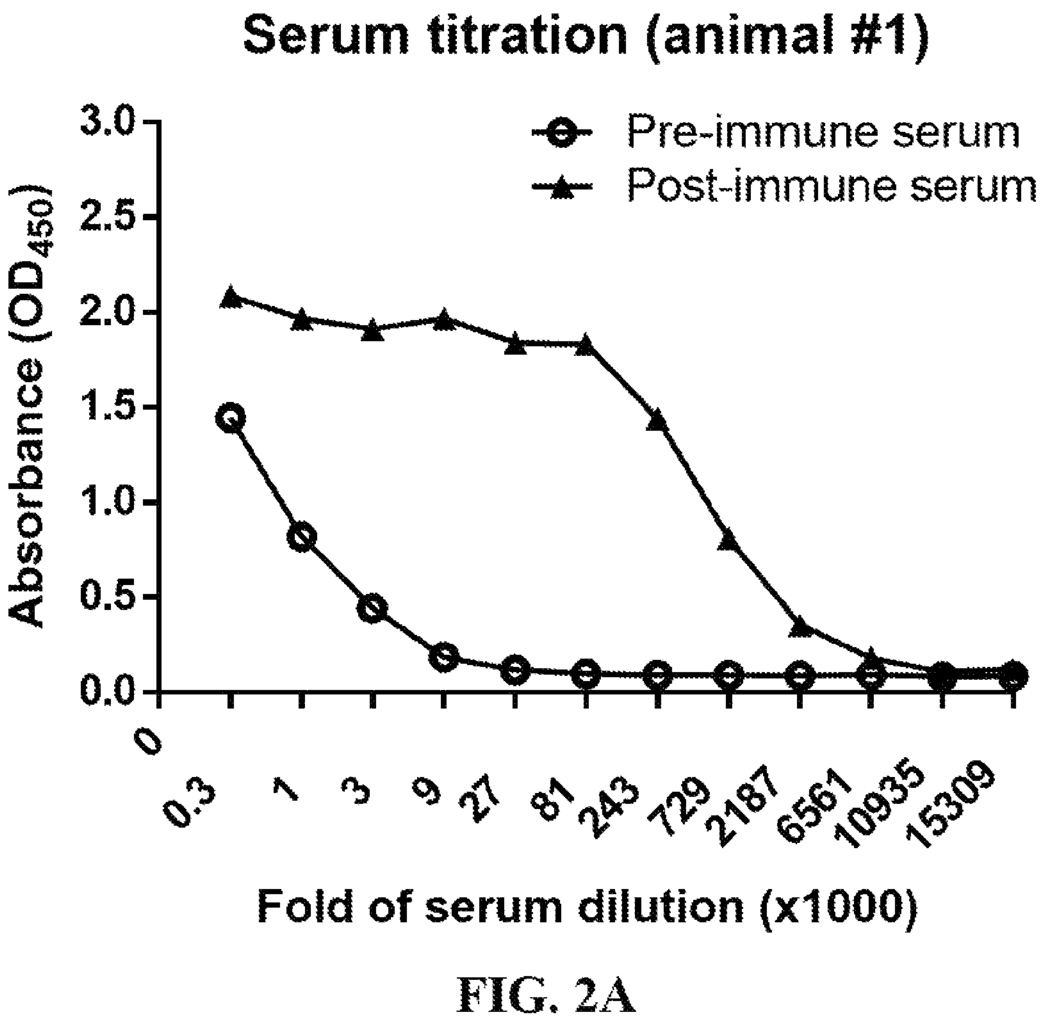
FIGS. 2A-2D show humoral immune response of an immunized camel against recombinant human GPC2 protein.

Disclosed herein are GPC2-specific camelid single domain antibodies which specifically bind human cell-surface GPC2. Disclosed herein are humanized $V_H$H single domain antibodies in monovalent or bivalent forms that bind cell-surface human GPC2. Also disclosed herein are constructs comprising the GPC2 single domain antibodies (for example, chimeric antigen receptor (CAR) T cells) capable of inhibiting GPC2-positive tumor cell growth and potently killing GPC2 positive-tumor cells. The present disclosure describes methods of treating GPC2-positive tumors using GPC2-specific single domain antibody-based chimeric antigen receptor T cells.

1. Definitions

Unless otherwise defined herein, technical and scientific terms used in the present description have the meanings that are commonly understood by those of ordinary skill in the art.

"A", "an" and "the": The articles as used herein refer to one or to more than one (i.e., to at least one) of the grammatical object of the article. By way of example, "an antibody" means one antibody or more than one antibody.

Antibody: The term as used herein refers to an immunoglobulin molecule that recognizes and specifically binds a target, such as a protein, polypeptide, peptide, carbohydrate, polynucleotide, lipid, or a combination of any of the foregoing, through at least one antigen-binding site wherein the antigen-binding site is usually within the variable region of the immunoglobulin molecule. As used herein, the term encompasses intact multispecific antibodies, intact monoclonal antibodies, single-domain antibodies (sdAbs; e.g., camelid antibodies, alpaca antibodies), single-chain Fv (scFv) antibodies, heavy chain antibodies (HCAbs), light chain antibodies (LCAbs), multispecific antibodies, bispecific antibodies, monospecific antibodies, monovalent antibodies, fusion proteins comprising an antigen-binding site of an antibody, and any other modified immunoglobulin molecule comprising an antigen-binding site (e.g., dual variable domain immunoglobulin molecules) as long as the antibodies exhibit the desired biological activity. Antibodies also include, but are not limited to, mouse antibodies, camel antibodies, chimeric antibodies, humanized antibodies, and human antibodies. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes. The term "immunoglobulin" (Ig) is used interchangeably with the term "antibody" herein. Unless expressly indicated otherwise, the term "antibody" as used herein include "antigen-binding fragments" of intact antibodies.

Full length antibody: the term is used herein to mean the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains VL and CL, and each heavy chain comprising immunoglobulin domains VH, CH1, CH2, and CH3. In some mammals, for example in camels and llamas, IgG antibodies consist of only two heavy chains (HCAb), each heavy chain comprising a variable domain attached to the Fc region (CH2 and CH3 domains).

Valent: this term as used herein denotes the presence of a specified number of binding sites in an antibody molecule. As such, the terms "monovalent," "bivalent," "tetravalent," and "hexavalent" denote the presence of one binding site, two binding sites, four binding sites, and six binding sites, respectively, in an antibody molecule. The bispecific antibodies disclosed herein are "bivalent." Monospecific bivalent antibodies, however, are within the scope of the present disclosure, in which the two antigen-binding sites bind the same antigen. The antigen-binding sites of monospecific bivalent antibodies can bind different epitopes on the antigen.

Monospecific antibody: this term refers to selective recognition of the antibody for a particular epitope of an antigen. Natural antibodies, for example, are monospecific. The term "monospecific" antibody as used herein denotes an antibody that has one or more binding sites each of which bind to the same epitope of the same antigen. The monospecific antibodies specific for GPC2 of the present disclosure may be monovalent or multi-valent, e.g., bivalent, tetravalent, or hexavalent.

Multispecific antibody: The term as used herein may include a plurality of immunoglobulin variable domain sequences, in which a first immunoglobulin variable domain sequence of the plurality has binding specificity for a first epitope and a second immunoglobulin variable domain sequence of the plurality has binding specificity for a second epitope. And the first and second epitopes are on the same antigen (e.g., the same protein or subunit of a multimeric protein) or on different antigens (e.g., different proteins or different subunits of a multimeric protein). A multispecific antibody molecule comprises a third, fourth or fifth immunoglobulin variable domain. A multispecific antibody molecule is a bispecific antibody molecule, a trispecific antibody molecule, or tetraspecific antibody molecule.

Bispecific antibody: The term may include a heavy chain variable domain sequence and a light chain variable domain sequence which have binding specificity for a first epitope and a heavy chain variable domain sequence and a light chain variable domain sequence which have binding specificity for a second epitope. A bispecific antibody molecule may have a single domain antibody, e.g., $V_HH$, or fragment thereof, having binding specificity for a first epitope and a single domain antibody, e.g., $V_HH$, or fragment thereof, having binding specificity for a second epitope. A bispecific antibody molecule may have a scFv, or fragment thereof, having binding specificity for a first epitope and a scFv, or fragment thereof, having binding specificity for a second epitope. And the first and second epitopes may be on the same antigen (e.g., the same protein or subunit of a multimeric protein) or on different antigens (e.g., different proteins or different subunits of a multimeric protein). A bispecific antibody molecule may have a half antibody, or fragment thereof, having binding specificity for a first epitope and a half antibody, or fragment thereof, having binding specificity for a second epitope.

Antigen-binding fragment: The term as used in connection with an antibody refers to a portion of an intact antibody and refers to the antigenic determining variable regions of an intact antibody. Examples of antibody fragments include, but are not limited to, Fab, Fab', $F(ab')_2$, Fv, linear antibodies, single chain antibody molecules (e.g., scFv), heavy chain antibodies (HCAbs), light chain antibodies (LCAbs), disulfide-linked scFv (dsscFv), diabodies, tribodies, tetrabodies, minibodies, dual variable domain antibodies (DVD), single variable domain antibodies (sdAbs; e.g., camelid antibodies, alpaca antibodies), single variable domain of heavy chain antibodies ($V_HH$), and multispecific antibodies formed from antibody fragments.

Epitope and antigenic determinant: The terms are used interchangeably herein and refer to the site on the surface of a target molecule to which a binding moiety binds, such as a localized region on the surface of an antigen. The target molecule can comprise, a protein, a peptide, a nucleic acid, a carbohydrate, or a lipid. An epitope having immunogenic activity is a portion of a target molecule that elicits an immune response in an animal. An epitope of a target molecule having antigenic activity is a portion of the target molecule to which an antibody binds, as determined by any method well known in the art, including, for example, by an immunoassay. Antigenic epitopes need not necessarily be immunogenic. Epitopes often consist of chemically active surface groupings of molecules such as amino acids or sugar side chains and have specific three dimensional structural characteristics as well as specific charge characteristics. The term, "epitope" includes linear epitopes and conformational epitopes. A region of a target molecule (e.g., a polypeptide) contributing to an epitope may be contiguous amino acids of the polypeptide or the epitope may come together from two or more non-contiguous regions of the target molecule. The epitope may or may not be a three-dimensional surface feature of the target molecule. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation.

Single-domain antibody: The term "single-domain antibody," "single-domain antibody moiety," "sdAb" or "sdAb moiety" refers to a single antigen-binding polypeptide having three complementary determining regions (CDRs), including full-length antibodies (e.g., HCAbs) and antigen-binding fragments thereof (e.g., $V_HH$). The sdAb alone is capable of binding to the antigen without pairing with a corresponding CDR-comprising polypeptide. In some cases, single-domain antibodies are engineered from camelid HCAbs, and their heavy chain variable domains are referred herein as "$V_HH$s". Some $V_HH$s may also be known as Nanobodies. Camelid sdAb is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). A basic $V_HH$ has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the present disclosure, a single domain antibody may be a naturally occurring single domain antibody known as heavy chain antibody devoid of light chains. Such single domain antibodies are disclosed in WO 9404678, for example. This variable domain may be derived from a heavy chain antibody naturally devoid of light chain known herein as a $V_HH$ or nanobody to distinguish it from the conventional VH of four chain immunoglobulins. Such a $V_HH$ molecule can be derived from antibodies raised in Camelidae species, for example in camel, llama, dromedary, alpaca and guanaco. Other species besides Camelidae may produce heavy chain antibodies naturally devoid of light chain; such $V_HH$s are within the scope of the present disclosure.

Monoclonal antibody: It is an antibody produced by a single clone of lymphocytes or by a cell into which the coding sequence of a single antibody has been transfected. Monoclonal antibodies are produced by methods known to those of skill in the art. Monoclonal antibodies include humanized monoclonal antibodies.

Chimeric antibody: The term refers to an antibody made by combining genetic material from a nonhuman source with genetic material from a human being. Or more generally, a chimeric antibody is an antibody having genetic material from a certain species with genetic material from another species.

Humanized antibody: It is an immunoglobulin including a human framework region and one or more CDRs from a non-human (for example a mouse, rabbit, rat, shark or synthetic) immunoglobulin. The non-human immunoglobulin providing the CDRs is termed a "donor," and the human immunoglobulin providing the framework is termed an "acceptor." Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A humanized antibody binds to the same antigen as the donor antibody that provides the CDRs. Humanized or other monoclonal antibodies can have additional conservative amino acid substitutions which have substantially no effect on antigen binding or other immunoglobulin functions.

Camelid antibody: The term as used herein, is intended to include antibodies having variable regions in which both the framework and CDR regions are derived from camelid germline heavy chain antibody sequences. Furthermore, if the antibody comprises a constant region, the constant region also is derived from camelid germline heavy chain antibody sequences. The camelid antibodies of the invention can include amino acid residues not encoded by camelid germline heavy chain antibody sequences (e.g., mutations introduced by random or site-specific mutagenesis in vitro or by somatic mutation in vivo). However, the term "camelid antibody", as used herein, is not intended to include antibodies in which CDR sequences derived from the germline of another mammalian species have been grafted onto camelid framework sequences.

VH and VL regions: The term can be subdivided into regions of hypervariability, termed "complementarity determining regions" (CDR), interspersed with regions that are more conserved, termed "framework regions" (FR or FW).

The extent of the framework region and CDRs: It has been precisely defined by a number of methods (see, Rabat, E. A., et al. (1991) Sequences of Proteins of Immunological Interest, Fifth Edition, U.S. Department of Health and Human Services, NIH Publication No. 91-3242; Chothia, C. et al. (1987) J. Mol. Biol. 196:901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg).

Complementarity determining region (CDR): As used herein refer to the sequences of amino acids within antibody variable regions which confer antigen specificity and binding affinity. In some embodiments, there are three CDRs in each heavy chain variable region (HCDR1, HCDR2, and HCDR3) and three CDRs in each light chain variable region (LCDR1, LCDR2, and LCDR3).

The amino acid residues of an sdAb (such as $V_HH$) are numbered according to the general numbering for $V_H$ domains given by Kabat et al. ("Sequence of proteins of immunological interest", US Public Health Services, MH Bethesda, Md., Publication No. 91), as applied to $V_HH$ domains from Camelids in the article of Riechmann and Muyldermans, J. Immunol. Methods 2000 Jun. 23; 240 (1-2): 185-195. According to this numbering, FR1 of a $V_HH$ comprises the amino acid residues at positions 1-30, CDR1 of a $V_HH$ comprises the amino acid residues at positions 31-35, FR2 of a $V_HH$ comprises the amino acids at positions 36-49, CDR2 of a $V_HH$ comprises the amino acid residues at positions 50-65, FR3 of a $V_HH$ comprises the amino acid residues at positions 66-94, CDR3 of a $V_HH$ comprises the amino acid residues at positions 95-102, and FR4 of a $V_HH$ comprises the amino acid residues at positions 103-113. In this respect, it should be noted that—as is well known in the art for $V_H$ domains and for $V_HH$ domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may comprise more amino acid residues than the number allowed for by the Kabat numbering).

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may comprise fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Framework region: Amino acid sequences interposed between CDRs. Framework regions include variable light and variable heavy framework regions. The framework regions serve to hold the CDRs in an appropriate orientation for antigen binding.

Substitution: A substitution comprises an amino acid not naturally present in a region of the antigen recognizing construct.

Substitution modification: A substitution modification described herein comprises an amino acid not naturally present in region the respective CDR region.

Amino acid substitution: The term refers to the replacement of one amino acid residue with another in a polypeptide sequence. A "conservative amino acid substitution" is one in which one amino acid residue is replaced with another amino acid residue having a side chain with similar chemical characteristics. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Generally, conservative substitutions in the sequences of the polypeptides, soluble proteins, and/or antibodies of the disclosure do not abrogate the binding of the polypeptide, soluble protein, or antibody comprising the amino acid sequence, to the target binding site. Methods of identifying amino acid conservative substitutions which do not eliminate binding are well-known in the art.

Conservative variant: "Conservative" amino acid substitutions are those substitutions that do not substantially affect or decrease the affinity of a protein, such as an antibody to GPC2. As one example, a monoclonal antibody that specifically binds GPC2 can include at most about 1, at most about 2, at most about 3, at most about 4, at most about 5, at most about 6, at most about 7, at most about 8, at most about 9, at most about 10, at most about 11, at most about 12, at most about 13, at most about 14, or at most about 15 conservative substitutions and specifically bind the GPC2 polypeptide. The term "conservative variant" also includes the use of a substituted amino acid in place of an unsubstituted parent amino acid, provided that the variant retains activity. Non-conservative substitutions are those that reduce an activity of a protein. Non-limiting examples of conservative substitutions may be found in, for example, Creighton (1984) Proteins. W.H. Freeman and Company, the contents of which are incorporated by reference in their entirety.

Conservative substitutions: It may include those, which are described by Dayhoff in "The Atlas of Protein Sequence and Structure. Vol. 5", Natl. Biomedical Research, the contents of which are incorporated by reference in their entirety. For example, in an aspect, amino acids, which belong to one of the following groups, can be exchanged for one another, thus, constituting a conservative exchange: Group 1: alanine (A), proline (P), glycine (G), asparagine (N), serine (S), threonine (T); Group 2: cysteine (C), serine (S), tyrosine (Y), threonine (T); Group 3: valine (V), isoleucine (I), leucine (L), methionine (M), alanine (A), phenyl-alanine (F); Group 4: lysine (K), arginine (R), histidine (H); Group 5: phenylalanine (F), tyro-sine (Y), tryptophan (W), histidine (H); and Group 6: aspartic acid (D), glutamic acid (E). In an aspect, a conservative amino acid substitution may be selected from the following of T→A, G→A, T→V, A→M, A→V, T→G, and/or T→S. In another aspect, a conservative amino acid substitution may include the substitution of an amino acid by another amino acid of the same class, for example, (1) nonpolar: Ala, Val, Leu, Ile, Pro, Met, Phe, Trp; (2) uncharged polar: Gly, Ser, Thr, Cys, Tyr, Asn, Gln; (3) acidic: Asp, Glu; and (4) basic: Lys, Arg, His. Other conservative amino acid substitutions may also be made as follows: (1) aromatic: Phe, Tyr, His; (2) proton donor: Asn, Gln, Lys, Arg, His, Trp; and (3) proton acceptor: Glu, Asp, Thr, Ser, Tyr, Asn, Gln (see, for example, U.S. Pat. No. 10,106,805, the contents of which are incorporated by reference in their entirety). In another aspect, conservative substitutions may be made in accordance with Table A. Methods for predicting tolerance to protein modification may be found in, for example, Guo et al., Proc. Natl. Acad. Sci., USA, 101(25):9205-9210 (2004), the contents of which are incorporated by reference in their entirety. In another aspect, conservative substitutions may be those shown in Table B under the heading of "conservative substitutions." If such substitutions result in a change in biological activity, then more substantial changes, denominated "exemplary substitutions" in Table B, may be introduced and the products screened if needed.

TABLE A

Conservative Amino Acid Substitutions

| Amino Acid | Substitutions (others are known in the art) |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

TABLE B

Amino Acid Substitutions

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Glu; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |

TABLE B-continued

Amino Acid Substitutions

| Original Residue (naturally occurring amino acid) | Conservative Substitutions | Exemplary Substitutions |
|---|---|---|
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Homologs and variants of a $V_L$ or a $V_H$ or a $V_HH$ or a $V_{NAR}$ of an antibody that specifically binds a GPC2 polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Degenerate variant: In the context of the present disclosure, a "degenerate variant" refers to a polynucleotide encoding a GPC2 polypeptide or an antibody that binds GPC2 that includes a sequence that is degenerate as a result of the genetic code. There are 20 natural amino acids, most of which are specified by more than one codon. Therefore, all degenerate nucleotide sequences are included as long as the amino acid sequence of the GPC2 polypeptide or antibody that binds GPC2 encoded by the nucleotide sequence is unchanged.

Binding affinity: Affinity of an antibody for an antigen. In some embodiments, affinity is calculated by a modification of the Scatchard method described by Frankel et al. Mol. Immunol., 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. In another embodiment, antibody affinity is measured by flow cytometry. An antibody that "specifically binds" an antigen (such as GPC2) is an antibody that binds the antigen with high affinity and does not significantly bind other unrelated antigens.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin comprising a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99}mTc$, $^{131}I$, $^{3}H$, $^{14}C$, $^{15}N$, $^{90}Y$, $^{99}Tc$, $^{11}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label. Linkers allow for proper folding of the sequences to generate the desired three-dimensional conformation and antigen binding profiles.

Conjugating, joining, bonding or linking: The terms refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Chimeric antigen receptor (CAR): A chimeric molecule that includes one or more antigen-binding portion (such as a single domain antibody or scFv) and a signaling domain, such as a signaling domain from a T cell receptor (e.g., CD3ζ). Typically, CARs are comprised of an antigen-binding moiety, a transmembrane domain and an intracellular domain. The intracellular domain typically includes a signaling chain having an immunoreceptor tyrosine-based activation motif (ITAM), such as CD3ζ or FcεRIγ. In some instances, the intracellular domain further includes the intracellular portion of at least one additional co-stimulatory domain, such as CD28, 4-1BB (CD137), ICOS, OX40 (CD134), CD27, and/or hematopoietic cell signal transducer (DAP10). In the context of the present application, the terms "cytoplasmic domain", "intracellular domain" and "intracellular signaling domain" are interchangeable.

Single CAR: A chimeric molecule that includes a single antigen-binding portion (such as a single domain antibody or scFv) and a signaling domain, such as a signaling domain from a T cell receptor (e.g., CD3ζ). Typically, single CARs may comprise a monospecific antigen-binding moiety, a transmembrane domain, and an intracellular domain.

Tandem CAR: A chimeric molecule that includes more than one antigen-binding portions (such as 2, 4, or 6 single domain antibodies or scFv) and a signaling domain, such as a signaling domain from a T cell receptor (e.g., CD3ζ). Typically, tandem CARs may comprise monospecific, bivalent antigen-binding moiety, e.g., two identical $V_H$H domains binding GPC2, or multi-specific, e.g., bispecific bivalent, antigen-binding moiety, e.g., two different $V_H$H domains binding GPC2 or one $V_H$H domain binding GPC2 and the other $V_H$H domain binding a molecule other than GPC2, e.g., GD2 and DLL3, a transmembrane domain, and an intracellular domain.

Dual CAR: Two separate CARs that may be bispecific, or two tandem CARs that each CAR may be monospecific or bispecific, or one single CAR and one tandem CAR that may be monospecific or bispecific. A dual CAR may have each of a first CAR and a second CAR having both co-stimulatory domain, such as CD28, 4-1BB (CD137), ICOS, OX40 (CD134), CD27, and DAP10, and a signaling domain, such as a signaling domain from a T cell receptor (e.g., CD3ζ).

Split CAR: different from dual CAR, in split CAR, a first CAR may comprise a co-stimulatory domain but lack a signaling domain from a T cell receptor; and a second CAR may comprises signaling domain from a T cell receptor but lack co-stimulatory domain.

Immune response: A response of a cell of the immune system, such as a B cell, T cell, or monocyte, to a stimulus. In some embodiments, the response is specific for a particular antigen (an "antigen-specific response"). In some embodiments, an immune response is a T cell response, such as a CD4+ response or a CD8+ response. In another embodiment, the response is a B cell response, and results in the production of specific antibodies.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. Remington's Pharmaceutical Sciences, by E. W. Martin, Mack Publishing Co., Easton, PA, 15th Edition, 1975, describes compositions and formulations suitable for pharmaceutical delivery of the compositions disclosed herein.

Preventing, treating or ameliorating a disease: "Preventing" a disease refers to inhibiting the full development of a disease. As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence(s) of cancer. The methods of the present application contemplate any one or more of these aspects of treatment. "Ameliorating" refers to the reduction in the number or severity of signs or symptoms of a disease, such as cancer.

Purified: The term purified does not require absolute purity; rather, it is intended as a relative term. Thus, for example, a purified peptide preparation is one in which the peptide or protein is more enriched than the peptide or protein is in its natural environment within a cell. In some embodiments, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extrachromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Recombinant: A recombinant nucleic acid is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Fusion protein: A protein comprising at least a portion of two different (heterologous) proteins.

Sample (or biological sample): A biological specimen comprising genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a tumor biopsy, such as a tumor tissue biopsy.

Subject: Living multi-cellular vertebrate organisms, a category that includes both human and veterinary subjects, including human and non-human mammals. "Subject", "individual" and "patient" are used herein interchangeably. In some embodiments, a subject is a mammal, including, but not limited to, human, bovine, horse, feline, canine, rodent, or primate. In some embodiments, the subject is a human.

Synthetic: Produced by artificial means in a laboratory, for example a synthetic nucleic acid or protein (for example, an antibody) can be chemically synthesized in a laboratory.

Therapeutically effective amount: Effective amount used herein refers to an amount of an agent, such as an anti-GPC2 construct, an engineered immune cell, or a pharmaceutical composition thereof, sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Transfection: A process introduces naked or purified nucleic acids into cells. Transfection may be carried out using calcium phosphate (i.e., tricalcium phosphate), by electroporation, by cell squeezing or by mixing a cationic lipid with the material to produce liposomes that fuse with the cell membrane and deposit their cargo inside.

Electroporation: A process uses a pulsed electric field to transiently permeabilize cell membranes, allowing macromolecules, such as DNA or RNA, to pass into cells.

Transduction: A process introduces foreign DNA into a cell by a virus or viral vector. Viruses may be, but not limited to, retroviruses, lentiviruses, adenoviruses, or adeno-associated viruses.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

GPC2-positive cancer: Examples of GPC2-positive cancers include, but are not limited to, neuroblastoma, acute lymphoblastic leukemia, embryonal rhabdomyosarcoma, alveolar rhabdomyosarcoma, Ewing's sarcoma, desmoplastic small round cell tumor, and osteosarcoma.

2. Anti-GPC2 Antibodies or Antigen Binding Fragments and CARs

Glypican-2 (GPC2): A member of the six-member glypican family of heparan sulfate (HS) proteoglycans that are attached to the cell surface by a GPI anchor (Filmus et al., Genome Biol 9:224, 2008). GPC2 is transiently expressed during neuronal development (Stipp et al., J Cell Biol 124:149-160, 1994; Lugert S, Kremer T, et al., Scientific Reports. 2017; 7: 46543.), participates in cell adhesion and is thought to regulate the growth and guidance of axons. In addition, GPC2 mRNA is highly expressed in neuroblastoma and other pediatric cancers (Orentas et al., Front Oncol 2:194, 2012). GPC2 is also known as cerebroglycan proteoglycan and glypican proteoglycan 2. GPC2 genomic, mRNA and protein sequences are publicly available (see, for example, NCBI Gene ID 221914).

2A: Anti-GPC2 Antibody or Antigen Binding Fragment

Heavy Chain Only Antibodies (HCAb) and Variable Domain ($V_HH$)

The antibodies of the present disclosure may include heavy chain only antibodies (HCAb). Camelids (camels, dromedary, and llamas) comprise in addition to normal heavy and light chain antibodies (2 light chains and 2 heavy chains in one antibody), single chain antibodies (comprising only heavy chains). The variable domains of HCAbs, referred to as $V_HH$s, nanobodies, or single-domain antibodies (sdAbs) represent the smallest naturally derived antigen-binding functional fragments (~15 kDa). Natural $V_HH$-comprising antibodies are missing the entire CH1 domain of the constant region of the heavy chain. The exon coding for the CH1 domain is present in the genome but is spliced out due to the loss of a functional splice acceptor sequence at the 5' side of the CH1 exon. As a result, the VDJ region is spliced onto the CH2 exon. When a $V_HH$ is recombined onto such constant regions (CH2, CH3), an antibody is produced that acts as a single chain antibody (i.e., an antibody of two heavy chains without a light chain interaction). Binding of an antigen is different from that seen with a conventional antibody, but high affinity is achieved the same way, i.e., through hypermutation of the variable region and selection of the cells expressing such high affinity antibodies. These $V_HH$s maintain affinities and antigen-binding specificities comparable to those of full-size mAbs.

Anti-GPC2 $V_HH$

Embodiments of the present disclosure include antibodies comprising a $V_HH$ domain that specifically bind GPC2. In some embodiments, the single domain antibody (about 15 kD) comprise a complementarity determining region (CDR) 1 having an amino acid sequence selected from the group consisting of SEQ ID NOs: 1-30, a CDR2 having an amino acid sequence selected from the group consisting of SEQ ID NOs: 31-61, and a CDR3 having an amino acid sequence selected from the group consisting of SEQ ID NOs: 62-92. For example, $V_HH$ single domain antibodies that specifically bind GPC2 may comprise CDR1, CDR2, and CDR3 as listed in Table 1.

Embodiments of the present disclosure may also include antibodies comprising $V_HH$ variants comprising one, two, or three conservative amino acid substitutions in CDR1 having an amino acid sequence selected from the group consisting of SEQ ID NOs: 1-30, and/or one, two, or three conservative amino acid substitutions in CDR2 having an amino acid sequence selected from the group consisting of SEQ ID NOs: 31-61, and/or one, two, or three conservative amino acid substitutions in CDR3 having an amino acid sequence selected from the group consisting of SEQ ID NOs: 62-92. Embodiments of the present disclosure may also include $V_H$H variants comprising one conservative amino acid substitution in CDR1 having an amino acid sequence selected from the group consisting of SEQ ID NOs: 1-30, and/or one conservative amino acid substitution in CDR2 having an amino acid sequence selected from the group consisting of SEQ ID NOs: 31-61, and/or one conservative amino acid substitution in CDR3 having an amino acid sequence selected from the group consisting of SEQ ID NOs: 62-92.

In some embodiments, there is provided an anti-GPC2 $V_H$H comprising: (a) a CDR1 comprising the amino acid sequence of SEQ ID NO: 23, or a variant thereof comprising up to about 3 (e.g., 1, 2, or 3) amino acid substitutions in the CDR1, (b) a CDR2 comprising the amino acid sequence of SEQ ID NO: 54, or a variant thereof comprising up to about 3 (e.g., 1, 2, or 3) amino acid substitutions in the CDR2; and (c) a CDR3 comprising the amino acid sequence of SEQ ID NO: 85, or a variant thereof comprising up to about 3 (e.g., 1, 2, or 3) amino acid substitutions in the CDR3. In some embodiments, there is provided an anti-GPC2 $V_H$H comprising: (a) a CDR1 comprising the amino acid sequence of SEQ ID NO: 23; (b) a CDR2 comprising the amino acid sequence of SEQ ID NO: 54; and (c) a CDR3 comprising the amino acid sequence of SEQ ID NO: 85, or a variant thereof comprising up to about 5 (e.g., 1, 2, 3, 4, or 5) amino acid substitutions in the CDRs. In some embodiments, there is provided an anti-GPC2 $V_H$H comprising: (a) a CDR1 comprising the amino acid sequence of SEQ ID NO: 23; (b) a CDR2 comprising the amino acid sequence of SEQ ID NO: 54; and (c) a CDR3 comprising the amino acid sequence of SEQ m NO:85. In some embodiments, there is provided a polypeptide comprising the amino acid sequences of SEQ ID NOs: 23, 54 and 85.

In some embodiments, there is provided an anti-GPC2 $V_H$H comprising: (a) a CDR1 comprising the amino acid sequence of SEQ ID NO: 27, or a variant thereof comprising up to about 3 (e.g., 1, 2, or 3) amino acid substitutions in the CDR1; (b) a CDR2 comprising the amino acid sequence of SEQ ID NO: 58, or a variant thereof comprising up to about 3 (e.g., 1, 2, or 3) amino acid substitutions in the CDR2; and (c) a CDR3 comprising the amino acid sequence of SEQ ID NO: 89, or a variant thereof comprising up to about 3 (e.g., 1, 2, or 3) amino acid substitutions in the CDR3. In some embodiments, there is provided an anti-GPC2 VIM comprising: (a) a CDR1 comprising the amino acid sequence of SEQ ID NO: 27; (b) a CDR2 comprising the amino acid sequence of SEQ ID NO: 58; and (c) a CDR3 comprising the amino acid sequence of SEQ ID NO: 89, or a variant thereof comprising up to about 5 (e.g., 1, 2, 3, 4, or 5) amino acid substitutions in the CDRs. In some embodiments, there is provided an anti-GPC2 $V_H$H comprising: (a) a CDR1 comprising the amino acid sequence of SEQ ID NO: 27; (b) a CDR2 comprising the amino acid sequence of SEQ ID NO: 58; and (c) a CDR3 comprising the amino acid sequence of SEQ ID NO:89. In some embodiments, there is provided a polypeptide comprising the amino acid sequences of SEQ ID NOs: 27; 58 and 89.

In some embodiments, there is provided an anti-GPC2 $V_H$H comprising: (a) a CDR1 comprising the amino acid sequence of SEQ ID NO: 3, or a variant thereof comprising up to about 3 (e.g., 1, 2, or 3) amino acid substitutions in the CDR1; (b) a CDR2 comprising the amino acid sequence of SEQ ID NO: 33, or a variant thereof comprising up to about 3 (e.g., 1, 2, or 3) amino acid substitutions in the CDR2; and (c) a CDR3 comprising the amino acid sequence of SEQ ID NO: 64, or a variant thereof comprising up to about 3 (e.g., 1, 2, or 3) amino acid substitutions in the CDR3. In some embodiments; there is provided an anti-GPC2 $V_H$H comprising: (a) a CDR1 comprising the amino acid sequence of SEQ ID NO: 3; (b) a CDR2 comprising the amino acid sequence of SEQ ID NO: 33; and (c) a CDR3 comprising the amino acid sequence of SEQ ID NO: 64, or a variant thereof comprising up to about 5 (e.g., 1, 2, 3, 4, or 5) amino acid substitutions in the CDRs. In some embodiments, there is provided an anti-GPC2 $V_H$H comprising: (a) a CDR1 comprising the amino acid sequence of SEQ ID NO: 3; (b) a CDR2 comprising the amino acid sequence of SEQ ID NO: 33; and (c) a CDR3 comprising the amino acid sequence of SEQ ID NO:64. In some embodiments, there is provided a polypeptide comprising the amino acid sequences of SEQ TD NOs: 3, 33 and 64.

In some embodiments, there is provided an anti-GPC2 $V_H$H comprising: (a) a CDR1 comprising the amino acid sequence of SEQ ID NO: 5, or a variant thereof comprising up to about 3 (e.g., 1, 2, or 3) amino acid substitutions in the CDR1; (b) a CDR2 comprising the amino acid sequence of SEQ ID NO: 35, or a variant thereof comprising up to about 3 (e.g., 1, 2, or 3) amino acid substitutions in the CDR2; and (c) a CDR3 comprising the amino acid sequence of SEQ ID NO: 66, or a variant thereof comprising up to about 3 (e.g., 1, 2, or 3) amino acid substitutions in the CDR3. In some embodiments, there is provided an anti-GPC2 $V_H$H comprising: (a) a CDR1 comprising the amino acid sequence of SEQ ID NO: 5; (b) a CDR2 comprising the amino acid sequence of SEQ ID NO: 35; and (c) a CDR3 comprising the amino acid sequence of SEQ ID NO: 66, or a variant thereof comprising up to about 5 (e.g., 1, 2, 3, 4, or 5) amino acid substitutions in the CDRs. In some embodiments, there is provided an anti-GPC2 $V_H$H comprising: (a) a CDR1 comprising the amino acid sequence of SEQ ID NO: 5; (b) a CDR2 comprising the amino acid sequence of SEQ ID NO: 35; and (c) a CDR3 comprising the amino acid sequence of SEQ ID NO:66. In some embodiments, there is provided a polypeptide comprising the amino acid sequences of SEQ ID NOs: 5, 35 and 66.

In some embodiments, there is provided an anti-GPC2 $V_H$H comprising: (a) a CDR1 comprising the amino acid sequence of SEQ ID NO: 11, or a variant thereof comprising up to about 3 (e.g., 1, 2, or 3) amino acid substitutions in the CDR1; (b) a CDR2 comprising the amino acid sequence of SEQ ID NO: 43, or a variant thereof comprising up to about 3 (e.g., 1, 2, or 3) amino acid substitutions in the CDR2; and (c) a CDR3 comprising the amino acid sequence of SEQ ID NO: 74, or a variant thereof comprising up to about 3 (e.g., 1, 2, or 3) amino acid substitutions in the CDR3. In some embodiments, there is provided an anti-GPC2 $V_H$H comprising: (a) a CDR1 comprising the amino acid sequence of SEQ ID NO: 11; (b) a CDR2 comprising the amino acid sequence of SEQ ID NO: 43; and (c) a CDR3 comprising the amino acid sequence of SEQ ID NO: 74, or a variant thereof comprising up to about 5 (e.g., 1, 2, 3, 4, or 5) amino acid substitutions in the CDRs. In some embodiments, there is provided an anti-GPC2 $V_H$H comprising: (a) a CDR1 comprising the amino acid sequence of SEQ ID NO: 11; (b) a CDR2 comprising the amino acid sequence of SEQ ID NO: 43; and (c) a CDR3 comprising the amino acid sequence of SEQ m NO:74. In some embodiments, there is provided a polypeptide comprising the amino acid sequences of SEQ ID NOs: 11, 43 and 74.

In some embodiments, the anti-GPC2 $V_H$H, including any of the embodiments described above (i.e., anti-GPC2 $V_H$H comprising specific CDR1, CDR2, and/or CDR3) comprises a $V_HH$ domain having at least about any one of 85%, 86%, 87%, 88%, 89%, 90%, 91%, 92%, 93%, 94%, 95%, 96%, 97%, 98%, 99%, or 100% sequence identity to the amino acid sequence of any one of SEQ ID NOs: 93-142. In some embodiments, a $V_HH$ sequence having at least about any one of 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-GPC2 $V_HH$ comprising that sequence retains the ability to bind to GPC2. In some embodiments, a total of 1 to 10 amino acids have been substituted, inserted and/or deleted in the amino acid sequence of any one of SEQ ID NOs: 93-142. In some embodiments, substitutions, insertions, or deletions occur in regions outside the CDRs (i.e., in the FRs). In some embodiments, the anti-GPC2 $V_HH$ comprises the amino acid sequence of any one of SEQ ID NOs: 93-142, optionally including post-translational modifications of that sequence.

In some embodiments, functional epitopes can be mapped by combinatorial alanine scanning. In this process, a combinatorial alanine-scanning strategy can be used to identify amino acids in the GPC2 protein that are necessary for interaction with anti-GPC2 sdAbs. In some embodiments, the epitope is conformational and crystal structure of anti-GPC2 sdAb bound to GPC2 may be employed to identify the epitopes.

In some embodiments, the present application provides antibodies (e.g., $V_HH$s) which compete with any one of the anti-GPC2 $V_HH$s described herein for binding to GPC2. In some embodiments, the present application provides antibodies (e.g., $V_HH$s) which compete with any one of the anti-GPC2 $V_HH$s provided herein for binding to an epitope on the GPC2. In some embodiments, an anti-GPC2 antibody (e.g., $V_HH$s) is provided that binds to the same epitope as an anti-GPC2 $V_HH$ comprising the amino acid sequence of any one of SEQ ID NOs: 93-142, In some embodiments, an GPC2 antibody (e.g., $V_HH$s) is provided that specifically binds to GPC2 competitively with an anti-GPC2 $V_HH$ comprising the amino acid sequence of any one of SEQ ID NOs:93-142.

In some embodiments, competition assays may be used to identify a monoclonal antibody that competes with an anti-GPC2 $V_HH$ described herein for binding to GPC2. Competition assays can be used to determine whether two antibodies bind the same epitope by recognizing identical or sterically overlapping epitopes or one antibody competitively inhibits binding of another antibody to the antigen. In certain embodiments, such a competing antibody binds to the same epitope that is bound by an antibody described herein. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). In some embodiments, two antibodies are said to bind to the same epitope if each blocks binding of the other by 50% or more. In some embodiments, the antibody that competes with an anti-GPC2 $V_HH$ described herein is a camelid, chimeric, humanized or human antibody. In some embodiments, the present application provides an antibody that competes with a camelid, chimeric, humanized, or human anti-GPC2 $V_HH$s as described herein.

In some embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CYTOTOX 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., Blood 101:1045-1052 (2003); and Cragg, M. S. and M. J. Glennie, *Blood* 103: 2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

Anti-GPC2 Bispecific Bivalent Antibody

Embodiments of the present disclosure may include bispecific antibodies, in which two antigen binding domains may be joined in a single bispecific molecule, i.e., bispecific bivalent anti-GPC2 antibodies. Anti-GPC2 bispecific bivalent antibodies of the present disclosure may comprise any two different $V_H$H single domains comprising CDR1, CDR2, and CDR3 listed in Table 1. That is, two different $V_H$H single domains bind GPC2. For example, anti-GPC2 bispecific bivalent antibodies may comprise AS70549-AS70771, or AS70549-AS70950, or AS70549-AS71402, or AS70549-AS71529, or AS70549-AS71661, etc. Anti-GPC2 bispecific bivalent antibodies of the present disclosure may also comprise a first $V_H$H single domain listed in Table 1 and a second $V_H$H single domain that binds to molecule other than GPC2, e.g., GD2 or DLL3. For example, anti-GPC2 bispecific bivalent antibodies may comprise a first $V_H$H single domain that binds to GPC2 (AS70549)—a second $V_H$H single domain that binds to GD2, or a first $V_H$H single domain that binds to GPC2 (AS70549)—a second $V_H$H single domain that binds to DLL3, or a first $V_H$H single domain that binds to GPC2 (AS70771)—a second $V_H$H single domain that binds to GD2, or a first $V_H$H single domain that binds to GPC2 (AS70771)—a second $V_H$H single domain that binds to DLL3, etc. Anti-GPC2 bispecific bivalent antibodies of the present disclosure may be in the form of Fv fragments (e.g., scFv) or HCAb or Fab. Anti-GPC2 bispecific bivalent antibodies may optionally include linker sequences, e.g., GS linker, linking between two different $V_H$H single domains. For example, anti-GPC2 bispecific bivalent antibodies may comprise AS71529VH5-AS72052VH5, AS72052VH5-AS71529VH5, AS70950VH6-AS71529VH6, AS71529VH6-AS70950VH6, AS70950VH6-AS70950VH6, AS78117VH4-AS71529VH6 or AS71529VH6-AS78117VH4.

2B: Anti-GPC2 CARs

Figure 5:
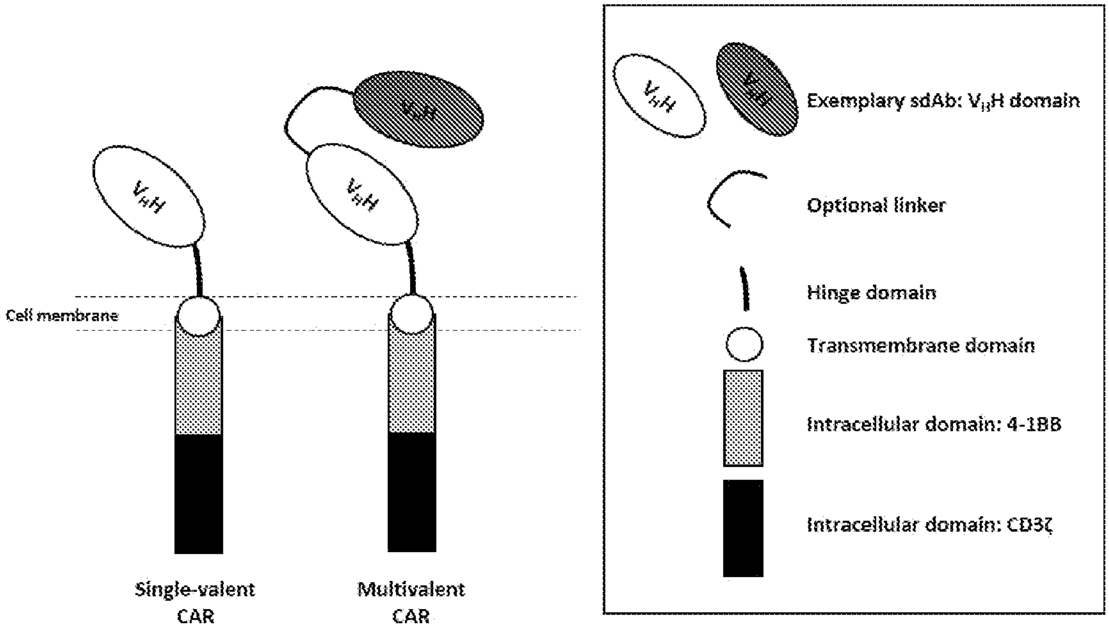
FIG. 5 shows schematic structures of exemplary $V_H$H-based CARs having one or two $V_H$H domains.

One aspect of the present application provides a chimeric antigen receptor comprising an extracellular domain comprising one or more anti-GPC2 sdAbs (e.g., $V_H$H), a transmembrane domain, and an intracellular signaling domain. Also provided is a chimeric antigen receptor system comprising: (a) a first chimeric antigen receptor comprising an extracellular domain comprising an anti-GPC2 sdAb (e.g., $V_H$H), a transmembrane domain, and an intracellular signaling domain; and (b) a second chimeric antigen receptor comprising an extracellular domain comprising a binding moiety that specifically binds to a second antigen that is different from GPC2 or a different epitope in GPC2. Any one of the anti-GPC2 antibody or antigen binding fragment described herein can be used in the chimeric receptors or chimeric antigen receptor systems described herein. Exemplary structures of chimeric receptors and chimeric antigen receptor systems are shown in FIG. 5.

Single Anti-GPC2 CAR

Embodiments of the present disclosure provide single anti-GPC2 CAR that has an extracellular antigen binding domain having a single GPC2 binding domain. In some embodiments, there is provided a chimeric antigen receptor targeting GPC2 (also referred herein as "anti-GPC2 chimeric receptor" or "anti-GPC2 CAR") comprising: (a) an extracellular domain comprising a single GPC2 binding domain comprising an anti-GPC2 $V_H$H domain comprising the CDR1, CDR2, and CDR3 listed in Table 1; (b) a transmembrane domain; and (c) an intracellular signaling domain. A hinge domain may optionally be used to link between $V_H$H single domain and transmembrane domain. In some embodiments, the transmembrane domain is selected from the group consisting of CD8α, CD4, CD28, 4-1BB, CD80, CD86, CD152, PD-1, CD2, CD27, ICOS and OX40. In some embodiments, the intracellular signaling domain comprises a primary intracellular signaling sequence of an immune effector cell (such as T cell). In some embodiments, the primary intracellular signaling sequence is derived from CD3 ζ, CD3γ, CD3δ, CD3ε, common FcR gamma (FCER1G), Fc gamma RIM, FcR beta (Fc Epsilon R1b), CD5, CD22, CD79a, CD79b, or CD66d. In some embodiments, the primary intracellular signaling sequence is derived from CD3ζ. In some embodiments, the intracellular signaling domain comprises an intracellular co-stimulatory sequence. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. Single anti-GPC2 CAR of the present disclosure may include CAS70549-BBz, CAS70771-BBz, CAS70950-BBz, CAS71402-BBz, CAS71529-BBz, CAS71661-BBz, CAS72021-BBz, CAS72052-BBz, CAS72383-BBz, CAS72479-BBz, CAS72499-BBz, CAS72531-BBz, CAS72669-BBz, CAS72794-BBz, CAS72805-BBz, CAS72806-BBz, CAS72835-BBz, CAS77906-BBz, CAS77916-BBz, CAS77932-BBz, CAS77934-BBz, CAS77978-BBz, CAS77986-BBz, CAS78117-BBz, CAS78215-BBz, CAS78810-BBz, CAS79101-BBz, CAS79236-BBz, CAS79274-BBz, CAS79285-BBz, CAS79317-BBz, CAS70950VH6-BBz, CAS70950VH7-BBz, CAS71529VH5-BBz, CAS71529VH6-BBz, CAS72052VH5-BBz, CAS72052VH6-BBz, CAS72669VH6-BBz, CAS78117VH4-BBz, CAS78117VH5-BBz, CAS78117VH6-BBz, CAS78117VH7-BBz, CAS79236VH4-BBz, CAS79236VH5-BBz, CAS79236VH6-BBz, CAS77916VH6-BBz, CAS77916VH7-BBz, CAS77916VH8-BBz, CAS77916VH9-BBz, CAS77916VH10-BBz, GPC2-CD28z, GPC2-CD27z, GPC2-ICOSz, GPC2-CD22 and GPC2-OX40z, preferably, CAS70950-BBz, CAS70950VH6-BBz, CAS71529-BBz, CAS71529VH6-BBz, CAS78117-BBz, CAS78117VH4-BBz, CAS79236-BBz, CAS79236VH6-BBz, GPC2-

CD28z, GPC2-CD27z, GPC2-ICOSz, GPC2-CD2z, GPC2-OX40z, or a combination thereof.

In some embodiments, there is provided a chimeric antigen receptor targeting GPC2 comprising: (a) an extracellular domain comprising an anti-GPC2 $V_H$H comprising a CDR1 comprising the amino acid sequence of SEQ ID NO:3, a CDR2 comprising the amino acid sequence of SEQ ID NO: 33, and a CDR3 comprising the amino acid sequence of SEQ ID NO: 64, or a variant thereof comprising up to about 5 amino acid substitutions in the CDRs; (b) a transmembrane domain; and (c) an intracellular signaling domain. In some embodiments, the anti-GPC2 $V_H$H moiety comprises a $V_H$H domain comprising the amino acid sequence of SEQ ID NO: 95,124 or 125, or a variant thereof comprising an amino acid sequence having at least about 95% sequence identity to the amino acid sequence of SEQ ID NO: 95,124 or 125. In some embodiments, the primary intracellular signaling sequence is derived from CD3ζ. In some embodiments, the intracellular signaling domain comprises an intracellular co-stimulatory sequence. In some embodiments, the intracellular co-stimulatory sequence comprises 4-1BB, CD28z, CD27z, ICOSz, CD2z or OX40z. In some embodiments, the anti-GPC2 chimeric antigen receptor further comprises a hinge domain (e.g., a CD8 hinge domain) located between the C-terminus of the extracellular domain and the N-terminus of the transmembrane domain. In some embodiments, the anti-GPC2 chimeric antigen receptor further comprises a signal peptide (such as a CD8 signal peptide). In some embodiments, the anti-GPC2 chimeric antigen receptor comprises a polypeptide comprising from the N-terminus to the C-terminus: a CD8 signal peptide, the anti-GPC2 $V_H$H moiety, a CD8 hinge domain, a CD8 transmembrane domain, and an intracellular signaling domain comprising an intracellular co-stimulatory sequence derived from 4-1BB and a CD3 ζ intracellular signaling sequence. In some embodiments, the anti-GPC2 chimeric antigen receptor comprises a polypeptide comprising from the N-terminus to the C-terminus: a CD8 signal peptide, the anti-GPC2 $V_H$H moiety, a CD28 hinge domain, a CD28 transmembrane domain, and an intracellular signaling domain comprising an intracellular co-stimulatory sequence derived from 4-1BB and a CD3 ζ intracellular signaling sequence. In some embodiments, the anti-GPC2 chimeric antigen receptor comprises a polypeptide comprising the amino acid sequence of SEQ ID NO: 190, 220 or 221, or a variant thereof comprising an amino acid sequence having at least about 95% sequence identity to the amino acid sequence of SEQ ID NO: 190, 220 or 221.

In some embodiments, there is provided a chimeric antigen receptor targeting GPC2 comprising: (a) an extracellular domain comprising an anti-GPC2 $V_H$H comprising a CDR1 comprising the amino acid sequence of SEQ ID NO:5, a CDR2 comprising the amino acid sequence of SEQ ID NO: 35, and a CDR3 comprising the amino acid sequence of SEQ ID NO: 66, or a variant thereof comprising up to about 5 amino acid substitutions in the CDRs; (b) a transmembrane domain; and (c) an intracellular signaling domain. In some embodiments, the anti-GPC2 $V_H$H moiety comprises a $V_H$H domain comprising the amino acid sequence of SEQ ID NO: 97,126 or 127, or a variant thereof comprising an amino acid sequence having at least about 95% sequence identity to the amino acid sequence of SEQ ID NO: 97,126 or 127. In some embodiments, the primary intracellular signaling sequence is derived from CD3ζ. In some embodiments, the intracellular signaling domain comprises an intracellular co-stimulatory sequence. In some embodiments, the intracellular co-stimulatory sequence comprises 4-1BB, CD28z, CD27z, ICOSz, CD2z or OX40z. In some embodiments, the anti-GPC2 chimeric antigen receptor further comprises a hinge domain (e.g., a CD8 hinge domain) located between the C-terminus of the extracellular domain and the N-terminus of the transmembrane domain. In some embodiments, the anti-GPC2 chimeric antigen receptor further comprises a signal peptide (such as a CD8 signal peptide). In some embodiments, the anti-GPC2 chimeric antigen receptor comprises a polypeptide comprising from the N-terminus to the C-terminus: a CD8 signal peptide, the anti-GPC2 $V_H$H moiety, a CD8 hinge domain, a CD8 transmembrane domain, and an intracellular signaling domain comprising an intracellular co-stimulatory sequence derived from 4-1BB and a CD3 ζ intracellular signaling sequence. In some embodiments, the anti-GPC2 chimeric antigen receptor comprises a polypeptide comprising from the N-terminus to the C-terminus: a CD8 signal peptide, the anti-GPC2 $V_H$H moiety, a CD28 hinge domain, a CD28 transmembrane domain, and an intracellular signaling domain comprising an intracellular co-stimulatory sequence derived from 4-1BB and a CD3 ζ intracellular signaling sequence. In some embodiments, the anti-GPC2 chimeric antigen receptor comprises a polypeptide comprising the amino acid sequence of SEQ ID NO: 193, 222 or 223, or a variant thereof comprising an amino acid sequence having at least about 95% sequence identity to the amino acid sequence of SEQ ID NO: 193, 222 or 223.

In some embodiments, there is provided a chimeric antigen receptor targeting GPC2 comprising: (a) an extracellular domain comprising an anti-GPC2 $V_H$H comprising a CDR1 comprising the amino acid sequence of SEQ ID NO:8, a CDR2 comprising the amino acid sequence of SEQ ID NO: 38, and a CDR3 comprising the amino acid sequence of SEQ ID NO: 69, or a variant thereof comprising up to about 5 amino acid substitutions in the CDRs; (b) a transmembrane domain; and (c) an intracellular signaling domain. In some embodiments, the anti-GPC2 $V_H$H moiety comprises a $V_H$H domain comprising the amino acid sequence of SEQ ID NO:100,128 or 129, or a variant thereof comprising an amino acid sequence having at least about 95% sequence identity to the amino acid sequence of SEQ ID NO: 100,128 or 129. In some embodiments, the primary intracellular signaling sequence is derived from CD3ζ. In some embodiments, the intracellular signaling domain comprises an intracellular co-stimulatory sequence. In some embodiments, the intracellular co-stimulatory sequence comprises 4-1BB, CD28z, CD27z, ICOSz, CD2z or OX40z. In some embodiments, the anti-GPC2 chimeric antigen receptor further comprises a hinge domain (e.g., a CD8 hinge domain) located between the C-terminus of the extracellular domain and the N-terminus of the transmembrane domain. In some embodiments, the anti-GPC2 chimeric antigen receptor further comprises a signal peptide (such as a CD8 signal peptide). In some embodiments, the anti-GPC2 chimeric antigen receptor comprises a polypeptide comprising from the N-terminus to the C-terminus: a CD8 signal peptide, the anti-GPC2 $V_H$H moiety, a CD8 hinge domain, a CD8 transmembrane domain, and an intracellular signaling domain comprising an intracellular co-stimulatory sequence derived from 4-1BB and a CD3 ζ intracellular signaling sequence. In some embodiments, the anti-GPC2 chimeric antigen receptor comprises a polypeptide comprising from the N-terminus to the C-terminus: a CD8 signal peptide, the anti-GPC2 $V_H$H moiety, a CD28 hinge domain, a CD28 transmembrane domain, and an intracellular signaling domain comprising an intracellular co-stimulatory sequence derived from 4-1BB and a CD3 ζ intracellular signaling sequence. In some embodiments, the anti-GPC2 chimeric antigen receptor comprises a polypeptide comprising the amino acid sequence of SEQ ID NO: 196, 224 or 225, or a variant thereof comprising an amino acid sequence having at least about 95% sequence identity to the amino acid sequence of SEQ ID NO: 196, 224 or 225.

In some embodiments, there is provided a chimeric antigen receptor targeting GPC2 comprising: (a) an extracellular domain comprising an anti-GPC2 $V_HH$ comprising a CDR1 comprising the amino acid sequence of SEQ ID NO:11, a CDR2 comprising the amino acid sequence of SEQ ID NO: 43, and a CDR3 comprising the amino acid sequence of SEQ ID NO: 74, or a variant thereof comprising up to about 5 amino acid substitutions in the CDRs; (b) a transmembrane domain; and (c) an intracellular signaling domain. In some embodiments, the anti-GPC2 $V_HH$ moiety comprises a $V_HH$ domain comprising the amino acid sequence of SEQ ID NO:105 or 130, or a variant thereof comprising an amino acid sequence having at least about 95% sequence identity to the amino acid sequence of SEQ ID NO: 105 or 130. In some embodiments, the primary intracellular signaling sequence is derived from CD3ζ. In some embodiments, the intracellular signaling domain comprises an intracellular co-stimulatory sequence. In some embodiments, the intracellular co-stimulatory sequence comprises 4-1BB, CD28z, CD27z, ICOSz, CD2z or OX40z. In some embodiments, the anti-GPC2 chimeric antigen receptor further comprises a hinge domain (e.g., a CD8 hinge domain) located between the C-terminus of the extracellular domain and the N-terminus of the transmembrane domain. In some embodiments, the anti-GPC2 chimeric antigen receptor further comprises a signal peptide (such as a CD8 signal peptide). In some embodiments, the anti-GPC2 chimeric antigen receptor comprises a polypeptide comprising from the N-terminus to the C-terminus: a CD8 signal peptide, the anti-GPC2 $V_HH$ moiety, a CD8 hinge domain, a CD8 transmembrane domain, and an intracellular signaling domain comprising an intracellular co-stimulatory sequence derived from 4-1BB and a CD3 ζ intracellular signaling sequence. In some embodiments, the anti-GPC2 chimeric antigen receptor comprises a polypeptide comprising from the N-terminus to the C-terminus: a CD8 signal peptide, the anti-GPC2 $V_HH$ moiety, a CD28 hinge domain, a CD28 transmembrane domain, and an intracellular signaling domain comprising an intracellular co-stimulatory sequence derived from 4-1BB and a CD3 ζ intracellular signaling sequence. In some embodiments, the anti-GPC2 chimeric antigen receptor comprises a polypeptide comprising the amino acid sequence of SEQ ID NO: 196, 224 or 225, or a variant thereof comprising an amino acid sequence having at least about 95% sequence identity to the amino acid sequence of SEQ ID NO: 201 or 226.

In some embodiments, there is provided a chimeric antigen receptor targeting GPC2 comprising: (a) an extracellular domain comprising an anti-GPC2 $V_HH$ comprising a CDR1 comprising the amino acid sequence of SEQ ID NO:23, a CDR2 comprising the amino acid sequence of SEQ ID NO: 54, and a CDR3 comprising the amino acid sequence of SEQ ID NO: 85, or a variant thereof comprising up to about 5 amino acid substitutions in the CDRs; (b) a transmembrane domain; and (c) an intracellular signaling domain. In some embodiments, the anti-GPC2 $V_HH$ moiety comprises a $V_HH$ domain comprising the amino acid sequence of SEQ ID NO:116, or 131-134, or a variant thereof comprising an amino acid sequence having at least about 95% sequence identity to the amino acid sequence of SEQ ID NO: 116, or 131-134. In some embodiments, the primary intracellular signaling sequence is derived from CD3ζ. In some embodiments, the intracellular signaling domain comprises an intracellular co-stimulatory sequence. In some embodiments, the intracellular co-stimulatory sequence comprises 4-1BB, CD28z, CD27z, ICOSz, CD2z or OX40z. In some embodiments, the anti-GPC2 chimeric antigen receptor further comprises a hinge domain (e.g., a CD8 hinge domain) located between the C-terminus of the extracellular domain and the N-terminus of the transmembrane domain. In some embodiments, the anti-GPC2 chimeric antigen receptor further comprises a signal peptide (such as a CD8 signal peptide). In some embodiments, the anti-GPC2 chimeric antigen receptor comprises a polypeptide comprising from the N-terminus to the C-terminus: a CD8 signal peptide, the anti-GPC2 $V_HH$ moiety, a CD8 hinge domain, a CD8 transmembrane domain, and an intracellular signaling domain comprising an intracellular co-stimulatory sequence derived from 4-1BB and a CD3 ζ intracellular signaling sequence. In some embodiments, the anti-GPC2 chimeric antigen receptor comprises a polypeptide comprising from the N-terminus to the C-terminus: a CD8 signal peptide, the anti-GPC2 $V_HH$ moiety, a CD28 hinge domain, a CD28 transmembrane domain, and an intracellular signaling domain comprising an intracellular co-stimulatory sequence derived from 4-1BB and a CD3 ζ intracellular signaling sequence. In some embodiments, the anti-GPC2 chimeric antigen receptor comprises a polypeptide comprising the amino acid sequence of SEQ ID NO: 212 or 227-230, or a variant thereof comprising an amino acid sequence having at least about 95% sequence identity to the amino acid sequence of SEQ ID NO: 212 or 227-230.

In some embodiments, there is provided a chimeric antigen receptor targeting GPC2 comprising: (a) an extracellular domain comprising an anti-GPC2 $V_HH$ comprising a CDR1 comprising the amino acid sequence of SEQ ID NO:27, a CDR2 comprising the amino acid sequence of SEQ ID NO: 58, and a CDR3 comprising the amino acid sequence of SEQ ID NO: 89, or a variant thereof comprising up to about 5 amino acid substitutions in the CDRs; (b) a transmembrane domain; and (c) an intracellular signaling domain. In some embodiments, the anti-GPC2 $V_HH$ moiety comprises a $V_HH$ domain comprising the amino acid sequence of SEQ ID NO:120, or 135-137, or a variant thereof comprising an amino acid sequence having at least about 95% sequence identity to the amino acid sequence of SEQ ID NO: 120, or 135-137. In some embodiments, the primary intracellular signaling sequence is derived from CD3 ζ. In some embodiments, the intracellular signaling domain comprises an intracellular co-stimulatory sequence. In some embodiments, the intracellular co-stimulatory sequence comprises 4-1BB, CD28z, CD27z, ICOSz, CD2z or OX40z. In some embodiments, the anti-GPC2 chimeric antigen receptor further comprises a hinge domain (e.g., a CD8 hinge domain) located between the C-terminus of the extracellular domain and the N-terminus of the transmembrane domain. In some embodiments, the anti-GPC2 chimeric antigen receptor further comprises a signal peptide (such as a CD8 signal peptide). In some embodiments, the anti-GPC2 chimeric antigen receptor comprises a polypeptide comprising from the N-terminus to the C-terminus: a CD8 signal peptide, the anti-GPC2 $V_HH$ moiety, a CD8 hinge domain, a CD8 transmembrane domain, and an intracellular signaling domain comprising an intracellular co-stimulatory sequence derived from 4-1BB and a CD3 ζ intracellular signaling sequence. In some embodiments, the anti-GPC2 chimeric antigen receptor comprises a polypeptide comprising from the N-terminus to the C-terminus: a CD8 signal peptide, the anti-GPC2 $V_HH$ moiety, a CD28 hinge domain, a CD28 transmembrane domain, and an intracellular signaling domain comprising an intracellular co-stimulatory sequence derived from 4-1BB and a CD3 ζ intracellular signaling sequence. In some embodiments, the anti-GPC2 chimeric antigen receptor comprises a polypeptide comprising the amino acid sequence of SEQ ID NO: 216 or 231-233, or a variant thereof comprising an amino acid sequence having at least about 95% sequence identity to the amino acid sequence of SEQ ID NO: 216 or 231-233.

Tandem CAR

Tandem CARs of the present disclosure may include CAS70950VH6-AS70950VH6-BBz (SEQ ID NO: 243). Tandem CARs of the present disclosure may also include anti-GPC2 bispecific bivalent CARs including CAS71529VH5-AS72052VH5-BBz (SEQ ID NO: 239), CAS72052VH5-AS71529VH5-BBz (SEQ ID NO: 240), CAS70950VH6-AS71529VH6-BBz (SEQ ID NO: 241), CAS71529VH6-AS70950VH6-BBz (SEQ ID NO: 242), CAS78117VH4-AS71529VH6-BBz (SEQ ID NO: 246) and CAS71529VH6-AS78117VH4-BBz (SEQ ID NO: 247).

In some embodiments, there is provided a tandem chimeric antigen receptor targeting GPC2 comprising: (a) an extracellular domain comprising a tandem anti-GPC2 $V_HH$; (b) a transmembrane domain; and (c) an intracellular signaling domain. In some embodiments, the anti-GPC2 $V_HH$ moiety comprises a $V_HH$ domain comprising the amino acid sequence of SEQ ID NO: 143-147, 244, or 245, or a variant thereof comprising an amino acid sequence having at least about 95% sequence identity to the amino acid sequence of SEQ ID NO: 143-147, 244, or 245. In some embodiments, the primary intracellular signaling sequence is derived from CD3ζ. In some embodiments, the intracellular signaling domain comprises an intracellular co-stimulatory sequence. In some embodiments, the intracellular co-stimulatory sequence comprises 4-1BB, CD28z, CD27z, ICOSz, CD2z or OX40z. In some embodiments, the anti-GPC2 chimeric antigen receptor further comprises a hinge domain (e.g., a CD8 hinge domain) located between the C-terminus of the extracellular domain and the N-terminus of the transmembrane domain. In some embodiments, the anti-GPC2 chimeric antigen receptor further comprises a signal peptide (such as a CD8 signal peptide). In some embodiments, the anti-GPC2 chimeric antigen receptor comprises a polypeptide comprising from the N-terminus to the C-terminus: a CD8 signal peptide, the anti-GPC2 $V_HH$ moiety, a CD8 hinge domain, a CD8 transmembrane domain, and an intracellular signaling domain comprising an intracellular co-stimulatory sequence derived from 4-1BB and a CD3 ζ intracellular signaling sequence. In some embodiments, the anti-GPC2 chimeric antigen receptor comprises a polypeptide comprising from the N-terminus to the C-terminus: a CD8 signal peptide, the anti-GPC2 $V_HH$ moiety, a CD28 hinge domain, a CD28 transmembrane domain, and an intracellular signaling domain comprising an intracellular co-stimulatory sequence derived from 4-1BB and a CD3 ζ intracellular signaling sequence. In some embodiments, the anti-GPC2 chimeric antigen receptor comprises a polypeptide comprising the amino acid sequence of SEQ ID NO: 243, 239-242, 246 or 247, or a variant thereof comprising an amino acid sequence having at least about 95% sequence identity to the amino acid sequence of SEQ ID NO: 243, 239-242, 246 or 247.

In some embodiments, the present application provides a multivalent (such as bivalent, trivalent, or of higher number of valencies) chimeric antigen receptor comprising: (a) an extracellular domain comprising an sdAb moiety specifically binding to a first epitope of GPC2 and a second binding moiety (e.g., sdAb or scFv) specifically binding to a second epitope of GPC2; (b) a transmembrane domain; and (c) an intracellular signaling domain, wherein the first epitope and the second epitope are different. In some embodiments, the first anti-GPC2 sdAb is located at the N-terminus of the second GPC2 binding moiety (e.g., the second anti-GPC2 sdAb). In some embodiments, the first anti-GPC2 sdAb is located at the C-terminus of the second GPC2 binding moiety (e.g., the second anti-GPC2 sdAb). In some embodiments, the multivalent chimeric antigen receptor specifically binds to two different epitopes on GPC2. In some embodiments, the multivalent chimeric antigen receptor specifically binds to three or more different epitopes on GPC2.

In some embodiments, the binding moieties, such as sdAbs (including the plurality of sdAbs, or the first sdAb and/or the second sdAb) are camelid, chimeric, human, or humanized. In some embodiments, the binding moieties or sdAbs are fused to each other via peptide bonds or peptide linkers. In some embodiments, each peptide linker is no more than about 50 (such as no more than about any one of 35, 25, 20, 15, 10, or 5) amino acids long. In some embodiments, the transmembrane domain is selected from the group consisting of CD8α, CD4, CD28, 4-1BB, CD80, CD86, CD152, PD-1, CD2, CD27, ICOS and OX40. In some embodiments, the intracellular signaling domain comprises a primary intracellular signaling sequence of an immune effector cell (such as T cell). In some embodiments, the primary intracellular signaling sequence is derived from CD3 ζ, CD3γ, CD3δ, CD3ε, common FcR gamma (FCER1G), Fc gamma RIM, FcR beta (Fc Epsilon R1b), CD5, CD22, CD79a, CD79b, or CD66d. In some embodiments, the primary intracellular signaling sequence is derived from CD3ζ. In some embodiments, the intracellular signaling domain comprises an intracellular co-stimulatory sequence. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28, 4-1BB, CD2, CD27, ICOS and OX40. In some embodiments, the multivalent chimeric antigen receptor further comprises a hinge domain (such as a CD8 hinge domain) located between the C-terminus of the extracellular domain and the N-terminus of the transmembrane domain. In some embodiments, the multivalent chimeric antigen receptor further comprises a signal peptide (such as a CD8 signal peptide). In some embodiments, the anti-GPC2 chimeric antigen receptor comprises a polypeptide comprising from the N-terminus to the C-terminus: a CD8 signal peptide, the extracellular domain, a CD8 or CD28 hinge domain, a CD8, CD28, CD2, CD27, ICOS or OX40 transmembrane domain, and an intracellular signaling domain comprising an intracellular co-stimulatory sequence derived from 4-1BB, CD28, CD2, CD27, ICOS or OX40 and a CD3 ζ intracellular signaling sequence. In some embodiments, the multivalent chimeric antigen receptor is monospecific. In some embodiments, the multivalent chimeric antigen receptor is multispecific, such as bispecific.

The multivalent chimeric receptors described herein may be especially suitable for targeting multimeric antigens via synergistic binding by the different antigen binding sites, or for enhancing binding affinity or avidity to the antigen. Any of the anti-GPC2 sdAbs described herein may be used in the extracellular domain of the multivalent chimeric receptors described herein.

Dual CAR

Dual CAR can be a combination of any two anti-GPC2 CARs, in which each of a first CAR and a second CAR may be a single CAR or a tandem CAR, i.e., single CAR/single CAR, single CAR/tandem CAR, or tandem CAR/tandem CAR. The levels of dual CAR T cell signalling may be regulated by manipulating the intracellular domains of each first and second CARs. For example, the intracellular domains of each of the first CAR and the second CAR may comprise a co-stimulatory domain, such as CD28, 4-1BB (CD137), ICOS, OX40 (CD134), CD27, and/or DAP10, and/or a signaling domain from a T cell receptor, such as a signaling domain from a T cell receptor (e.g., CD3ζ). For example, dual CAR of the present disclosure may include a first CAR and a second CAR each having an intracellular domain comprising a co-stimulatory domain and a signaling domain from a T cell receptor. Thus, when dual CAR bind antigens (e.g., bispecific), the T cell signals may be transmitted through two signaling domains from a T cell receptor.

Dual CAR can be a combination of any two single anti-GPC2 CARs selected, independently, from the group consisting of CAS70549-BBz, CAS70771-BBz, CAS70950-BBz, CAS71402-BBz, CAS71529-BBz, CAS71661-BBz, CAS72021-BBz, CAS72052-BBz, CAS72383-BBz, CAS72479-BBz, CAS72499-BBz, CAS72531-BBz, CAS72669-BBz, CAS72794-BBz, CAS72805-BBz, CAS72806-BBz, CAS72835-BBz, CAS77906-BBz, CAS77916-BBz, CAS77932-BBz, CAS77934-BBz, CAS77978-BBz, CAS77986-BBz, CAS78117-BBz, CAS78215-BBz, CAS78810-BBz, CAS79101-BBz, CAS79236-BBz, CAS79274-BBz, CAS79285-BBz, CAS79317-BBz, CAS70950VH6-BBz, CAS70950VH7-BBz, CAS71529VH5-BBz, CAS71529VH6-BBz, CAS72052VH5-BBz, CAS72052VH6-BBz, CAS72669VH6-BBz, CAS78117VH4-BBz, CAS78117VH5-BBz, CAS78117VH6-BBz, CAS78117VH7-BBz, CAS79236VH4-BBz, CAS79236VH5-BBz, CAS79236VH6-BBz, CAS77916VH6-BBz, CAS77916VH7-BBz, CAS77916VH8-BBz, CAS77916VH9-BBz, CAS77916VH10-BBz, GPC2-CD28z, C2-CD27z, GPC2-ICOSz, GPC2-CD2z, and GPC2-OX40z, preferably, CAS70950-BBz, CAS70950VH6-BBz, CAS71529-BBz, CAS71529VH6-BBz, CAS78117-BBz, CAS78117VH4-BBz, CAS79236-BBz, CAS79236VH6-BBz, GPC2-CD28z, GPC2-CD27z, GPC2-ICOSz, GPC2-CD2z, GPC2-OX40z, CAS71529VH5-AS72052VH5-BBz, CAS72052VH5-AS71529VH5-BBz, CAS70950VH6-AS71529VH6-BBz, CAS71529VH6-AS70950VH6-BBz, CAS70950VH6-AS70950VH6-BBz, CAS78117VH4-AS71529VH6-BBz and CAS71529VH6-AS78117VH4-BBz.

Dual CAR can also be a combination of a first single anti-GPC2 CARs selected from the group consisting of CAS70549-BBz, CAS70771-BBz, CAS70950-BBz, CAS71402-BBz, CAS71529-BBz, CAS71661-BBz, CAS72021-BBz, CAS72052-BBz, CAS72383-BBz, CAS72479-BBz, CAS72499-BBz, CAS72531-BBz, CAS72669-BBz, CAS72794-BBz, CAS72805-BBz, CAS72806-BBz, CAS72835-BBz, CAS77906-BBz, CAS77916-BBz, CAS77932-BBz, CAS77934-BBz, CAS77978-BBz, CAS77986-BBz, CAS78117-BBz, CAS78215-BBz, CAS78810-BBz, CAS79101-BBz, CAS79236-BBz, CAS79274-BBz, CAS79285-BBz, CAS79317-BBz, CAS70950VH6-BBz, CAS70950VH7-BBz, CAS71529VH5-BBz, CAS71529VH6-BBz, CAS72052VH5-BBz, CAS72052VH6-BBz, CAS72669VH6-BBz, CAS78117VH4-BBz, CAS78117VH5-BBz, CAS78117VH6-BBz, CAS78117VH7-BBz, CAS79236VH4-BBz, CAS79236VH5-BBz, CAS79236VH6-BBz, CAS77916VH6-BBz, CAS77916VH7-BBz, CAS77916VH8-BBz, CAS77916VH9-BBz, CAS77916VH10-BBz, GPC2-CD28z, GPC2-CD27z, GPC2-ICOSz, GPC2-CD2z, GPC2-OX40z, CAS71529VH5-AS72052VH5-BBz, CAS72052VH5-AS71529VH5-BBz, CAS70950VH6-AS71529VH6-BBz, CAS71529VH6-AS70950VH6-BBz, CAS70950VH6-AS70950VH6-BBz, CAS78117VH4-AS71529VH6-BBz and CAS71529VH6-AS78117VH4-BBz, preferably, CAS70950-BBz, CAS70950VH6-BBz, CAS71529-BBz, CAS71529VH6-BBz, CAS78117-BBz, CAS78117VH4-BBz, CAS79236-BBz, CAS79236VH6-BBz, GPC2-CD28z, GPC2-CD27z, GPC2-ICOSz, GPC2-CD2z, GPC2-OX40z CAS71529VH5-AS72052VH5-BBz, CAS72052VH5-AS71529VH5-BBz, CAS70950VH6-AS71529VH6-BBz, CAS71529VH6-AS70950VH6-BBz, CAS70950VH6-AS70950VH6-BBz, CAS78117VH4-AS71529VH6-BBz and CAS71529VH6-AS78117VH4-BBz and a second CAR that binds molecule other than GPC2, e.g., GD2 and DLL3, and comprises a co-stimulatory domain, such as CD28, 4-1BB (CD137), ICOS, OX40 (CD134), CD27, and/or DAP10, and a signaling domain from a T cell receptor, such as a signaling domain from a T cell receptor (e.g., CD3ζ).

In some embodiments, there is provided a dual chimeric antigen receptor system comprising: (a) a first chimeric antigen receptor comprising an extracellular domain comprising an anti-GPC2 sdAb (such as any one of the anti-GPC2 $V_H$Hs described herein), a transmembrane domain, and an intracellular signaling domain comprising an intracellular co-stimulatory sequence derived from 4-1BB or CD28 and a CD3 ζ intracellular signaling sequence; and (b) a second chimeric antigen receptor comprising an extracellular domain comprising an anti-GD2 or DLL3 sdAb or scFv, a transmembrane domain, and an intracellular signaling domain comprising an intracellular co-stimulatory sequence derived from 4-1BB or CD28 and a CD3 ζ intracellular signaling sequence. In some embodiments, the transmembrane domain is selected from the group consisting of CD8α, CD4, CD28, 4-1BB, CD80, CD86, CD152 and PD-1. In some embodiments, the primary intracellular signaling sequence is derived from CD3ζ. In some embodiments, the intracellular co-stimulatory sequence is derived from a co-stimulatory molecule selected from the group consisting of CD27, CD28, 4-1BB, OX40, CD40, PD-1, integrin subunit alpha L (LFA-1), ICOS, CD2, CD7, LIGHT, NKG2C, B7-H3, TNF receptor superfamily member (TNFRSF)9, TNFRSF4, TNFRSF8, CD40 ligand (CD40LG), integrin subunit beta (ITGB)2, killer cell lectin like receptor (KLR)C2, TNFRSF18, TNFRSF14, hepatitis A virus cellular receptor (HAVCR)1, galectin 9 (LGALS9), hematopoietic cell signal transducer (DAP10), transmembrane immune signaling adaptor TYROBP (DAP12), CD83, ligands of CD83 and combinations thereof. In some embodiments, the first chimeric antigen receptor and/or the second chimeric antigen receptor further comprises a hinge domain (such as a CD8 hinge domain) located between the C-terminus of the extracellular domain and the N-terminus of the transmembrane domain. In some embodiments, the first chimeric antigen receptor and/or the second chimeric antigen receptor further comprises a signal peptide (such as a CD8 signal peptide). Any suitable anti-GD2 or DLL3 sdAb or scFv may be used for the dual chimeric antigen receptor systems described herein.

Split CAR

Split CAR are different from dual CAR in that a first CAR may comprise a co-stimulatory domain but without a signaling domain from a T cell receptor; and a second CAR may comprise a signaling domain from a T cell receptor but without a co-stimulatory domain. Thus, when split CAR bind antigens (e.g., bispecific), T cell signals may be transmitted through a co-stimulatory domain of the first CAR and a signaling domain from a T cell receptor of the second CAR. For example, split CAR of the present disclosure may have a first CAR comprising a $V_HH$ single binding domain that binds GPC2 having an amino acid sequence selected from SEQ ID NO: 93-142 and a second CAR comprising a $V_HH$ single binding domain that binds a molecule other than GPC2, e.g., GD2 and DLL3. The first CAR can also be monospecific or bispecific bivalent tandem CAR. The first CAR may have a signaling domain from a T cell receptor, e.g., CD3ζ, and the second CAR may have a co-stimulatory domain, e.g., CD28 or 4-1BB, and vice versa.

In some embodiments, there is provided a split chimeric antigen receptor system comprising: (a) a first chimeric antigen receptor comprising an extracellular domain comprising an anti-GPC2 sdAb (such as any one of the anti-GPC2 $V_HH$s described herein), a transmembrane domain, and an intracellular signaling domain comprising a primary intracellular signaling sequence of an immune effector cell (e.g., T cell), wherein optionally the intracellular signaling domain does not comprise an intracellular co-stimulatory sequence; (b) a second chimeric antigen receptor comprising an extracellular domain comprising a second binding moiety (e.g., sdAb, scFv, or an extracellular domain of a receptor) that specifically binds to a second antigen or epitope, a transmembrane domain, and an intracellular signaling domain comprising an intracellular co-stimulatory sequence, wherein optionally the intracellular signaling domain does not comprise a primary intracellular signaling sequence. In some embodiments, the second antigen is GD2 or DLL3.

In some embodiments, the transmembrane domain is selected from the group consisting of CD8α, CD4, CD28, 4-1BB, CD80, CD86, CD152 and PD-1. In some embodiments, the primary intracellular signaling sequence is derived from CD3ζ, CD3γ, CD3δ, CD3ε, common FcR gamma (FCER1G), Fc gamma RIIa, FcR beta (Fc Epsilon Rib), CD5, CD22, CD79a, CD79b, or CD66d. In some embodiments, the primary intracellular signaling sequence is derived from CD3ζ. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28 or 4-1BB. In some embodiments, the first chimeric antigen receptor and/or the second chimeric antigen receptor further comprises a hinge domain (such as a CD8 hinge domain) located between the C-terminus of the extracellular domain and the N-terminus of the transmembrane domain. In some embodiments, the first chimeric antigen receptor and/or the second chimeric antigen receptor further comprises a signal peptide (such as a CD8 signal peptide). In some embodiments, the first chimeric antigen receptor comprises a polypeptide comprising from the N-terminus to the C-terminus: a CD8 signal peptide, the anti-GPC2 sdAb, a CD8 hinge domain, a CD8 transmembrane domain, and an intracellular signaling domain comprising a CD3 ζ intracellular signaling sequence. In some embodiments, the second chimeric antigen receptor comprises a polypeptide comprising from the N-terminus to the C-terminus: a CD8 signal peptide, the second binding domain, a CD8 hinge domain, a CD8 transmembrane domain, and an intracellular signaling domain comprising an intracellular co-stimulatory sequence derived from 4-1BB or CD28.

In some embodiments, there is provided a split chimeric antigen receptor system comprising: (a) a first chimeric antigen receptor comprising an extracellular domain comprising an anti-GPC2 sdAb (such as any one of the anti-GPC2 sdAb $V_HH$s described herein), a transmembrane domain, and an intracellular domain comprising an intracellular signaling domain comprising an intracellular co-stimulatory sequence, wherein optionally the intracellular signaling domain does not comprise a primary intracellular signaling sequence; (b) a second chimeric antigen receptor comprising an extracellular domain comprising a second binding moiety (e.g., sdAb, scFv, or an extracellular domain of a receptor) that specifically binds to a second antigen or epitope, a transmembrane domain, and an intracellular signaling domain comprising a primary intracellular signaling sequence of an immune effector cell (e.g., T cell), wherein optionally the intracellular signaling domain does not comprise an intracellular co-stimulatory sequence. In some embodiments, the second antigen is GD2 or DLL3. In some embodiments, the transmembrane domain is selected from the group consisting of CD8α, CD4, CD28, 4-1BB, CD80, CD86, CD152 and PD-1. In some embodiments, the primary intracellular signaling sequence is derived from CD3 ζ, CD3γ, CD3δ, CD3ε, common FcR gamma (FCER1G), Fc gamma RIM, FcR beta (Fc Epsilon R1b), CD5, CD22, CD79a, CD79b, or CD66d. In some embodiments, the primary intracellular signaling sequence is derived from CD3ζ. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from CD28 or 4-1BB. In some embodiments, the first chimeric antigen receptor and/or the second chimeric antigen receptor further comprises a hinge domain (such as a CD8 hinge domain) located between the C-terminus of the extracellular domain and the N-terminus of the transmembrane domain. In some embodiments, the first chimeric antigen receptor and/or the second chimeric antigen receptor further comprises a signal peptide (such as a CD8 signal peptide). In some embodiments, the first chimeric antigen receptor comprises a polypeptide comprising from the N-terminus to the C-terminus: a CD8 signal peptide, the anti-GPC2 sdAb, a CD8 hinge domain, a CD8 transmembrane domain, and an intracellular signaling domain comprising an intracellular co-stimulatory sequence derived from 4-1BB or CD28. In some embodiments, the second chimeric antigen receptor comprises a polypeptide comprising from the N-terminus to the C-terminus: a CD8 signal peptide, the second binding domain, a CD8 hinge domain, a CD8 transmembrane domain, and an intracellular signaling domain comprising a CD3ζ intracellular signaling sequence.

Immune effector cells such as T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 2006/0121005, the contents of which are hereby incorporated herein by reference in their entireties. Examples of immune effector cells include T cells, e.g., alpha/beta T cells and gamma/delta T cells, B cells, natural killer (NK) cells, natural killer T (NKT) cells, mast cells, and myeloid-derived phagocytes. In some embodiments, the immune cells are T cells, such as cytotoxic T cell and/or helper T cell. In some embodiments, the T cells are $CD4^+$/$CD8^-$, $CD4^-$/$CD8^+$, $CD4^+$/$CD8^+$, $CD4^-$/$CD8^-$, or combinations thereof. In some embodiments, the T cells produce IL-2, TFN, and/or TNF upon expressing the CAR and binding to the target cells, such as $GPC2^+$ tumor cells. In some embodiments, the CD8+ T cells lyse antigen-specific target cells upon expressing the CAR and binding to the target cells. In some embodiments, the immune cells are γδ T cells.

Methods of making CAR-expressing cells are described, e.g., in US 2016/0185861, the content of which is hereby incorporated herein by reference in its entirety.

Method of Treatment

In some embodiments, there is provided a method of treating a GPC2-positive disease consisting of acute lymphoblastic leukemia cell, Ewing's sarcoma cell, neuroblastoma, Embryonal rhabdomyosarcoma, alveolar rhabdomyosarcoma, lung cancer, brain cancer, uterine cancer, cervical cancer, colorectal cancer, stomach cancer, head and neck cancer, breast cancer, pancreatic cancer, ovarian cancer, kidney cancer, esophageal cancer, testicular cancer, and skin cancer. In some embodiments, there is provided a method of treating a disease (such as cancer, e.g., neuroblastoma, small cell lung cancer and medulloblastoma) in an individual (such as a human individual), comprising administering to the individual an effective amount of a pharmaceutical composition comprising an engineered immune cell (e.g., T cell) comprising: an anti-GPC2 chimeric antigen receptor comprising: (a) an extracellular domain comprising an anti-GPC2 $V_HH$ (such as any one of the anti-GPC2 $V_HH$ described herein); (b) a transmembrane domain; and (c) an intracellular signaling domain. In some embodiments, the intracellular signaling domain comprises a primary intracellular signaling sequence of an immune effector cell (such as T cell). In some embodiments, the primary intracellular signaling sequence is derived from CD3 ζ, FcRγ, FcRβ, CD3γ, CD3δ, CD3ε, CD5, CD22, CD79a, CD79b, or CD66d. In some embodiments, the primary intracellular signaling sequence is derived from CD3 ζ. In some embodiments, the intracellular signaling domain comprises an intracellular co-stimulatory sequence. In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof. In some embodiments, the intracellular co-stimulatory sequence is derived from In some embodiments, the intracellular co-stimulatory sequence comprises 4-1BB, CD28z, CD27z, ICOSz, CD22 or OX40z. In some embodiments, the anti-GPC2 chimeric antigen receptor comprises: (a) an extracellular domain comprising an anti-GPC2 $V_HH$ (such as any one of the anti-GPC2 $V_HH$ or tandem anti-GPC2 $V_HH$ described herein); (b) a transmembrane domain; and (c) an intracellular signaling domain comprising a CD3ζ intracellular signaling sequence and an intracellular co-stimulatory sequence derived from CD28 or 4-1BB. In some embodiments, the anti-GPC2 $V_HH$ comprises any one of the following: (1) a CDR1 comprising the amino acid sequence of SEQ ID NO: 1-30, a CDR2 comprising the amino acid sequence of SEQ ID NO: 31-61, and a CDR3 comprising the amino acid sequence of SEQ ID NO: 62-92, or a variant thereof comprising up to about 5 amino acid substitutions in the CDRs; In some embodiments, the anti-GPC2 $V_HH$ comprises a $V_HH$ domain comprising the amino acid sequence of any one of SEQ ID NOs: 93-142, 143-147 and 244-245, or a variant thereof comprising an amino acid sequence having at least about 95% sequence identity to the amino acid sequence of any one of SEQ ID NOs: 93-142, 143-147 and 244-245. In some embodiments, the anti-GPC2 chimeric antigen receptor comprises the amino acid sequence of any one of SEQ ID NOs: 189-238, and 248-252, or a variant thereof comprising an amino acid sequence having at least about 95% sequence identity to the amino acid sequence of any one of SEQ ID NOs: 189-238, and 248-252. In some embodiments, the GPC2 chimeric antigen receptor comprises the amino acid sequence of SEQ ID NO: 239-243, and 246-247. In some embodiments, the engineered immune cell expresses a safety-switch antigen or epitope, such as CD52, EGFR, or CD20. In some embodiments, the method further comprises subsequently administering an effective amount of a therapeutic antibody specifically binding to the safety-switch antigen or epitope.

In some embodiments, a disease or disorder may be treated and/or disrupted to modulate genetically engineered cells in vivo, e.g., to boost, augment, or increase the expansion of genetically engineered cells, e.g., T cells expressing CARs of the present disclosure, administered to a subject, by administering an agent to the subject. In particular embodiments, the agent is a pharmaceutical agent. In some embodiments, the agent is a therapeutic agent. In some embodiments, the agent is an immunomodulatory agent. In some embodiments, the agent is a chemotherapeutic agent. In some embodiments, the agent, such as an immunomodulatory agent, is capable of inhibiting or blocking a function of a molecule, or signaling pathway involving said molecule. In some embodiments, the molecule may be expressed on an immune cells or may be part of an immune synapse, such as is expressed on a T cell or antigen presenting cell or other cell associated with an immune response. In some such aspects, the molecule is an immune-inhibitory molecule or the molecule is an immune checkpoint molecule. In some embodiments, the immune checkpoint molecule or pathway is PD-1, CD274 molecule (PD-L1), programmed cell death 1 ligand 2 (PD-L2), cytotoxic T-lymphocyte associated protein 4 (CTLA-4), lymphocyte-activation gene 3 (LAG-3), hepatitis A virus cellular receptor 2 (TIM3), V-set immunoregulatory receptor (VISTA), adenosine 2A Receptor (A2AR), or adenosine or a pathway involving any of the foregoing.

Exemplary immune checkpoint inhibitors include Tremelimumab (CTLA-4 blocking antibody, also known as ticilimumab, CP-675,206), anti-OX40, PD-L1 monoclonal antibody (Anti-B7-H1; MEDI4736, also called durvalumab), MK-3475 (PD-1 blocker), nivolumab (anti-PD-1 antibody), CT-011 (anti-PD-1 antibody), BY55 monoclonal antibody, AMP224 (anti-PD-L1 antibody), BMS-936559 (anti-PD-L1 antibody), MPLDL3280A (anti-PD-L1 antibody), MSB0010718C (anti-PD-L1 antibody) and ipilimumab (anti-CTLA-4 antibody, also known as Yervoy®, MDX-010 and MDX-101). Exemplary of immunomodulatory antibodies include, but are not limited to, Daclizumab (Zenapax), Bevacizumab (AVASTIN®), Basiliximab, Ipilimumab, Nivolumab, pembrolizumab, MPDL3280A, Pidilizumab (CT-011), MK-3475, BMS-936559, MPDL3280A (Atezolizumab), tremelimumab, IMP321, BMS-986016, LAG525, urelumab, PF-05082566, TRX518, MK-4166, dacetuzumab (SGN-40), lucatumumab (HCD122), SEACD40, CP-870, CP-893, MEDI6469, MEDI6383, MOXR0916, AMP-224, MSB0010718C (Avelumab), MEDI4736 (durvalumab), PDR001, rHIgM12B7, Ulocuplumab, BKT140, Varlilumab (CDX-1127), ARGX-110, MGA271, lirilumab (BMS-986015, IPH2101), IPH2201, ARGX-115, Emactuzumab, CC-90002 and MNRP1685Aor an antibody-binding fragment thereof. Other exemplary immunomodulators include, e.g, afutuzumab; pegfilgrastim; 3-(4-amino-1-oxo-1,3-dihydro-2H-isoindol-2-yl)piperidine-2,6-dione (CAS: 191732-72-6); thalidomide, actimid (CC4047); and IRX-2 (mixture of human cytokines including interleukin 1, interleukin 2, and interferon gamma, CAS 951209-71-5, available from IRX Therapeutics).

In some embodiments, the immunomodulatory agent is thalidomide (2-(2,6-dioxopiperidin-3-yl)-1H-isoindole-1,3 (2H)-dione) or an analog or derivative of thalidomide. In certain embodiments, a thalidomide derivative includes structural variants of thalidomide that have a similar biological activity. Exemplary thalidomide derivatives include, but are not limited to 3-(4-amino-1-oxo-1,3 dihydro-2H-isoindol-2-yl)piperidine-2,6-dione), pomalidomide, CC-1088, CDC-501, and CDC-801, and the compounds disclosed in U.S. Pat. Nos. 5,712,291; 7,320,991; and 8,716,315; U.S. Appl. No. 2016/0313300; and PCT Pub. Nos. WO 2002/068414 and WO 2008/154252; the contents of which are hereby incorporated by reference in their entireties.

In some embodiments, the immunomodulatory agent is 3-(4-amino-1-oxo-1,3 dihydro-2H-isoindol-2-yl)piperidine-2,6-dione, pomalidomide, avadomide, a stereoisomer of 3-(4-amino-1-oxo-1,3 dihydro-2H-isoindol-2-yl)piperidine-2,6-dione, pomalidomide, avadomide or a pharmaceutically acceptable salt, solvate, hydrate, co-crystal, clathrate, or polymorph thereof. In some embodiments, the immunomodulatory compound is 3-(4-amino-1-oxo-1,3 dihydro-2H-isoindol-2-yl)piperidine-2,6-dione, a stereoisomer of 3-(4-amino-1-oxo-1,3 dihydro-2H-isoindol-2-yl)piperidine-2,6-dione or a pharmaceutically acceptable salt, solvate, hydrate, co-crystal, clathrate, or polymorph thereof. In some embodiments, the immunomodulatory compound is 3-(4-amino-1-oxo-1,3-dihydro-2H-isoindol-2-yl)piperidine-2,6-dione).

In certain embodiments, the disease or disorder may be treated and/or disrupted by administering to the subject the compound, 3-(4-amino-1-oxo-1,3-dihydro-2H-isoindol-2-yl)piperidine-2,6-dione) and T cells expressing CARs of the present disclosure. CARS may be at least one single-valent CAR selected from the group consisting of CAS70549-BBz, CAS70771-BBz, CAS70950-BBz, CAS71402-BBz, CAS71529-BBz, CAS71661-BBz, CAS72021-BBz, CAS72052-BBz, CAS72383-BBz, CAS72479-BBz, CAS72499-BBz, CAS72531-BBz, CAS72669-BBz, CAS72794-BBz, CAS72805-BBz, CAS72806-BBz, CAS72835-BBz, CAS77906-BBz, CAS77916-BBz, CAS77932-BBz, CAS77934-BBz, CAS77978-BBz, CAS77986-BBz, CAS78117-BBz, CAS78215-BBz, CAS78810-BBz, CAS79101-BBz, CAS79236-BBz, CAS79274-BBz, CAS79285-BBz, CAS79317-BBz, CAS70950VH6-BBz, CAS70950VH7-BBz, CAS71529VH5-BBz, CAS71529VH6-BBz, CAS72052VH5-BBz, CAS72052VH6-BBz, CAS72669VH6-BBz, CAS78117VH4-BBz, CAS78117VH5-BBz, CAS78117VH6-BBz, CAS78117VH7-BBz, CAS79236VH4-BBz, CAS79236VH5-BBz, CAS79236VH6-BBz, CAS77916VH6-BBz, CAS77916VH7-BBz, CAS77916VH8-BBz, CAS77916VH9-BBz, and CAS77916VH10-BBz, GPC2-CD28z, C2-CD27z, GPC2-ICOSz, GPC2-CD2z, and GPC2-OX40z, preferably, CAS70950-BBz, CAS70950VH6-BBz, CAS71529-BBz, CAS71529VH6-BBz, CAS78117-BBz, CAS78117VH4-BBz, CAS79236-BBz, CAS79236VH6-BBz, GPC2-CD28z, GPC2-CD27z, GPC2-ICOSz, GPC2-CD2z and GPC2-OX40z, and/or monovalent tandem CAR including CAS70950VH6-AS70950VH6-BBz, and/or multi-valent tandem CARs including CAS71529VH5-AS72052VH5-BBz, CAS72052VH5-AS71529VH5-BBz, CAS70950VH6-AS71529VH6-BBz, CAS71529VH6-AS70950VH6-BBz, CAS78117VH4-AS71529VH6-BBz and CAS71529VH6-AS78117VH4-BBz, preferably CAS70950VH6-AS71529VH6-BBz, CAS71529VH6-AS70950VH6-BBz, CAS78117VH4-AS71529VH6-BBz and CAS71529VH6-AS78117VH4-BBz.

3-(4-amino-1-oxo-1,3 dihydro-2H-isoindol-2-yl)piperidine-2,6-dione is FDA approved for the treatment of multiple myeloma, myelodysplastic syndrome associated with deletion 5q, and most recently in relapsed/refractory mantle-cell lymphoma (MCL). 3-(4-amino-1-oxo-1,3 dihydro-2H-isoindol-2-yl)piperidine-2,6-dione generally is a synthetic derivative of thalidomide, and is currently understood to have multiple immunomodulatory effects, including enforcement of immune synapse formation between T cell and antigen presenting cells (APCs). For example, in some cases, 3-(4-amino-1-oxo-1,3 dihydro-2H-isoindol-2-yl)piperidine-2,6-dione modulates T cell responses and results in increased interleukin (IL)-2 production in $CD4^+$ and $CD8^+$ T cells, induces the shift of T helper (Th) responses from Th2 to Th1, inhibits expansion of regulatory subset of T cells (Tregs), and improves functioning of immunological synapses in follicular lymphoma and chronic lymphocytic leukemia (CLL) (Otahal et al, Oncoimmunology (2016) 5(4): e1115940). 3-(4-amino oxo-1,3 dihydro-2H-isoindol-2-yl) piperidine-2,6-dione also has direct tumoricidal activity in patients with multiple myeloma (MM) and directly and indirectly modulates survival of CLL tumor cells by affecting supportive cells, such as nurse-like cells found in the microenvironment of lymphoid tissues. 3-(4-amino-1-oxo-1,3 dihydro-2H-isoindol-2-yl)piperidine-2,6-dione also can enhance T-cell proliferation and interferon-y production in response to activation of T cells via CD3 ligation or dendritic cell-mediated activation. In addition, 3-(4-amino-1-oxo-1,3 dihydro-2H-isoindol-2-yl)piperidine-2,6-dione is thought to decrease proliferation of pro-inflammatory cytokines including TNF-α, IL-1, IL-6, and IL-12 and enhance antibody-dependent cellular cytotoxicity (ADCC) via increased NK cell activation. 3-(4-amino-1-oxo-1,3 dihydro-2H-isoindol-2-yl)piperidine-2,6-dione can also induce malignant B cells to express higher levels of immunostimulatory molecules such as CD80, CD86, HLA-DR, CD95, and CD40 (Fecteau et al. Blood (2014) 124(10): 1637-1644). Cereblon, an E3 ubiquitin ligase, was identified as the primary target for thalidomide induced teratogenesis (Ito et al, T, (2010) Science 327:1345-1350). 3-(4-amino-1- oxo-1,3 dihydro-2H-isoindol-2-yl)piperidine-2,6-dione also targets cereblon and it has been shown that this leads to the reduction of c-Myc and IRF4 expression while also increasing expression of p21 that leads to G1 cell-cycle arrest (Lopez-Girona et al, (2012) Leukemia 26: 2326-2335).

In certain embodiments, the pharmaceutical agent is 3-(4-amino-1-oxo-1,3 dihydro-2H-isoindol-2-yl)piperidine-2,6-dione or a thalidomide derivative. In particular embodiments the pharmaceutical agent is 3-(4-amino-1-oxo-1,3 dihydro-2H-isoindol-2-yl)piperidine-2,6-dione. In some embodiments, 3-(4-amino-1-oxo-1,3 dihydro-2H-isoindol-2-yl)piperidine-2,6-dione or a thalidomide derivative is administered at a dosage of from about 0.1 μM to about 10 mM, from about 0.5 μM to about 5 mM, from about 1 μM to about 2 mM, from about 1 μM to about 1 mM, from about 1 μM to about 500 μM, from about 1 μM to about 400 μM, from about 1 μM to about 300 μM, from about 1 μM to about 200 μM, from about 1 μM to about 100 μM, from about 1 μM to about 50 μM, from about 1 μM to about 40 μM, from about 1 μM to about 30 μM, from about 1 μM to about 20 μM, from about 1 μM to about 15 μM, from about 1 μM to about 10 μM, from about 5 μM to about 15 μM, or from about 5 μM to about 10 μM. In some embodiments, 3-(4-amino-1-oxo-1,3 dihydro-2H-isoindol-2-yl)piperidine-2,6-dione or a thalidomide derivative is administered at a dosage of from about 1 mg to about 20 mg, e.g., from about 1 mg to about 10 mg, from about 2.5 mg to about 7.5 mg, from about 5 mg to about 15 mg, such as about 5 mg, 10 mg, 15 mg or 20 mg. In some embodiments, 3-(4-amino-1-oxo-1,3 dihydro-2H-isoindol-2-yl)piperidine-2,6-dione is administered at a dose of from about 10 to 5 mg/kg, e.g., about 100 μg/kg to about 2 mg/kg, about 200 mg/kg to about 1 mg/kg, about 400 mg/kg to about 600 mg/kg, such as about 500 mg/kg. In particular embodiments, the dose of 3-(4-amino-1-oxo-1,3 dihydro-2H-isoindol-2-yl)piperidine-2,6-dione is or is about 10 mg. In certain embodiments, a lesion is treated and/or disrupted by administering a single dose of 3-(4-amino-1-oxo-1,3 dihydro-2H-isoindol-2-yl)piperidine-2,6-dione to the subject. In particular embodiments, a lesion is treated and/or disrupted by administering multiple doses of 3-(4-amino-1-oxo-1,3 dihydro-2H-isoindol-2-yl)piperidine-2,6-dione to the subject. In particular embodiments, the multiple doses of 3-(4-amino-1-oxo-1,3 dihydro-2H-isoindol-2-yl) piperidine-2,6-dione are administered over one or more treatment cycles. In some embodiments, the treatment cycles comprise a drug holiday. In certain embodiments, the 3-(4-amino-1-oxo-1,3 dihydro-2H-isoindol-2-yl)piperidine-2,6-dione is administered once daily for 14 days over a 21 day treatment cycle. In certain embodiments, the 3-(4-amino-1-oxo-1,3 dihydro-2H-isoindol-2-yl)piperidine-2,6-dione is administered once daily for 21 days over a 28 day treatment cycle.

Administration of the anti-GPC2 constructs or pharmaceutical compositions thereof may be carried out in any convenient manner, including by injection, ingestion, transfusion, implantation or transplantation. The pharmaceutical compositions may be administered to a patient transarterially, subcutaneously, intradermally, intratumorally, intranodally, intramedullary, intramuscularly, intravenously, or intraperitoneally. In some embodiments, the pharmaceutical composition is administered systemically. In some embodiments, the pharmaceutical composition is administered to an individual by infusion, such as intravenous infusion. Infusion techniques for immunotherapy are known in the art (see, e.g., Rosenberg et al., New Eng. J. of Med. 319: 1676 (1988)). In some embodiments, the pharmaceutical composition is administered to an individual by intradermal or subcutaneous injection. In some embodiments, the compositions are administered by intravenous injection. In some embodiments, the compositions are injected directly into a tumor, or a lymph node. In some embodiments, the pharmaceutical composition is administered locally to a site of tumor, such as directly into tumor cells, or to a tissue having tumor cells.

Dosages and desired drug concentration of pharmaceutical compositions of the present application may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46. It is within the scope of the present application that different formulations will be effective for different treatments and different disorders, and that administration intended to treat a specific organ or tissue may necessitate delivery in a manner different from that to another organ or tissue.

In some embodiments, wherein the pharmaceutical composition comprises any one of the anti-GPC2 constructs described herein, the pharmaceutical composition is administered at a dosage of about 10 ng/kg up to about 100 mg/kg of body weight of the individual or more per day, for example, at about 1 mg/kg/day to 10 mg/kg/day, depending upon the route of administration.

In some embodiments, wherein the pharmaceutical composition comprises any one of the engineered immune cells described herein, the pharmaceutical composition is administered at a dosage of at least about any of $10^4$, $10^5$, $10^6$, $10^7$, $10^8$, or $10^9$ cells/kg of body weight of the individual. In some embodiments, the pharmaceutical composition is administered at a dosage of any of about $10^4$ to about $10^5$, about $10^5$ to about $10^6$, about $10^6$ to about $10^7$, about $10^7$ to about $10^8$, about $10^8$ to about $10^9$, about $10^4$ to about $10^9$, about $10^4$ to about $10^6$, about $10^6$ to about $10^8$, or about $10^5$ to about $10^7$ cells/kg of body weight of the individual. In some embodiments, the pharmaceutical composition is administered at a dose of at least about any $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$ ells/kg or more.

In some embodiments, the pharmaceutical composition is administered for a single time. In some embodiments, the pharmaceutical composition is administered for multiple times (such as any of 2, 3, 4, 5, 6, or more times). In some embodiments, the pharmaceutical composition is administered once per week to once per year. In some embodiments, the interval between administrations is about 1 week to a year. The optimal dosage and treatment regime for a particular patient can readily be determined by one skilled in the art of medicine by monitoring the patient for signs of disease and adjusting the treatment accordingly.

Moreover, dosages may be administered by one or more separate administrations, or by continuous infusion. In some embodiments, the pharmaceutical composition is administered in split doses, such as about any one of 2, 3, 4, 5, or more doses. In some embodiments, the split doses are administered over about a week. In some embodiments, the dose is equally split. In some embodiments, the split doses are about 20%, about 30% and about 50% of the total dose. In some embodiments, the interval between consecutive split doses is about 1 day, 2 days, 3 days or longer. For repeated administrations over several days or longer, depending on the condition, the treatment is sustained until a desired suppression of disease symptoms occurs. However, other dosage regimens may be useful. The progress of this therapy is easily monitored by conventional techniques and assays.

In some embodiments, the amount of the pharmaceutical composition is effective to cause an objective clinical response in the individual. In some embodiments, the amount of the pharmaceutical composition is effective to cause disease remission (partial or complete) in the individual. In some embodiments, the amount of the pharmaceutical composition is effective to prevent relapse or disease progression of the cancer in the individual. In some embodiments, the amount of the pharmaceutical composition is effective to prolong survival (such as disease free survival) in the individual. In some embodiments, the pharmaceutical composition is effective to improve quality of life in the individual.

In some embodiments, the amount of the pharmaceutical composition is effective to inhibit growth or reducing the size of a solid or lymphatic tumor. In some embodiments, the size of the solid or lymphatic tumor is reduced for at least about 10% (including for example at least about any of 20%, 30%, 40%, 60%, 70%, 80%, 90%, or 100%). In some embodiments, a method of inhibiting growth or reducing the size of a solid or lymphatic tumor in an individual is provided.

In some embodiments, the amount of the pharmaceutical composition is effective to inhibit tumor metastasis in the individual. In some embodiments, at least about 10% (including for example at least about any of 20%, 30%, 40%, 60%, 70%, 80%, 90%, or 100%) metastasis is inhibited. In some embodiments, a method of inhibiting metastasis to lymph node is provided. In some embodiments, a method of inhibiting metastasis to the lung is provided. In some embodiments, a method of inhibiting metastasis to the liver is provided. Metastasis can be assessed by any known methods in the art, such as by blood tests, bone scans, x-ray scans, CT scans, PET scans, and biopsy.

EXAMPLES

The examples below are intended to be purely exemplary of the invention and should therefore not be considered to limit the invention in any way. The following examples and detailed description are offered by way of illustration and not by way of limitation.

Example 1

Animal Immunization and Titration 1.1 Animal Immunization

Two camels were immunized using recombinant Human Glypican 2 Protein (R&D Systems, #2304-GP) as an immunogen. The animals were immunized subcutaneously in the neck for six times. Complete Freund's Adjuvant (SIGMA, #F5881) was used in combination with 200 μg/dose immunogen during primary immunization. The Incomplete Freund's Adjuvant (SIGMA, #F5506) 200 μg/dose immunogen were used in the boost immunizations. Animals were immunized at 1 to 2-week intervals. One animal also received 2 injections of transgenic HEK293T/hGPC2 cells ($1\times10^7$, constructed in house reference to Example 3) that stably expressing hGPC2 at the 4th and 5th immunization. Peripheral blood samples were collected at the pre-immunization stage and after the 3rd and 5th immunization. The IgG subclasses were fractionated from serum using Protein G and Protein A resins, and the antigen specific humoral immune response was verified by ELISA-based and cell-based assays (FIG. 2A-FIG. 2D), showing an adequate elicit of response in correlation with presence of heavy chain immunoglobulins (HCAbs). To confirm the titer of antigen-specific single-domain antibodies (sdAbs), 100 mL blood samples were collected 5 days after the last immunization. Lymphocytes and blood sera were separated and stored at −80° C.

1.2 IgG Fractionation

IgG-subclass fractionation was carried out according to GenScript's Standard Operating Procedure. The IgG subclasses were fractionated from terminal bleed serum using Protein G and Protein A resins. The 1 mL serum sample was loaded onto a 1 mL HITRAP® Protein G HP column, and the column was washed with 10 mL phosphate buffer (20 mM, pH 7.0). The IgG3 (MW 100,000 Da) fraction was eluted with 0.15M NaCl, 0.58% acetic acid (pH 3.5), and the eluate was neutralized with 1M Tris-HCl (pH 9.0) to pH 7.4. Subsequently, the IgG1 (MW 170,000 Da) fraction was eluted with 0.1 M glycine-HCl (pH 2.7), and the eluate was neutralized with 1M Tris-HCl (pH 8.5) to pH 7.4. The flow-through of HITRAP® Protein G HP column was then loaded onto a 1 mL HITRAP® Protein A HP column, and the column was washed with 20 mL phosphate buffer (20 mM, pH 7.0). The IgG2 (MW 100,000 Da) fraction was eluted with 0.15 M NaCl, 0.58% acetic acid (pH 4.5), and the eluate was neutralized with 1M Tris-HCl (pH 9.0) to pH 7.4. The concentrations of the purified IgG1, IgG2 and IgG3 antibodies were determined by OD280, and the purity of each was assessed by both reducing and non-reducing SDS-PAGE analysis.

1.3 Immune Response Assay

Figure 2B:
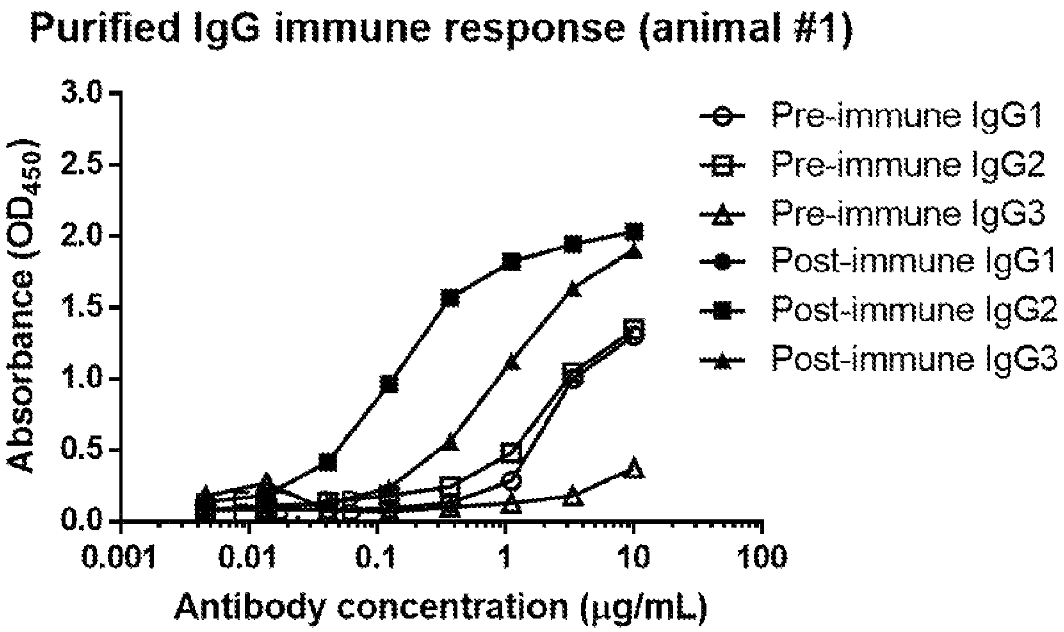
Figure 2C:
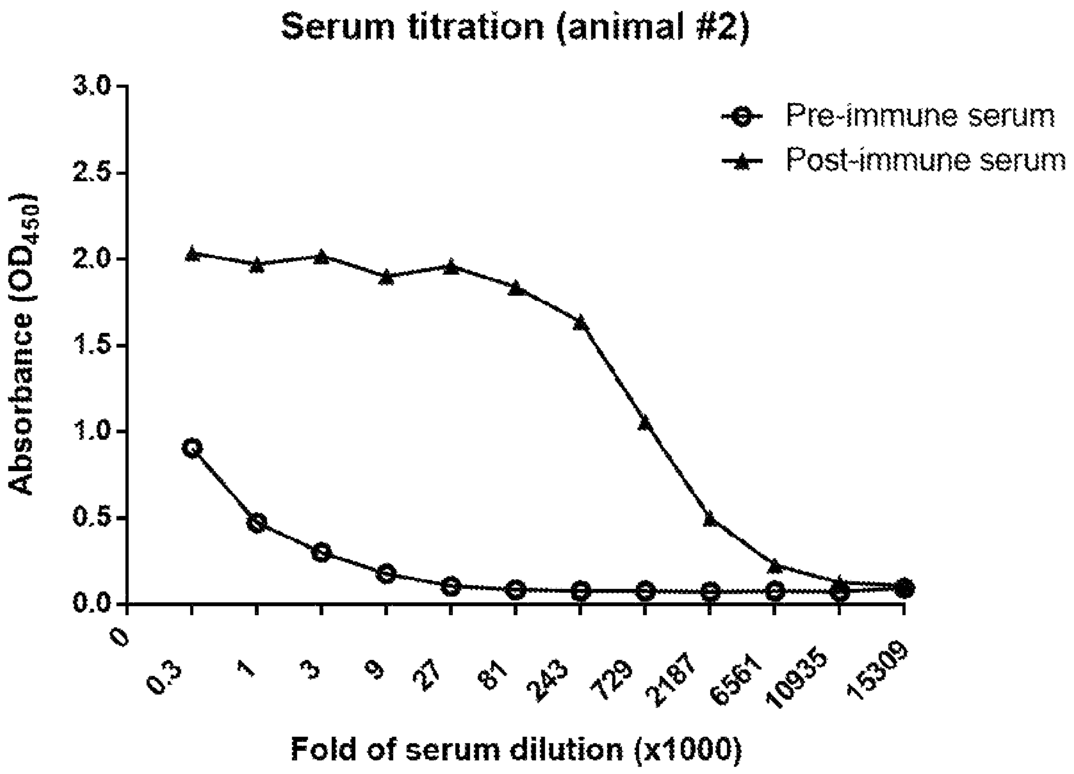
Figure 2D:
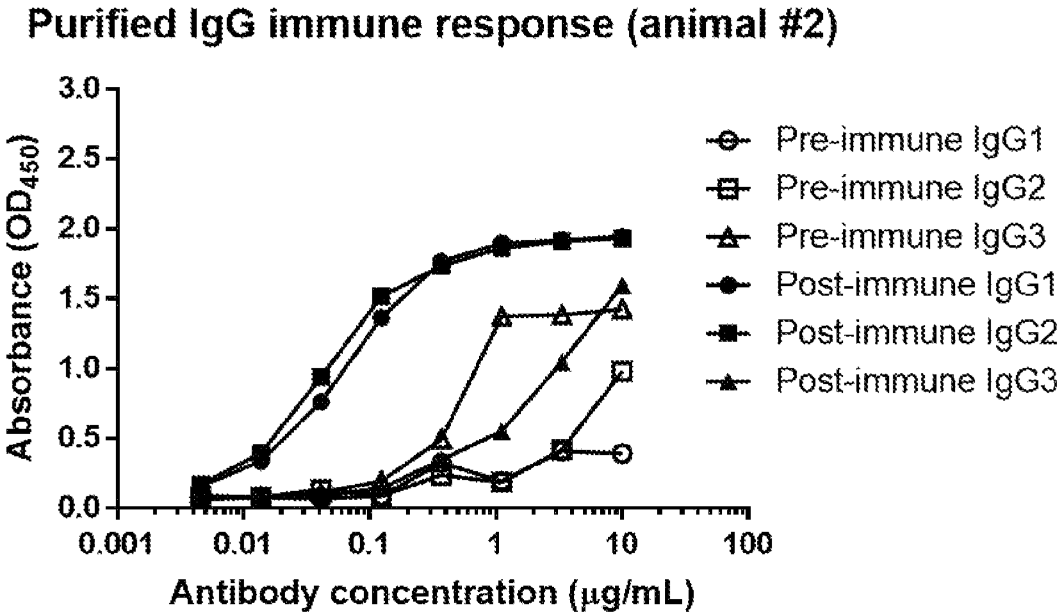
Figure 3A:
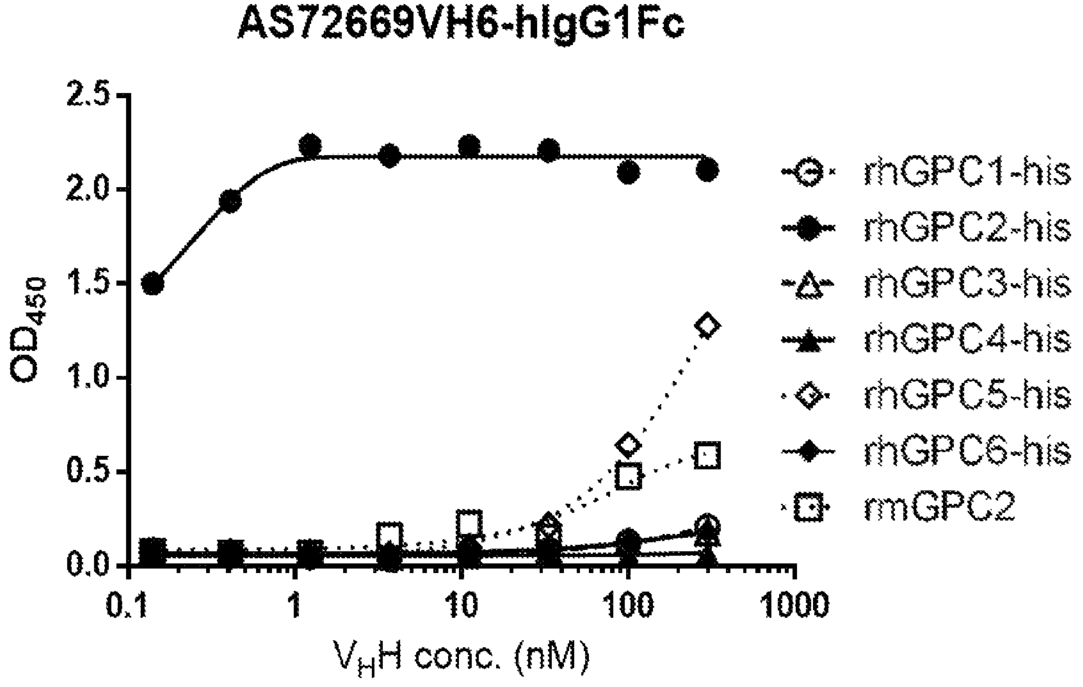
FIGS. 3A-3G show cross-reactivity of humanized anti-human GPC2 monoclonal $V_H$H binders to human GPC1, GPC2, GPC3, GPC4, GPC5 GPC6 and mouse GPC2.
Figure 3B:
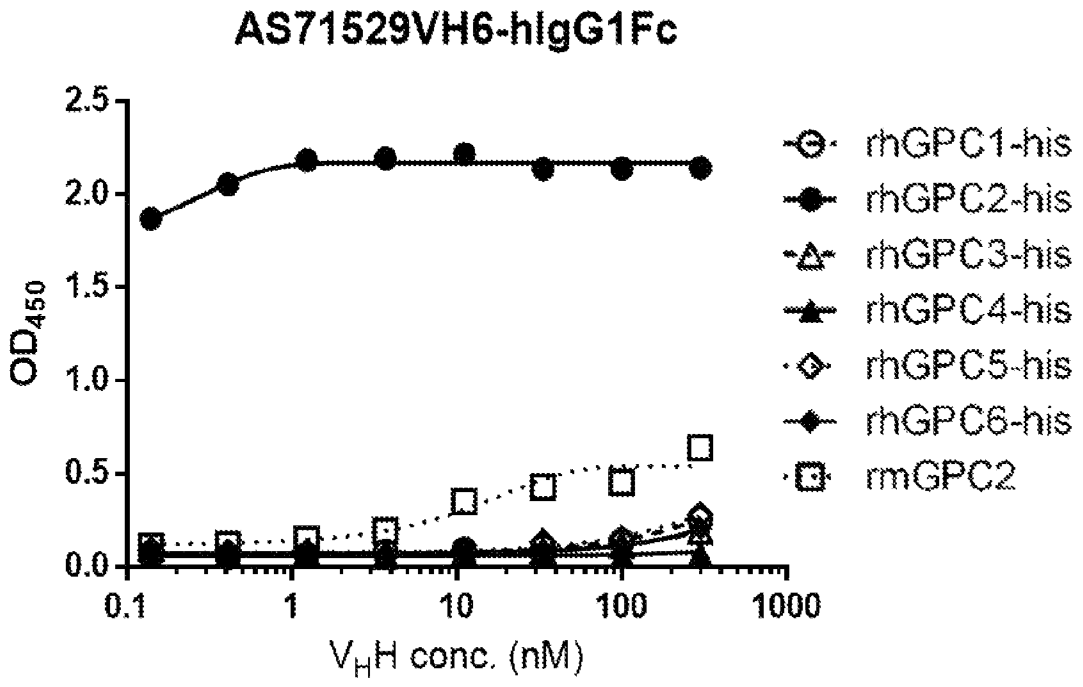
Figure 3C:
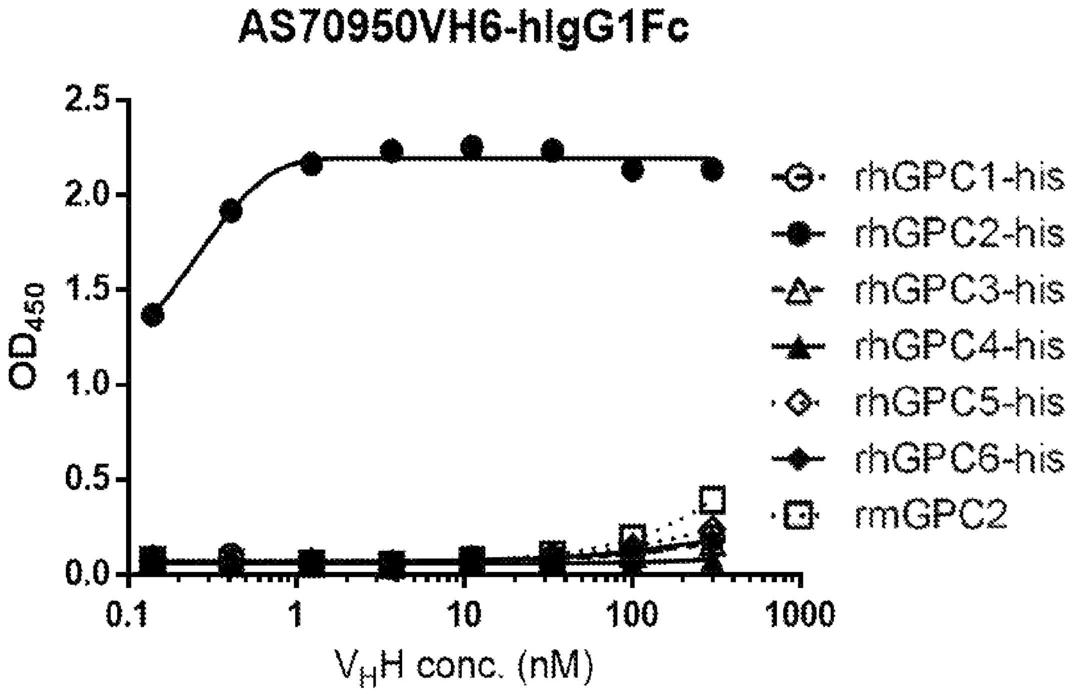
Figure 3D:
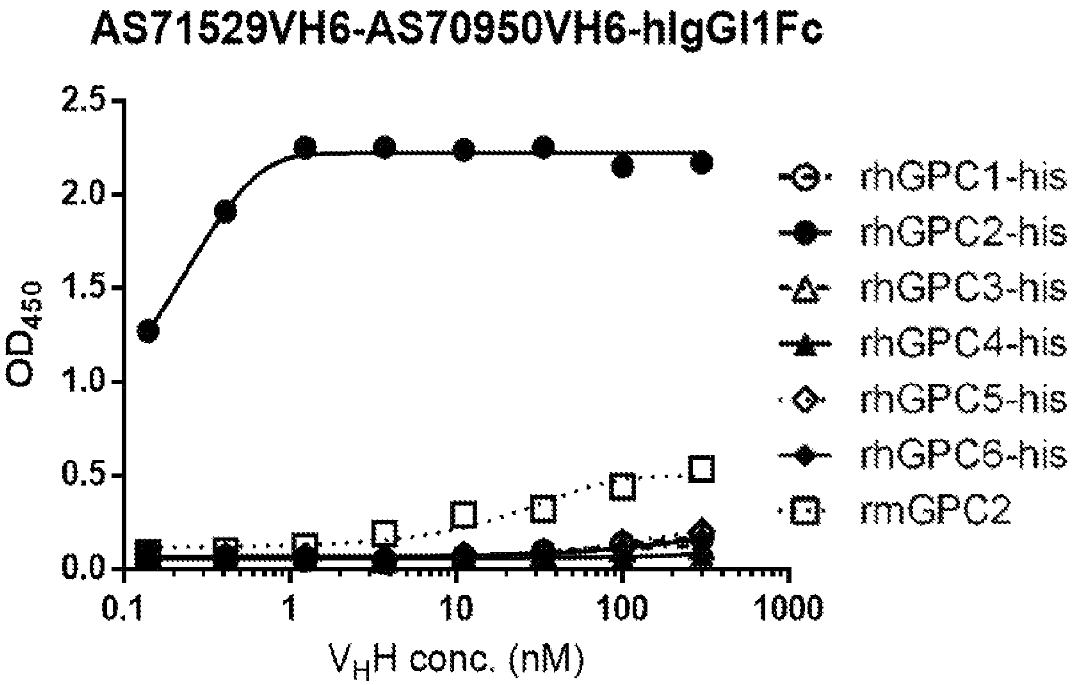
Figure 3E:
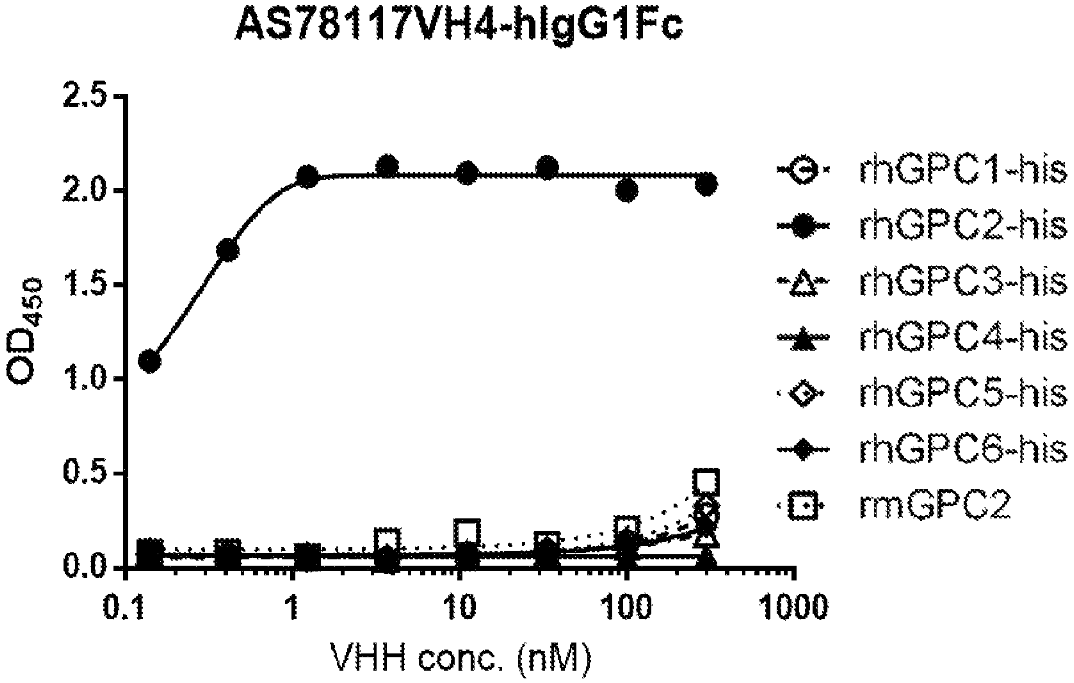
Figure 3F:
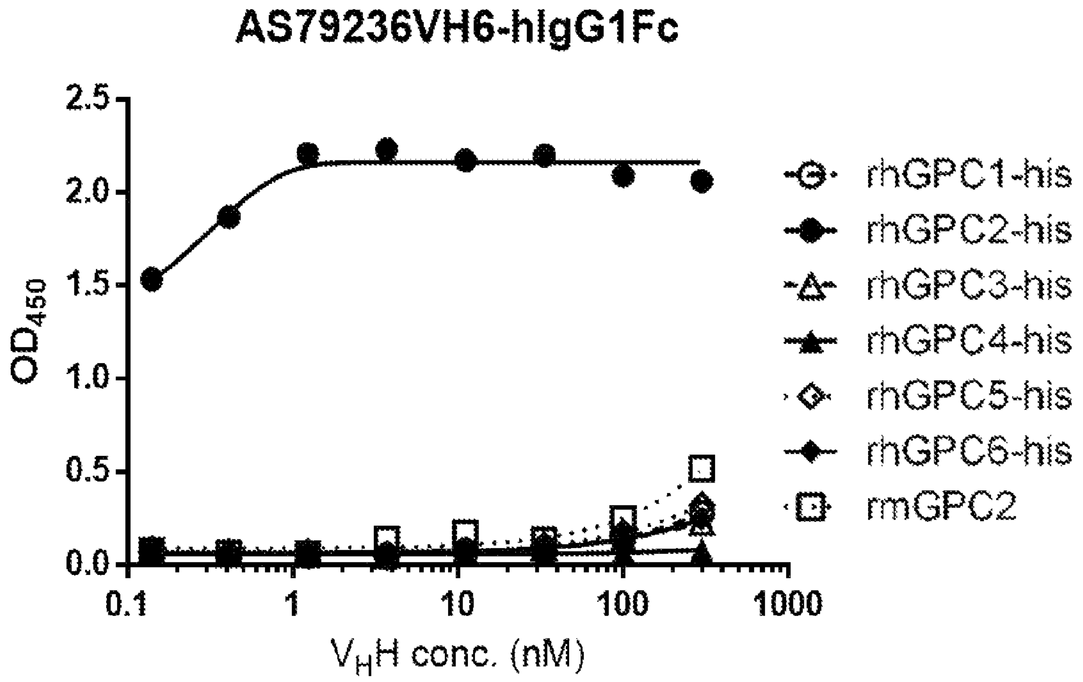
Figure 3G:
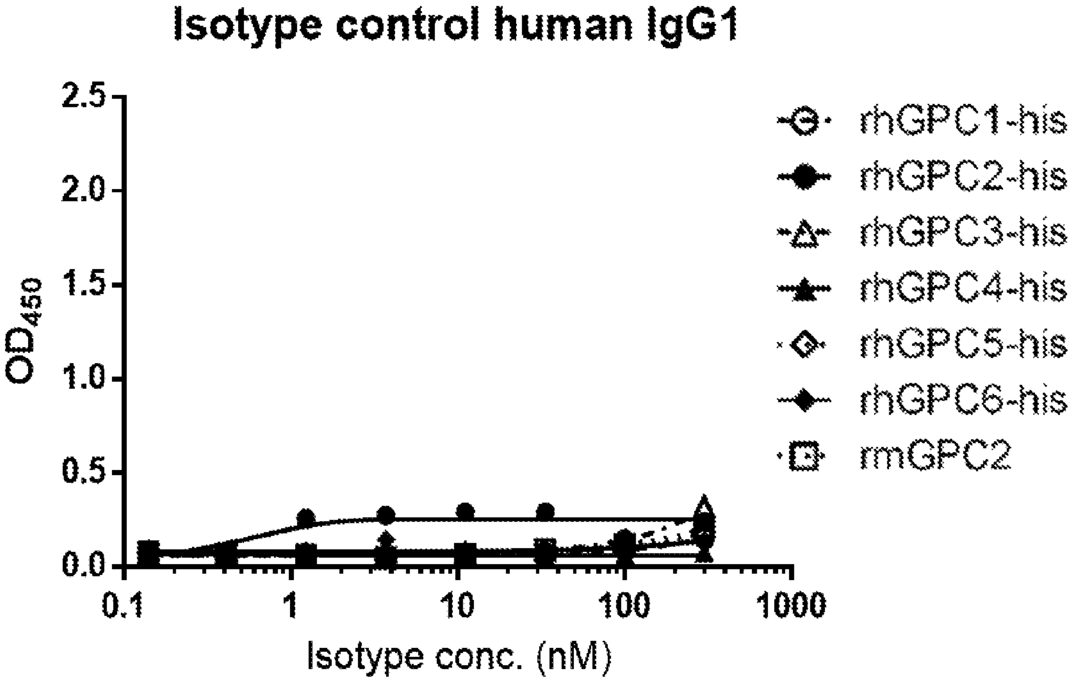

Immune response of the camels were evaluated by ELISA, in which the serum samples and purified IgGs were assayed for binding to immobilized immunogens. Sera collected pre-immunization, after 3rd and 5th immunization and at terminal bleed were evaluated. The antigens were diluted in coating buffer. The microtiter plate was coated with diluted antigen at 4° C. overnight. The plate was then washed 3 times with washing buffer followed by blocking at room temperature for 2 hours. The plate was subsequently washed 4 times with washing buffer. A series of diluted sera or IgGs were added to the plate and incubated at room temperature for 1.5 hours. The plate was then washed 4 times with washing buffer. HRP-conjugated anti-llama IgG secondary antibody (NOVUS, #NB7242) was added to the plate and incubated at room temperature for 1 hour. After washing, the TMB substrate was added to each well and incubated for 10 minutes before stopping with 1M HCl. To quantify binding, absorbance at 450 nm was measured for each well using a spectrometer. As shown in FIGS. 2A and 2C, post-immune sera from the immunized animals bind to the recombinant GPC2 protein at higher dilutions than the pre-immune sera, data indicates positive humoral immune response against human GPC2. In FIG. 2B and FIG. 2D, all exemplary anti-GPC2 $V_H$H-hIgG1Fc proteins bind to recombinant GPC2 protein in a dose dependent manner as the absorbance at 450 nm is positively correlated with the concentration of $V_H$H-hIgG1Fc proteins.

Example 2

$V_HH$ Phage Display Library Construction 2.1 RNA Extraction

Lymphocytes were isolated from the peripheral blood samples of immunized camels using a lymphocyte separation medium (TBD, #LTS1076). Total RNA was isolated from each sample using TRIzol® Reagent (LIFE technologies, #15596-026) according to manufacturer's instruction. Quantity and quality of the total RNA were assessed by gel electrophoresis and quantified by measuring absorbance at OD260/280.

2.2 $V_HH$ Amplification and Phage Library Construction

The RNA was reverse transcribed to generate a cDNA library with an oligo(dT)20 primer for each blood sample using PrimeScript™ 1st Strand cDNA Synthesis Kit (Takara, #6110A) according to the manufacturer's protocol. Nucleotide sequences encoding $V_HH$ were amplified from the cDNA library using specific primers. The $V_HH$ fragments were amplified according to GenScript's standard operating procedure. The variable regions of the heavy-chain immunoglobulins were amplified using polymerase chain reaction (PCR). The DNA products were analyzed by agarose gel electrophoresis. $V_HH$ PCR fragments were subsequently digested from agarose gel and ligated into the phagemid vector. The recombinant plasmids with $V_HH$ gene fragments were electro-transferred into *E. coli* cells. The transformed cells were diluted and plated on 2*YT plates supplemented with 100 mg/mL ampicillin. The successfully transfected *E. coli* carrying an ampicillin-resistance gene that allow them to form colonies on YT plates. The number of colonies were counted to estimate the size of display library. Single clones were picked randomly and sequenced to examine the quality of the library. To produce cells for plasmid isolation, transfected *E. coli* cells were plated on YT plates supplemented with 100 mg/mL ampicillin and 2% glucose. Colonies were scraped and aliquots of transfected cells were stored in glycerol at −80° C. as stock for library plasmid isolation.

Example 3

Phage Display Panning 3.1 Panning

The library stock was grown to log phase, and then the library was rescued and precipitated with PEG/NaCl, re-suspended in PBS and stored at −80° C. The constructed VIM phage library was panned against recombinant human GPC2 protein (R&D, #2304-GP) or HEK293T/hGPC2 cell line (constructed in house reference to Example 3) to obtain output phage with the counter selection of human GPC1/GPC3 (R&D, #4519-GP; R&D, #2119-GP) proteins or HEK293T blank cell (ATCC, #CRL-1573). Each output was analyzed for enrichment factor (# of phage present in eluate relative to control), diversity and percentage of GPC2 protein and cell positive clones (by ELISA & FACS).

Based on these parameters, the best output was sub-cloned as a pool into a soluble expression vector for high-throughput screening. Colonies were picked and grown in 96 deep well plates (1 mL volume) and induced by adding IPTG (AMRESCO, 40487-100G) and 0.05% Triton for single-domain antibody (sdAb) expression in the supernatant. The supernatant was analyzed for their ability to bind to GPC2 protein (by ELISA), the positive binders were sequenced and the unique clones were selected for further characterization.

3.2 Phage ELISA

Phage ELISA was performed to identify clones specific to the target antigens. Individual output phage clones were grown in 96-deep-well plate and rescued by M13K07 helper phage (NEB, #N0315S) overnight. To identify clones that bind to antigen proteins, 96-well ELISA microtiter plates were coated with recombinant human GPC2 protein or control proteins (GPC1/GPC3) respectively in coating buffer overnight at 4° C., and the plates were then blocked with blocking buffer. After blocking, approximately 50 μL per well of phage supernatant from the overnight cell culture was added to the plates for 1.5-hour incubation at 4° C. The plates were washed four times, and the HRP-conjugated anti-M13 monoclonal antibody was added to the plates for 45 minutes incubation at 4° C. The plates were again washed five times and substrate solution was added to the wells for developing. Absorption at 450 nm was measured for each well. After panning, ELISA positive phage clones were randomly selected and DNA was prepared from output phage using a plasmid extraction kit.

3.3 Phage FACS

To identify clones that bind with GPC2 expressing cells. HEK293T clones that stably express human GPC2, Cynomolgus monkey GPC2, *Pteropus vampyrus GPC*2 were prepared by transfecting HEK293 T cells (ATCC, #CRL-1573) with plvx-EF1α-puro plasmids comprising sequences of human GPC2 (NM 152742.3), Cynomolgus monkey (*Macaca fascicularis*) GPC2 (NW 005092963.1) or *Pteropus vampyrus GPC*2 ORF (NW_011888974.1). Phage supernatant was added to the GPC2-expressing HEK293T stable cells and SH-SY5Y tumor cell (ATCC, #CRL-2266), the residual phage that bound on cell surface was detected by M13 Bacteriaphage Antibody (Sino biological, #11973-MM05T-H). Cells were analyzed by flow cytometry.

Table 1 shows CDR1, CDR2, and CDR3 in camel $V_HH$ in accordance with some embodiments of the present disclosure.

TABLE 1

| Antibody | ID | CDR1 Sequence | ID | CDR2 Sequence | ID | CDR3 Sequence |
|---|---|---|---|---|---|---|
| AS70549 | 1 | RYTGRSSC | 31 | IYSDDGVT | 62 | ATRTTYPGVCPDNAAWYD Y |
| AS70771 | 2 | GYTGK | 32 | IDDAGGT | 63 | AADTFRWFMRRSGPINGSD YAY |
| AS70950 | 3 | EFTYKNTC | 33 | IDSDGNT | 64 | AAGAYCGRLLLWIGNYAY |
| AS71402 | 4 | GYTYNRN | 34 | MYTGSGTT | 65 | AADTARRGGSWSGPFKYD Y |

TABLE 1-continued

| Antibody | ID | CDR1 Sequence | ID | CDR2 Sequence | ID | CDR3 Sequence |
|---|---|---|---|---|---|---|
| AS71529 | 5 | EYRYSSRYC | 35 | IDSNGSA | 66 | AADHLAYDCYSGATSVFRY |
| AS71661 | 6 | GTTFAHYNM | 36 | ISKYGGTT | 67 | AIGVLPSSTAICAGAANY |
| AS72021 | 7 | RNTYSSYC | 37 | IDNVKT | 68 | AAHLELCYYTDPMYQYEYNY |
| AS72052 | 8 | GFRYASYC | 38 | IHSDGII | 69 | AAGAYCGADAILTLYDYAF |
| AS72383 | 9 | GLTFDDSG | 39 | ITWNGRST | 70 | AAAFITKTGCSYE |
| AS72479 | 10 | ETTDCRYV | 40 | ITSGGST | 71 | ESDPGWSGYHARRC |
| AS72499 | 11 | RFTYSSYC | 41 | IEKDDST | 72 | AARIPGGNCGVVARMAY |
| AS72531 | 12 | GLTFAHYNM | 42 | ISKYGGT | 73 | AIGVLSSTARGPGAANY |
| AS72669 | 11 | RFTYSSYC | 43 | FYTGGGRT | 74 | VAGFYCSGGYWEGDFGY |
| AS72794 | 13 | GFTFDDYA | 44 | ISASGTTT | 75 | AADRFRDYCSDSWSHLYNYEYMH |
| AS72805 | 14 | RLRVSNNC | 45 | LGSDGRT | 76 | AAADFSSGGYCNIASVYHSYFPY |
| AS72806 | 15 | GYTYMPPC | 46 | IYGRGGST | 77 | AADNLCYATGILRSAYDYSY |
| AS72835 | 16 | GGYTSRTVC | 47 | IYRSGTT | 78 | AASPGYSDAACVSVPQANR |
| AS77906 | 17 | GVVKCDVE | 48 | IEAGGHT | 79 | VAAPRYYTLSCPKDF |
| AS77916 | 18 | GYTSSWNC | 49 | IANRGHST | 80 | ATDTWACVGISTDFEY |
| AS77932 | 19 | GYWYSVAW | 50 | VLNGGGRR | 81 | AAGNGVGHPLGPSEYNY |
| AS77934 | 20 | GYTYSSYS | 51 | FFYSGGPT | 82 | AARRSNTNDYCFYPTYTY |
| AS77978 | 21 | GATSCRWR | 52 | IANGAT | 83 | AADPRVYTSRCDRTY |
| AS77986 | 22 | ASGYTYSSDS | 53 | ISTGGRST | 84 | AADGPSMTAIQALGDLYPVDFAW |
| AS78117 | 23 | RYTYATYS | 54 | LDSVGAT | 85 | VVDPASAKVTYGSWSTPSYAY |
| AS78215 | 24 | RYTFSSNC | 55 | IASASGYT | 86 | AARAGPCWSWAQADLYNY |
| AS78810 | 25 | GYTYYD | 56 | ISSSSST | 87 | AAGRYVGRKLEVYDYAY |
| AS79101 | 26 | GDTYSNYC | 57 | IDSDGSR | 88 | ATDPKVACARVVEYGGGWYR |
| AS79236 | 27 | GYTYSSYC | 58 | IDAGGRT | 89 | AVDVRTRCGGTWDGEAVYFPY |
| AS79274 | 28 | KYAFCTYD | 59 | IDSRGNT | 90 | AAQIVGGALRCPRFAMY |
| AS79285 | 29 | RYTVSNYC | 60 | ISTDGTT | 91 | AGVYGLIWYYKPCPAQREWALQRYGY |
| AS79317 | 30 | GYSSSSVC | 61 | IYVTLGSI | 92 | AAGGCGYRGVADVPEFTY |
| AS70950VH6 | 3 | EFTYKNTC | 33 | IDSDGNT | 64 | AAGAYCGRLLLWIGNYAY |

TABLE 1-continued

| Antibody | ID | CDR1 Sequence | ID | CDR2 Sequence | ID | CDR3 Sequence |
|---|---|---|---|---|---|---|
| AS70950VH7 | 3 | EFTYKNTC | 33 | IDSDGNT | 64 | AAGAYCGRLLLWIGNYAY |
| AS71529VH5 | 5 | EYRYSSRYC | 35 | IDSNGSA | 66 | AADHLAYDCYSGATSVFRY |
| AS71529VH6 | 5 | EYRYSSRYC | 35 | IDSNGSA | 66 | AADHLAYDCYSGATSVFRY |
| AS72052VH5 | 8 | GFRYASYC | 38 | IHSDGII | 69 | AAGAYCGADAILTLYDYAF |
| AS72052VH6 | 8 | GFRYASYC | 38 | IHSDGII | 69 | AAGAYCGADAILTLYDYAF |
| AS72669VH6 | 11 | RFTYSSYC | 43 | FYTGGGRT | 74 | VAGFYCSGGYWEGDFGY |
| AS78117VH4 | 23 | RYTYATYS | 54 | LDSVGAT | 85 | VVDPASAKVTYGSWSTPSYAY |
| AS78117VH5 | 23 | RYTYATYS | 54 | LDSVGAT | 85 | VVDPASAKVTYGSWSTPSYAY |
| AS78117VH6 | 23 | RYTYATYS | 54 | LDSVGAT | 85 | VVDPASAKVTYGSWSTPSYAY |
| AS78117VH7 | 23 | RYTYATYS | 54 | LDSVGAT | 85 | VVDPASAKVTYGSWSTPSYAY |
| AS79236VH4 | 27 | GYTYSSYC | 58 | IDAGGRT | 89 | AVDVRTRCGGTWDGEAVYFPY |
| AS79236VH5 | 27 | GYTYSSYC | 58 | IDAGGRT | 89 | AVDVRTRCGGTWDGEAVYFPY |
| AS79236VH6 | 27 | GYTYSSYC | 58 | IDAGGRT | 89 | AVDVRTRCGGTWDGEAVYFPY |
| AS77916VH6 | 18 | GYTSSWNC | 49 | IANRGHST | 80 | ATDTWACVGISTDFEY |
| AS77916VH7 | 18 | GYTSSWNC | 49 | IANRGHST | 80 | ATDTWACVGISTDFEY |
| AS77916VH8 | 18 | GYTSSWNC | 49 | IANRGHST | 80 | ATDTWACVGISTDFEY |
| AS77916VH9 | 18 | GYTSSWNC | 49 | IANRGHST | 80 | ATDTWACVGISTDFEY |
| AS77916VH10 | 18 | GYTSSWNC | 49 | IANRGHST | 80 | ATDTWACVGISTDFEY |

Camel $V_H$H amino acid sequences in accordance with some embodiments of the present disclosure may include AS70549 (SEQ ID NO: 93), AS70771 (SEQ ID NO: 94), AS70950 (SEQ ID NO: 95), AS71402 (SEQ ID NO: 96), AS71529 (SEQ ID NO: 97), AS71661 (SEQ ID NO: 98), AS72021 (SEQ ID NO: 99), AS72052 (SEQ ID NO: 100), AS72383 (SEQ ID NO: 101), AS72479 (SEQ ID NO: 102), AS72499 (SEQ ID NO: 103), AS72531 (SEQ ID NO: 104), AS72669 (SEQ ID NO: 105), AS72794 (SEQ ID NO: 106), AS72805 (SEQ ID NO: 107), AS72806 (SEQ ID NO: 108), AS72835 (SEQ ID NO: 109), AS77906 (SEQ ID NO: 110), AS77916 (SEQ ID NO: 111), AS77932 (SEQ ID NO: 112), AS77934 (SEQ ID NO: 113), AS77978 (SEQ ID NO: 114), AS77986 (SEQ ID NO: 115), AS78117 (SEQ ID NO: 116), AS78215 (SEQ ID NO: 117), AS78810 (SEQ ID NO: 118), AS79101 (SEQ ID NO: 119), AS79236 (SEQ ID NO: 120), AS79274 (SEQ ID NO: 121), AS79285 (SEQ ID NO: 122), and AS79317 (SEQ ID NO: 123).

Camel $V_H$H nucleic acid sequences may include AS70549 (SEQ ID NO: 148), AS70771 (SEQ ID NO: 149), AS70950 (SEQ ID NO: 150), AS71402 (SEQ ID NO: 151), AS71529 (SEQ ID NO: 152), AS71661 (SEQ ID NO: 153), AS72021 (SEQ ID NO: 154), AS72052 (SEQ ID NO: 155), AS72383 (SEQ ID NO: 156), AS72479 (SEQ ID NO: 157), AS72499 (SEQ ID NO: 158), AS72531 (SEQ ID NO: 159), AS72669 (SEQ ID NO: 160), AS72794 (SEQ ID NO: 161), AS72805 (SEQ ID NO: 162), AS72806 (SEQ ID NO: 163), AS72835 (SEQ ID NO:164), AS77906 (SEQ ID NO: 165), AS77916 (SEQ ID NO: 166), AS77932 (SEQ ID NO: 167), AS77934 (SEQ ID NO: 168), AS77978 (SEQ ID NO: 169), AS77986 (SEQ ID NO: 170), AS78117 (SEQ ID NO: 171), AS78215 (SEQ ID NO: 172), AS78810 (SEQ ID NO: 173), AS79101 (SEQ ID NO: 174), AS79236 (SEQ ID NO: 175), AS79274 (SEQ ID NO: 176), AS79285 (SEQ ID NO: 177), and AS79317 (SEQ ID NO: 178).

Example 4

Humanization and Affinity Measurement

The variable domain sequences of parental antibody were searched in the database of human germline using NCBI Ig-Blast (ncbi.nlm.nih.gov/projects/igblast/) to find human acceptors (i.e., human variable domains with high homology to the parental antibody). The CDRs of human acceptors were replaced with their camel counterparts, residues potentially critical for antigen binding or antibody scaffold formation were left untouched, resulting in a panel of humanized variants which are indicated with "VH" in their names.

The DNA sequences of parental and humanized variants were cloned into pcDNA3.4 vector, then plasmids were transfected into HEK293-6E cell, supernatants were collected and affinity ranking was tested by Surface Plasmon Resonance (SPR) using Biacore T200.

Humanized $V_H$H amino acid sequences in accordance with some embodiments of the present disclosure may include AS70950VH6 (SEQ ID NO: 124), AS70950VH7 (SEQ ID NO: 125), AS71529VH5 (SEQ ID NO: 126), AS71529VH6 (SEQ ID NO: 127), AS72052VH5 (SEQ ID NO: 128), AS72052VH6 (SEQ ID NO: 129), AS72669VH6 (SEQ ID NO: 130), AS78117VH4 (SEQ ID NO: 131), AS78117VH5 (SEQ ID NO: 132), AS78117VH6 (SEQ ID NO: 133), AS78117VH7 (SEQ ID NO: 134), AS79236VH4 (SEQ ID NO: 135), AS79236VH5 (SEQ ID NO: 136), AS79236VH6 (SEQ ID NO: 137), AS77916VH6 (SEQ ID NO: 138), AS77916VH7 (SEQ ID NO: 139), AS77916VH8 (SEQ ID NO: 140), AS77916VH9 (SEQ ID NO: 141), AS77916VH10 (SEQ ID NO: 142), AS71529VH5-AS72052VH5 (SEQ ID NO: 143), AS72052VH5-AS71529VH5 (SEQ ID NO: 144), AS70950VH6-AS71529VH6 (SEQ ID NO: 145), AS71529VH6-AS70950VH6 (SEQ ID NO: 146), and AS70950VH6-AS70950VH6 (SEQ ID NO: 147).

Example 5

Affinity and Specificity of anti-GPC2 $V_H$Hs 5.1 Surface Plasmon Resonance (SPR) Assay Each of the exemplary anti-GPC2 $V_H$H sequences was cloned into a vector comprising a human IgG1Fc fragment (hlgG1Fc) sequence to facilitate recombinant expression of anti-GPC2 $V_H$H-hlgG1Fc. Recombinant proteins were obtained and purified for SPR assays. The affinity of each anti-GPC2 $V_H$H-hIgG1Fc for GPC2 was determined by SPR using a BIACORE® T200 analytical system (GE Healthcare). Briefly, recombinant human GPC2-His protein was covalently coupled to a CM5(s) sensor chip using an amine coupling kit. Exemplary $V_H$H-hIgG1Fc proteins were serially diluted in running buffer (10 mM HEPES, 150 mM NaCl, 3 mM EDTA, 0.05% Tween-20, pH 7.4) and injected over the chip cell at a flowrate of 100 μL/min for 100 seconds followed by buffer-only injection for 300 seconds to allow for antibody dissociation. The dissociation rate constants (KD) were determined using the BIACORE® T200 evaluation software version 3.0 (Langmuir binding, local fit, 1:1 binding model). The binding affinities of the six $V_H$H-hlgG1Fcs are shown in Table 1.

TABLE 1

Binding affinity of anti-GPC2 $V_H$H-hIgG1Fc to recombinant human GPC2-his protein

| Binders | ka (1/Ms) | kd (1/s) | KD (M) |
|---|---|---|---|
| AS78117VH4-hIgG1Fc | 2.0E+05 | 1.7E−04 | 8.2E−10 |
| AS79236VH6-hIgG1Fc | 5.3E+05 | 1.9E−04 | 3.7E−10 |
| AS70950VH6-hIgG1Fc | 3.90E+05 | 1.10E−04 | 2.70E−10 |
| AS71529VH6-hIgG1Fc | 8.50E+05 | 4.40E−03 | 5.10E−09 |
| AS71529VH6-AS70950VH6-hIgG1Fc | 3.20E+05 | 6.10E−05 | 1.90E−10 |
| AS72669VH6-hIgG1Fc | 5.20E+05 | 7.70E−05 | 1.50E−10 |

5.2 Specific Binding Assay

To evaluate the specificity of humanized anti-GPC2 $V_H$H5 to recombinant human GPC2 protein, an ELISA-based binding assay was conducted to determine the differential target proteins binding of anti-GPC2 $V_H$H5. Briefly, microplates were coated with 2 μg/mL recombinant human GPC1-His (RD System, Cat #4519-GP), GPC2-His (RD System, Cat #2304-GP), GPC3-His (ACRO, Cat #GP3-H5223), GPC4-Fc (RD System, Cat #9195-GP), GPC5-His (RD System, Cat #2607-G5/CF), GPC6-His (RD System, Cat #2845-GP) or recombinant mouse GPC2-His (RD System, Cat #2355-GP) proteins. Recombinant human protein coated plates were blocked with skim milk. Serially diluted humanized $V_H$H-hIgG1Fc recombinant antibodies were added to each well of the plates and incubated at 4° C. for 1.5 h. Samples were further labelled with HRP-conjugated goat anti human IgG (H+L) secondary antibody (Genescript, Cat #A00166-1) and signal was developed with 3,3',5,5'-Tetramethylbenzidine (TMB) substrate according to manufacturer's instruction. For the GPC4, $V_H$H-His recombinant antibodies and anti-His tag secondary antibody (Genescript, Cat #A00612) were added to the GPC4-Fc coated plates instead. Optic density at 450 nm was measured by plate reader.

As shown in FIG. 3A-FIG. 3G, all humanized $V_H$H-hIgG1Fc proteins (AS78117VH4-hIgG1Fc, AS79236VH6-hIgG1Fc, AS70950VH6-hIgG1Fc and AS71529VH6-hIgG1Fc) bind to recombinant human GPC2 protein with high affinity. In comparison, human IgG1 served as negative control and showed no binding with GPC family proteins, suggested the positive signals are antibody-specific. In particularly, AS78117VH4-hIgG1Fc, AS79236VH6-hIgG1Fc and AS70950VH6-hIgG1Fc showed better specificity to human GPC2 protein than the reported D3-GPC2-IgG1 [5] as they had no cross-reactivity with other recombinant human and murine GPC family proteins. Together, data suggested the humanized $V_H$H-hIgG1Fc proteins can specifically recognize human GPC2 protein.

5.3 Binding of Recombinant $V_H$H-his Proteins to Target Cells

Recombinant anti-GPC2 $V_H$H-His proteins were constructed by fusing the anti-GPC2 $V_H$H sequence to a mouse Ig heavy chain signal peptide sequence (N'-MGWSWILL-FLLSVTAGVHS-C; SEQ ID NO: 179) at the N terminus, and a 6×His-tag (N'-HHHHHH-C; SEQ ID NO: 180) at the C terminus. The codons were further optimized for optimal expression in mammalian engineered immune effector cells. The obtained nucleotide sequences were then cloned into a mammalian expression vector pCDNA3.4 to provide expression plasmids.

Figure 4A:
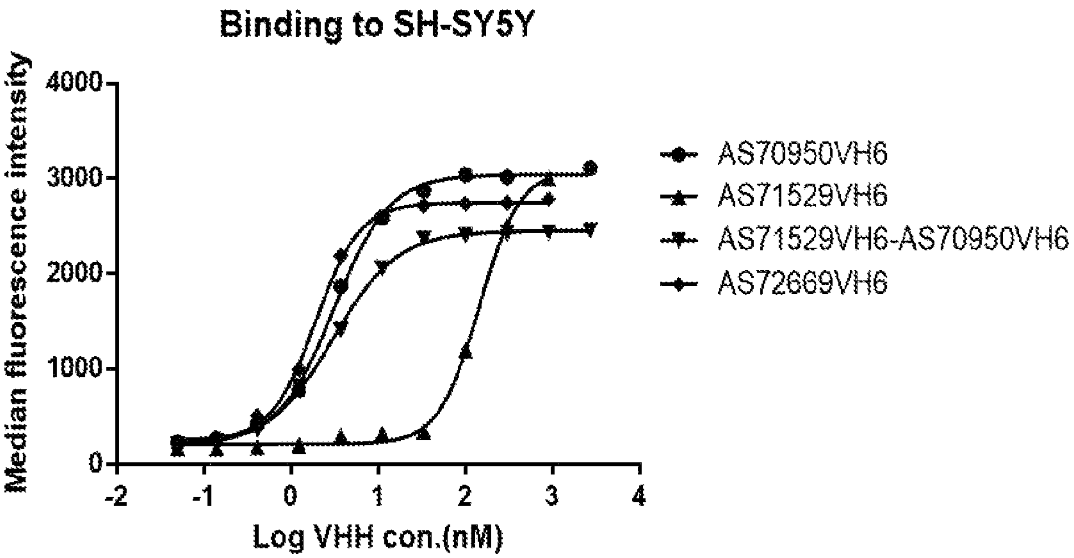
FIGS. 4A-4C show binding affinity of four anti-GPC2 $V_H$H antibodies for GPC2-expressing cell lines.
Figure 4B:
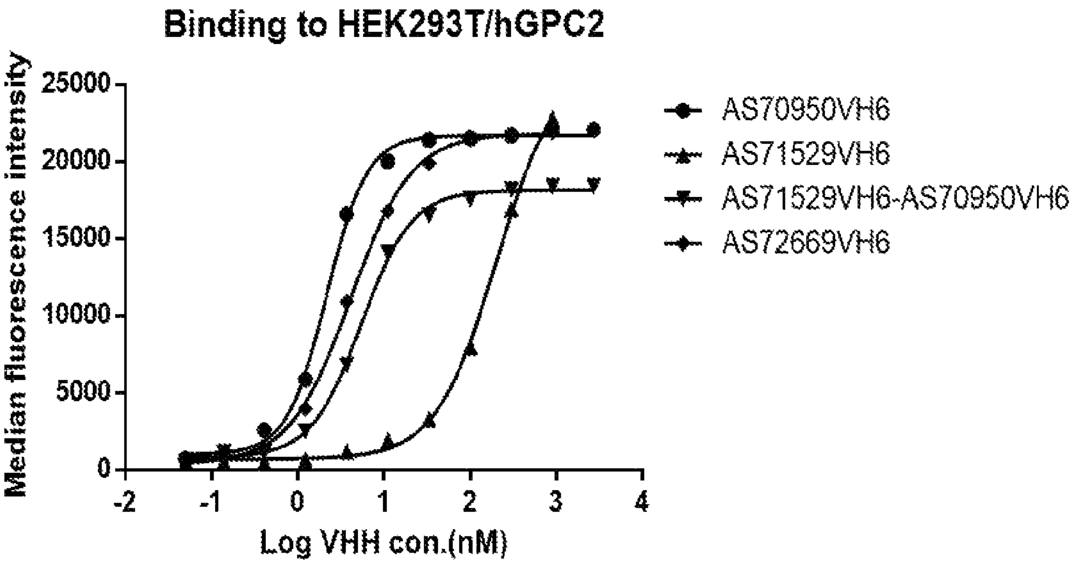
Figure 4C:
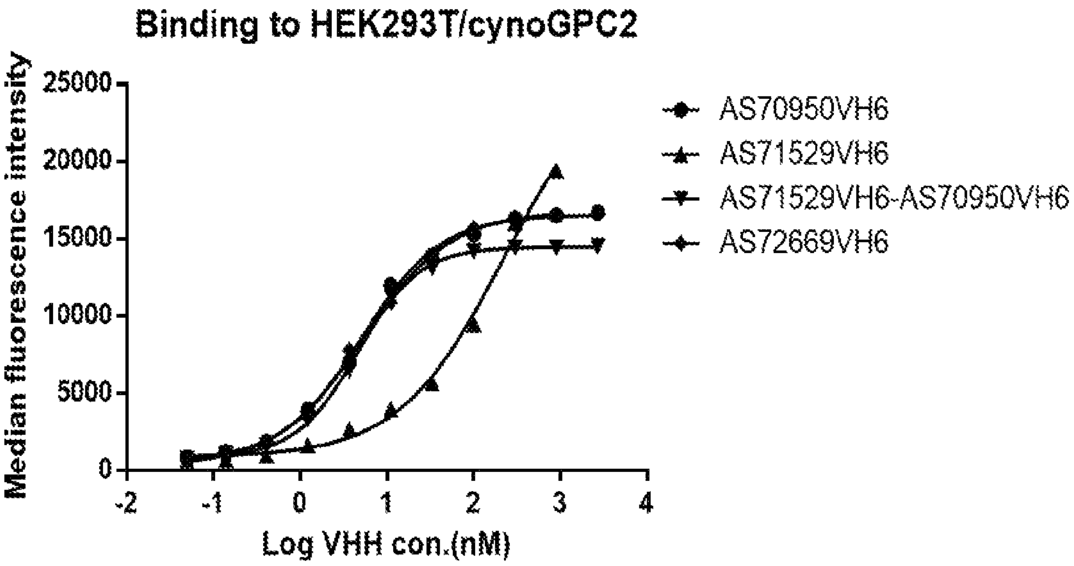

Binding affinities of humanized $V_H$H proteins AS70950VH6, AS71529VH6, AS72669VH6 and AS71529VH6-AS70950VH6 anti-GPC2 $V_H$H-HIS proteins to human GPC2 expressing cells (SH-SY5Y and HEK293T/ hGPC2) and cynomolgus monkey GPC2 expressing cell (HEK293T/cynoGPC2) were determined using flow cytometry. Briefly, serially diluted anti-GPC2 $V_H$H-HIS proteins were incubated with $2\times10^5$ target cells at 4° C. for 30 mins. After washing, cells were further labelled with THE™ His tag Antibody (iFluor 647) (Genescript, #A01802) at 4° C. for 30 mins. Fluorescence intensity was measured by flow cytometry. A four parameters variable slope curve was fitted to each group using GraphPad Prism for Windows Version 6.02. As shown in FIG. 4A-FIG. 4C, exemplary AS70950VH6, AS71529VH6, AS72669VH6 and AS71529VH6-AS70950VH6 specifically bind to SH-SY5Y, HEK293T/hGPC2 and HEK293T/cynoGPC2 in a dose-dependent manner.

Example 6

Generation of Monovalent GPC2-Specific CART Cells 6.1 Generation of CAR

Monovalent $V_H$H-based CARs comprising the isolated anti-GPC2 $V_H$H antibody fragment can be constructed by cloning the $V_H$H encoding nucleic acid sequence in-frame to the hinge domain of CD8α hinge and transmembrane domain that was fused to the 4-1BB and CD3 ζ intracellular signaling domains (FIG. 5). Nucleic acid sequence was cloned into a lentiviral vector backbone bearing the EF1α promoter.

Components of CAR in accordance with some embodiments of the present disclosure may include the following:

| SEQ ID NO: | Component of CAR | Sequence |
|---|---|---|
| 181 | Linker | GGGGSGGGGSGGGGS |
| 182 | CD8α signal peptide | MALPVTALLLPLALLLHAARP |
| 183 | CD8α hinge | TTTPAPRPPTPAPTIASQPLSLRPEACRPAAGGAVHTRGLDFACD |
| 184 | CD8α transmembrane domain | IYIWAPLAGTCGVLLLSLVITLYC |
| 253 | CD28 transmembrane domain | FWVLVVVGGVLACYSLLVTVAFIIFWV |
| 254 | CD27 transmembrane domain | ILVIFSGMFLVFTLAGALFLH |
| 255 | ICOS transmembrane domain | FWLPIGCAAFVVVCILGCILI |
| 256 | CD2 transmembrane domain | IYLIIGICGGGSLLMVFVALLVFYIT |
| 257 | OX40 transmembrane domain | VAAILGLGLVLGLLGPLAILL |
| 185 | 4-1BB intracellular domain | KRGRKKLLYIFKQPFMRPVQTTQEEDGCSCRFPEEEEGGCEL |
| 186 | CD28 intracellular domain | RSKRSRLLHSDYMNMTPRRPGPTRKHYQPYAPPRDFAAYRS |
| 258 | CD27 intracellular domain | QRRKYRSNKGESPVEPAEPCHYSCPREEEGSTIPIQEDYRKPEPACSP |
| 259 | ICOS intracellular domain | CWLTKKKYSSSVHDPNGEYMFMRAVNTAKKSRLTDVTL |
| 260 | CD2 intracellular domain | KRKKQRSRRNDEELETRAHRVATEERGRKPHQIPASTPQNPATSQHPPPPP GHRSQAPSHRPPPPGHRVQHQPQKRPPAPSGTQVHQQKGPPLPRPRVQP KPPHGAAENSLSPSSN |
| 261 | OX40 intracellular domain | ALYLLRRDQRLPPDAHKPPGGGSFRTPIQEEQADAHSTLAKI |
| 187 | CD3ζintracellular domain | RVKFSRSADAPAYKQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR |
| 188 | P2A element | GSGATNFSLLKQAGDVEENPGP |

Exemplary monovalent $V_H$H-based CARs comprising camel VIM sequences in accordance with some embodiments of the present disclosure may include CAS70549-BBz (SEQ ID NO: 189), CAS70771-BBz (SEQ ID NO: 190), CAS70950-BBz (SEQ ID NO: 191), CAS71402-BBz (SEQ ID NO: 192), CAS71529-BBz (SEQ ID NO: 193), CAS71661-BBz (SEQ ID NO: 194), CAS72021-BBz (SEQ ID NO: 195), CAS72052-BBz (SEQ ID NO: 196), CAS72383-BBz (SEQ ID NO: 197), CAS72479-BBz (SEQ ID NO: 198), CAS72499-BBz (SEQ ID NO: 199), CAS72531-BBz (SEQ ID NO: 200), CAS72669-BBz (SEQ ID NO: 201), CAS72794-BBz (SEQ ID NO: 202), CAS72805-BBz (SEQ ID NO: 203), CAS72806-BBz (SEQ ID NO: 204), CAS72835-BBz (SEQ ID NO: 205), CAS77906-BBz (SEQ ID NO: 206), CAS77916-BBz (SEQ ID NO: 207), CAS77932-BBz (SEQ ID NO: 208), CAS77934-BBz (SEQ ID NO: 209), CAS77978-BBz (SEQ ID NO: 210), CAS77986-BBz (SEQ ID NO: 211), CAS78117-BBz (SEQ ID NO: 212), CAS78215-BBz (SEQ ID NO: 213), CAS78810-BBz (SEQ ID NO: 214), CAS79101-BBz (SEQ ID NO: 215), CAS79236-BBz (SEQ ID NO: 216), CAS79274-BBz (SEQ ID NO: 217), CAS79285-BBz (SEQ ID NO: 218), and CAS79317-BBz (SEQ ID NO: 219). Exemplary monovalent $V_H$H-based CARs comprising camel VIM sequences in accordance with some embodiments of the present disclosure may include CAS70549-BBz (SEQ ID NO: 189), CAS70771-BBz, (SEQ ID NO: 190), CAS70950-BBz (SEQ ID NO: 191), CAS71402-BBz (SEQ ID NO: 192), CAS71529-BBz (SEQ ID NO: 193), CAS71661-BBz (SEQ ID NO: 194), CAS72021-BBz (SEQ ID NO: 195), CAS72052-BBz (SEQ ID NO: 196), CAS72383-BBz (SEQ ID NO: 197), CAS72479-BBz (SEQ ID NO: 198), CAS72499-BBz (SEQ ID NO: 199), CAS72531-BBz (SEQ ID NO: 200), CAS72669-BBz (SEQ ID NO: 201), CAS72794-BBz (SEQ ID NO: 202), CAS72805-BBz (SEQ ID NO: 203), CAS72806-BBz (SEQ ID NO: 204), CAS72835-BBz (SEQ ID NO: 205), CAS77906-BBz (SEQ ID NO: 206), CAS77916-BBz (SEQ ID NO: 207), CAS77932-BBz (SEQ ID NO: 208), CAS77934-BBz (SEQ ID NO: 209), CAS77978-BBz (SEQ ID NO: 210), CAS77986-BBz (SEQ ID NO: 211), CAS78117-BBz (SEQ ID NO: 212), CAS78215-BBz (SEQ ID NO: 213), CAS78810-BBz (SEQ ID NO: 214), CAS79101-BBz (SEQ ID NO: 215), CAS79236-BBz (SEQ ID NO: 216), CAS79274-BBz (SEQ ID NO: 217), CAS79285-BBz (SEQ ID NO: 218) and CAS79317-BBz (SEQ ID NO: 219).

Exemplary monovalent $V_H$H-based CARs comprising humanized camel $V_H$H sequences in accordance with some embodiments of the present disclosure may include CAS70950VH6-BBz, CAS70950VH7-BBz, CAS71529VH5-BBz, CAS71529VH6-BBz, CAS72052VH5-BBz, CAS72052VH6-BBz, CAS72669VH6-BBz, CAS78117VH4-BBz, CAS78117VH5-BBz, CAS78117VH6-BBz, CAS78117VH7-BBz, CAS79236VH4-BBz, CAS79236VH5-BBz, CAS79236VH6-BBz, CAS77916VH6-BBz, CAS77916VH7-BBz, CAS77916VH8-BBz, CAS77916VH9-BBz, CAS77916VH10-BBz, GPC2-CD28z, GPC2-CD27z, GPC2-ICOSz, GPC2-CD2z and GPC2-OX40z.

6.2 Lentivirus Production, T-Cell Transduction and Expansion

To produce viral supernatant, HEK-293T cells were co-transfected with GPC2-CAR lentiviral vectors psPAX2 (Addgene #12260) and pMD2.G (Addgene #12259) at a pre-optimized ratio with polyetherimide (PEI) per the manufacturer's protocol. The supernatant was collected overnight after transfection. The virus-comprising supernatants were filtered through a 0.45 μm PES filter, followed by ultra-centrifugation for lentivirus concentration. Viral aliquots were stored at −80° C.

Human PBMCs were purchased from HemaCare Corporation and primary human T cells were isolated using Miltenyi human PanT cell isolation kits (Miltenyi, #130096535). The purified T cells, which comprised >98% CD3+ cells, were activated and expanded using Miltenyi anti-CD3/CD28 micro-beads (Miltenyi, #130091441) for 24-48 hours at a 2:1 cell-to-bead ratio and suspended at $0.5\times10^6$ cells/mL in growth medium supplemented with 300 U/mL IL-2. The pre-activated T cells were then transduced with lentivirus stock in the presence of 8 μg/mL polybrene by centrifugation at 1000 g, 32° C. for 1.5 h. The transduced cells were then transferred to the cell culture incubator for transgene expression under suitable conditions. Cells were counted every other day and fed with fresh growth medium every 2-3 days.

6.3 In Vitro Cytotoxicity Assay

The pre-activated T cells were transduced with lentivirus stock in the presence of 8 mg/mL polybrene and 300 IU/mL IL-2. T cells and lentivirus were centrifuged at 1000 g, 32° C. for 1 h and placed in humidified cell culture incubator for transgene expression under suitable conditions. On day 5 or day 7 or day 10 post-transduction, transduced T cells were harvested and co-incubated with tumor cells at an effector (CAR T) to target cell ratio of 10:1 or 5:1 or 2:1 or 1:1 or 0.2:1 for 20 hours. Target cells were human neuroblastoma cell line SH-SY5Y (ATCC, #CRL-2266), human neuroblastoma cell line IMR-32 cells (ATCC, #CCL-127), or human epidermoid carcinoma cell line A-431 (ATCC, #CRL-1555). To assay the cytotoxicity of CAR T cells on tumor cells, the Cytotoxicity Detection Kit (LDH) (Roche, #11644793001) assay reagents were prepared according to manufacturer's protocol. Reaction mix was added to the cell-free supernatant of each sample to detect the LDH released from cells. Optical densities at OD492 nm and OD650 nm were measured by PHERStar Microplate Reader. Baseline LDH released from the target cell in the absence of effector cells and effector cell in the absence of target cells were subtracted from the total LDH amount. The target maximum release was obtained by adding Triton-X100 at a final concentration of 1% to target cells in the absence of effector cells at the time when the cytotoxicity assays initiated. Supernatant from target cells in the absence of effector cells was used for target minimum release. The specific cytotoxicity was calculated by the formula: % Target cell lysis=100*[(OD CAR T cell+Target cell)−(OD CAR T cell)−(OD Target cell)+(OD Buffer background)]/(OD Target Maximum release−OD Target Minimum release).

Figure 6A:
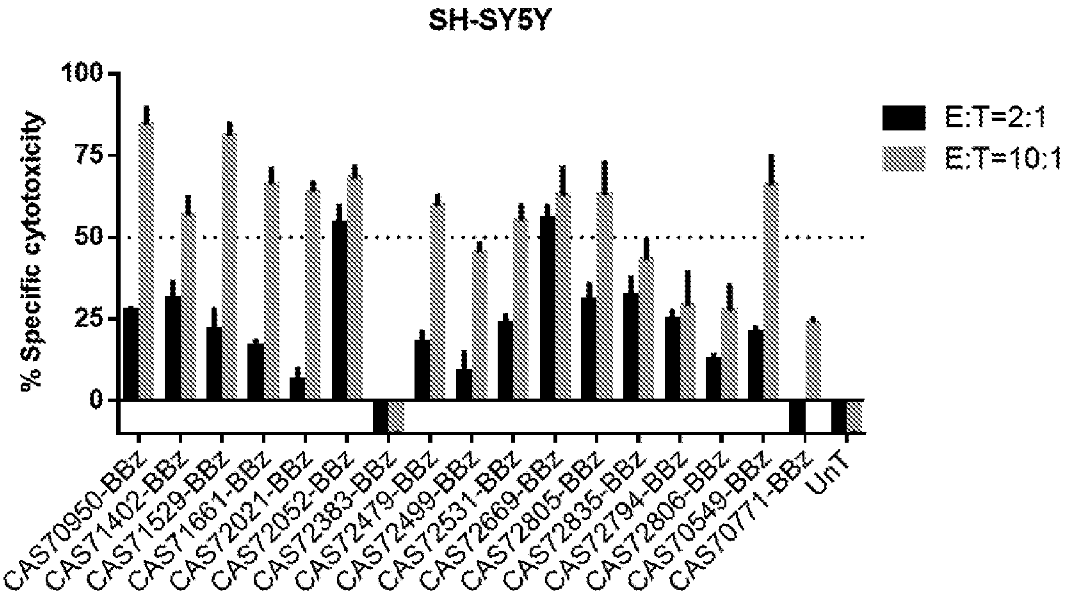
FIGS. 6A-6D show cytotoxic activity of monovalent anti-GPC2 CAR T cells in SH-SY5Y neuroblastoma cells.
Figure 6B:
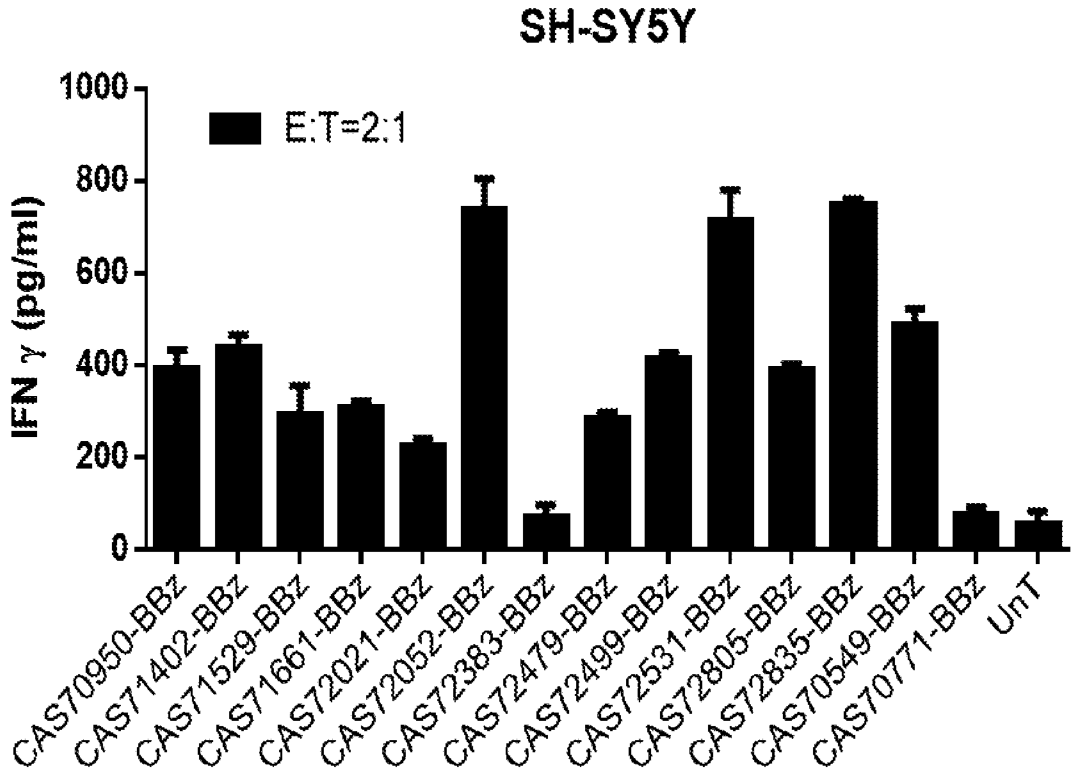
Figure 6C:
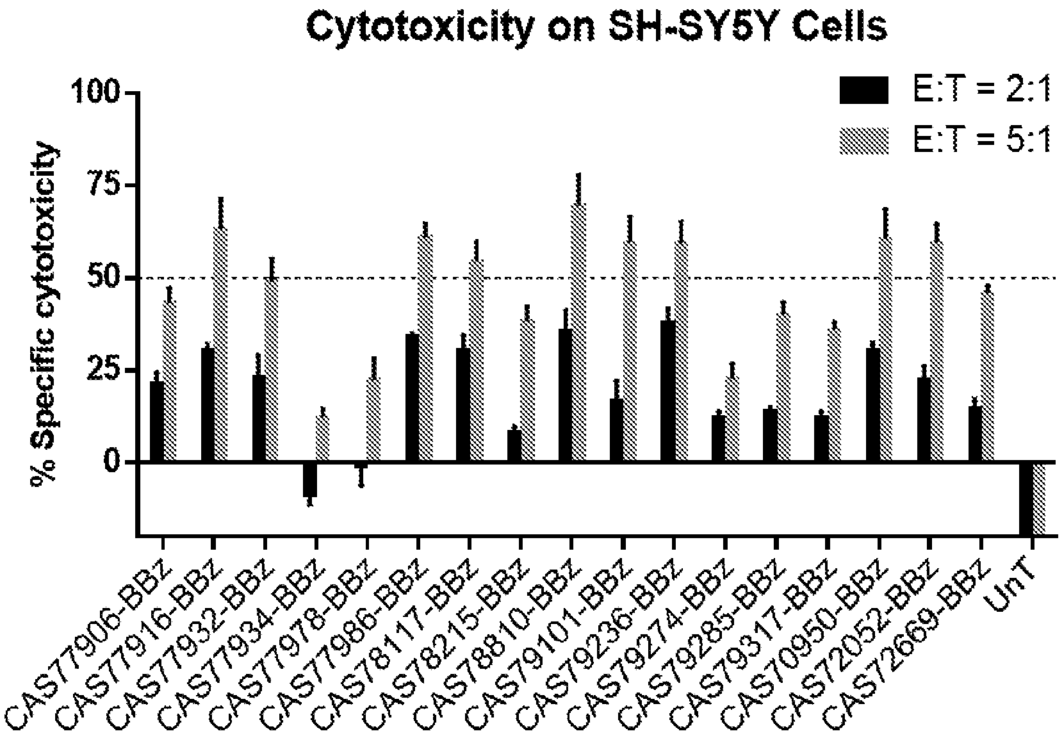
Figure 6D:
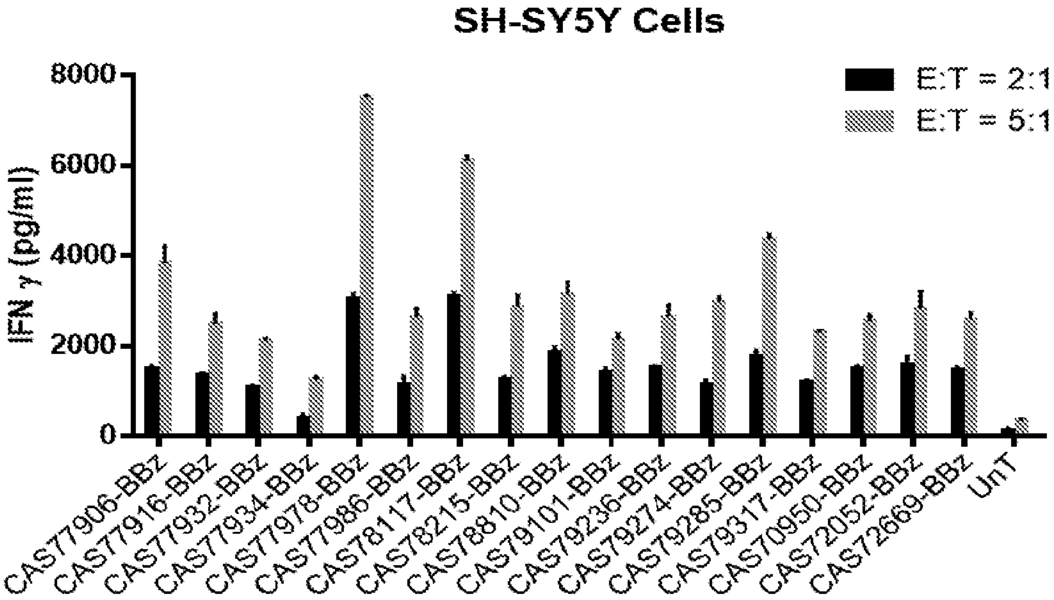

Exemplary monovalent CAR T cells targeting GPC2 were selected and tested in the cytotoxicity assay. As shown in FIG. 6A, a first group of monovalent GPC2 CAR T cells are tested. CAR T cells of CAS70950-BBz, CAS71402-BBz, CAS71529-BBz, CAS71661-BBz, CAS72021-BBz, CAS72052-BBz, CAS72383-BBz, CAS72479-BBz, CAS72499-BBz, CAS72531-BBz, CAS72669-BBz, CAS72805-BBz, CAS72835-BBz, CAS72794-BBz, CAS72806-BBz, CAS70549-BBz and CAS70771-BBz exhibited different levels of cytotoxicity and cytokine release against neuroblastoma cell line SH-SY5Y cells, with over 50% monovalent $V_H$H-based CAR T cells showing >50% cytotoxicity against SH-SY5Y. Among the eleven exemplary constructs (CAS70950-BBz, CAS71402-BBz, CAS71529-BBz, CAS71661-BBz, CAS72021-BBz, CAS72052-BBz, CAS72479-BBz, CAS72531-BBz, CAS72669-BBz, CAS72805-BBz and CAS70549-BBz) CAR T cells that showed more than 50% cytotoxicity against SH-SY5Y and exhibited similar cytotoxicity, four constructs (CAS70950-BBz, CAS71529-BBz, CAS72052-BBz and CAS72669-BBz) were selected as examples for further testing A second group of monovalent GPC2 CAR T cells are tested and their cytotoxicity against SH-SY5Y was compared to three selected constructs (CAS70950-BBz, CAS72052-BBz and CAS72669-BBz) from the first group. As shown in FIG. 6C, CAR T cells of CAS77906-BBz, CAS77916-BBz, CAS77932-BBz, CAS77934-BBz, CAS77978-BBz, CAS77986-BBz, CAS78117-BBz, CAS78215-BBz, CAS78810-BBz, CAS79101-BBz, CAS79236-BBz, CAS79274-BBz, CAS79285-BBz, CAS79317-BBz, are tested and three CAR T cell constructs that showed potent antitumor efficacy from previous study. CAR T cells exhibited different levels of cytotoxicity and cytokine release against neuroblastoma cell line SH-SY5Y cells, with over 50% monovalent $V_H$H-based CAR T cells showing more than 50% cytotoxicity against SH-SY5Y. Two (CAS78117-BBz and CAS79236-BBz) of the seven exemplary constructs (CAS77916-BBz, CAS78117-BBz, CAS77932-BBz, CAS77986-BBz, CAS78810-BBz, CAS79101-BBz and CAS79236-BBz) CAR T cells that showed better cytotoxicity and were equivalent to the CAS70950-BBz, CAS72052-BBz and CAS72669-BBz CAR T cells were selected as examples for further testing.

Figure 7A:
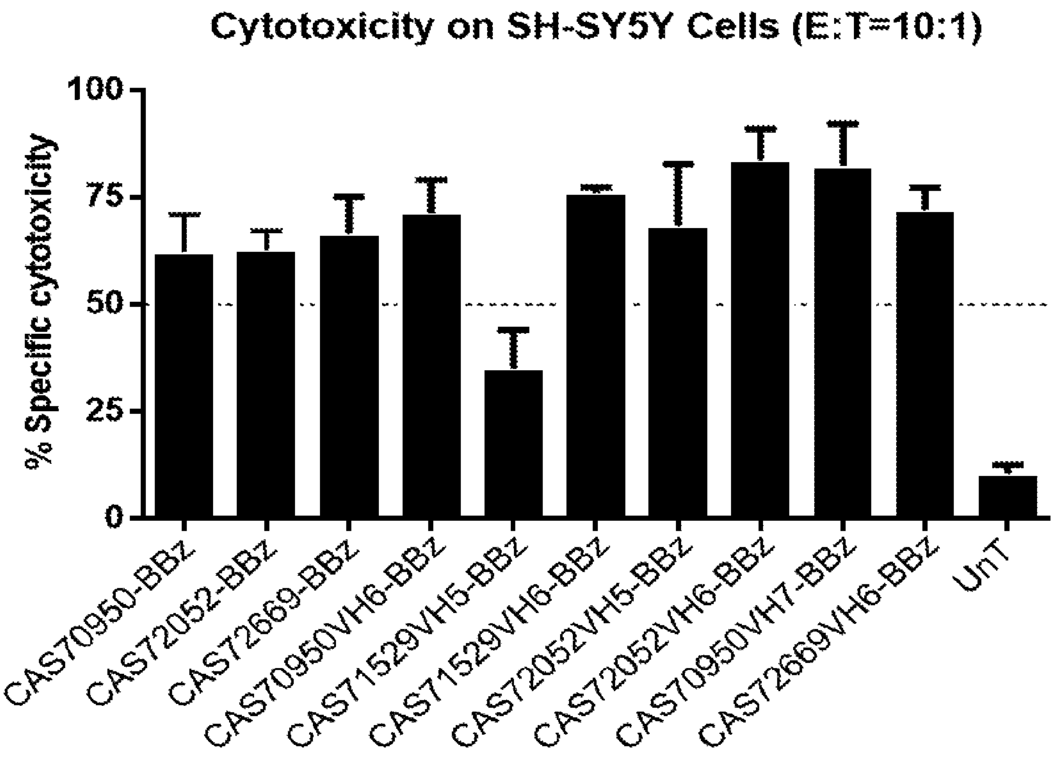
FIGS. 7A-7J show cytotoxic activity of humanized monovalent anti-GPC2 CAR T cells in SH-SY5Y and IMR-32 neuroblastoma cells and A-431 epidermoid carcinoma cells.
Figure 7B:
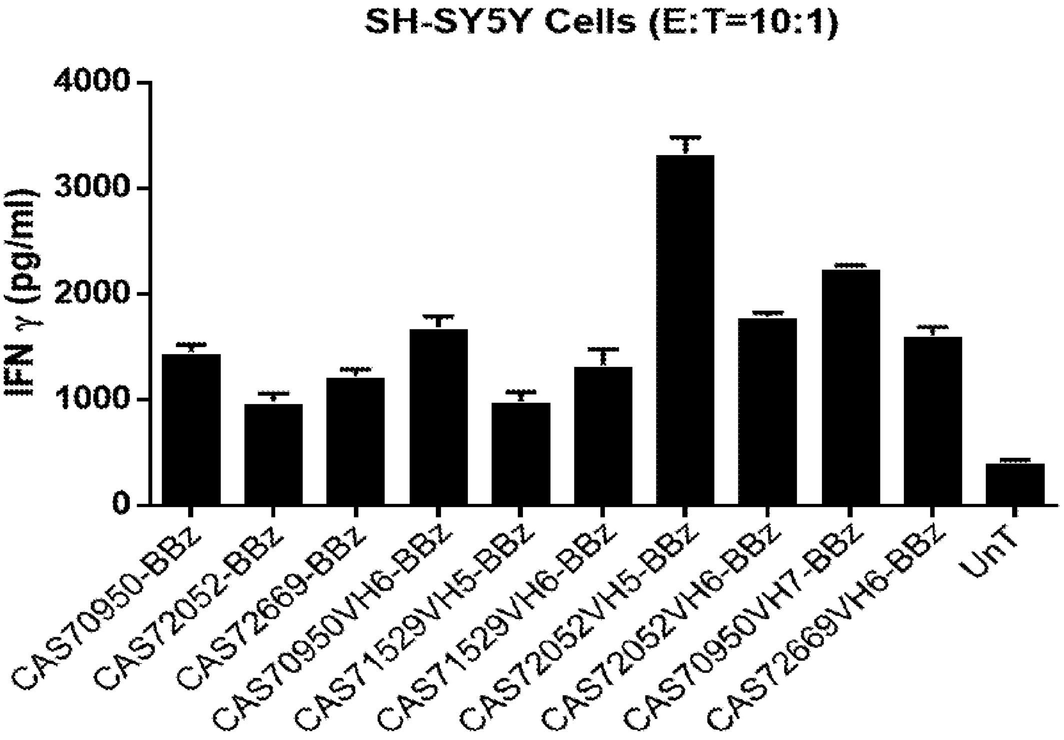

In the first humanization attempt, a group of exemplary humanized monovalent GPC2 CAR T cells are assessed for in vitro cytotoxicity. As shown in FIG. 7A and FIG. 7B, the humanized constructs CAS70950VH6-BBz, CAS70950VH7-BBz, CAS71529VH5-BBz, CAS71529VH6-BBz, CAS72052VH5-BBz, CAS72052VH6-BBz and CAS72669VH6-BBz CAR T cells were compared to their parental constructs CAS70950-BBz, CAS72052-BBz and CAS72669-BBz CAR T cells. CAR T cells exhibit different levels of cytotoxicity and cytokine release against neuroblastoma cell line SH-SY5Y cells, with over 70% monovalent $V_H$H-based CAR T cells showing more than 50% cytotoxicity against SH-SY5Y. Among the six exemplary humanized constructs (CAS70950VH6-BBz, CAS70950VH7-BBz, CAS71529VH6-BBz, CAS72052VH5-BBz, CAS72052VH6-BBz and CAS72669VH6-BBz) CAR T cells that showed more than 50% cytotoxicity against SH-SY5Y, three constructs (CAS70950VH6-BBz, CAS71529VH6-BBz and CAS72669VH6-BBz) were selected as examples for further testing.

Figure 7C:
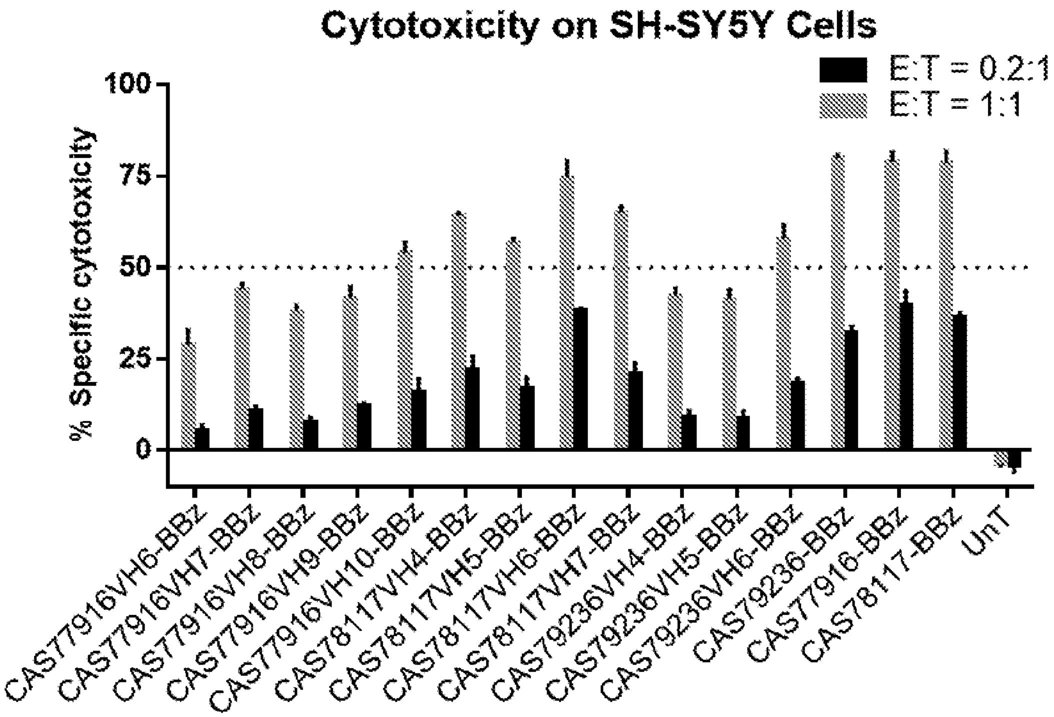
Figure 7D:
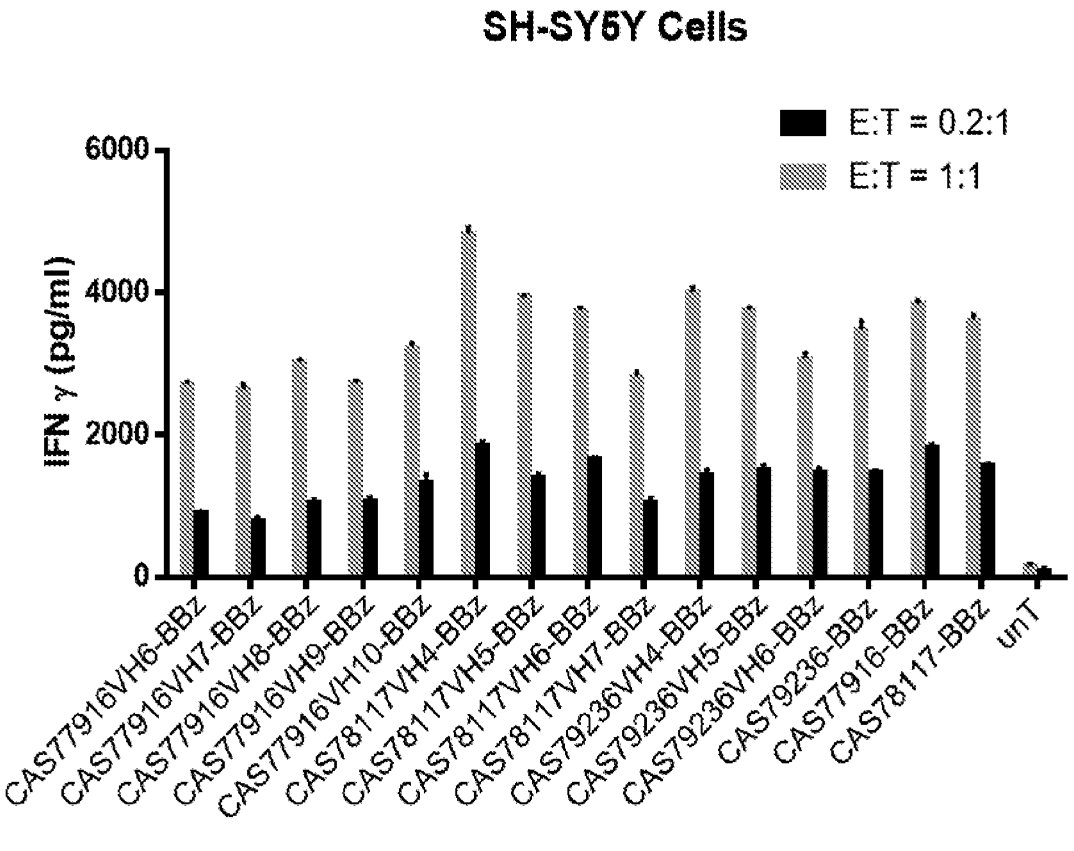

In the second humanization attempt, exemplary humanized monovalent GPC2 CAR T cells were assessed for in vitro cytotoxicity. As shown in FIG. 7C and FIG. 7D, humanized monovalent GPC2 CAR T cells of CAS77916VH6-BBz, CAS77916VH7-BBz, CAS77916VH8-BBz, CAS77916VH9-BBz, CAS77916VH10-BBz, CAS78117VH4-BBz, CAS78117VH5-BBz, CAS78117VH6-BBz, CAS78117VH7-BBz, CAS79236VH4-BBz, CAS79236VH5-BBz, CAS79236VH6-BBz were compared to their parental constructs CAS79236-BBz, CAS77916-BBz and CAS78117-BBz. Over 50% monovalent $V_H$H-based CAR T cells showing more than 50% cytotoxicity against SH-SY5Y. Among the six exemplary humanized constructs (CAS77916VH10-BBz, CAS78117VH4-BBz, CAS78117VH5-BBz, CAS78117VH6-BBz, CAS78117VH7-BBz, CAS79236VH6-BBz) that showed more than 50% cytotoxicity against SH-SY5Y and exhibited similar cytotoxicity as their parental constructs CAR T cells, CAS78117VH4-BBz and CAS79236VH6-BBz were selected as examples for further testing.

Figure 7E:
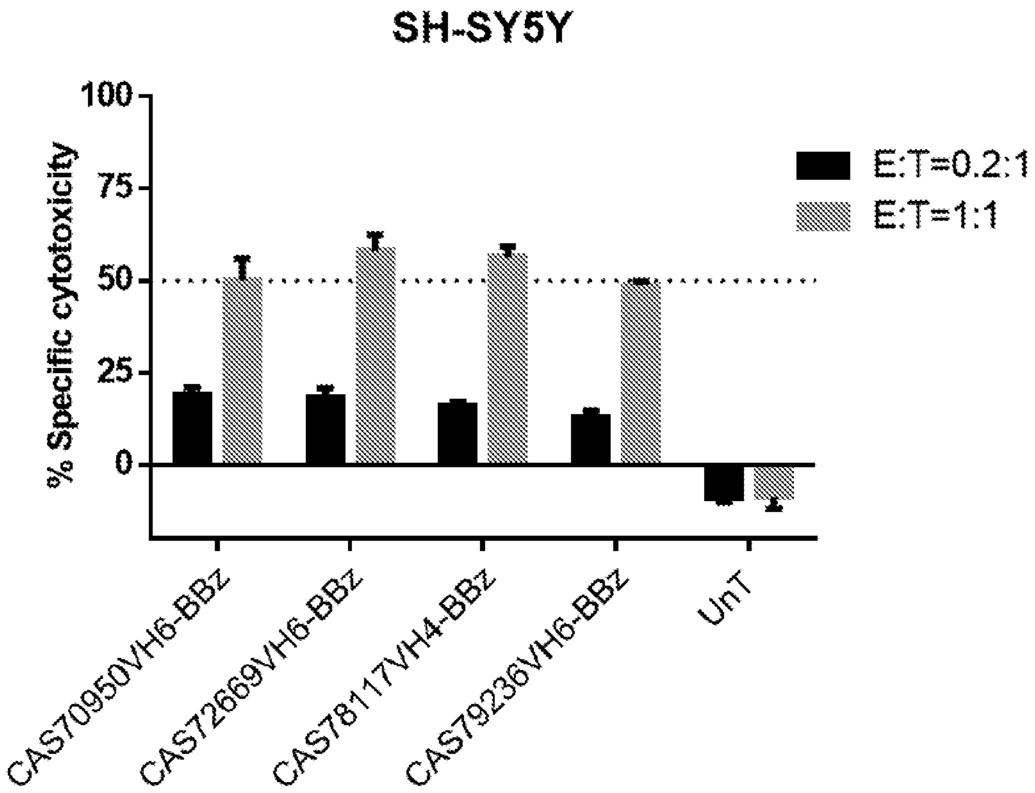
Figure 7F:
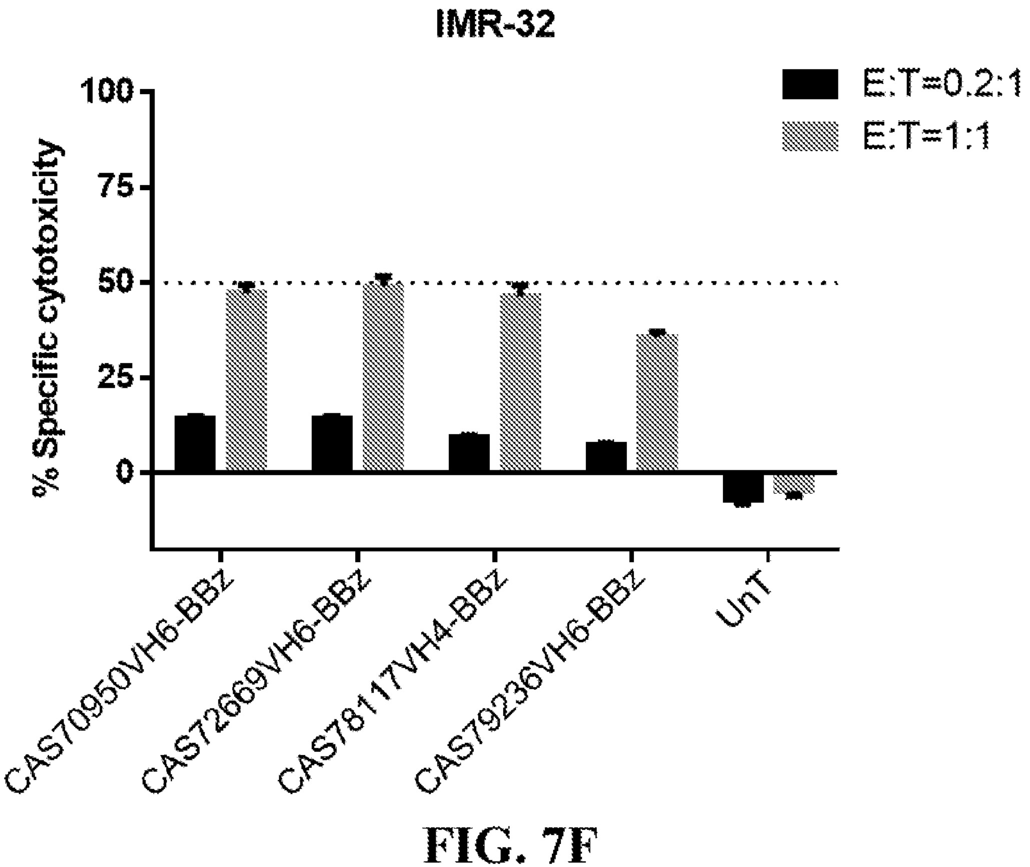

In another embodiment, the selected exemplary humanized CAR T cell constructs from the previous two humanizations were compared in in vitro assay. The humanized $V_H$H based (CAS70950VH6-BBz, CAS72669VH6-BBz, CAS78117VH4-BBz and CAS79236VH6-BBz) CAR T cells exhibit potent cytotoxicity against multiple GPC2 positive neuroblastoma cell lines SH-SY5Y (FIG. 7E) and IMR-32 (FIG. 7F) with at least 7-folds increase in IMR-32 killing and 12-folds increase in SH-SY5Y killing by CAR T cell treatments as compared with the untransduced control T cells (UnT). The cytotoxicity of humanized $V_H$H-based CAR T cells (CAS70950VH6-BBz, CAS72669VH6-BBz, CAS78117VH4-BBz and CAS79236VH6-BBz) were showing equivalent level of cytotoxicity against GPC2 positive tumor cells.

Figure 7G:
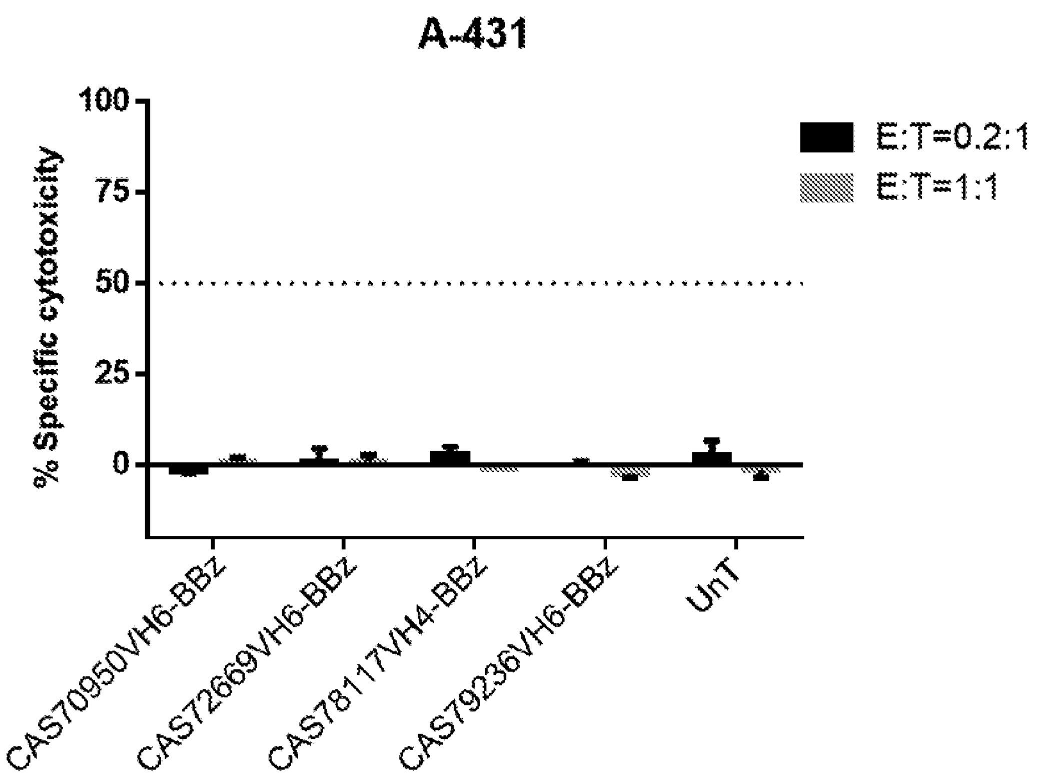
Figure 7H:
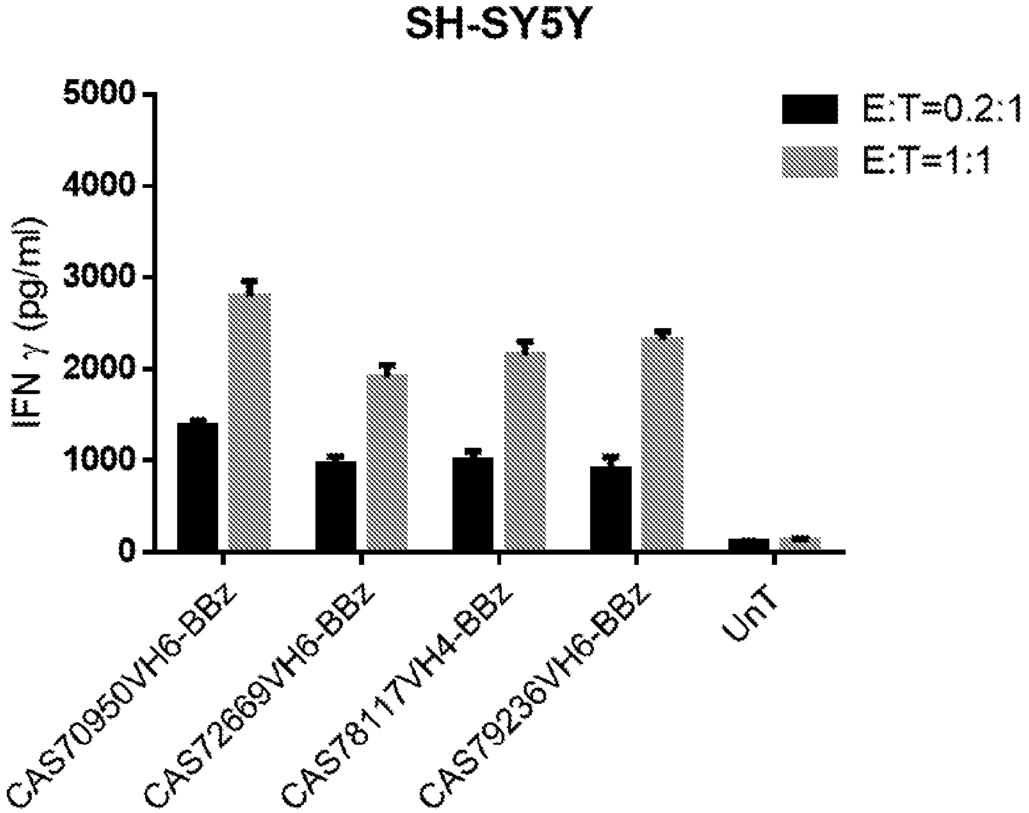
Figure 7I:
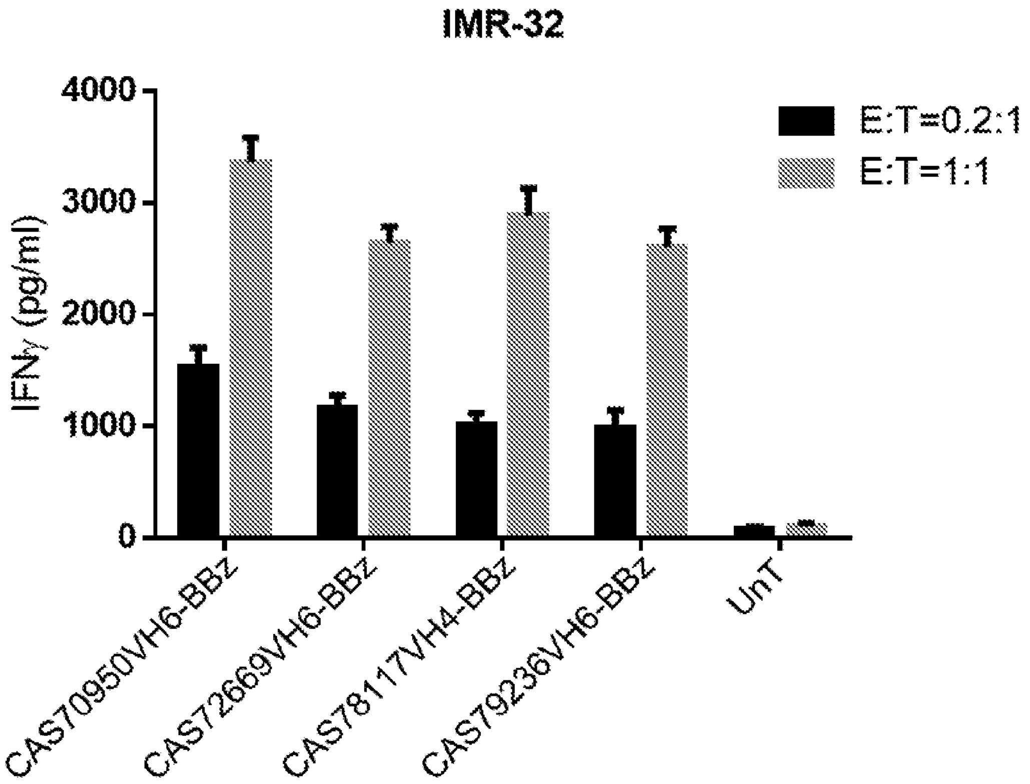
Figure 7J:
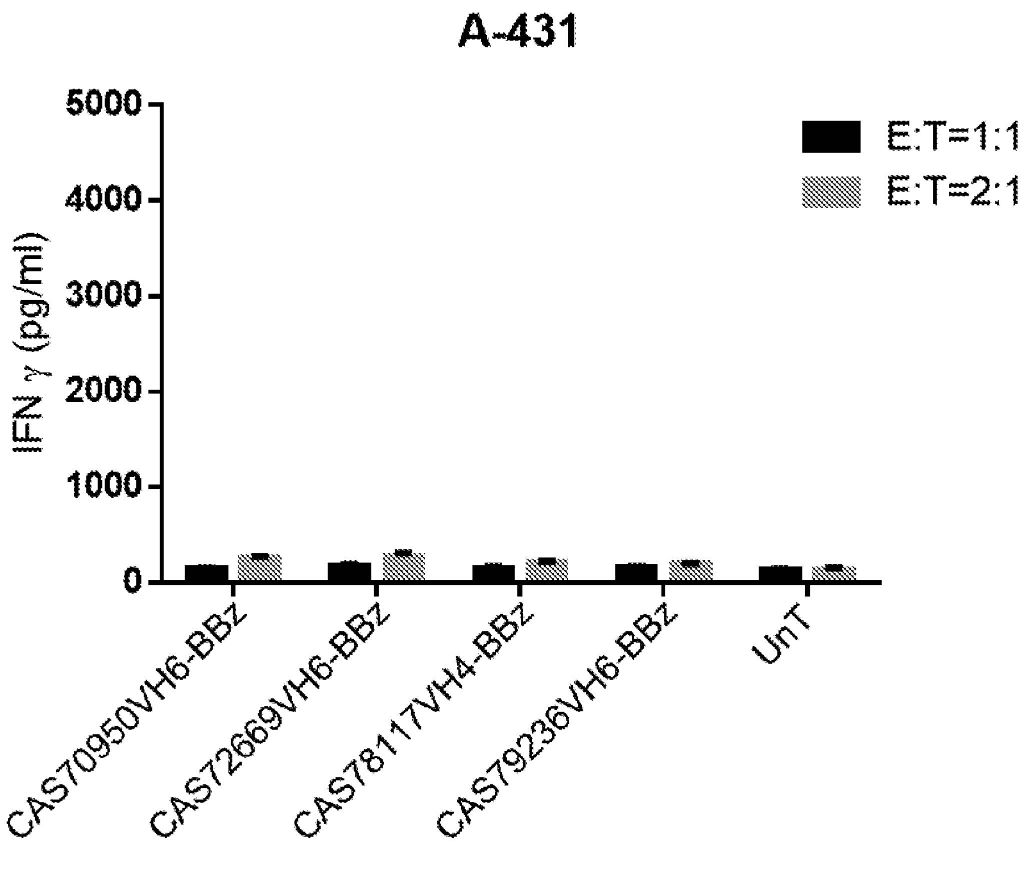

In another embodiment, the exemplary humanized $V_H$H based (CAS70950VH6-BBz, CAS72669VH6-BBz, CAS78117VH4-BBz and CAS79236VH6-BBz) CART cells were selected to investigate if CAR T cells had non-specific cytotoxicity against GPC2 negative tumor cell. Similar to that of the UnT controls, FIG. 7G showed no cytotoxicity against GPC2 negative human epidermoid carcinoma cell line A-431 was observed in CAS70950VH6-BBz, CAS72669VH6-BBz, CAS78117VH4-BBz and CAS79236VH6-BBz. This observation indicated that constructs CAS70950VH6-BBz, CAS72669VH6-BBz, CAS78117VH4-BBz and CAS79236VH6-BBz were target specific and potent against GPC2 positive cells, with no significant toxicity against GPC2 negative A-431 cell.

6.4 IFNγ Release

In addition to the cytotoxicity data above, supernatants from the in vitro co-culture assays were also collected to assess CAR T cells-induced cytokine release, e.g., release of interferon gamma (i.e., IFNγ), as another indicator of cytotoxicity, was quantified using a HTRF human IFNγ AlphaLISA kit (Perkin Elmer, #62HIFNGPEH) per manufacturer's instruction. As shown in FIG. 6B, FIG. 6D, FIG. 7B, FIG. 7D and FIG. 7H-FIG. 7J, CAR T cells released high levels of IFNγ upon co-culturing with GPC2-positive target cells SH-SY5Y and IMR-32. No significant cytokine release were detected against GPC2-negative cell line A-431. Untransduced T cells (UnT) did not induce release of IFNγ in the co-culture. Therefore the cytokine release data is consistent with the in vitro cytotoxicity data, suggested that cytokine release from the selected CAR T cells was GPC-2 specific.

Example 7

Preparation of Exemplary Multi-Valent GPC2 Chimeric Antigen Receptors

As described in Example 6, nucleic acid sequences that encode multiple different $V_H$Hs conjugated via peptide linkers were ligated into a CAR signal domain backbone vector comprising a hinge domain of CD8α hinge and transmembrane domain that was fused to the 4-1BB and CD3 ζ intracellular signaling domains. Nucleic acid sequence was cloned into a lentiviral vector backbone bearing the EF1α promoter.

Using protocols described in Example 6, the lentiviral vectors carrying CAR genes were packaged and titrated as described. Human T cells were isolated using Miltenyi human PanT cell isolation kits and activated using Miltenyi anti-CD3/CD28 micro-beads. The pre-activated T cells were then transduced with lentivirus stock in the presence of 8 μg/mL polybrene by centrifugation at 1000 g, 32° C. for 1.5 h. The transduced cells were then transferred to the cell culture incubator for transgene expression under suitable conditions.

Exemplary multi-valent and monovalent $V_H$H-based tandem CARs comprising multiple different humanized $V_H$H sequences in accordance with some embodiments of the present disclosure may include CAS71529VH5-AS72052VH5-BBz (SEQ ID NO: 239), CAS72052VH5-AS71529VH5-BBz (SEQ ID NO: 240), CAS70950VH6-AS71529VH6-BBz (SEQ ID NO: 241), CAS71529VH6-AS70950VH6-BBz (SEQ ID NO: 242), and CAS70950VH6-AS70950VH6-BBz (SEQ ID NO: 243) CAS78117VH4-AS71529VH6-BBz (SEQ ID NO: 246) and CAS71529VH6-AS78117VH4-BBz (SEQ ID NO: 247).

7.1 In Vitro Cytotoxicity Assay

On day 5 or day 8 or day 10 post-transduction, transduced T cells were harvested and co-incubated with tumor cells at an effector (CAR T) to target cell ratio of 10:1 or 1:1 or 0.2:1 for 20 hours. To assay the cytotoxicity of CAR T cells on tumor cells, the Cytotoxicity Detection Kit (LDH) (Roche, #11644793001) was added to the culture supernatant and the specific cytotoxicity for each CAR T cell construct was measured as described in Example 6.

Figure 8A:
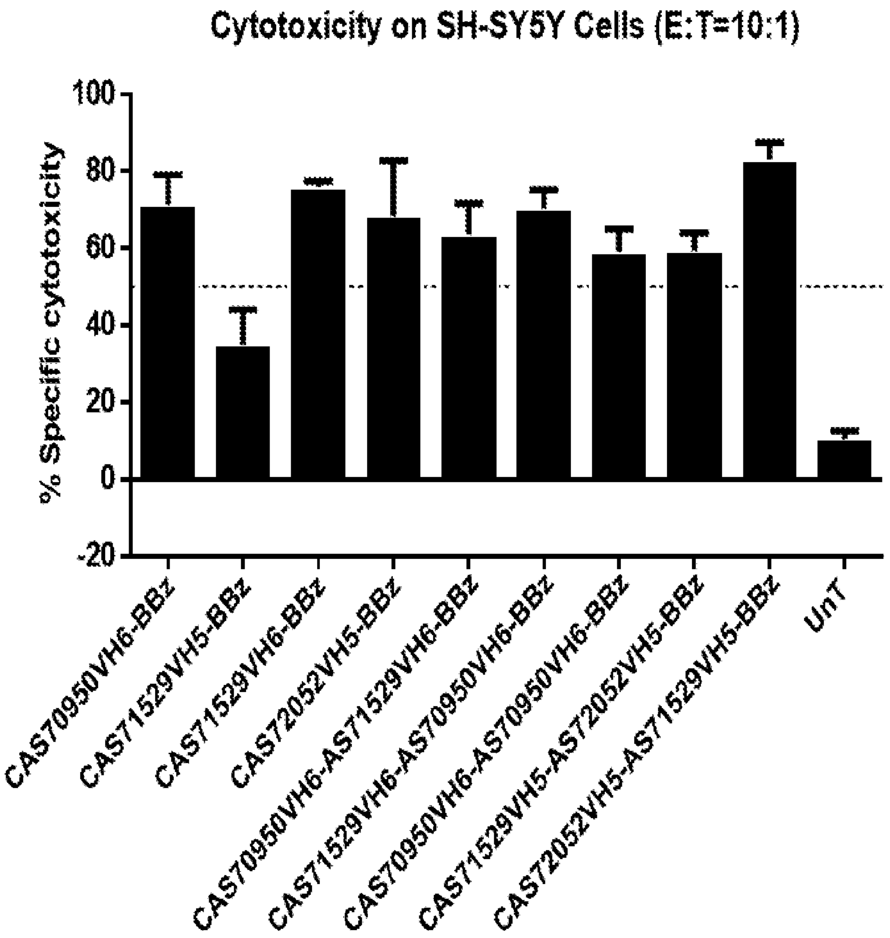
FIGS. 8A-8F show cytotoxic activity of humanized monovalent and multi-valent anti-GPC2 CAR T cells in SH-SY5Y and IMR-32 neuroblastoma cells and A-431 epidermoid carcinoma cells.

In an embodiment, bivalent GPC2 tandem CAR T cells (CAS70950VH6-AS71529VH6-BBz, CAS71529VH6-AS70950VH6-BBz, CAS71529VH5-AS72052VH5-BBz, CAS72052VH5-AS71529VH5-BBz) and monovalent GPC2 tandem CAR T cells (CAS70950VH6-AS70950VH6-BBz) were compared to their parental monovalent GPC2 CAR T cells (CAS70950VH6-BBz, CAS71529VH5-BBz, CAS71529VH6-BBz, CAS72052VH5-BBz) against SH-SY5Y cells at an effector to target ratio of 10:1 for 20 hours. As shown in FIG. 8A, the specific percentage lysis of GPC2 tandem CAR T cells were 63.66±8.02% by CAS70950VH6-AS71529VH6-BBz-expressing CAR T cells, 70.33±4.93% by CAS71529VH6-AS70950VH6-BBz-expressing CAR T cells, 59.00±6.08% by CAS70950VH6-AS70950VH6-BBz-expressing CAR T cells, 59.33±4.72% by CAS71529VH5-AS72052VH5-BBz-expressing CAR T cells, 83.00±4.58% by CAS72052VH5-AS71529VH5-BBz-expressing CAR T cells, similar to that of their parental monovalent CAR T cells (CAS70950VH6-BBz, CAS71529VH5-BBz, CAS71529VH6-BBz and CAS72052VH5-BBz). Together, the data suggested that the bivalent CAR T cells had potent antitumor activity against GPC2 positive cells.

To investigate if the cytotoxicity of humanized $V_H$H based CAR T cells was GPC2 target-specific, cytolytic assay was established using monovalent humanized $V_H$H based CAR T cells (CAS71529VH5-BBz, CAS71529VH6-BBz, CAS72052VH5-BBz, CAS70950VH6-BBz) and humanized $V_H$H based bivalent GPC2 CAR T cells (CAS70950VH6-AS71529VH6-BBz, CAS71529VH6-AS70950VH6-BBz, CAS71529VH5-AS72052VH5-BBz, CAS72052VH5-AS71529VH5-BBz) were co-cultured with GPC2-positive neuroblastoma cell lines (SH-SY5Y and IMR-32), and GPC2-negative epidermoid carcinoma cell line A-431, at 1:1 effector to target ratio.

Figure 8B:
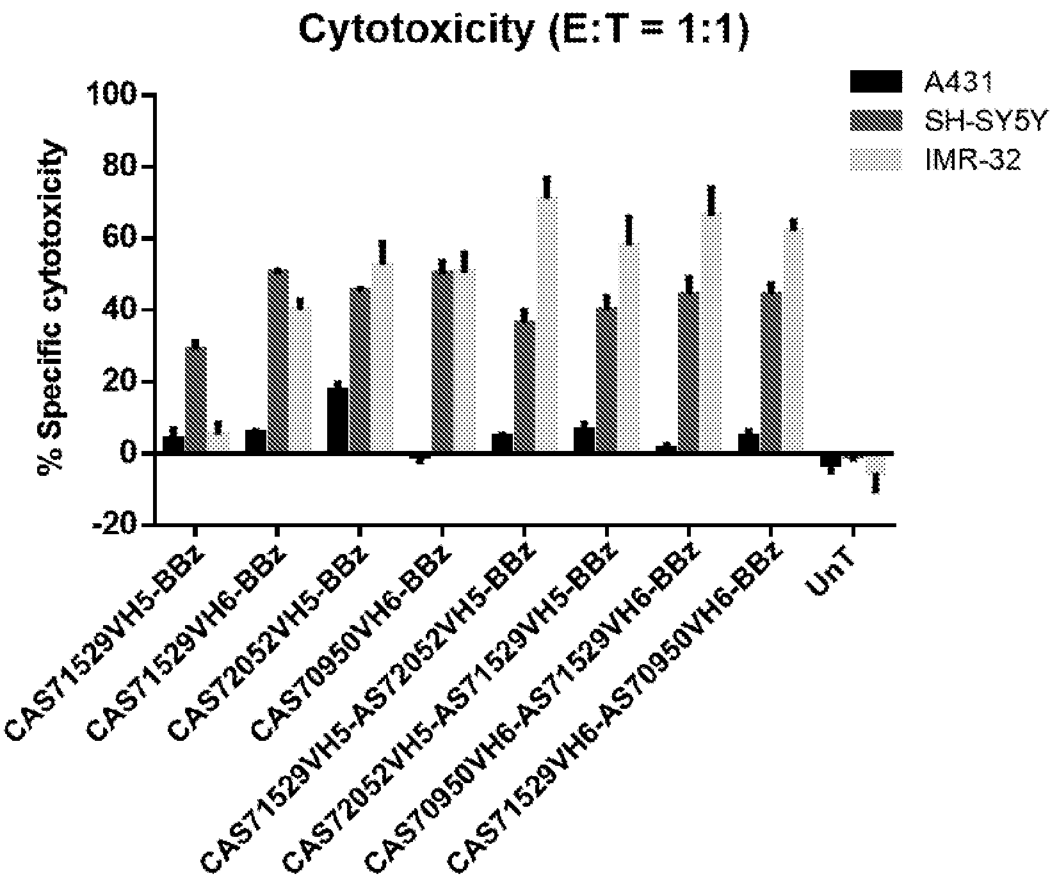

FIG. 8B showed that cytotoxicity of monovalent and bivalent GPC2 CAR T cells against SH-SY5Y cells and IMR-32 cells was more than 40%, except that CAS71529VH5-BBz expressing CAR T had lytic activity less than 30% against SH-SY5Y and IMR-32 cells. Lytic activity of monovalent GPC2 CART cells and bivalent GPC2 CART cells against A-431 was less than 10%, and minimal cell lysis was observed in SH-SY5Y, IMR-32 and A-431 cells treated with un-transduced T cells (FIG. 8B). Collectively, data suggests that the humanized $V_H$H based bivalent and monovalent CAR T cells could recognize GPC2-positive tumor cells in an antigen-specific manner and exhibit equivalent cytotoxicity against GPC2-positive tumor cells. The humanized $V_H$H based bivalent and monovalent CAR T cells showed minimum or no lytic activity against GPC2 negative cells.

Figure 8C:
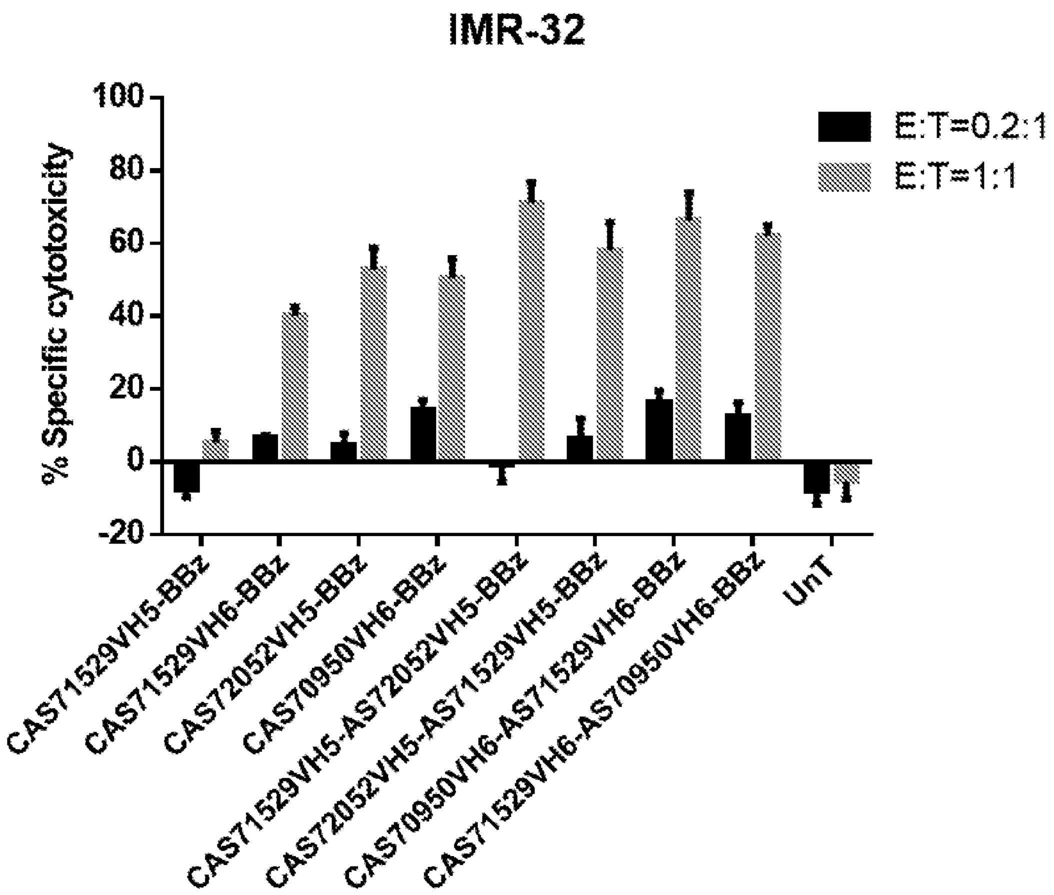

Having established the target specificity of GPC2 CAR T cells, studies were conducted to determine whether GPC2 CAR T cells had dose dependent cytotoxicity against GPC2 positive tumor cell. A 20-hours cytolytic assay was established using humanized $V_H$H based monovalent GPC2 CAR T cells (CAS71529VH5-BBz, CAS71529VH6-BBz, CAS72052VH5-BBz, CAS70950VH6-BBz) and humanized $V_H$H based bivalent GPC2 CAR T cells (CAS70950VH6-AS71529VH6-BBz, CAS71529VH6-AS70950VH6-BBz, CAS71529VH5-AS72052VH5-BBz, CAS72052VH5-AS71529VH5-BBz) expressing T cells co-cultured with GPC2-positive neuroblastoma IMR-32 cells, at 0.2:1 and 1:1 effector to target ratio. As shown in FIG. 8C, the lytic activity of bivalent GPC2 CAR T cells against IMR-32 cells ranged from "49% to 66%" at the E:T ratio of 1:1, with an average of 58%, which was higher than the averaged activity (37%) of monovalent GPC2 CAR T cells. In comparison, average cytotoxicity was less than 10% against IMR-32 cells when treated with monovalent and bivalent GPC2 CAR T cells at 0.2:1 effector to target ratio. Cytotoxicity of GPC2 CAR T cells against IMR-32 was dose-dependent. Furthermore, minimal cell lysis was observed in IMR-32 cells treated with un-transduced T cells. All $V_H$H based monovalent and bivalent GPC2 CAR T cells showed similar level of cytotoxicity against IMR-32 (FIG. 8C). Collectively, bivalent CAR T cells (CAS70950VH6-AS71529VH6-BBz, CAS71529VH6-AS70950VH6-BBz, CAS71529VH5-AS72052VH5-BBz, CAS72052VH5-AS71529VH5-BBz) exhibit equivalent or better cytolytic activity than the monovalent CAR T cells (CAS71529VH5-BBz, CAS71529VH6-BBz, CAS72052VH5-BBz, CAS70950VH6-BBz) when co-cultured with IMR-32 cells.

7.2 IFNγ Release

Figure 8D:
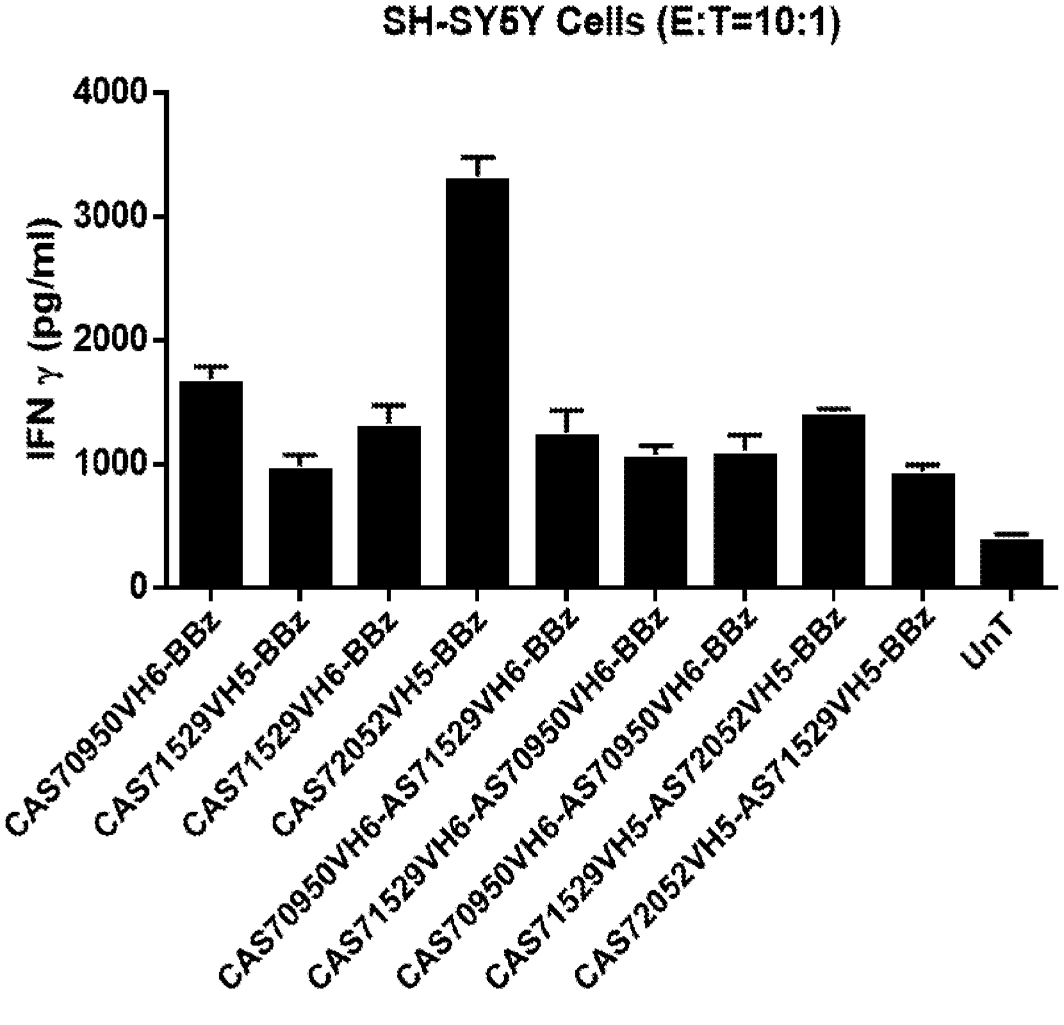
Figure 8E:
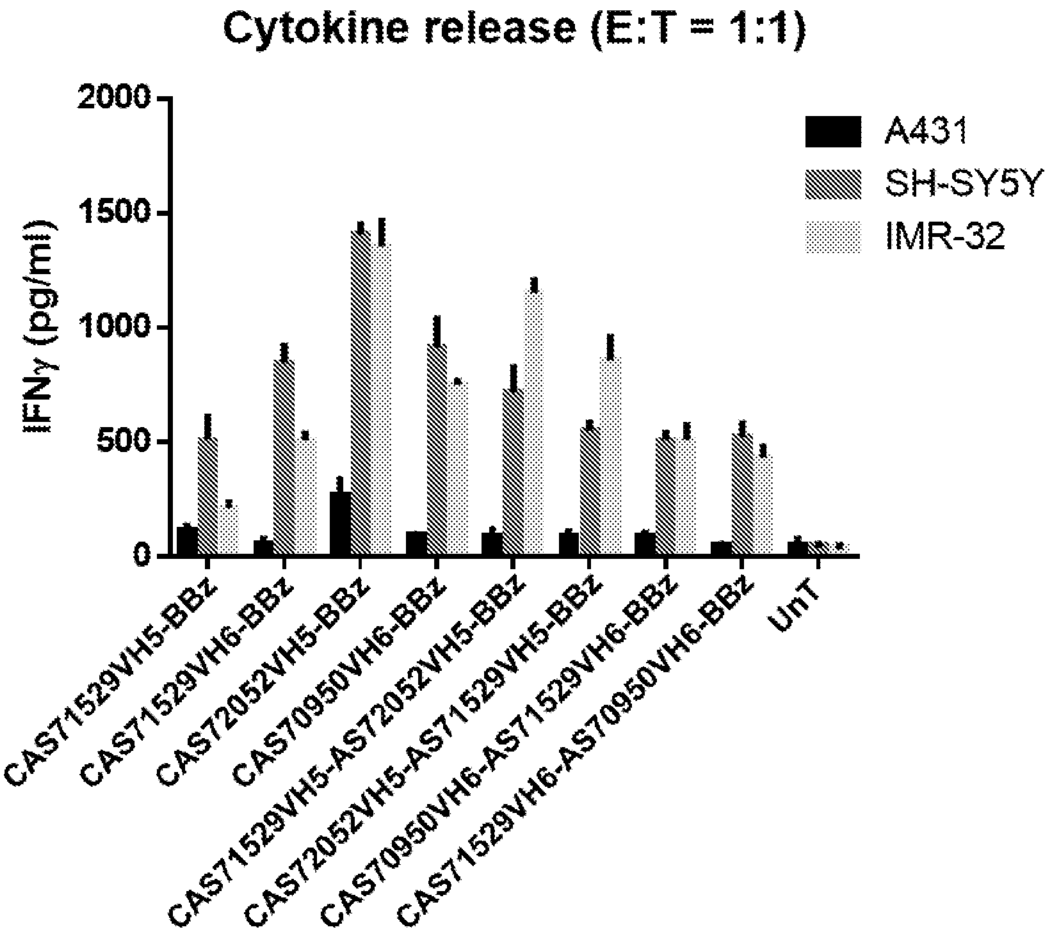
Figure 8F:
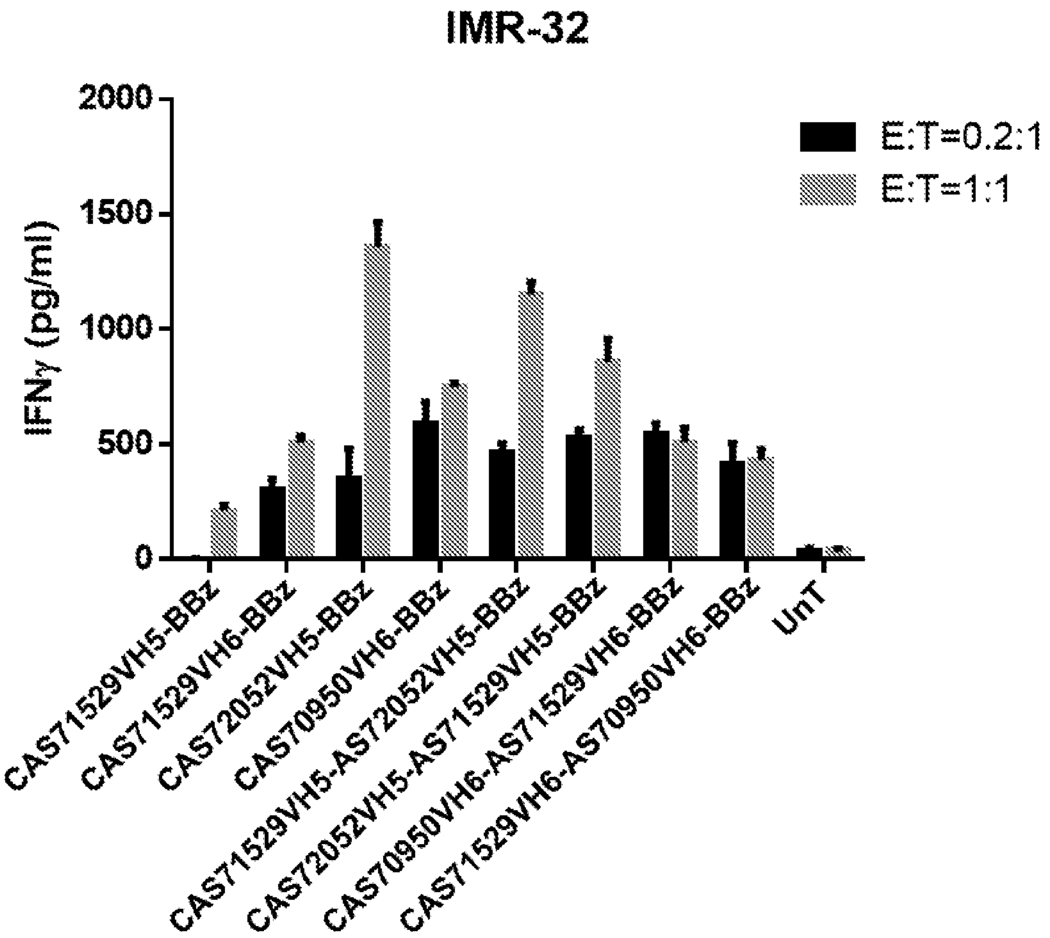

Supernatants from the in vitro co-culture assays were collected to assess CAR T cells-induced cytokine release, e.g., interferon gamma (i.e., IFNγ) release as described in Example 6. As shown in FIG. 8D-FIG. 8F, T cells expressing monovalent (CAS71529VH5-BBz, CAS71529VH6-BBz, CAS72052VH5-BBz, CAS70950VH6-BBz) and bivalent GPC2 CAR T cells (CAS70950VH6-AS71529VH6-BBz, CAS71529VH6-AS70950VH6-BBz, CAS71529VH5-AS72052VH5-BBz, CAS72052VH5-AS71529VH5-BBz) released high levels of IFNγ when co-cultured with GPC2-positive target cells SH-SY5Y and IMR-32. IFNγ was not induced in GPC2-negative A-431 cells. Untransduced T cells (UnT) did not induce release of IFNγ in the co-culture. Data suggested that the cytokine release from the selected CAR T cells was GPC-2 specific. Cytokine release data was consistent with the in vitro cytotoxicity data.

Example 8

In Vivo Efficacy of GPC2 CAR T in Tumor Xenograft Mice

Figure 9A:
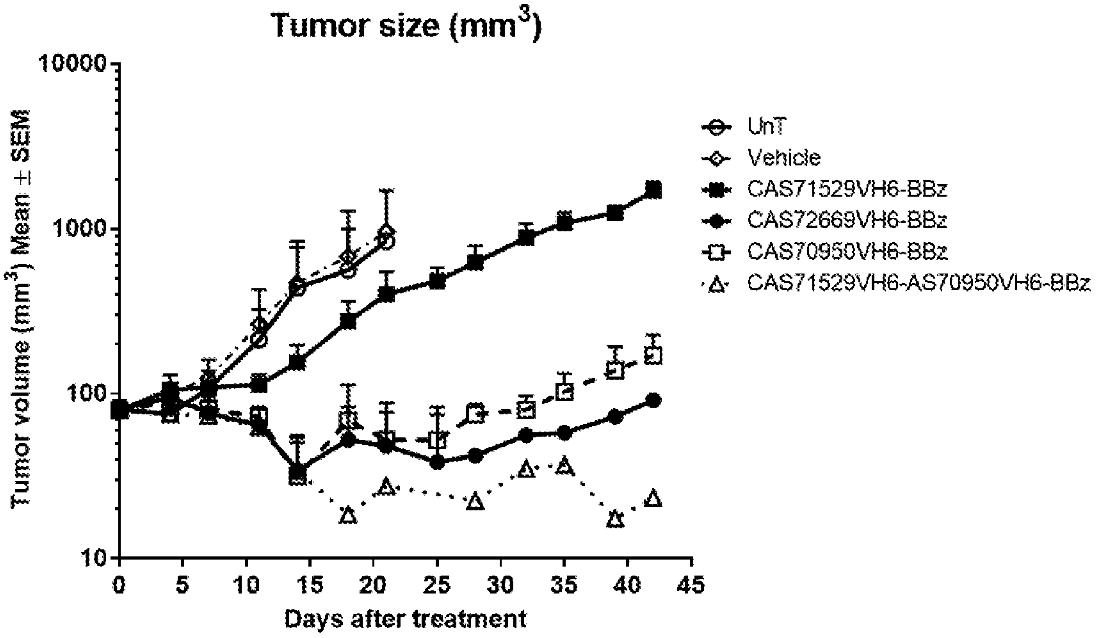
FIGS. 9A-9C show inhibition of neuroblastoma xenograft tumor growth by anti-GPC2 CART cells.
Figure 9B:
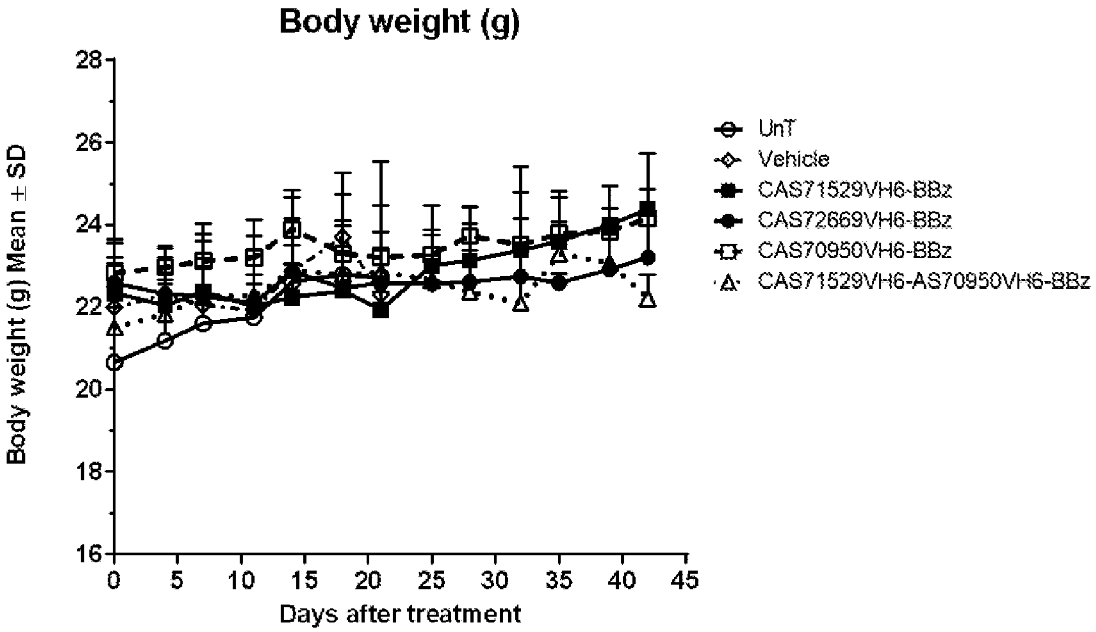

To evaluate the antitumor activities of GPC2-specific CAR T cells in vivo, NCG mice (NOD-Prkdc Cd5 I12rg Cd/NjuCrl) were subcutaneously injected with neuroblastoma SH-SY5Y cells. A single dose of untransduced T cells ($10\times10^6$) or CAR T cells ($5\times10^6$) was administered intravenously to tumor engrafted mice 9 days after tumor inoculation (FIG. 9A). Tumor length (L) and width (W) was measured by caliper every 3-4 days after CAR T cells treatment. Tumor volume was estimated using formula: $V=(W^2\times L)/2$. Fourteen days after treatment, the NCG mice treated with CAS70950VH6-BBz, CAS72669VH6-BBz and CAS70950VH6-AS71529VH6-BBz CAR expressing T cells all showed reduced tumor burden comparing with the untransduced T cell-treated group (FIG. 9A). Tumor regression of CAS70950VH6-BBz, CAS72669VH6-BBz and CAS70950VH6-AS71529VH6-BBz CAR T cells was more pronounced than the CAS71529VH6-BBz. At the end of obversion, 100% of monovalent CAR T cells (CAS70950VH6-BBz, CAS72669VH6-BBz) and 80% of multi-valent CAR T cells (CAS70950VH6-AS71529VH6-BBz) treated mice were alive (FIG. 9A). At day 42 post treatment, 2/5 mice (40%) treated with CAS72669VH6-BBz expressing CAR T cells were tumor-free and 3/5 mice (60%) treated with CAS70950VH6-AS71529VH6-BBz expressing CAR T cells were tumor-free without recurrence. In particularly, CAS70950VH6-BBz, CAS72669VH6-BBz and CAS70950VH6-AS71529VH6-BBz showed potent anti-tumor activity in a CAR T dosage six-folds lower than that reported for the LH7 CAR T ($30\times10^6$ CAR T cells per mouse) [4]. The data highlighted the superiority of $V_H$H-based CAR T cells in tumor regression and protection of mice from disease progression. Remarkably, no significant weight loss was observed from NCG mice receiving GPC2-targeted CAR T cells, suggested $5\times10^6$ GPC2-targeted CAR T cells are well tolerated by NCG mice (FIG. 9B).

Figure 9C:
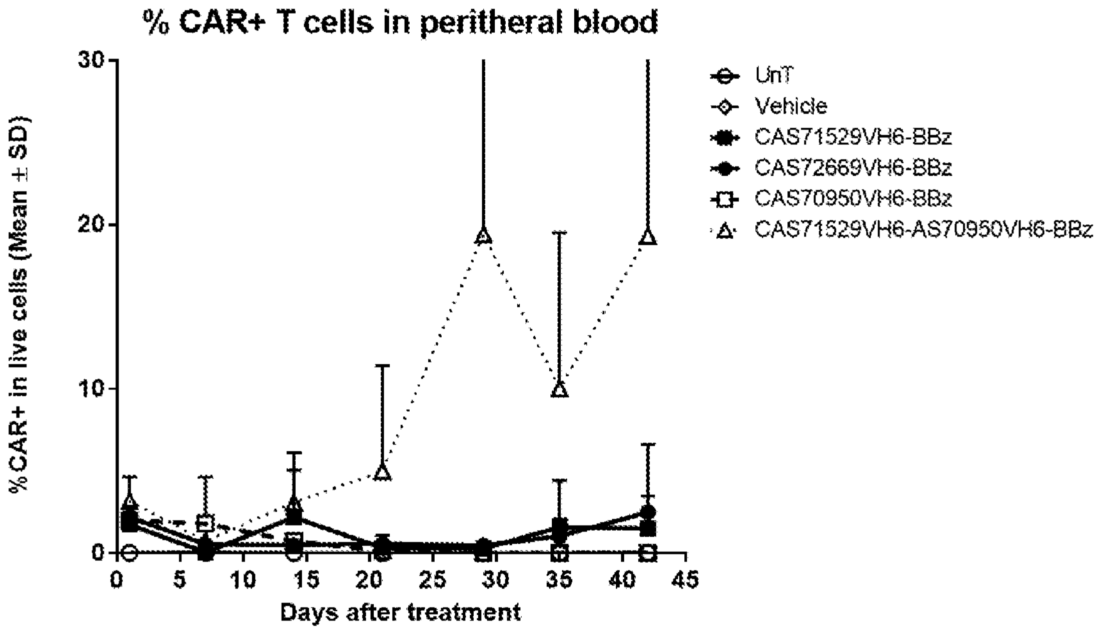

Moreover, the expansion and persistence of CAR T cells in vivo are also considered as critical predictors of durable clinical tumor regression in patients with cancer [8]. To understand the basic kinetics of infused CAR T cells, the percentage of CAR T cells in peripheral blood of NCG mice was assessed using flow cytometry. As shown in FIG. 9C, elevated percentage of CAR T cells in peripheral blood of NCG mice was observed from day 14 post treatment. Average 5.00±6.42% of CAR T cells were found in the peripheral blood of NCG mice treated with $5\times10^6$ CAS70950VH6-AS71529VH6-BBz CAR T cells, whereas less than 1% CAR T cells were detected in CAS70950VH6-BBz, CAS72669VH6-BBz and CAS71529VH6-BBz expressing CAR T groups. Expansion of CAR T cells in the CAS70950VH6-AS71529VH6-BBz group was inversely correlated with tumor size over time.

Example 9

3-(4-amino-1-oxo-1,3 dihydro-2H-isoindol-2-yl) piperidine-2,6-dione Enhances the Function of CAR T Cells Against Tumor Cell Line 3-(4-amino-1-oxo-1,3 dihydro-2H-isoindol-2-yl)piperidine-2,6-dione is an immunomodulatory drug approved to treat multiple myeloma (MM). Its formula is as follow:

(Compound A)

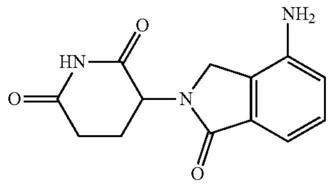

It was demonstrated that a combination therapy of molecule of formula I and anti-BCMA CAR T improved CAR T-mediated multiple myeloma clearance in preclinical models [9, 10]. Given the advantages of Compound A in combination treatment, the effect of Compound A on GPC2 CAR T function was further explored in neuroblastoma tumor cell co-culture model and xenograft tumor model.

Figure 10:
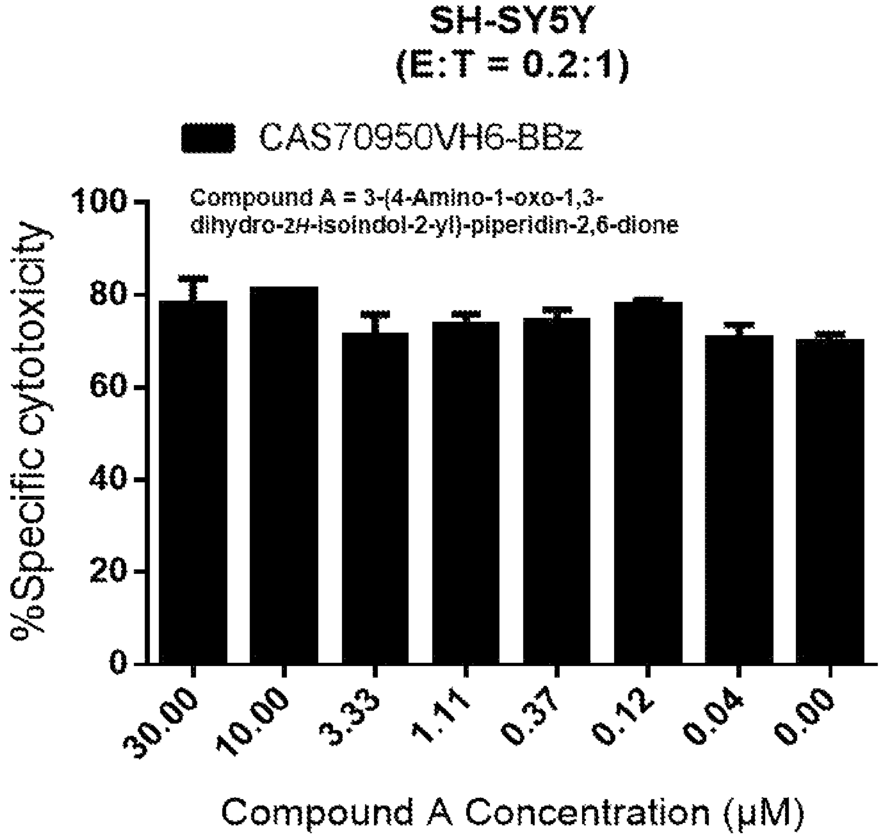
FIG. 10 shows an effect of Compound A on the cytotoxic activity of humanized CAS70950VH6-BBz CAR T cells in SH-SY5Y neuroblastoma cells.

To evaluate if Compound A influence to the cytotoxicity of CAR T against tumor cell, Compound A (CAS Number: 191732-72-6, Sigma-Aldrich, St. Louis) stock was serially diluted to final concentration of 30, 10, 3.33, 1.11, 0.37, 0.12 and 0.04 μM using complete growth medium. In the presence of Compound A gradient, CAR T cells were co-incubated with tumor cells at an effector (CAR T) to target cell ratio of 0.2:1 for 20 hours. CAR T cells and tumor cells co-cultured without addition of Compound A served as a control. Cytotoxicity of CAR T cells on tumor cells was estimated using the Cytotoxicity Detection Kit (LDH) (Roche, #11644793001) as described in Example 6. FIG. 10 showed that cytotoxicity of monovalent GPC2 CAR T cells (CAS70950VH6-BBz) against SH-SY5Y cells was not impaired by various concentrations of Compound A.

Figure 11A:
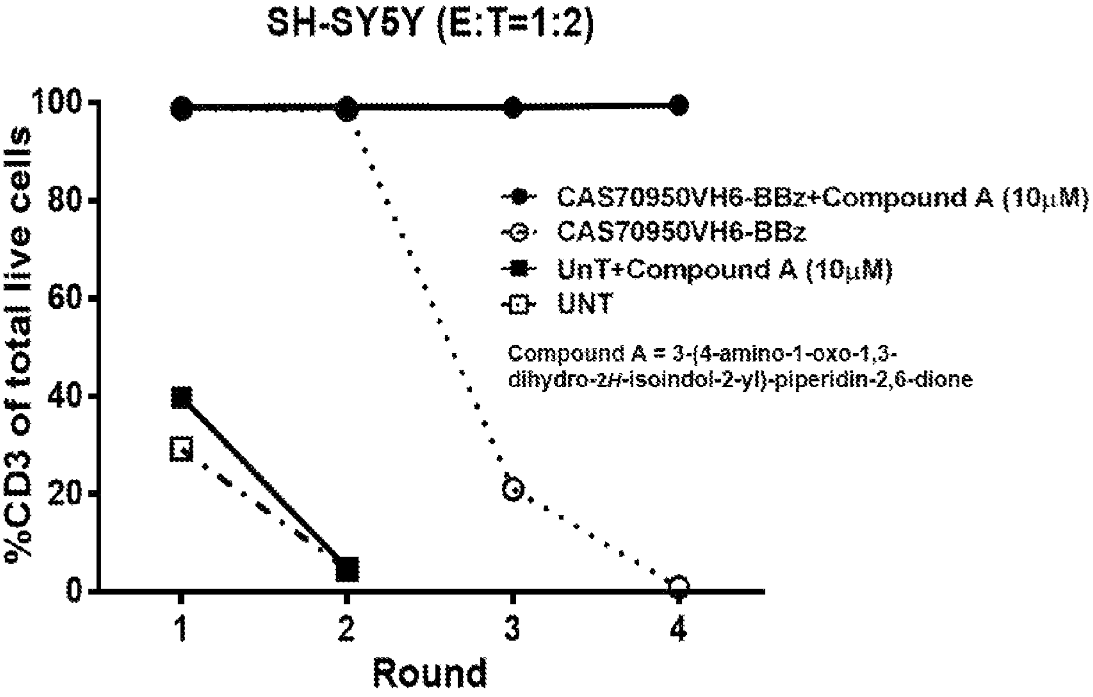
FIGS. 11A-11C show in vitro repetitive challenge assay of humanized CAS70950VH6-BBz CAR T cells in presence of Compound A.
Figure 11B:
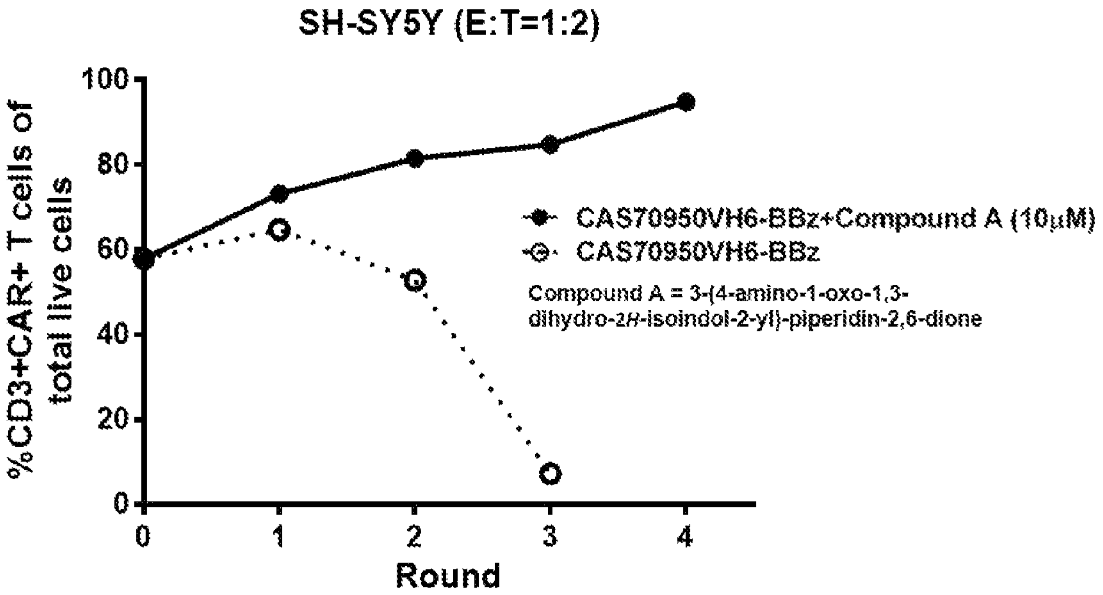
Figure 11C:
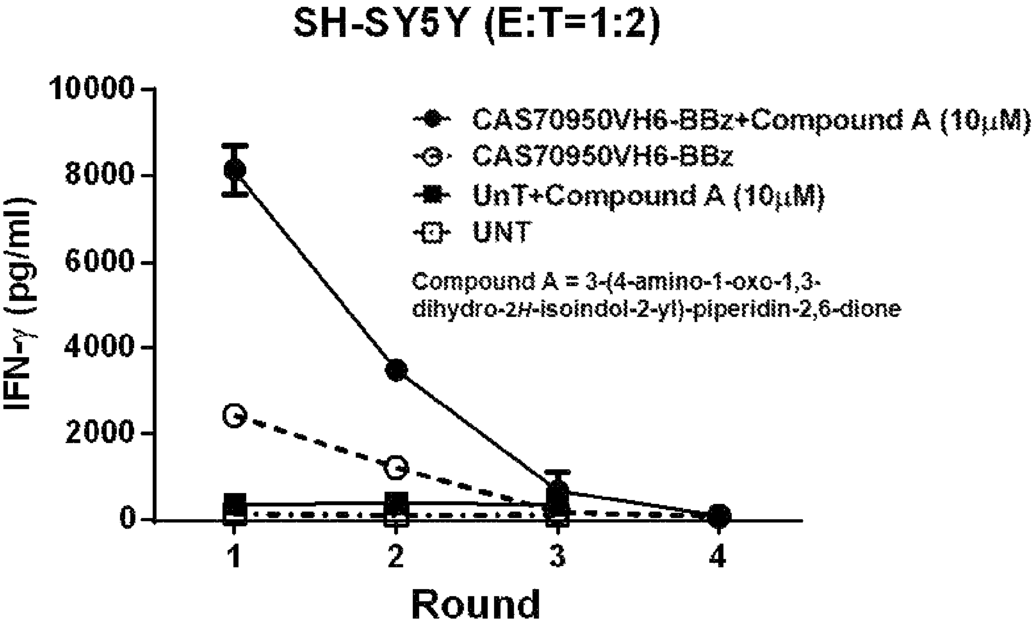

To evaluate the effect of 3-(4-amino-1-oxo-1,3 dihydro-2H-isoindol-2-yl)piperidine-2,6-dione (Compound A) on CAR T cell recursive killing potential, T cell expansion and survival, an in vitro repetitive challenge assay was employed [11]. Exemplary CAS70950VH6-BBz CAR T cells on day 11 post-transduction were co-cultured with SH-SY5Y tumor cells at an effector (CAR T) to target cell ratio of 1:2. The co-culture media was supplemented with 10 μM Compound A throughout this study. CAR T cells were re-challenged with tumor cells every 3 days (round 1, round 2, round 3 and round 4). CAR T cells and tumor cells co-cultured without addition of Compound A was used as a control. The percentages of $CD3^+$ T cells, percentages of $CD3^+CAR^+$ T cells were analyzed by flow cytometer. The amount of IFNγ in the co-culture supernatant was quantified using HTRF human IFNγ AlphaLISA kit (Perkin Elmer, #62HIFNGPEH) as described in Example 6. Under these experimental conditions, multiple SH-SY5Y tumor cell challenges resulted in a decreased CAS70950VH6-BBz CAR T cell cytotoxicity, shown by the decrease percentages of total CD3+ T cells and $CD3^+CAR^+$ T cells over time (FIG. 11A and FIG. 11B). By contrast, CAS70950VH6-BBz CAR T cells supplemented with 10 μM Compound A maintained their effector activity and promoted $CD3^+CAR^+$ T cells survival and expansion after repetitive tumor challenges (FIG. 11A and FIG. 11B). 3-(4-amino-1-oxo-1,3 dihydro-2H-isoindol-2-yl)piperidine-2,6-dione (Compound A) treatment also promoted higher amount of IFNγ released from the CAS70950VH6-BBz CAR T cells compared to the non-treated CAR T cells. Furthermore, the un-transduced T cell (UnT) controls treated with or without 10 μM Compound A failed to control the tumor cell growth and T cells exhausted after second round of tumor cell challenge (FIG. 11A). Data suggested the tumor cell control was a CAR dependent process.

To evaluate the synergetic anti-tumor effect of Compound A in combination with GPC2-specific CAR T cells in vivo, NCG mice (NOD-Prkdc Cd5 I12rg Cd/NjuCrl) were subcutaneously injected with neuroblastoma SH-SY5Y cells for 13 days prior to CAR T infusion. A single dose of untransduced T cells ($6\times10^6$ total T cells/mouse) or CARP T cells (CAS70950VH6-BBz, $1.5\times10^6$ CAR+ T cells/mouse) was administered intravenously to tumor xenograft mice and multi-dose of Compound A was administrated intraperitoneally at 7.5 mg of Compound A per kg of body weight o.p.d. for 21 days. Tumor length (L) and width (W) was measured by caliper every 3-4 days after CAR T cells treatment. Tumor volume was estimated using formula: V=(W2×L)/2.

Figure 12A:
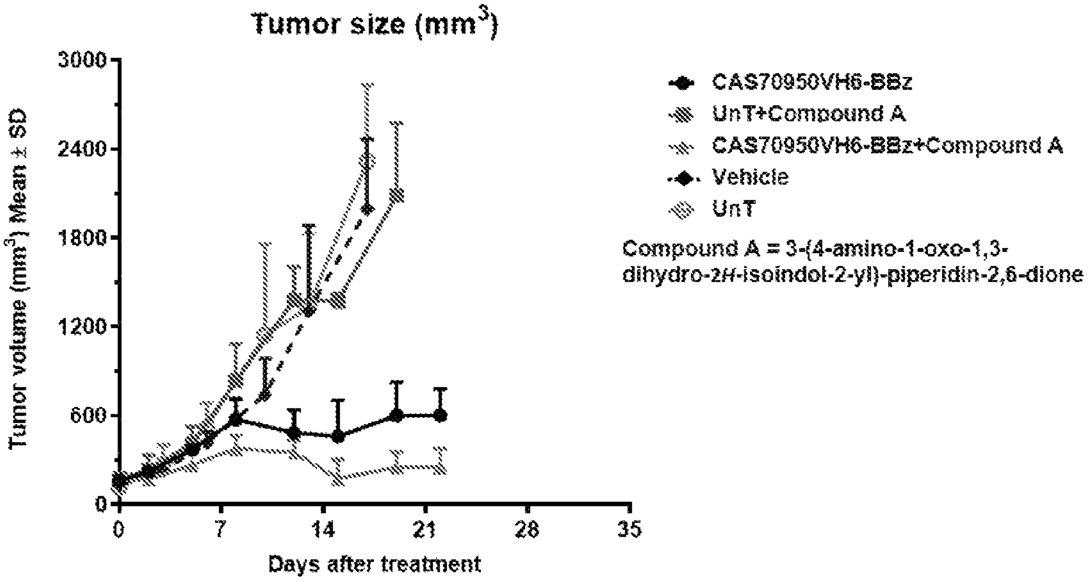
FIGS. 12A-12C show inhibition of neuroblastoma xenograft tumor growth by a combination of humanized CAS70950VH6-BBz CAR T cells and Compound A.
Figure 12B:
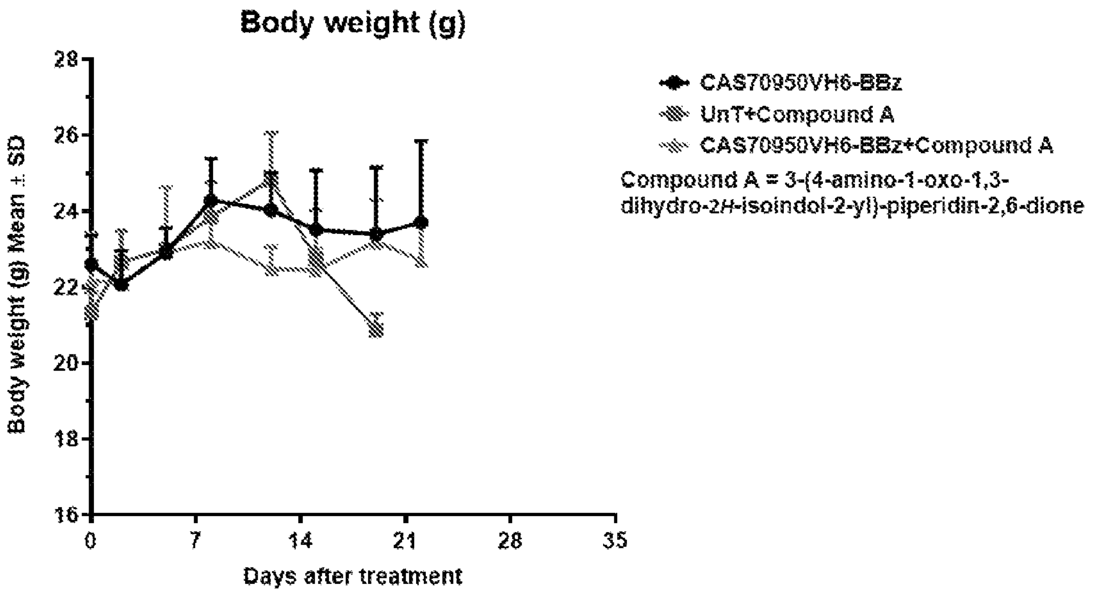
Figure 12C:
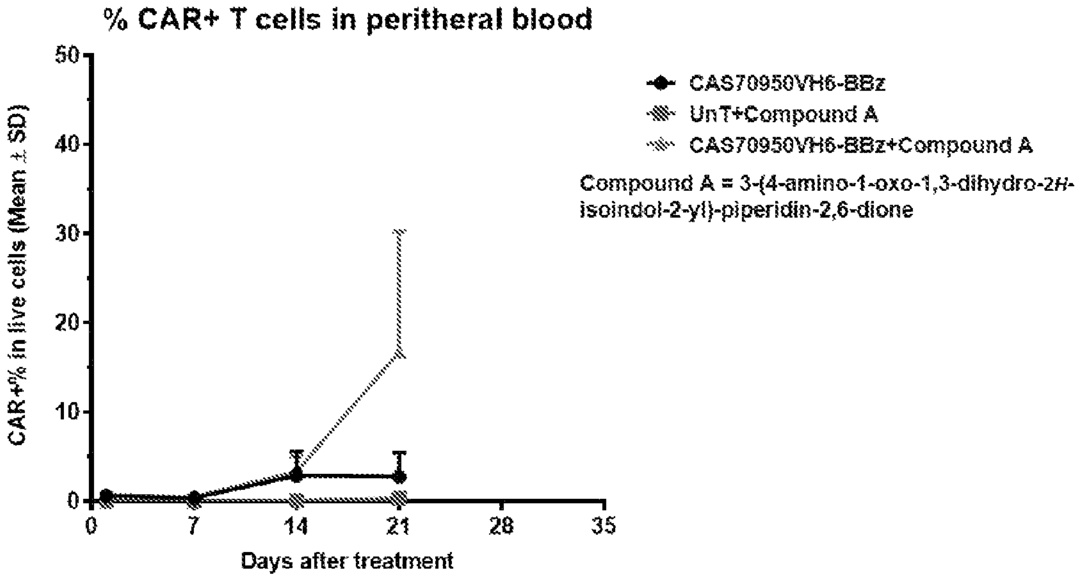

Twelve days after treatment, the NCG mice treated with CAS70950VH6-BBz CAR T cells showed delayed tumor growth comparing with the untransduced T cell-treated group (FIG. 12A). While Compound A alone did not achieve any tumor suppression, its combination with CAR-T cells resulted in more pronounced tumor regression. The data clearly demonstrated that Compound A significantly enhanced antitumor function of CAR T cells against SH-SY5Y derived neuroblastoma tumors. Remarkably, no significant weight loss was observed from NCG mice receiving GPC2-targeted CAR T cells and its combination with Compound A, suggested both treatments were well tolerated by NCG mice (FIG. 12B). As shown in FIG. 12C, elevated percentage of CAR T cells in peripheral blood of NCG mice was observed from day 14 post treatment. While CAR T cell expansion was observed lasting from day 14 to 21 with about 2.80% CAR+ T cell, Compound A co-administration significantly promoted CARP T cells expansion by about 6 fold (16.78%) at day 21 post treatment. Notably, percentage of CARP T cells positively correlated with the tumor growth between groups of CAR T cell alone and its combination with Compound A.

Example 10

Figure 13A:
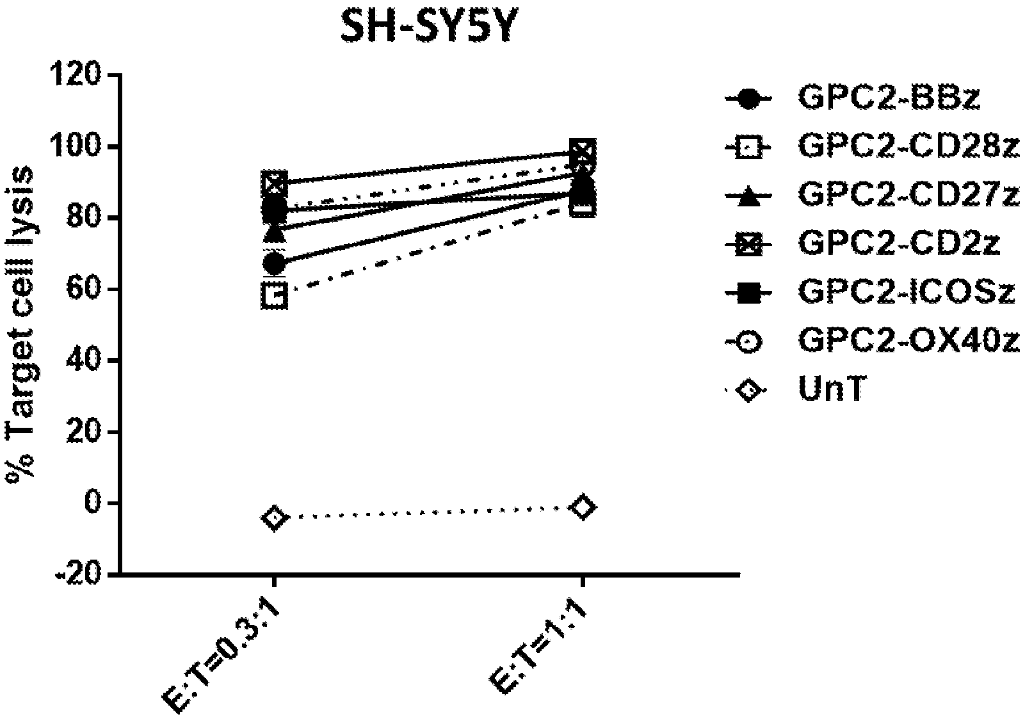
FIGS. 13A-13B show GPC2 CAR Ts with 4-1BB, CD28, CD27, CD2, ICOS, or OX40 co-stimulatory domain can all exert potent cytotoxicity and producing IFNγ against SH-SY5Y.

In Vitro Cytotoxicity and CAR T Persistence of GPC2 CAR Ts Harboring Different Co-Stimulatory Domains GPC2 CAR Ts harboring different co-stimulatory domains were tested for their cytotoxic efficacies against NBL tumor cell line SH-SY5Y following the experimental procedures described in Example 6 and Example 7. Exemplary GPC2 CAR T GPC2-BBz (GPC2 CAR T comprised 4-1BB and CD3 ζ intracellular signaling domains) was used as a positive control and was compared to GPC2-CD28z (SEQ ID NO: 248, GPC2 CAR T comprised CD28 and CD3 ζ intracellular signaling domains), GPC2-CD27z (SEQ ID NO: 249, GPC2 CAR T comprised CD27 and CD3 ζ intracellular signaling domains), GPC2-CD2z (SEQ ID NO:251, GPC2 CAR T comprised CD2 and CD3 ζ intracellular signaling domains), GPC2-ICOSz (SEQ ID NO:250, GPC2 CAR T comprised ICOS and CD3 ζ intracellular signaling domains) and GPC2-OX40z (SEQ ID NO:252, GPC2 CAR T comprised OX40 and CD3 ζ intracellular signaling domains). As shown in FIG. 13A, all tested GPC2 CAR Ts showed potent cytotoxicity against SH-SY5Y. CAR Ts harbouring different co-stimulatory domain showed comparable level of cytotoxicity as the positive control GPC2-BBz CAR T.

Figure 13B:
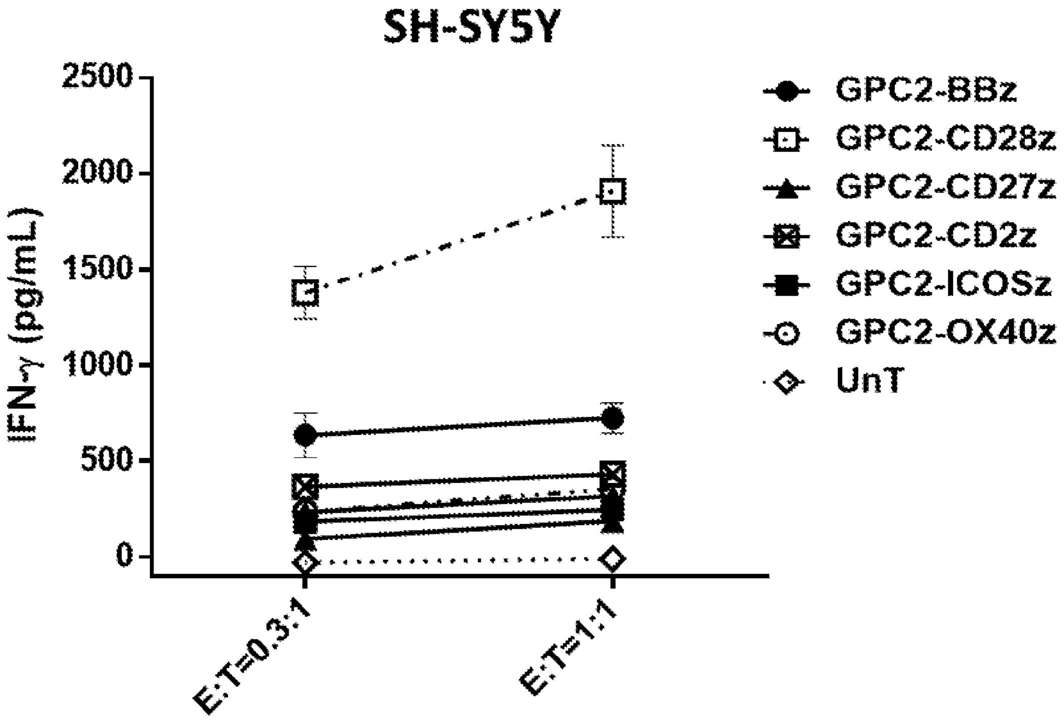

Furthermore, level of IFNγ produced from the cytotoxicity assay was quantified following the experimental procedures described in Example 6 and Example 7. All tested GPC2 CAR T cells showed elevated level of IFNγ production against SH-SY5Y comparing to that of the negative control (UnT) (FIG. 13B). Intriguingly GPC2-CD28z CAR T had higher level of IFNγ production than the GPC2-BBz, GPC2-CD27z, GPC2-CD2z, GPC2-ICOSz and GPC2-OX40z (FIG. 13B). Together, data suggests that GPC2 CAR Ts harbouring different co-stimulatory domains can all exert potent cytotoxicity and produce IFNγ against GPC2 positive tumor cell line.

Figure 14A:
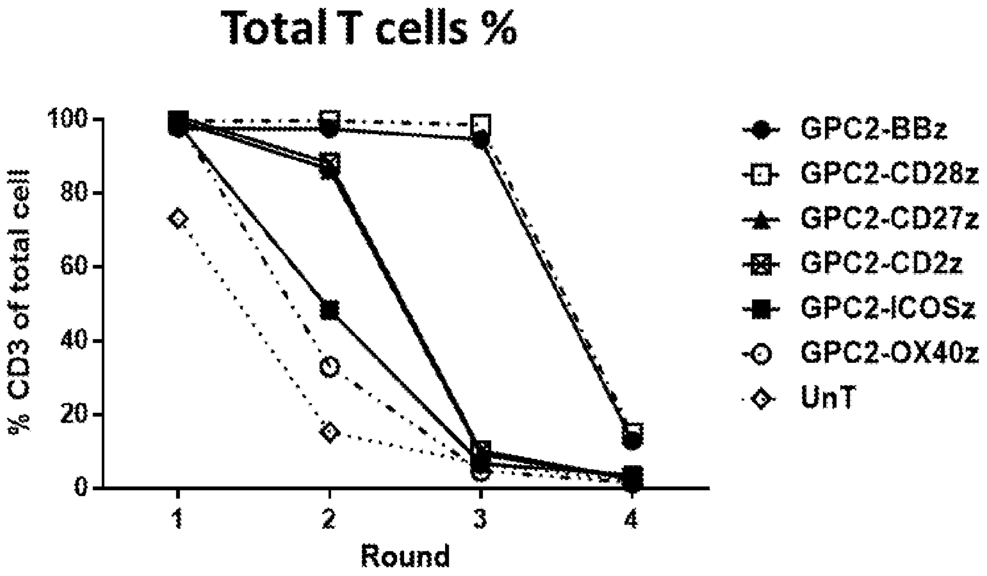
FIGS. 14A-14C show long term persistence and fold of CAR T cells expansion of GPC2 CAR Ts with 4-1BB, CD28, CD27, CD2, ICOS, or OX40 co-stimulatory domain when serially challenged with SH-SY5Y.
Figure 14B:
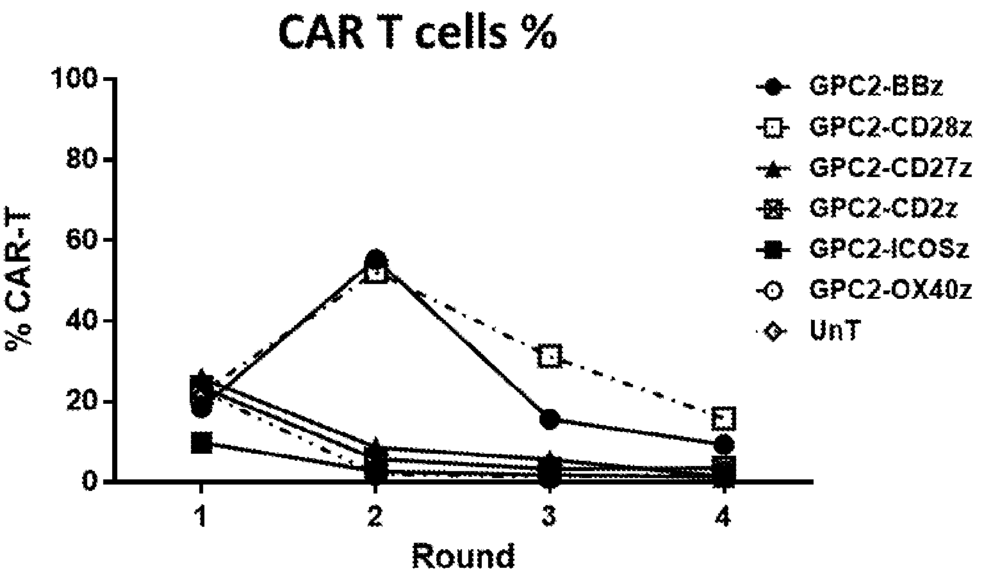
Figure 14C:
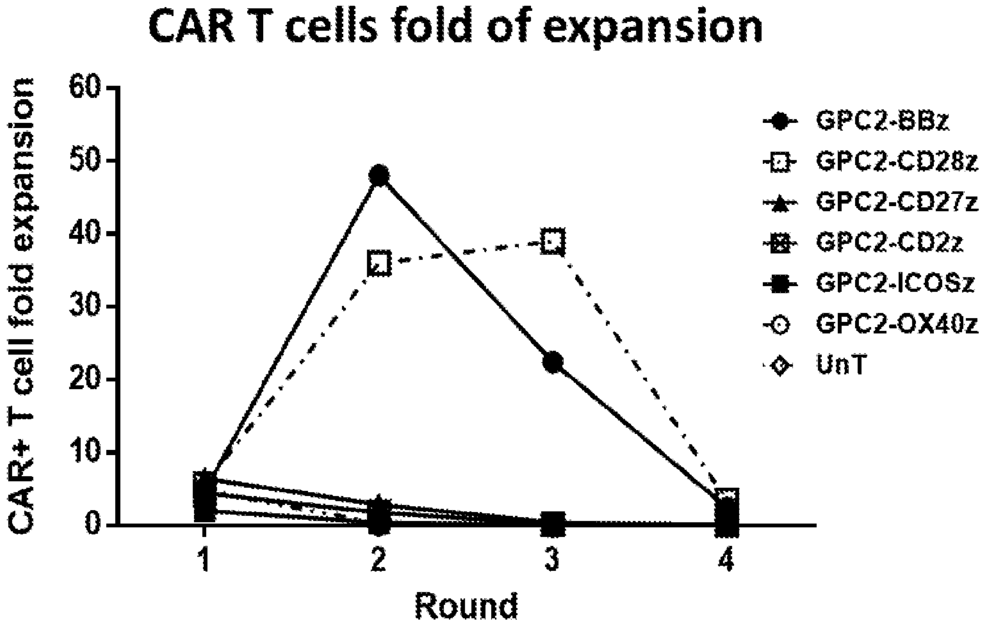

To evaluate the persistence of GPC2 CAR T cells, exemplary CAR T cells were selected and tested in the serial challenge assay. Briefly, $4\times10^5$ SH-SY5Y cells and $1.33\times10^5$ CART cells transduced with GPC2-BBz, GPC2-CD28z, GPC2-CD27z, GPC2-CD2z, GPC2-ICOSz or GPC2-OX40z lentiviral vectors were co-cultured in 12 well plates using fresh growth medium without IL-2 (E:T ratio=1:3). Cells were harvested after three days co-culture and samples were taken for cell counting using AOPI and T cell quantified by FACs. CAR T cells were replated with fresh SH-SY5Y cells at a 1:2 E:T ratio in growth medium without IL-2 to start the next round of tumor co-culture. Samples were taken for cell counting and T cell quantification at the end of each challenge every three days. GPC2-BBz served as a positive control while the untransduced T cell (UnT) was used as a negative control. As shown in FIG. 14A, CAR T cells were repeatedly stimulated with SH-SY5Y and all GPC2 CAR T cells showed better persistence when comparing with the UnT negative control. GPC2-CD28z had comparable level of long term persistence and CAR T cells expansion as the positive control GPC2-BBz (FIG. 14A and FIG. 14C). Although a gradual decline in CAR positive T cells percentage was observed in GPC2-CD27z, GPC2-CD2z, GPC2-ICOSz and GPC2-OX40z CAR T cells, the GPC2-BBz and GPC2-CD28z CAR T cells expanded and reaching a peak level of CAR positive T cells percentage after 2 rounds of target cell challenges (FIG. 14B). The CD28 co-stimulatory domain helped to maintain a more stable level of CAR positive T cells than other costimulatory domains after 4 rounds of target cell challenge (FIG. 14B).

Collectively, the data suggest 4-1BB, CD28, CD27, CD2, ICOS and OX40 co-stimulatory signaling domains are all capable to support the cytotoxic function of GPC2 CAR T against GPC2 positive target cell. GPC2 CAR T cells with 4-1BB or CD28 costimulatory domain, however, have better T cell expansion and long term persistence under serial tumor cell challenges comparing to those harboring CD2, CD27, ICOS and OX40 signaling domains.

Example 11

GPC2 CAR Ts are effective against neuroblastoma, small cell lung cancer (SCLC) and medulloblastoma tumor cells.

Figure 15:
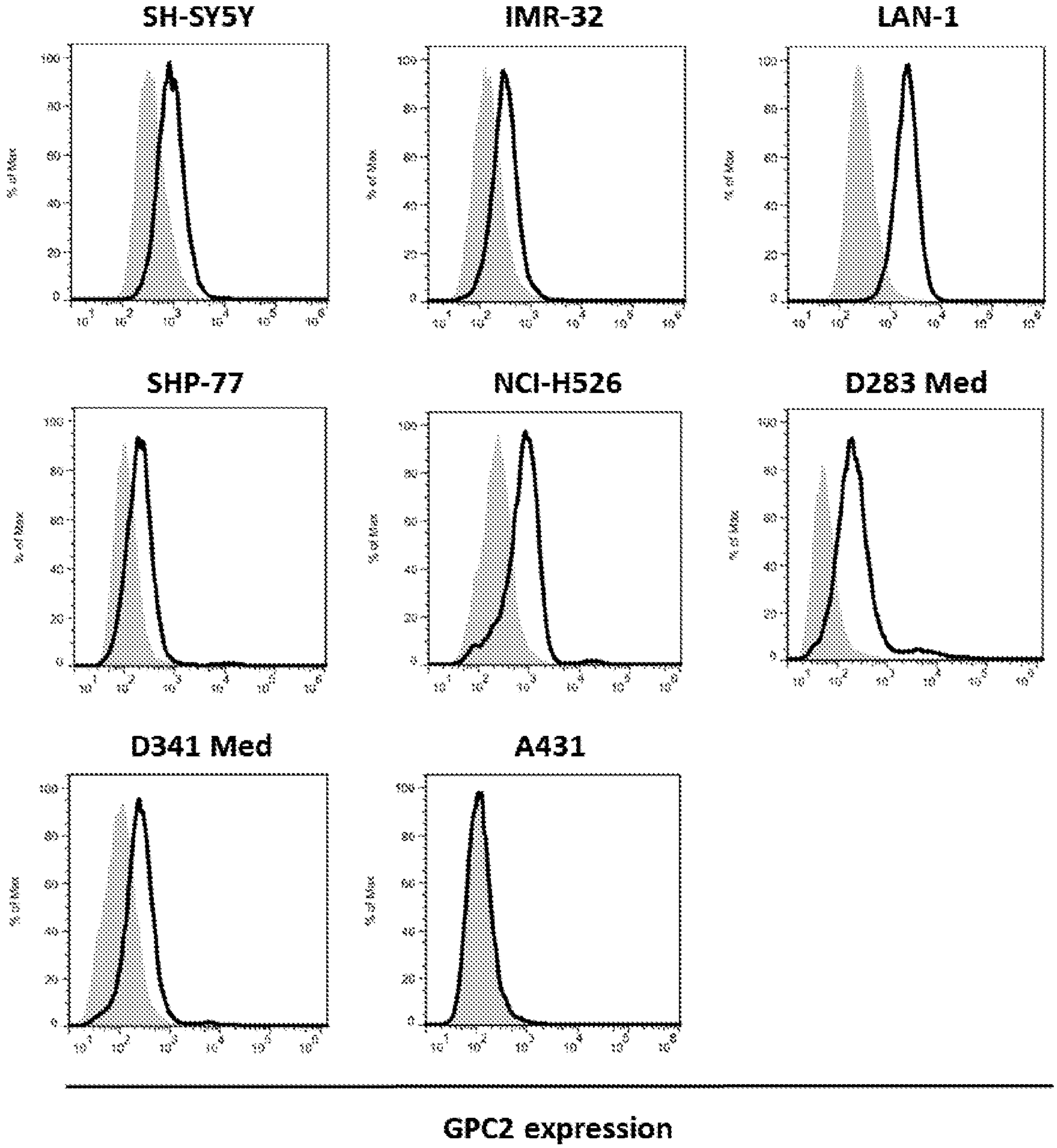
FIG. 15 shows GPC2 expression in human neuroblastoma, small cell lung cancer, medulloblastoma and epidermoid carcinoma tumor cell lines.

To measure the level of GPC2 expression, human neuroblastoma cell lines SH-SY5Y (ATCC, #CRL-2266) and human neuroblastoma cell line IMR-32 cells (ATCC, #CCL-127) were cultured in EMEM media supplemented with 10% FBS. Human neuroblastoma cell line LAN-1 cells (ECACC, #06041201) were cultured in mixture of EMEM and Ham's F12 (1:1 ratio) media with 10% FBS. Human epidermoid carcinoma cell line A-431 (ATCC, #CRL-1555) was cultured in DMEM media supplemented with 10% FBS. Human SCLC tumor cell lines SHP-77 (ATCC, #CRL-2195) and NCI-H526 (ATCC, #CRL-5811) were cultured in RPMI-1640 media supplemented with 10% FBS. Human medulloblastoma tumor cell line D283 Med (ATCC, #HTB-185) was cultured in EMEM media supplemented with 10% FBS and D341 Med (ATCC, #HTB-187) was cultured in EMEM media supplemented with 20% FBS. Tumor cell surface expression of GPC2 was analyzed by flow cytometry. As shown in FIG. 15, neuroblastoma cell lines SH-SY5Y, IMR-32 and LAN-1 were GPC2 positive. SCLC cell lines NCI-H526 was GPC2 positive and SHP-77 was GPC2 low positive (FIG. 15). Medulloblastoma cell lines D283 Med and D341 Med were GPC2 positive (FIG. 15). A-431 was GPC2 negative (FIG. 15). The GPC2 positive tumor cell lines were selected and tested in in vitro cytotoxicity assay.

Figure 16:
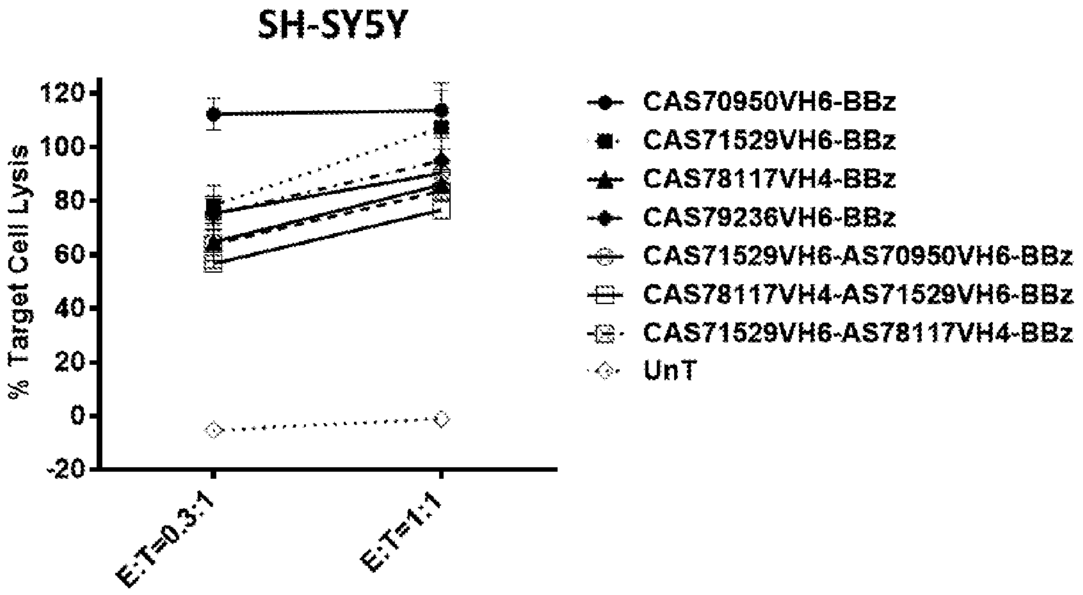
FIG. 16 shows in vitro cytotoxicity of GPC2 CAR Ts against neuroblastoma cell line SH-SY5Y.
Figure 17:
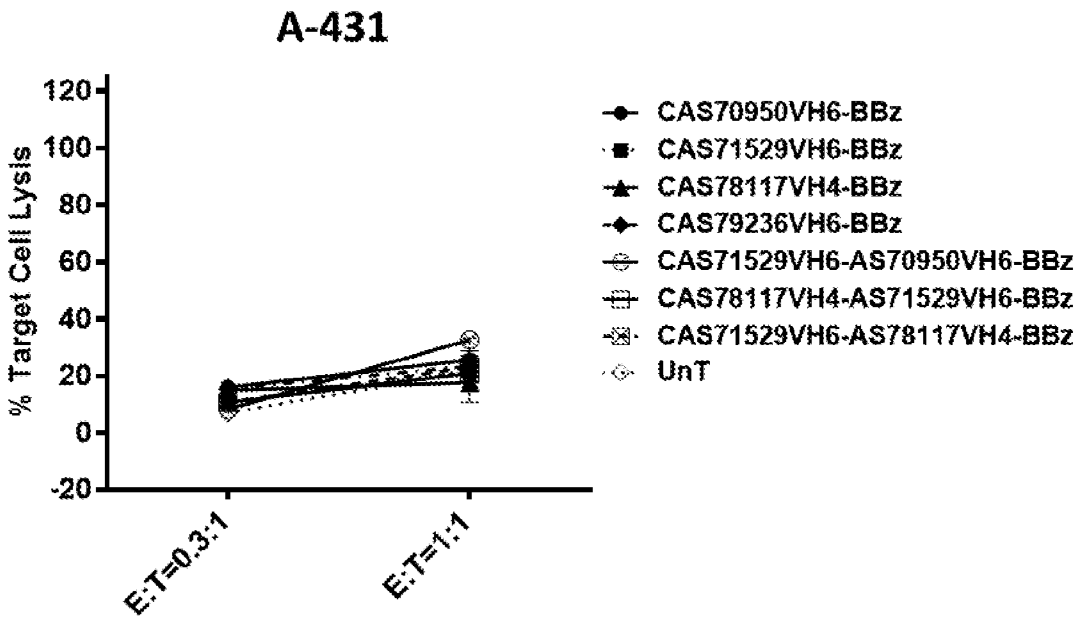
FIG. 17 shows in vitro cytotoxicity of GPC2 CAR Ts against human epidermoid carcinoma tumor cell lines A-431.
Figure 18:
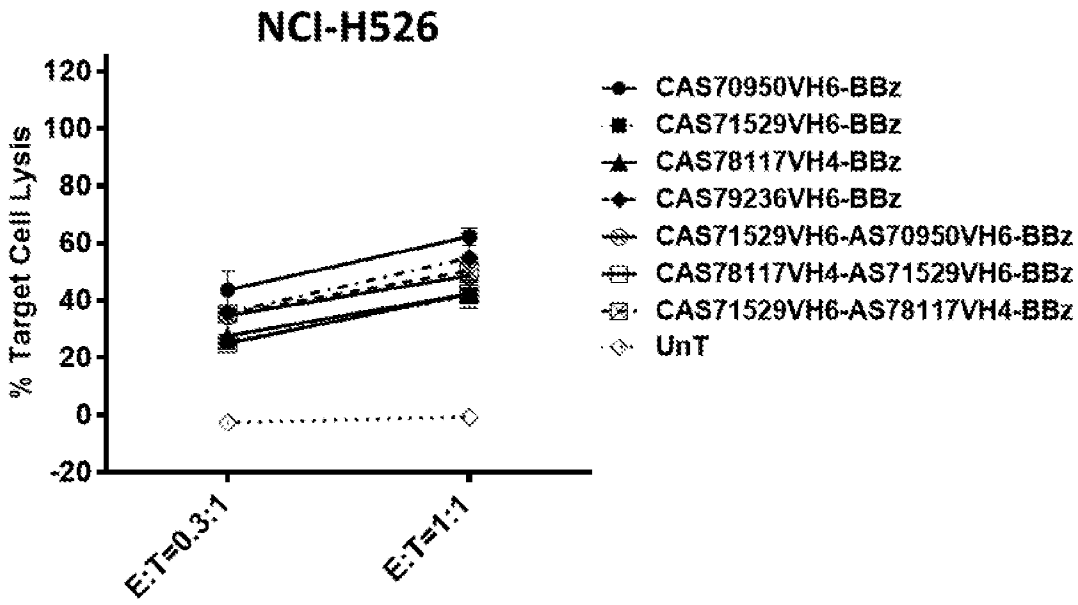
FIG. 18 shows in vitro cytotoxicity of GPC2 CAR Ts against human small cell lung cancer cell lines NCI-H526.
Figure 19:
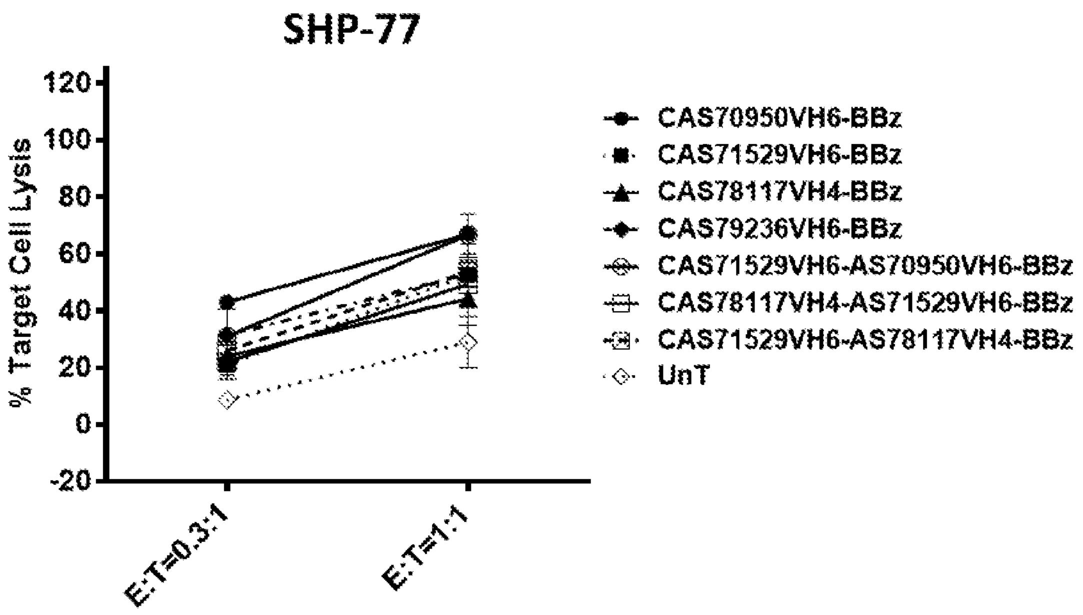
FIG. 19 shows in vitro cytotoxicity of GPC2 CAR Ts against human small cell lung cancer cell lines SHP-77.
Figure 20:
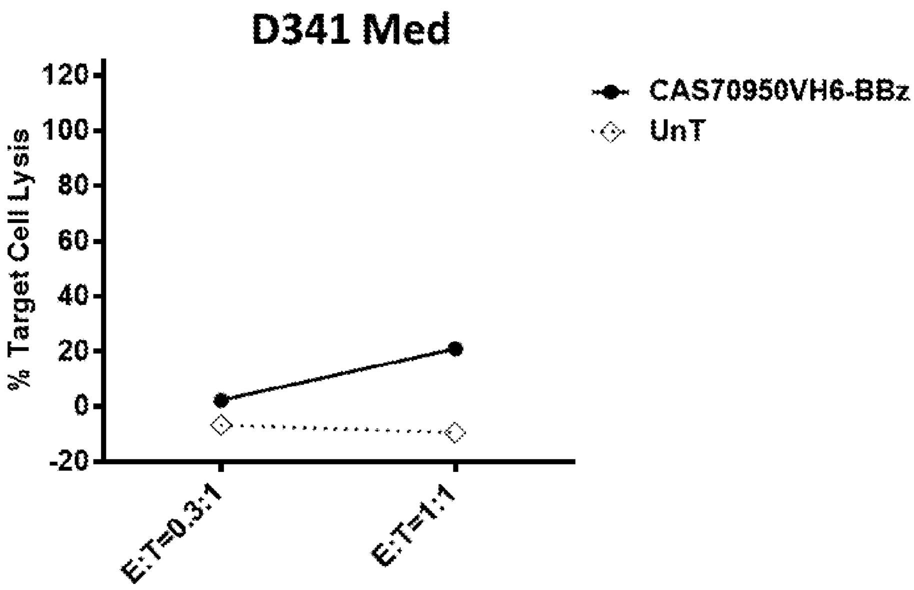
FIG. 20 shows in vitro cytotoxicity of exemplary GPC2 CAR T against human medulloblastoma cell lines D341 Med.
Figure 21:
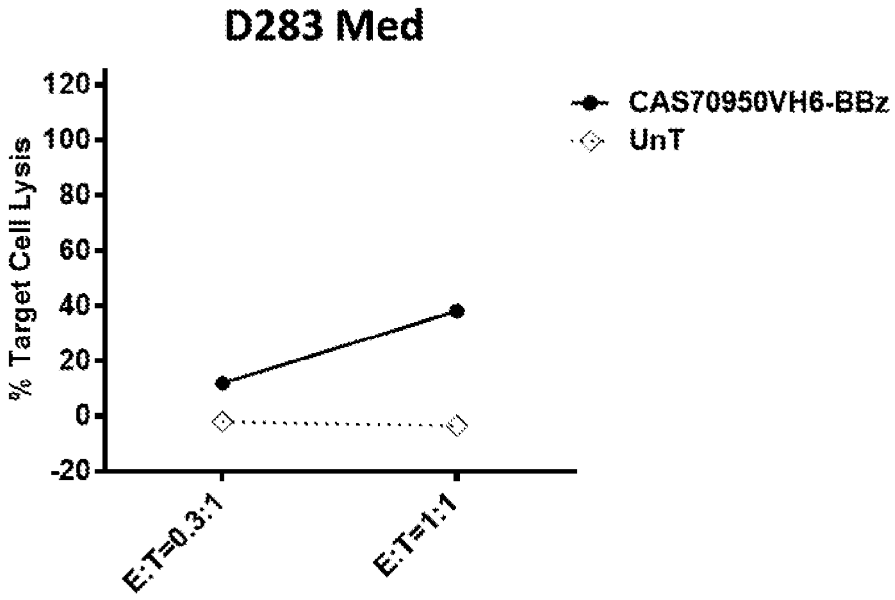
FIG. 21 shows in vitro cytotoxicity of exemplary GPC2 CAR T against human medulloblastoma cell lines D283 Med.

To evaluate the cytotoxic efficacy of GPC2 CAR Ts against tumor cells, the GPC2 positive NBL tumor cell line SH-SY5Y was used as a positive control and the GPC2 negative cell line A-431 was used as a negative control. As shown in FIG. 16 and FIG. 17, all GPC2 CAR Ts showed potent cytotoxicity against SH-SY5Y but not to the negative control A-431. Data indicated all GPC2 CAR Ts had potent cytotoxic efficacy against GPC2 positive target cell. Furthermore, elevated level of cytotoxicity was also observed in all GPC2 CAR Ts tested against the SCLC cell lines NCI-H526 and SHP-77 in a dose-dependent manner comparing to the untransduced T cell control (UnT) (FIG. 18 and FIG. 19). Exemplary GPC2 CAR T (CAS70950VH6-BBz) was also tested against human medulloblastoma tumor cells. As shown in FIG. 20 and FIG. 21, CAS70950VH6-BBz CAR T had elevated level of cytotoxicity against D341 Med and D283 Med cell lines comparing to UnT.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

| SEQUENCE LISTING |
| --- |
| AMINO ACID SEQUENCE |
| AS70549 (SEQ ID NO: 93)<br>QVRLVESGGGSVQAGGSLTLSCAYSRYTGRSSCMAWFRRPPGKKRERVASIYSDDGVTVYADSVKG<br>RFTITQDSAQNTLYLQMNSLDPEDTAMYYCATRTTYPGVCPDNAAWYDYWGQGTQVTVSS |
| AS70771 (SEQ ID NO: 94)<br>QVQLVESGGGSVQAGGSLRLSCAASGYTGKMAWFRQAPGKEREGVAAIDDAGGTNYIDSVKGRFTI<br>SKDNAENTLYLRMNSLKPEDTAIYYCAADTFRWFMRRSGPINGSDYAYWGQGTQVTVSS |
| AS70950 (SEQ ID NO: 95)<br>QVQLVESGGGSAQSGGSLRLSCAISEFTYKNTCVGWFRQAPGKEREGVAAIDSDGNTNYVDSVKGR<br>FTISQGNAKNTVYLQMNSLKPEDTAMYYCAAGAYCGRLLLWIGNYAYWGQGTQVTVSS |
| AS71402 (SEQ ID NO: 96)<br>QMQLVESGGGSVQAGGSLRLSCVVSGYTYNRNMAWFRQAPGKEREGVAAMYTGSGTTDYADSVK<br>GRFTISHDNAKNTLYLQMNSLKPEDTATYYCAADTARRGGSWSGPFKYDYWGQGTQVTVSS |
| AS71529 (SEQ ID NO: 97)<br>EVQLVESGGGSVQAGGSLRLSCVVSEYRYSSRYCMGWFRQAPGKEREGVAAIDSNGSADYVDSVK<br>GRFTISKDNAKNTLYLQINSVRPEDTAMYYCAADHLAYDCYSGATSVFRYWGQGTQVTVSS |
| AS71661 (SEQ ID NO: 98)<br>QVQLVESGGGLVQAGGSLRLSCSPSGTTFAHYNMVGWFRQAPGKDREGVSCISKYGGTTYYADSV<br>KGRFTIYRDNAKNTLFLQMNSLKPEDTAMYYCAIGVLPSSTAICAGAANYWGQGTQVTVSS |
| AS72021 (SEQ ID NO: 99)<br>EVQLAESGGGSVQAGGSLRLSCVVSRNTYSSYCMSWFRQAPGKEREGVAAIDNVKTSYADSVKGRF<br>TISKDNAKNTLYLQMNSLKPEDTAMYYCAAHLELCYYTDPMYQYEYNYWGQGTQVTVSS |
| AS72052 (SEQ ID NO: 100)<br>QVRLVESGGGSVQAGGSLRLSCAVSGFRYASYCMGWFRQAPGKEREGVAAIHSDGIIRYAESVKGR<br>FTISKDNAKNTLYLQLNSLKPEDNAMYSCAAGAYCGADAILTLYDYAFWGQGTQVTVSS |
| AS72383 (SEQ ID NO: 101)<br>QVRLVESGGGLVQAGGSQRLSCTASGLTFDDSGMGWFRQAPGKGREGVSCITWNGRSTYYADSVK<br>GRFTISRDNSKNTLYLQMNSLKPEDTAMYYCAAAFITKTGCSYEYDYSGQGTQVTVSS |
| AS72479 (SEQ ID NO: 102)<br>QVKLVESGGGSVQAGGSLRLSCAASETTDCRYVWRWYREDPGMEREFVSSITSGGSTWYADSVKG<br>RFTISQDNAKSTLYLQMNSLKPEDSGMYYCESDPGWSGYHARRCEVYRGQGIQVTVSS |
| AS72499 (SEQ ID NO: 103)<br>QVRLVESGGGSVQAGGSLRLSCVVSRFTYSSYCMGWFRQAPGKEREGVAGIEKDDSTYYADSVKG<br>RFTISKDNAKNTLYLQMNSLKPEDTAMYYCAARIPGGNCGVVARMAYWDYWGKGTLVTVSS |
| AS72531 (SEQ ID NO: 104)<br>QVQLVESGGGLVQAGGSLRLSCTASGLTFAHYNMVGWFRQAPGKDREGVSCISKYGGTIYYADSV<br>KGRFTIDRNNAKNTLYLQMNSLKPEDTAMYYCAIGVLSSTARGPGAANYWGQGTQVTVSS |
| AS72669 (SEQ ID NO: 105)<br>EVQLVESGGGSVQAGGSLKLSCAASRFTYSSYCMGWIRQAPGKEREGVAIFYTGGGRTYYADSVKG<br>RFTISQDTAKNTLYLQMNSLKPEDTGIYYCVAGFYCSGGYWEGDFGYWGQGTQVTVSS |
| AS72794 (SEQ ID NO: 106)<br>QVQLVESGGGLVQAGGSLRLSCTASGFTFDDYAMSWFRQAPGKEREGVSCISASGTTTYYGDSVKG<br>RFTISRDNAKTTLILQMSSLKPEDTAMYYCAADRFRDYCSDSWSHLYNYEYMHWGQGTQVTVSS |

-continued

SEQUENCE LISTING

AS72805 (SEQ ID NO: 107)
QVQLVESGGDSVQAGGSLTLSCVASRLRVSNNCMGWFRQAPGNEREGVATLGSDGRTIYADSVKG
RFTISKDNVANTLYLQMNGLKLDDTALYYCAAADFSSGGYCNIASVYHSYFPYWGQGTQVTVSS

AS72806 (SEQ ID NO: 108)
QVQLVESGGGSVQAGGSLRLSCAASGYTYMPPCMGWFRQAPGKEREGVATIYGRGGSTYYADSVK
GRFTISQDNAKNTLYLQMNNLEPEDTAMYYCAADNLCYATGILRSAYDYSYWGQGTQVTVSS

AS72835 (SEQ ID NO: 109)
QVHLMESGGGSVQAGGSLRLSCAVSGGYTSRTVCMGWFRQTPGKEREVLAAIYRSGTTYYHDSVK
GRFTISRDGDKNTVYLQMDSLKPEDTAMYYCAASPGYSDAACVSVPQANRWGQGTQVTVSS

AS77906 (SEQ ID NO: 110)
QVRLVESGGGSVQAGESLRLSCARSGVVKCDVEMRWYRQSPGKEREFVALIEAGGHTEYADSVKG
RFTISQDNAKMLFYLQMNSLKPEDTAKYYCVAAPRYYTLSCPKDFWGRGTQVTVSS

AS77916 (SEQ ID NO: 111)
QVHLMESGGGSVQAGGSLRLSCATSGYTSSWNCMGWFRQPPGKEREGVATIANRGHSTYYADSVK
GRFTISQGNAKNTVYLQMNSLKPEDTAMYYCATDTWACVGISTDFEYWGQGTQVTVSS

AS77932 (SEQ ID NO: 112)
QVQLKESGGGSVQAGGSLRLSCAVSGYWYSVAWMGWFRQTPGKEREGVAAVLNGGGRRYYADS
VKGRFTISQDNSKNTLYLQMNSLKPEDTAMYYCAAGNGVGHPLGPSEYNYWGQGTQVTVSS

AS77934 (SEQ ID NO: 113)
EVQLVESGGGSVQAGGSLRLSCAASGYTYSSYSIAWFRQAPGKEREGVAGFFYSGGPTCYADSVKG
RFTISQDNAKNTLYLQMNSLKPEDTAMYYCAARRSNTNDYCFYPTYTYWGQGTQVTVSS

AS77978 (SEQ ID NO: 114)
QVRLVESGGGSVQAGGSLRLSCAASGATSCRWRMSWYRQAPGKEREFVSSIANGATEYADSVKGR
FTISQDNARNTMYLQMNSLSPEDTAMYYCAADPRVYTSRCDRTYLGQGTQVTVSS

AS77986 (SEQ ID NO: 115)
QVQLVESGGGSVQAGGSLRLSCAASASGYTYSSDSMAWFRQAPGKEREGVAGISTGGRSTYYADSV
KGRFTISQDNAKTTVYLHMNSLKPEDTAMYYCAADGPSMTAIQALGDLYPVDFAWWGQGTQVTVS
S

AS78117 (SEQ ID NO: 116)
QVKLVESGGGSVQAGGALRLSCIVRRYTYATYSMAWFRQSPGKEREGVAGLDSVGATGYAESVKG
RFTISKDNAKNILYLQMNSLKPEDTAMYYCVVDPASAKVTYGSWSTPSYAYWGQGTQVTVSS

AS78215 (SEQ ID NO: 117)
QVKLVESGGGSVQAGGALRLSCAASRYTFSSNCMGWFRQAPGKEREGVATIASASGYTDYHDSVK
GRFAISRDNAKNTVYLQMNSLKPEDTATYYCAARAGPCWSWAQADLYNYWGQGTQVTVSS

AS788I0 (SEQ ID NO: 118)
QVHLVESGGGSVQAGGSLRLSCAASGYTYYDMGWFRLAPGKEREGIAAISSSSSTYYADSVKGRFTI
SRDSNTLYLQMNSLKPEDTAMYSCAAGRYVGRKLEVYDYAYWGQGTQVTVSS

AS79101 (SEQ ID NO: 119)
QVQLVESGGGSVQAGGSLRLSCAASGDTYSNYCMGWFRQAPGKEREEVAAIDSDGSRRYPDSVKG
RFTISKDNAKKILYLQMNSLKPEDTAMYFCATDPKVACARVVEYGGGWYRWGQGTQVTVSS

AS79236 (SEQ ID NO: 120)
QVKLVESGGGSVQAGGSLRLSCAVSGYTYSSYCMAWFRQAPGEEREGVASIDAGGRTTYVDSVKG
RFTISKDNAKTSLYLQMNSLKPEDTAMYYCAVDVRTRCGGTWDGEAVYFPYWGQGTQVTVSS

AS79274 (SEQ ID NO: 121)
QVHLVESGGGSVQAGGSLRLSCAASKYAFCTYDMSWFRQAPGKEREVVSSIDSRGNTNYSDSVKGR
FTISQDHAKNTLYLQMNSLKPEDTAMYTCAAQIVGGALRCPRFAMYWGQGTQVTVSS

AS79285 (SEQ ID NO: 122)
QVRLVESGGGSVQAGGSLALSCETSRYTVSNYCMGWFRQVSGKEVEGVALISTDGTTTYADSVKGR
FTISKDNAKNTLYLQMNSLKSEDTAMYFCAGVYGLIWYYKPCPAQREWALQRYGYWGQGTQVTV
SS

AS79317 (SEQ ID NO: 123)
EVQLAESGGGSVQPGGSLRLSCAASGYSSSSVCMGWFRQAPGKEREGVAIIYVTLGSIAYADSVKGR
FTISRDNAKNTLDLEMNSLKPDDTALYYCAAGGCGYRGVADVPEFTYRGQGTQVTVSS

AS70950VH6 (SEQ ID NO: 124)
EVQLVESGGGLVQPGGSLRLSCAISEFTYKNTCVGWFRQAPGKGREGVAAIDSDGNTNYVDSVKGR
FTISQDNSKNTVYLQMNSLRAEDTAMYYCAAGAYCGRLLLWIGNYAYWGQGTLVTVSS

-continued

SEQUENCE LISTING

AS70950VH7 (SEQ ID NO: 125)
EVQLVESGGGLVQPGGSLRLSCAASEFTYKNTCVGWFRQAPGKGREGVAAIDSDGNTNYVDSVKG
RFTISRDNSKNTVYLQMNSLRAEDTAMYYCAAGAYCGRLLLWIGNYAYWGQGTLVTVSS

AS71529VH5 (SEQ ID NO: 126)
EVQLVESGGGLVQPGGSLRLSCAVSEYRYSSRYCMGWFRQAPGKGLEGVSAIDSNGSADYVDSVKG
RFTISKDNSKNTLYLQMNSLRAEDTAVYYCAADHLAYDCYSGATSVFRYWGQGTLVTVSS

AS71529VH6 (SEQ ID NO: 127)
EVQLVESGGGLVQPGGSLRLSCAVSEYRYSSRYCMGWFRQAPGKGREGVAAIDSNGSADYVDSVK
GRFTISKDNSKNTLYLQMNSLRAEDTAMYYCAADHLAYDCYSGATSVFRYWGQGTLVTVSS

AS72052VH5 (SEQ ID NO: 128)
QVQLVESGGGVVQPGGSLRLSCAVSGFRYASYCMGWFRQAPGKGLEGVAAIHSDGIIRYAESVKGR
FTISKDNSKNTLYLQMNSLRAEDTAVYYCAAGAYCGADAILTLYDYAFWGQGTLVTVSS

AS72052VH6 (SEQ ID NO: 129)
QVQLVESGGGVVQPGGSLRLSCAVSGFRYASYCMGWFRQAPGKGLEGVAAIHSDGIIRYAESVKGR
FTISKDNSKNTLYLQMNSLRAEDTAMYSCAAGAYCGADAILTLYDYAFWGQGTLVTVSS

AS72669VH6 (SEQ ID NO: 130)
QVQLVESGGGVVQPGGSLRLSCAASRFTYSSYCMGWIRQAPGKGREGVAIFYTGGGRTYYADSVKG
RFTISQDNSKNTLYLQMNSLRAEDTAVYYCVAGFYCSGGYWEGDFGYWGQGTLVTVSS

AS78117VH4 (SEQ ID NO: 131)
EVQLVESGGGLVQPGGSLRLSCIVSRYTYATYSMAWFRQAPGKGLEGVSGLDSVGATGYAESVKGR
FTISRDNSKNTLYLQMNSLRAEDTAVYYCVVDPASAKVTYGSWSTPSYAYWGQGTLVTVSS

AS78117VH5 (SEQ ID NO: 132)
EVQLVESGGGLVQPGGSLRLSCIVSRYTYATYSMAWFRQAPGKGLEGVSGLDSVGATGYAESVKGR
FTISKDNSKNTLYLQMNSLRAEDTAVYYCVVDPASAKVTYGSWSTPSYAYWGQGTLVTVSS

AS78117VH6 (SEQ ID NO: 133)
EVQLVESGGGLVQPGGSLRLSCIVSRYTYATYSMAWFRQAPGKGLEGVSGLDSVGATGYAESVKGR
FTISKDNSKNTLYLQMNSLRAEDTAMYYCVVDPASAKVTYGSWSTPSYAYWGQGTLVTVSS

AS78117VH7 (SEQ ID NO: 134)
EVQLVESGGGLVQPGGSLRLSCIVSRYTYATYSMAWFRQAPGKGLEGVAGLDSVGATGYAESVKG
RFTISKDNSKNTLYLQMNSLRAEDTAMYYCVVDPASAKVTYGSWSTPSYAYWGQGTLVTVSS

AS79236VH4 (SEQ ID NO: 135)
EVQLVESGGGLVQPGGSLRLSCAASGYTYSSYCMAWFRQAPGKGLEGVASIDAGGRTTYVDSVKG
RFTISRDNAKNSLYLQMNSLRAEDTAVYYCAVDVRTRCGGTWDGEAVYFPYWGQGTLVTVSS

AS79236VH5 (SEQ ID NO: 136)
EVQLVESGGGLVQPGGSLRLSCAVSGYTYSSYCMAWFRQAPGKGLEGVASIDAGGRTTYVDSVKG
RFTISKDNAKNSLYLQMNSLRAEDTAVYYCAVDVRTRCGGTWDGEAVYFPYWGQGTLVTVSS

AS79236VH6 (SEQ ID NO: 137)
EVQLVESGGGLVQPGGSLRLSCAVSGYTYSSYCMAWFRQAPGKGLEGVASIDAGGRTTYVDSVKG
RFTISKDNAKNSLYLQMNSLRAEDTAMYYCAVDVRTRCGGTWDGEAVYFPYWGQGTLVTVSS

AS77916VH6 (SEQ ID NO: 138)
EVQLVESGGGLVQPGGSLRLSCATSGYTSSWNCMGWFRQAPGKGLEGVATIANRGHSTYYADSVK
GRFTISQDNSKNTLYLQMNSLRAEDTAVYYCATDTWACVGISTDFEYWGQGTLVTVSS

AS77916VH7 (SEQ ID NO: 139)
EVQLVESGGGLVQPGGSLRLSCATSGYTSSWNCMGWFRQAPGKGLEGVATIANRGHSTYYADSVK
GRFTISQDNSKNTLYLQMNSLRAEDTAMYYCATDTWACVGISTDFEYWGQGTLVTVSS

AS77916VH8 (SEQ ID NO: 140)
EVQLVESGGGLVQPGGSLRLSCATSGYTSSWNCMGWFRQAPGKGLEGVATIANRGHSTYYADSVK
GRFTISQDNSKNTVYLQMNSLRAEDTAVYYCATDTWACVGISTDFEYWGQGTLVTVSS

AS77916VH9 (SEQ ID NO: 141)
EVQLVESGGGLVQPGGSLRLSCATSGYTSSWNCMGWFRQAPGKGREGVATIANRGHSTYYADSVK
GRFTISQDNSKNTLYLQMNSLRAEDTAVYYCATDTWACVGISTDFEYWGQGTLVTVSS

AS77916VH10 (SEQ ID NO: 142)
EVQLVESGGGLVQPGGSLRLSCATSGYTSSWNCMGWFRQAPGKGREGVATIANRGHSTYYADSVK
GRFTISQDNSKNTVYLQMNSLRAEDTAVYYCATDTWACVGISTDFEYWGQGTLVTVSS

AS71529VH5-AS72052VH5 (SEQ ID NO: 143)
EVQLVESGGGLVQPGGSLRLSCAVSEYRYSSRYCMGWFRQAPGKGLEGVSAIDSNGSADYVDSVKG
RFTISKDNSKNTLYLQMNSLRAEDTAVYYCAADHLAYDCYSGATSVFRYWGQGTLVTVSSGGGGS

-continued

SEQUENCE LISTING

GGGGSGGGGSQVQLVESGGGVVQPGGSLRLSCAVSGFRYASYCMGWFRQAPGKGLEGVAAIHSDG
IIRYAESVKGRFTISKDNSKNTLYLQMNSLRAEDTAVYYCAAGAYCGADAILTLYDYAFWGQGTLV
TVSS

AS72052VH5-AS71529VH5 (SEQ ID NO: 144)
QVQLVESGGGVVQPGGSLRLSCAVSGFRYASYCMGWFRQAPGKGLEGVAAIHSDGIIRYAESVKGR
FTISKDNSKNTLYLQMNSLRAEDTAVYYCAAGAYCGADAILTLYDYAFWGQGTLVTVSSGGGGSG
GGGSGGGGSEVQLVESGGGLVQPGGSLRLSCAVSEYRYSSRYCMGWFRQAPGKGLEGVSAIDSNGS
ADYVDSVKGRFTISKDNSKNTLYLQMNSLRAEDTAVYYCAADHLAYDCYSGATSVFRYWGQGTLV
TVSS

AS70950VH6-AS71529VH6 (SEQ ID NO: 145)
EVQLVESGGGLVQPGGSLRLSCAISEFTYKNTCVGWFRQAPGKGREGVAAIDSDGNTNYVDSVKGR
FTISQDNSKNTVYLQMNSLRAEDTAMYYCAAGAYCGRLLLWIGNYAYWGQGTLVTVSSGGGGSG
GGGSGGGGSEVQLVESGGGLVQPGGSLRLSCAVSEYRYSSRYCMGWFRQAPGKGREGVAAIDSNG
SADYVDSVKGRFTISKDNSKNTLYLQMNSLRAEDTAMYYCAADHLAYDCYSGATSVFRYWGQGTL
VTVSS

AS71529VH6-AS70950VH6 (SEQ ID NO: 146)
EVQLVESGGGLVQPGGSLRLSCAVSEYRYSSRYCMGWFRQAPGKGREGVAAIDSNGSADYVDSVK
GRFTISKDNSKNTLYLQMNSLRAEDTAMYYCAADHLAYDCYSGATSVFRYWGQGTLVTVSSGGGG
SGGGGSGGGGSEVQLVESGGGLVQPGGSLRLSCAISEFTYKNTCVGWFRQAPGKGREGVAAIDSDG
NTNYVDSVKGRFTISQDNSKNTVYLQMNSLRAEDTAMYYCAAGAYCGRLLLWIGNYAYWGQGTL
VTVSS

AS70950VH6-AS70950VH6 (SEQ ID NO: 147)
EVQLVESGGGLVQPGGSLRLSCAISEFTYKNTCVGWFRQAPGKGREGVAAIDSDGNTNYVDSVKGR
FTISQDNSKNTVYLQMNSLRAEDTAMYYCAAGAYCGRLLLWIGNYAYWGQGTLVTVSSGGGGSG
GGGSGGGGSEVQLVESGGGLVQPGGSLRLSCAISEFTYKNTCVGWFRQAPGKGREGVAAIDSDGNT
NYVDSVKGRFTISQDNSKNTVYLQMNSLRAEDTAMYYCAAGAYCGRLLLWIGNYAYWGQGTLVT
VSS

AS78117VH4-AS71529VH6 (SEQ ID NO: 244)
EVQLVESGGGLVQPGGSLRLSCIVSRYTYATYSMAWFRQAPGKGLEGVSGLDSVGATGYAESVKGR
FTISRDNSKNTLYLQMNSLRAEDTAVYYCVVDPASAKVTYGSWSTPSYAYWGQGTLVTVSSGGGG
SGGGGSGGGGSEVQLVESGGGLVQPGGSLRLSCAVSEYRYSSRYCMGWFRQAPGKGREGVAAIDS
NGSADYVDSVKGRFTISKDNSKNTLYLQMNSLRAEDTAMYYCAADHLAYDCYSGATSVFRYWGQ
GTLVTVSS

AS71529VH6-AS78117VH4 (SEQ ID NO: 245)
EVQLVESGGGLVQPGGSLRLSCAVSEYRYSSRYCMGWFRQAPGKGREGVAAIDSNGSADYVDSVK
GRFTISKDNSKNTLYLQMNSLRAEDTAMYYCAADHLAYDCYSGATSVFRYWGQGTLVTVSSGGGG
SGGGGSGGGGSEVQLVESGGGLVQPGGSLRLSCIVSRYTYATYSMAWFRQAPGKGLEGVSGLDSVG
ATGYAESVKGRFTISRDNSKNTLYLQMNSLRAEDTAVYYCVVDPASAKVTYGSWSTPSYAYWGQG
TLVTVSS

CAS70549-BBz (SEQ ID NO: 189)
MALPVTALLLPLALLLHAARPQVRLVESGGGSVQAGGSLTLSCAYSRYTGRSSCMAWFRRPPGKKR
ERVASIYSDDGVTVYADSVKGRFTITQDSAQNTLYLQMNSLDPEDTAMYYCATRTTYPGVCPDNAA
WYDYWGQGTQVTVSSTTTPAPRPPTPAPTIASQPLSLRPEACRPAAGGAVHTRGLDFACDIYIWAPL
AGTCGVLLLSLVITLYCKRGRKKLLYIFKQPFMRPVQTTQEEDGCSCRFPEEEEGGCELRVKFSRSAD
APAYKQGQNQLYNELNLGRREEYDVLDKRRGRDPEMGGKPRRKNPQEGLYNELQKDKMAEAYSEI
GMKGERRRGKGHDGLYQGLSTATKDTYDALHMQALPPR

CAS70771-BBz (SEQ ID NO: 190)
MALPVTALLLPLALLLHAARPQVQLVESGGGSVQAGGSLRLSCAASGYTGKMAWFRQAPGKEREG
VAAIDDAGGTNYIDSVKGRFTISKDNAENTLYLRMNSLKPEDTAIYYCAADTFRWFMRRSGPINGSD
YAYWGQGTQVTVSSTTTPAPRPPTPAPTIASQPLSLRPEACRPAAGGAVHTRGLDFACDIYIWAPLAG
TCGVLLLSLVITLYCKRGRKKLLYIFKQPFMRPVQTTQEEDGCSCRFPEEEEGGCELRVKFSRSADAP
AYKQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPR

CAS70950-BBz (SEQ ID NO: 191)
MALPVTALLLPLALLLHAARPQVQLVESGGGSAQSGGSLRLSCAISEFTYKNTCVGWFRQAPGKERE
GVAAIDSDGNTNYVDSVKGRFTISQGNAKNTVYLQMNSLKPEDTAMYYCAAGAYCGRLLLWIGNY
AYWGQGTQVTVSSTTTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGCELRVKFSRSADAPA
YKQGQNQLYNELNLGRREEYDVLDKRRGRDPEMGGKPRRKNPQEGLYNELQKDKMAEAYSEIGM
KGERRRGKGHDGLYQGLSTATKDTYDALHMQALPPR

CAS71402-BBz (SEQ ID NO: 192)
MALPVTALLLPLALLLHAARPQMQLVESGGGSVQAGGSLRLSCVVSGYTYNRNMAWFRQAPGKER
EGVAAMYTGSGTTDYADSVKGRFTISHDNAKNTLYLQMNSLKPEDTATYYCAADTARRGGSWSGP
FKYDYWGQGTQVTVSSTTTPAPRPPTPAPTIASQPLSLRPEACRPAAGGAVHTRGLDFACDIYIWAPL
AGTCGVLLLSLVITLYCKRGRKKLLYIFKQPFMRPVQTTQEEDGCSCRFPEEEEGGCELRVKFSRSAD
APAYKQGQNQLYNELNLGRREEYDVLDKRRGRDPEMGGKPRRKNPQEGLYNELQKDKMAEAYSEI
GMKGERRRGKGHDGLYQGLSTATKDTYDALHMQALPPR

-continued

SEQUENCE LISTING

CAS71529-BBz (SEQ ID NO: 193)
MALPVTALLLPLALLLHAARPEVQLVESGGGSVQAGGSLRLSCVVSEYRYSSRYCMGWFRQAPGKE
REGVAAIDSNGSADYVDSVKGRFTISKDNAKNTLYLQINSVRPEDTAMYYCAADHLAYDCYSGATS
VFRYWGQGTQVTVSSTTTPAPRPPTPAPTIASQPLSLRPEACRPAAGGAVHTRGLDFACDIYIWAPLA
GTCGVLLLSLVITLYCKRGRKKLLYIFKQPFMRPVQTTQEEDGCSCRFPEEEEGGCELRVKFSRSADA
PAYKQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPR

CAS71661-BBz (SEQ ID NO: 194)
MALPVTALLLPLALLLHAARPQVQLVESGGGLVQAGGSLRLSCSPSGTTFAHYNMVGWFRQAPGK
DREGVSCISKYGGTTYYADSVKGRFTIYRDNAKNTLFLQMNSLKPEDTAMYYCAIGVLPSSTAICAG
AANYWGQGTQVTVSSTTTPAPRPPTPAPTIASQPLSLRPEACRPAAGGAVHTRGLDFACDIYIWAPLA
GTCGVLLLSLVITLYCKRGRKKLLYIFKQPFMRPVQTTQEEDGCSCRFPEEEEGGCELRVKFSRSADA
PAYKQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPR

CAS72021-BBz (SEQ ID NO: 195)
MALPVTALLLPLALLLHAARPEVQLAESGGGSVQAGGSLRLSCVVSRNTYSSYCMSWFRQAPGKER
EGVAAIDNVKTSYADSVKGRFTISKDNAKNTLYLQMNSLKPEDTAMYYCAAHLELCYYTDPMYQY
EYNYWGQGTQVTVSSTTTPAPRPPTPAPTIASQPLSLRPEACRPAAGGAVHTRGLDFACDIYIWAPLA
GTCGVLLLSLVITLYCKRGRKKLLYIFKQPFMRPVQTTQEEDGCSCRFPEEEEGGCELRVKFSRSADA
PAYKQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPR

CAS72052-BBz (SEQ ID NO: 196)
MALPVTALLLPLALLLHAARPQVRLVESGGGSVQAGGSLRLSCAVSGFRYASYCMGWFRQAPGKE
REGVAAIHSDGIIRYAESVKGRFTISKDNAKNTLYLQLNSLKPEDNAMYSCAAGAYCGADAILTLYD
YAFWGQGTQVTVSSTTTPAPRPPTPAPTIASQPLSLRPEACRPAAGGAVHTRGLDFACDIYIWAPLAG
TCGVLLLSLVITLYCKRGRKKLLYIFKQPFMRPVQTTQEEDGCSCRFPEEEEGGCELRVKFSRSADAP
AYKQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPR

CAS72383-BBz (SEQ ID NO: 197)
MALPVTALLLPLALLLHAARPQVRLVESGGGLVQAGGSQRLSCTASGLTFDDSGMGWFRQAPGKG
REGVSCITWNGRSTYYADSVKGRFTISRDNSKNTLYLQMNSLKPEDTAMYYCAAAFITKTGCSYEY
DYSGQGTQVTVSSTTTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGCELRVKFSRSADAPA
YKQGQNQLYNELNLGRREEYDVLDKRRGRDPEMGGKPRRKNPQEGLYNELQKDKMAEAYSEIGM
KGERRRGKGHDGLYQGLSTATKDTYDALHMQALPPR

CAS72479-BBz (SEQ ID NO: 198)
MALPVTALLLPLALLLHAARPQVKLVESGGGSVQAGGSLRLSCAASETTDCRYVWRWYREDPGME
REFVSSITSGGSTWYADSVKGRFTISQDNAKSTLYLQMNSLKPEDSGMYYCESDPGWSGYHARRCE
VYRGQGIQVTVSSTTTPAPRPPTPAPTIASQPLSLRPEACRPAAGGAVHTRGLDFACDIYIWAPLAGTC
GVLLLSLVITLYCKRGRKKLLYIFKQPFMRPVQTTQEEDGCSCRFPEEEEGGCELRVKFSRSADAPAY
KQGQNQLYNELNLGRREEYDVLDKRRGRDPEMGGKPRRKNPQEGLYNELQKDKMAEAYSEIGMK
GERRRGKGHDGLYQGLSTATKDTYDALHMQALPPR

CAS72499-BBz (SEQ ID NO: 199)
MALPVTALLLPLALLLHAARPQVRLVESGGGSVQAGGSLRLSCVVSRFTYSSYCMGWFRQAPGKER
EGVAGIEKDDSTYYADSVKGRFTISKDNAKNTLYLQMNSLKPEDTAMYYCAARIPGGNCGVVARM
AYWDYWGKGTLVTVSSTTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEEEEGGCELRVKFSRSA
DAPAYKQGQNQLYNELNLGRREEYDVLDKRRGRDPEMGGKPRRKNPQEGLYNELQKDKMAEAYS
EIGMKGERRRGKGHDGLYQGLSTATKDTYDALHMQALPPR

CAS72531-BBz (SEQ ID NO: 200)
MALPVTALLLPLALLLHAARPQVQLVESGGGLVQAGGSLRLSCTASGLTFAHYNMVGWFRQAPGK
DREGVSCISKYGGTIYYADSVKGRFTIDRNNAKNTLYLQMNSLKPEDTAMYYCAIGVLSSTARGPGA
ANYWGQGTQVTVSSTTTPAPRPPTPAPTIASQPLSLRPEACRPAAGGAVHTRGLDFACDIYIWAPLAG
TCGVLLLSLVITLYCKRGRKKLLYIFKQPFMRPVQTTQEEDGCSCRFPEEEEGGCELRVKFSRSADAP
AYKQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPR

CAS72669-BBz (SEQ ID NO: 201)
MALPVTALLLPLALLLHAARPEVQLVESGGGSVQAGGSLKLSCAASRFTYSSYCMGWIRQAPGKER
EGVAIFYTGGGRTYYADSVKGRFTISQDTAKNTLYLQMNSLKPEDTGIYYCVAGFYCSGGYWEGDF
GYWGQGTQVTVSSTTTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGCELRVKFSRSADAPA
YKQGQNQLYNELNLGRREEYDVLDKRRGRDPEMGGKPRRKNPQEGLYNELQKDKMAEAYSEIGM
KGERRRGKGHDGLYQGLSTATKDTYDALHMQALPPR

CAS72794-BBz (SEQ ID NO: 202)
MALPVTALLLPLALLLHAARPQVQLVESGGGLVQAGGSLRLSCTASGFTFDDYAMSWFRQAPGKER
EGVSCISASGTTTYYGDSVKGRFTISRDNAKTTLILQMSSLKPEDTAMYYCAADRFRDYCSDSWSHL
YNYEYMHWGQGTQVTVSSTTTPAPRPPTPAPTIASQPLSLRPEACRPAAGGAVHTRGLDFACDIYIW

SEQUENCE LISTING

APLAGTCGVLLLSLVITLYCKRGRKKLLYIFKQPFMRPVQTTQEEDGCSCRFPEEEEGGCELRVKFSR
SADAPAYKQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR

CAS72805-BBz (SEQ ID NO: 203)
MALPVTALLLPLALLLHAARPQVQLVESGGDSVQAGGSLTLSCVASRLRVSNNCMGWFRQAPGNE
REGVATLGSDGRTIYADSVKGRFTISKDNVANTLYLQMNGLKLDDTALYYCAAADFSSGGYCNIAS
VYHSYFPYWGQGTQVTVSSTTTPAPRPPTPAPTIASQPLSLRPEACRPAAGGAVHTRGLDFACDIYIW
APLAGTCGVLLLSLVITLYCKRGRKKLLYIFKQPFMRPVQTTQEEDGCSCRFPEEEEGGCELRVKFSR
SADAPAYKQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR

CAS72806-BBz (SEQ ID NO: 204)
MALPVTALLLPLALLLHAARPQVQLVESGGGSVQAGGSLRLSCAASGYTYMPPCMGWFRQAPGKE
REGVATIYGRGGSTYYADSVKGRFTISQDNAKNTLYLQMNNLEPEDTAMYYCAADNLCYATGILRS
AYDYSYWGQGTQVTVSSTTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEEEEGGCELRVKFSRSA
DAPAYKQGQNQLYNELNLGRREEYDVLDKRRGRDPEMGGKPRRKNPQEGLYNELQKDKMAEAYS
EIGMKGERRRGKGHDGLYQGLSTATKDTYDALHMQALPPR

CAS72835-BBz (SEQ ID NO: 205)
MALPVTALLLPLALLLHAARPQVHLMESGGGSVQAGGSLRLSCAVSGGYTSRTVCMGWFRQTPGK
EREVLAAIYRSGTTYYHDSVKGRFTISRDGDKNTVYLQMDSLKPEDTAMYYCAASPGYSDAACVSV
PQANRWGQGTQVTVSSTTTPAPRPPTPAPTIASQPLSLRPEACRPAAGGAVHTRGLDFACDIYIWAPL
AGTCGVLLLSLVITLYCKRGRKKLLYIFKQPFMRPVQTTQEEDGCSCRFPEEEEGGCELRVKFSRSAD
APAYKQGQNQLYNELNLGRREEYDVLDKRRGRDPEMGGKPRRKNPQEGLYNELQKDKMAEAYSEI
GMKGERRRGKGHDGLYQGLSTATKDTYDALHMQALPPR

CAS77906-BBz (SEQ ID NO: 206)
MALPVTALLLPLALLLHAARPQVRLVESGGGSVQAGESLRLSCARSGVVKCDVEMRWYRQSPGKE
REFVALIEAGGHTEYADSVKGRFTISQDNAKMLFYLQMNSLKPEDTAKYYCVAAPRYYTLSCPKDF
WGRGTQVTVSSTTTPAPRPPTPAPTIASQPLSLRPEACRPAAGGAVHTRGLDFACDIYIWAPLAGTCG
VLLLSLVITLYCKRGRKKLLYIFKQPFMRPVQTTQEEDGCSCRFPEEEEGGCELRVKFSRSADAPAYK
QGQNQLYNELNLGRREEYDVLDKRRGRDPEMGGKPRRKNPQEGLYNELQKDKMAEAYSEIGMKG
ERRRGKGHDGLYQGLSTATKDTYDALHMQALPPR

CAS77916-BBz (SEQ ID NO: 207)
MALPVTALLLPLALLLHAARPQVHLMESGGGSVQAGGSLRLSCATSGYTSSWNCMGWFRQPPGKE
REGVATIANRGHSTYYADSVKGRFTISQGNAKNTVYLQMNSLKPEDTAMYYCATDTWACVGISTDF
EYWGQGTQVTVSSTTTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGCELRVKFSRSADAPA
YKQGQNQLYNELNLGRREEYDVLDKRRGRDPEMGGKPRRKNPQEGLYNELQKDKMAEAYSEIGM
KGERRRGKGHDGLYQGLSTATKDTYDALHMQALPPR

CAS77932-BBz (SEQ ID NO: 208)
MALPVTALLLPLALLLHAARPQVQLKESGGGSVQAGGSLRLSCAVSGYWYSVAWMGWFRQTPGK
EREGVAAVLNGGGRRYYADSVKGRFTISQDNSKNTLYLQMNSLKPEDTAMYYCAAGNGVGHPLGP
SEYNYWGQGTQVTVSSTTTPAPRPPTPAPTIASQPLSLRPEACRPAAGGAVHTRGLDFACDIYIWAPL
AGTCGVLLLSLVITLYCKRGRKKLLYIFKQPFMRPVQTTQEEDGCSCRFPEEEEGGCELRVKFSRSAD
APAYKQGQNQLYNELNLGRREEYDVLDKRRGRDPEMGGKPRRKNPQEGLYNELQKDKMAEAYSEI
GMKGERRRGKGHDGLYQGLSTATKDTYDALHMQALPPR

CAS77934-BBz (SEQ ID NO: 209)
MALPVTALLLPLALLLHAARPEVQLVESGGGSVQAGGSLRLSCAASGYTYSSYSIAWFRQAPGKERE
GVAGFFYSGGPTCYADSVKGRFTISQDNAKNTLYLQMNSLKPEDTAMYYCAARRSNTNDYCFYPTY
TYWGQGTQVTVSSTTTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGCELRVKFSRSADAPA
YKQGQNQLYNELNLGRREEYDVLDKRRGRDPEMGGKPRRKNPQEGLYNELQKDKMAEAYSEIGM
KGERRRGKGHDGLYQGLSTATKDTYDALHMQALPPR

CAS77978-BBz (SEQ ID NO: 210)
MALPVTALLLPLALLLHAARPQVRLVESGGGSVQAGGSLRLSCAASGATSCRWRMSWYRQAPGKE
REFVSSIANGATEYADSVKGRFTISQDNARNTMYLQMNSLSPEDTAMYYCAADPRVYTSRCDRTYL
GQGTQVTVSSTTTPAPRPPTPAPTIASQPLSLRPEACRPAAGGAVHTRGLDFACDIYIWAPLAGTCGV
LLLSLVITLYCKRGRKKLLYIFKQPFMRPVQTTQEEDGCSCRFPEEEEGGCELRVKFSRSADAPAYKQ
GQNQLYNELNLGRREEYDVLDKRRGRDPEMGGKPRRKNPQEGLYNELQKDKMAEAYSEIGMKGE
RRRGKGHDGLYQGLSTATKDTYDALHMQALPPR

CAS77986-BBz (SEQ ID NO: 211)
MALPVTALLLPLALLLHAARPQVQLVESGGGSVQAGGSLRLSCAASASGYTYSSDSMAWFRQAPGK
EREGVAGISTGGRSTYYADSVKGRFTISQDNAKTTVYLHMNSLKPEDTAMYYCAADGPSMTAIQAL
GDLYPVDFAWWGQGTQVTVSSTTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSCRFPEEEEGGCELRVK
FSRSADAPAYKQGQNQLYNELNLGRREEYDVLDKRRGRDPEMGGKPRRKNPQEGLYNELQKDKM
AEAYSEIGMKGERRRGKGHDGLYQGLSTATKDTYDALHMQALPPR

-continued

SEQUENCE LISTING

CAS78117-BBz (SEQ ID NO: 212)
MALPVTALLLPLALLLHAARPQVKLVESGGGSVQAGGALRLSCIVRRYTYATYSMAWFRQSPGKER
EGVAGLDSVGATGYAESVKGRFTISKDNAKNILYLQMNSLKPEDTAMYYCVVDPASAKVTYGSWS
TPSYAYWGQGTQVTVSSTTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEEEEGGCELRVKFSRSA
DAPAYKQGQNQLYNELNLGRREEYDVLDKRRGRDPEMGGKPRRKNPQEGLYNELQKDKMAEAYS
EIGMKGERRRGKGHDGLYQGLSTATKDTYDALHMQALPPR

CAS78215-BBz (SEQ ID NO: 213)
MALPVTALLLPLALLLHAARPQVKLVESGGGSVQAGGALRLSCAASRYTFSSNCMGWFRQAPGKER
EGVATIASASGYTDYHDSVKGRFAISRDNAKNTVYLQMNSLKPEDTATYYCAARAGPCWSWAQAD
LYNYWGQGTQVTVSSTTTPAPRPPTPAPTIASQPLSLRPEACRPAAGGAVHTRGLDFACDIYIWAPLA
GTCGVLLLSLVITLYCKRGRKKLLYIFKQPFMRPVQTTQEEDGCSCRFPEEEEGGCELRVKFSRSADA
PAYKQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPR

CAS78810-BBz (SEQ ID NO: 214)
MALPVTALLLPLALLLHAARPQVHLVESGGGSVQAGGSLRLSCAASGYTYYDMGWFRLAPGKERE
GIAAISSSSSTYYADSVKGRFTISRDSNTLYLQMNSLKPEDTAMYSCAAGRYVGRKLEVYDYAYWG
QGTQVTVSSTTTPAPRPPTPAPTIASQPLSLRPEACRPAAGGAVHTRGLDFACDIYIWAPLAGTCGVL
LLSLVITLYCKRGRKKLLYIFKQPFMRPVQTTQEEDGCSCRFPEEEEGGCELRVKFSRSADAPAYKQG
QNQLYNELNLGRREEYDVLDKRRGRDPEMGGKPRRKNPQEGLYNELQKDKMAEAYSEIGMKGER
RRGKGHDGLYQGLSTATKDTYDALHMQALPPR

CAS79101-BBz (SEQ ID NO: 215)
MALPVTALLLPLALLLHAARPQVQLVESGGGSVQAGGSLRLSCAASGDTYSNYCMGWFRQAPGKE
REEVAAIDSDGSRRYPDSVKGRFTISKDNAKKILYLQMNSLKPEDTAMYFCATDPKVACARVVEYG
GGWYRWGQGTQVTVSSTTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEEEEGGCELRVKFSRSA
DAPAYKQGQNQLYNELNLGRREEYDVLDKRRGRDPEMGGKPRRKNPQEGLYNELQKDKMAEAYS
EIGMKGERRRGKGHDGLYQGLSTATKDTYDALHMQALPPR

CAS79236-BBz (SEQ ID NO: 216)
MALPVTALLLPLALLLHAARPQVKLVESGGGSVQAGGSLRLSCAVSGYTYSSYCMAWFRQAPGEER
EGVASIDAGGRTTYVDSVKGRFTISKDNAKTSLYLQMNSLKPEDTAMYYCAVDVRTRCGGTWDGE
AVYFPYWGQGTQVTVSSTTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEEEEGGCELRVKFSRSA
DAPAYKQGQNQLYNELNLGRREEYDVLDKRRGRDPEMGGKPRRKNPQEGLYNELQKDKMAEAYS
EIGMKGERRRGKGHDGLYQGLSTATKDTYDALHMQALPPR

CAS79274-BBz (SEQ ID NO: 217)
MALPVTALLLPLALLLHAARPQVHLVESGGGSVQAGGSLRLSCAASKYAFCTYDMSWFRQAPGKE
REVVSSIDSRGNTNYSDSVKGRFTISQDHAKNTLYLQMNSLKPEDTAMYTCAAQIVGGALRCPRFA
MYWGQGTQVTVSSTTTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGCELRVKFSRSADAPA
YKQGQNQLYNELNLGRREEYDVLDKRRGRDPEMGGKPRRKNPQEGLYNELQKDKMAEAYSEIGM
KGERRRGKGHDGLYQGLSTATKDTYDALHMQALPPR

CAS79285-BBz (SEQ ID NO: 218)
MALPVTALLLPLALLLHAARPQVRLVESGGGSVQAGGSLALSCETSRYTVSNYCMGWFRQVSGKEV
EGVALISTDGTTTYADSVKGRFTISKDNAKNTLYLQMNSLKSEDTAMYFCAGVYGLIWYYKPCPAQ
REWALQRYGYWGQGTQVTVSSTTTPAPRPPTPAPTIASQPLSLRPEACRPAAGGAVHTRGLDFACDI
YIWAPLAGTCGVLLLSLVITLYCKRGRKKLLYIFKQPFMRPVQTTQEEDGCSCRFPEEEEGGCELRVK
FSRSADAPAYKQGQNQLYNELNLGRREEYDVLDKRRGRDPEMGGKPRRKNPQEGLYNELQKDKM
AEAYSEIGMKGERRRGKGHDGLYQGLSTATKDTYDALHMQALPPR

CAS79317-BBz (SEQ ID NO: 219)
MALPVTALLLPLALLLHAARPEVQLAESGGGSVQPGGSLRLSCAASGYSSSSVCMGWFRQAPGKER
EGVAIIYVTLGSIAYADSVKGRFTISRDNAKNTLDLEMNSLKPDDTALYYCAAGGCGYRGVADVPEF
TYRGQGTQVTVSSTTTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGCELRVKFSRSADAPA
YKQGQNQLYNELNLGRREEYDVLDKRRGRDPEMGGKPRRKNPQEGLYNELQKDKMAEAYSEIGM
KGERRRGKGHDGLYQGLSTATKDTYDALHMQALPPR

CAS70950VH6-BBz (SEQ ID NO: 220)
MALPVTALLLPLALLLHAARPEVQLVESGGGLVQPGGSLRLSCAISEFTYKNTCVGWFRQAPGKGRE
GVAAIDSDGNTNYVDSVKGRFTISQDNSKNTVYLQMNSLRAEDTAMYYCAAGAYCGRLLLWIGNY
AYWGQGTLVTVSSTTTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGCELRVKFSRSADAPA
YKQGQNQLYNELNLGRREEYDVLDKRRGRDPEMGGKPRRKNPQEGLYNELQKDKMAEAYSEIGM
KGERRRGKGHDGLYQGLSTATKDTYDALHMQALPPR

CAS70950VH7-BBz (SEQ ID NO: 221)
MALPVTALLLPLALLLHAARPEVQLVESGGGLVQPGGSLRLSCAASEFTYKNTCVGWFRQAPGKGR
EGVAAIDSDGNTNYVDSVKGRFTISRDNSKNTVYLQMNSLRAEDTAMYYCAAGAYCGRLLLWIGN
YAYWGQGTLVTVSSTTTPAPRPPTPAPTIASQPLSLRPEACRPAAGGAVHTRGLDFACDIYIWAPLAG

-continued

SEQUENCE LISTING

TCGVLLLSLVITLYCKRGRKKLLYIFKQPFMRPVQTTQEEDGCSCRFPEEEEGGCELRVKFSRSADAP
AYKQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPR

CAS71529VH5-BBz (SEQ ID NO: 222)
MALPVTALLLPLALLLHAARPEVQLVESGGGLVQPGGSLRLSCAVSEYRYSSRYCMGWFRQAPGKG
LEGVSAIDSNGSADYVDSVKGRFTISKDNSKNTLYLQMNSLRAEDTAVYYCAADHLAYDCYSGATS
VFRYWGQGTLVTVSSTTTPAPRPPTPAPTIASQPLSLRPEACRPAAGGAVHTRGLDFACDIYIWAPLA
GTCGVLLLSLVITLYCKRGRKKLLYIFKQPFMRPVQTTQEEDGCSCRFPEEEEGGCELRVKFSRSADA
PAYKQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPR

CAS71529VH6-BBz (SEQ ID NO: 223)
MALPVTALLLPLALLLHAARPEVQLVESGGGLVQPGGSLRLSCAVSEYRYSSRYCMGWFRQAPGKG
REGVAAIDSNGSADYVDSVKGRFTISKDNSKNTLYLQMNSLRAEDTAMYYCAADHLAYDCYSGAT
SVFRYWGQGTLVTVSSTTTPAPRPPTPAPTIASQPLSLRPEACRPAAGGAVHTRGLDFACDIYIWAPL
AGTCGVLLLSLVITLYCKRGRKKLLYIFKQPFMRPVQTTQEEDGCSCRFPEEEEGGCELRVKFSRSAD
APAYKQGQNQLYNELNLGRREEYDVLDKRRGRDPEMGGKPRRKNPQEGLYNELQKDKMAEAYSEI
GMKGERRRGKGHDGLYQGLSTATKDTYDALHMQALPPR

CAS72052VH5-BBz (SEQ ID NO: 224)
MALPVTALLLPLALLLHAARPQVQLVESGGGVVQPGGSLRLSCAVSGFRYASYCMGWFRQAPGKG
LEGVAAIHSDGIIRYAESVKGRFTISKDNSKNTLYLQMNSLRAEDTAVYYCAAGAYCGADAILTLYD
YAFWGQGTLVTVSSTTTPAPRPPTPAPTIASQPLSLRPEACRPAAGGAVHTRGLDFACDIYIWAPLAG
TCGVLLLSLVITLYCKRGRKKLLYIFKQPFMRPVQTTQEEDGCSCRFPEEEEGGCELRVKFSRSADAP
AYKQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPR

CAS72052VH6-BBz (SEQ ID NO: 225)
MALPVTALLLPLALLLHAARPQVQLVESGGGVVQPGGSLRLSCAVSGFRYASYCMGWFRQAPGKG
LEGVAAIHSDGIIRYAESVKGRFTISKDNSKNTLYLQMNSLRAEDTAMYSCAAGAYCGADAILTLYD
YAFWGQGTLVTVSSTTTPAPRPPTPAPTIASQPLSLRPEACRPAAGGAVHTRGLDFACDIYIWAPLAG
TCGVLLLSLVITLYCKRGRKKLLYIFKQPFMRPVQTTQEEDGCSCRFPEEEEGGCELRVKFSRSADAP
AYKQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPR

CAS72669VH6-BBz (SEQ ID NO: 226)
MALPVTALLLPLALLLHAARPQVQLVESGGGVVQPGGSLRLSCAASRFTYSSYCMGWIRQAPGKGR
EGVAIFYTGGGRTYYADSVKGRFTISQDNSKNTLYLQMNSLRAEDTAVYYCVAGFYCSGGYWEGD
FGYWGQGTLVTVSSTTTPAPRPPTPAPTIASQPLSLRPEACRPAAGGAVHTRGLDFACDIYIWAPLAG
TCGVLLLSLVITLYCKRGRKKLLYIFKQPFMRPVQTTQEEDGCSCRFPEEEEGGCELRVKFSRSADAP
AYKQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPR

CAS78117VH4-BBz (SEQ ID NO: 227)
MALPVTALLLPLALLLHAARPEVQLVESGGGLVQPGGSLRLSCIVSRYTYATYSMAWFRQAPGKGL
EGVSGLDSVGATGYAESVKGRFTISRDNSKNTLYLQMNSLRAEDTAVYYCVVDPASAKVTYGSWST
PSYAYWGQGTLVTVSSTTTPAPRPPTPAPTIASQPLSLRPEACRPAAGGAVHTRGLDFACDIYIWAPL
AGTCGVLLLSLVITLYCKRGRKKLLYIFKQPFMRPVQTTQEEDGCSCRFPEEEEGGCELRVKFSRSAD
APAYKQGQNQLYNELNLGRREEYDVLDKRRGRDPEMGGKPRRKNPQEGLYNELQKDKMAEAYSEI
GMKGERRRGKGHDGLYQGLSTATKDTYDALHMQALPPR

CAS78117VH5-BBz (SEQ ID NO: 228)
MALPVTALLLPLALLLHAARPEVQLVESGGGLVQPGGSLRLSCIVSRYTYATYSMAWFRQAPGKGL
EGVSGLDSVGATGYAESVKGRFTISKDNSKNTLYLQMNSLRAEDTAVYYCVVDPASAKVTYGSWS
TPSYAYWGQGTLVTVSSTTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEEEEGGCELRVKFSRSA
DAPAYKQGQNQLYNELNLGRREEYDVLDKRRGRDPEMGGKPRRKNPQEGLYNELQKDKMAEAYS
EIGMKGERRRGKGHDGLYQGLSTATKDTYDALHMQALPPR

CAS78117VH6-BBz (SEQ ID NO: 229)
MALPVTALLLPLALLLHAARPEVQLVESGGGLVQPGGSLRLSCIVSRYTYATYSMAWFRQAPGKGL
EGVSGLDSVGATGYAESVKGRFTISKDNSKNTLYLQMNSLRAEDTAMYYCVVDPASAKVTYGSWS
TPSYAYWGQGTLVTVSSTTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEEEEGGCELRVKFSRSA
DAPAYKQGQNQLYNELNLGRREEYDVLDKRRGRDPEMGGKPRRKNPQEGLYNELQKDKMAEAYS
EIGMKGERRRGKGHDGLYQGLSTATKDTYDALHMQALPPR

CAS78117VH7-BBz (SEQ ID NO: 230)
MALPVTALLLPLALLLHAARPEVQLVESGGGLVQPGGSLRLSCIVSRYTYATYSMAWFRQAPGKGL
EGVAGLDSVGATGYAESVKGRFTISKDNSKNTLYLQMNSLRAEDTAMYYCVVDPASAKVTYGSWS
TPSYAYWGQGTLVTVSSTTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEEEEGGCELRVKFSRSA
DAPAYKQGQNQLYNELNLGRREEYDVLDKRRGRDPEMGGKPRRKNPQEGLYNELQKDKMAEAYS
EIGMKGERRRGKGHDGLYQGLSTATKDTYDALHMQALPPR

-continued

SEQUENCE LISTING

CAS79236VH4-BBz (SEQ ID NO: 231)
MALPVTALLLPLALLLHAARPEVQLVESGGGLVQPGGSLRLSCAASGYTYSSYCMAWFRQAPGKGL
EGVASIDAGGRTTYVDSVKGRFTISRDNAKNSLYLQMNSLRAEDTAVYYCAVDVRTRCGGTWDGE
AVYFPYWGQGTLVTVSSTTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEEEEGGCELRVKFSRSA
DAPAYKQGQNQLYNELNLGRREEYDVLDKRRGRDPEMGGKPRRKNPQEGLYNELQKDKMAEAYS
EIGMKGERRRGKGHDGLYQGLSTATKDTYDALHMQALPPR

CAS79236VH5-BBz (SEQ ID NO: 232)
MALPVTALLLPLALLLHAARPEVQLVESGGGLVQPGGSLRLSCAVSGYTYSSYCMAWFRQAPGKGL
EGVASIDAGGRTTYVDSVKGRFTISKDNAKNSLYLQMNSLRAEDTAVYYCAVDVRTRCGGTWDGE
AVYFPYWGQGTLVTVSSTTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEEEEGGCELRVKFSRSA
DAPAYKQGQNQLYNELNLGRREEYDVLDKRRGRDPEMGGKPRRKNPQEGLYNELQKDKMAEAYS
EIGMKGERRRGKGHDGLYQGLSTATKDTYDALHMQALPPR

CAS79236VH6-BBz (SEQ ID NO: 233)
MALPVTALLLPLALLLHAARPEVQLVESGGGLVQPGGSLRLSCAVSGYTYSSYCMAWFRQAPGKGL
EGVASIDAGGRTTYVDSVKGRFTISKDNAKNSLYLQMNSLRAEDTAMYYCAVDVRTRCGGTWDGE
AVYFPYWGQGTLVTVSSTTTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRFPEEEEGGCELRVKFSRSA
DAPAYKQGQNQLYNELNLGRREEYDVLDKRRGRDPEMGGKPRRKNPQEGLYNELQKDKMAEAYS
EIGMKGERRRGKGHDGLYQGLSTATKDTYDALHMQALPPR

CAS77916VH6-BBz (SEQ ID NO: 234)
MALPVTALLLPLALLLHAARPEVQLVESGGGLVQPGGSLRLSCATSGYTSSWNCMGWFRQAPGKGL
EGVATIANRGHSTYYADSVKGRFTISQDNSKNTLYLQMNSLRAEDTAVYYCATDTWACVGISTDFE
YWGQGTLVTVSSTTTPAPRPPTPAPTIASQPLSLRPEACRPAAGGAVHTRGLDFACDIYIWAPLAGTC
GVLLLSLVITLYCKRGRKKLLYIFKQPFMRPVQTTQEEDGCSCRFPEEEEGGCELRVKFSRSADAPAY
KQGQNQLYNELNLGRREEYDVLDKRRGRDPEMGGKPRRKNPQEGLYNELQKDKMAEAYSEIGMK
GERRRGKGHDGLYQGLSTATKDTYDALHMQALPPR

CAS77916VH7-BBz (SEQ ID NO: 235)
MALPVTALLLPLALLLHAARPEVQLVESGGGLVQPGGSLRLSCATSGYTSSWNCMGWFRQAPGKGL
EGVATIANRGHSTYYADSVKGRFTISQDNSKNTLYLQMNSLRAEDTAMYYCATDTWACVGISTDFE
YWGQGTLVTVSSTTTPAPRPPTPAPTIASQPLSLRPEACRPAAGGAVHTRGLDFACDIYIWAPLAGTC
GVLLLSLVITLYCKRGRKKLLYIFKQPFMRPVQTTQEEDGCSCRFPEEEEGGCELRVKFSRSADAPAY
KQGQNQLYNELNLGRREEYDVLDKRRGRDPEMGGKPRRKNPQEGLYNELQKDKMAEAYSEIGMK
GERRRGKGHDGLYQGLSTATKDTYDALHMQALPPR

CAS77916VH8-BBz (SEQ ID NO: 236)
MALPVTALLLPLALLLHAARPEVQLVESGGGLVQPGGSLRLSCATSGYTSSWNCMGWFRQAPGKGL
EGVATIANRGHSTYYADSVKGRFTISQDNSKNTVYLQMNSLRAEDTAVYYCATDTWACVGISTDFE
YWGQGTLVTVSSTTTPAPRPPTPAPTIASQPLSLRPEACRPAAGGAVHTRGLDFACDIYIWAPLAGTC
GVLLLSLVITLYCKRGRKKLLYIFKQPFMRPVQTTQEEDGCSCRFPEEEEGGCELRVKFSRSADAPAY
KQGQNQLYNELNLGRREEYDVLDKRRGRDPEMGGKPRRKNPQEGLYNELQKDKMAEAYSEIGMK
GERRRGKGHDGLYQGLSTATKDTYDALHMQALPPR

CAS77916VH9-BBz (SEQ ID NO: 237)
MALPVTALLLPLALLLHAARPEVQLVESGGGLVQPGGSLRLSCATSGYTSSWNCMGWFRQAPGKG
REGVATIANRGHSTYYADSVKGRFTISQDNSKNTLYLQMNSLRAEDTAVYYCATDTWACVGISTDF
EYWGQGTLVTVSSTTTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGCELRVKFSRSADAPA
YKQGQNQLYNELNLGRREEYDVLDKRRGRDPEMGGKPRRKNPQEGLYNELQKDKMAEAYSEIGM
KGERRRGKGHDGLYQGLSTATKDTYDALHMQALPPR

CAS77916VH10-BBz (SEQ ID NO: 238)
MALPVTALLLPLALLLHAARPEVQLVESGGGLVQPGGSLRLSCATSGYTSSWNCMGWFRQAPGKG
REGVATIANRGHSTYYADSVKGRFTISQDNSKNTVYLQMNSLRAEDTAVYYCATDTWACVGISTDF
EYWGQGTLVTVSSTTTPAPRPPTPAPTIASQPLSLRPEACRPAAGGAVHTRGLDFACDIYIWAPLAGT
CGVLLLSLVITLYCKRGRKKLLYIFKQPFMRPVQTTQEEDGCSCRFPEEEEGGCELRVKFSRSADAPA
YKQGQNQLYNELNLGRREEYDVLDKRRGRDPEMGGKPRRKNPQEGLYNELQKDKMAEAYSEIGM
KGERRRGKGHDGLYQGLSTATKDTYDALHMQALPPR

CAS71529VH5-AS72052VH5-BBz (SEQ ID NO: 239)
MALPVTALLLPLALLLHAARPEVQLVESGGGLVQPGGSLRLSCAVSEYRYSSRYCMGWFRQAPGKG
LEGVSAIDSNGSADYVDSVKGRFTISKDNSKNTLYLQMNSLRAEDTAVYYCAADHLAYDCYSGATS
VFRYWGQGTLVTVSSGGGGSGGGGSGGGGSQVQLVESGGGVVQPGGSLRLSCAVSGFRYASYCMG
WFRQAPGKGLEGVAAIHSDGIIRYAESVKGRFTISKDNSKNTLYLQMNSLRAEDTAVYYCAAGAYC
GADAILTLYDYAFWGQGTLVTVSSTTTPAPRPPTPAPTIASQPLSLRPEACRPAAGGAVHTRGLDFAC
DIYIWAPLAGTCGVLLLSLVITLYCKRGRKKLLYIFKQPFMRPVQTTQEEDGCSCRFPEEEEGGCELR
VKFSRSADAPAYKQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPR

-continued

SEQUENCE LISTING

CAS72052VH5-AS71529VH5-BBz (SEQ ID NO: 240)
MALPVTALLLPLALLLHAARPQVQLVESGGGVVQPGGSLRLSCAVSGFRYASYCMGWFRQAPGKG
LEGVAAIHSDGIIRYAESVKGRFTISKDNSKNTLYLQMNSLRAEDTAVYYCAAGAYCGADAILTLYD
YAFWGQGTLVTVSSGGGGSGGGGSGGGGSEVQLVESGGGLVQPGGSLRLSCAVSEYRYSSRYCMG
WFRQAPGKGLEGVSAIDSNGSADYVDSVKGRFTISKDNSKNTLYLQMNSLRAEDTAVYYCAADHL
AYDCYSGATSVFRYWGQGTLVTVSSTTTPAPRPPTPAPTIASQPLSLRPEACRPAAGGAVHTRGLDFA
CDIYIWAPLAGTCGVLLLSLVITLYCKRGRKKLLYIFKQPFMRPVQTTQEEDGCSCRFPEEEEGGCEL
RVKFSRSADAPAYKQGQNQLYNELNLGRREEYDVLDKRRGRDPEMGGKPRRKNPQEGLYNELQKD
KMAEAYSEIGMKGERRRGKGHDGLYQGLSTATKDTYDALHMQALPPR

CAS70950VH6-AS71529VH6-BBz (SEQ ID NO: 241)
MALPVTALLLPLALLLHAARPEVQLVESGGGLVQPGGSLRLSCAISEFTYKNTCVGWFRQAPGKGRE
GVAAIDSDGNTNYVDSVKGRFTISQDNSKNTVYLQMNSLRAEDTAMYYCAAGAYCGRLLLWIGNY
AYWGQGTLVTVSSGGGGSGGGGSGGGGSEVQLVESGGGLVQPGGSLRLSCAVSEYRYSSRYCMGW
FRQAPGKGREGVAAIDSNGSADYVDSVKGRFTISKDNSKNTLYLQMNSLRAEDTAMYYCAADHLA
YDCYSGATSVFRYWGQGTLVTVSSTTTPAPRPPTPAPTIASQPLSLRPEACRPAAGGAVHTRGLDFAC
DIYIWAPLAGTCGVLLLSLVITLYCKRGRKKLLYIFKQPFMRPVQTTQEEDGCSCRFPEEEEGGCELR
VKFSRSADAPAYKQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPR

CAS71529VH6-AS70950VH6-BBz (SEQ ID NO: 242)
MALPVTALLLPLALLLHAARPEVQLVESGGGLVQPGGSLRLSCAVSEYRYSSRYCMGWFRQAPGKG
REGVAAIDSNGSADYVDSVKGRFTISKDNSKNTLYLQMNSLRAEDTAMYYCAADHLAYDCYSGAT
SVFRYWGQGTLVTVSSGGGGSGGGGSGGGGSEVQLVESGGGLVQPGGSLRLSCAISEFTYKNTCVG
WFRQAPGKGREGVAAIDSDGNTNYVDSVKGRFTISQDNSKNTVYLQMNSLRAEDTAMYYCAAGA
YCGRLLLWIGNYAYWGQGTLVTVSSTTTPAPRPPTPAPTIASQPLSLRPEACRPAAGGAVHTRGLDF
ACDIYIWAPLAGTCGVLLLSLVITLYCKRGRKKLLYIFKQPFMRPVQTTQEEDGCSCRFPEEEEGGCE
LRVKFSRSADAPAYKQGQNQLYNELNLGRREEYDVLDKRRGRDPEMGGKPRRKNPQEGLYNELQK
DKMAEAYSEIGMKGERRRGKGHDGLYQGLSTATKDTYDALHMQALPPR

CAS70950VH6-AS70950VH6-BBz (SEQ ID NO: 243)
MALPVTALLLPLALLLHAARPEVQLVESGGGLVQPGGSLRLSCAISEFTYKNTCVGWFRQAPGKGRE
GVAAIDSDGNTNYVDSVKGRFTISQDNSKNTVYLQMNSLRAEDTAMYYCAAGAYCGRLLLWIGNY
AYWGQGTLVTVSSGGGGSGGGGSGGGGSEVQLVESGGGLVQPGGSLRLSCAISEFTYKNTCVGWFR
QAPGKGREGVAAIDSDGNTNYVDSVKGRFTISQDNSKNTVYLQMNSLRAEDTAMYYCAAGAYCGR
LLLWIGNYAYWGQGTLVTVSSTTTPAPRPPTPAPTIASQPLSLRPEACRPAAGGAVHTRGLDFACDIY
IWAPLAGTCGVLLLSLVITLYCKRGRKKLLYIFKQPFMRPVQTTQEEDGCSCRFPEEEEGGCELRVKF
SRSADAPAYKQGQNQLYNELNLGRREEYDVLDKRRGRDPEMGGKPRRKNPQEGLYNELQKDKMA
EAYSEIGMKGERRRGKGHDGLYQGLSTATKDTYDALHMQALPPR

CAS78117VH4-AS71529VH6-BBz (SEQ ID NO: 246)
MALPVTALLLPLALLLHAARPEVQLVESGGGLVQPGGSLRLSCIVSRYTYATYSMAWFRQAPGKGL
EGVSGLDSVGATGYAESVKGRFTISRDNSKNTLYLQMNSLRAEDTAVYYCVVDPASAKVTYGSWST
PSYAYWGQGTLVTVSSGGGGSGGGGSGGGGSEVQLVESGGGLVQPGGSLRLSCAVSEYRYSSRYC
MGWFRQAPGKGREGVAAIDSNGSADYVDSVKGRFTISKDNSKNTLYLQMNSLRAEDTAMYYCAA
DHLAYDCYSGATSVFRYWGQGTLVTVSSTTTPAPRPPTPAPTIASQPLSLRPEACRPAAGGAVHTRG
LDFACDIYIWAPLAGTCGVLLLSLVITLYCKRGRKKLLYIFKQPFMRPVQTTQEEDGCSCRFPEEEEG
GCELRVKFSRSADAPAYKQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR

CAS71529VH6-AS78117VH4-BBz (SEQ ID NO: 247)
MALPVTALLLPLALLLHAARPEVQLVESGGGLVQPGGSLRLSCAVSEYRYSSRYCMGWFRQAPGKG
REGVAAIDSNGSADYVDSVKGRFTISKDNSKNTLYLQMNSLRAEDTAMYYCAADHLAYDCYSGAT
SVFRYWGQGTLVTVSSGGGGSGGGGSGGGGSEVQLVESGGGLVQPGGSLRLSCIVSRYTYATYSMA
WFRQAPGKGLEGVSGLDSVGATGYAESVKGRFTISRDNSKNTLYLQMNSLRAEDTAVYYCVVDPA
SAKVTYGSWSTPSYAYWGQGTLVTVSSTTTPAPRPPTPAPTIASQPLSLRPEACRPAAGGAVHTRGL
DFACDIYIWAPLAGTCGVLLLSLVITLYCKRGRKKLLYIFKQPFMRPVQTTQEEDGCSCRFPEEEEGG
CELRVKFSRSADAPAYKQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR

GPC2-CD28z (SEQ ID NO: 248)
MALPVTALLLPLALLLHAARPEVQLVESGGGLVQPGGSLRLSCAISEFTYKNTCVGWFRQAPGKGRE
GVAAIDSDGNTNYVDSVKGRFTISQDNSKNTVYLQMNSLRAEDTAMYYCAAGAYCGRLLLWIGNY
AYWGQGTLVTVSSIEVMYPPPYLDNEKSNGTIIHVKGKHLCPSPLFPGPSKPFWVLVVVGGVLACYS
LLVTVAFIIFWVRSKRSRLLHSDYMNMTPRRPGPTRKHYQPYAPPRDFAAYRSRVKFSRSADAPAYK
QGQNQLYNELNLGRREEYDVLDKRRGRDPEMGGKPRRKNPQEGLYNELQKDKMAEAYSEIGMKG
ERRRGKGHDGLYQGLSTATKDTYDALHMQALPPR

GPC2-CD27z (SEQ ID NO: 249)
MALPVTALLLPLALLLHAARPEVQLVESGGGLVQPGGSLRLSCAISEFTYKNTCVGWFRQAPGKGRE
GVAAIDSDGNTNYVDSVKGRFTISQDNSKNTVYLQMNSLRAEDTAMYYCAAGAYCGRLLLWIGNY
AYWGQGTLVTVSSTTTPAPRPPTPAPTIASQPLSLRPEACRPAAGGAVHTRGLDFACDILVIFSGMFL
VFTLAGALFLHQRRKYRSNKGESPVEPAEPCHYSCPREEEGSTIPIQEDYRKPEPACSPRVKFSRSADA
PAYKQGQNQLYNELNLGRREEYDVLDKRRGRDPEMGGKPRRKNPQEGLYNELQKDKMAEAYSEIG
MKGERRRGKGHDGLYQGLSTATKDTYDALHMQALPPR

-continued

SEQUENCE LISTING

GPC2-ICOSz (SEQ ID NO: 250)
MALPVTALLLPLALLLHAARPEVQLVESGGGLVQPGGSLRLSCAISEFTYKNTCVGWFRQAPGKGRE
GVAAIDSDGNTNYVDSVKGRFTISQDNSKNTVYLQMNSLRAEDTAMYYCAAGAYCGRLLLWIGNY
AYWGQGTLVTVSSTTTPAPRPPTPAPTIASQPLSLRPEACRPAAGGAVHTRGLDFACDFWLPIGCAAF
VVVCILGCILICWLTKKKYSSSVHDPNGEYMFMRAVNTAKKSRLTDVTLRVKFSRSADAPAYKQGQ
NQLYNELNLGRREEYDVLDKRRGRDPEMGGKPRRKNPQEGLYNELQKDKMAEAYSEIGMKGERRR
GKGHDGLYQGLSTATKDTYDALHMQALPPR

GPC2-CD2z (SEQ ID NO: 251)
MALPVTALLLPLALLLHAARPEVQLVESGGGLVQPGGSLRLSCAISEFTYKNTCVGWFRQAPGKGRE
GVAAIDSDGNTNYVDSVKGRFTISQDNSKNTVYLQMNSLRAEDTAMYYCAAGAYCGRLLLWIGNY
AYWGQGTLVTVSSTTTPAPRPPTPAPTIASQPLSLRPEACRPAAGGAVHTRGLDFACDIYLIIGICGGG
SLLMVFVALLVFYITKRKKQRSRRNDEELETRAHRVATEERGRKPHQIPASTPQNPATSQHPPPPPGH
RSQAPSHRPPPPGHRVQHQPQKRPPAPSGTQVHQQKGPPLPRPRVQPKPPHGAAENSLSPSSNRVKFS
RSADAPAYKQGQNQLYNELNLGRREEYDVLDKRRGRDPEMGGKPRRKNPQEGLYNELQKDKMAE
AYSEIGMKGERRRGKGHDGLYQGLSTATKDTYDALHMQALPPR

GPC2-OX40z (SEQ ID NO: 252)
MALPVTALLLPLALLLHAARPEVQLVESGGGLVQPGGSLRLSCAISEFTYKNTCVGWFRQAPGKGRE
GVAAIDSDGNTNYVDSVKGRFTISQDNSKNTVYLQMNSLRAEDTAMYYCAAGAYCGRLLLWIGNY
AYWGQGTLVTVSSTTTPAPRPPTPAPTIASQPLSLRPEACRPAAGGAVHTRGLDFACDVAAILGLGLV
LGLLGPLAILLALYLLRRDQRLPPDAHKPPGGGSFRTPIQEEQADAHSTLAKIRVKFSRSADAPAYKQ
GQNQLYNELNLGRREEYDVLDKRRGRDPEMGGKPRRKNPQEGLYNELQKDKMAEAYSEIGMKGE
RRRGKGHDGLYQGLSTATKDTYDALHMQALPPR

NUCLEIC ACID SEQUENCE

AS70549 (SEQ ID NO: 148)
CAGGTGCGGCTGGTGGAGAGCGGAGGAGGCTCCGTGCAGGCAGGAGGCTCTCTGACCCTGAGC
TGCGCCTACTCCCGGTATACAGGCAGAAGCTCCTGTATGGCCTGGTTCCGGAGACCCCCTGGCA
AGAAGAGGGAGAGGGTGGCATCCATCTACTCTGACGATGGCGTGACCGTGTATGCCGACTCTGT
GAAGGGCAGGTTTACCATCACACAGGATAGCGCCCAGAACACACTGTACCTGCAGATGAACAG
CCTGGACCCCGAGGATACCGCCATGTACTATTGCGCCACACGCACCACATATCCAGGCGTGTGC
CCAGACAACGCAGCATGGTACGATTATTGGGGCCAGGGCACCCAGGTGACAGTGTCTAGC

AS70771 (SEQ ID NO: 149)
CAGGTGCAGCTGGTGGAGTCTGGAGGAGGCAGCGTGCAGGCAGGAGGCTCCCTGAGGCTGTCTT
GCGCAGCAAGCGGATACACCGGCAAGATGGCCTGGTTCAGGCAGGCACCAGGCAAGGAGAGGG
AGGGAGTGGCCGCCATCGACGATGCCGGCGGCACAAACTACATCGACAGCGTGAAGGGCCGGT
TTACCATCTCCAAGGATAACGCCGAGAATACACTGTATCTGAGAATGAACAGCCTGAAGCCCGA
GGACACCGCCATCTACTATTGTGCCGCCGATACATTCAGATGGTTTATGCGGAGATCCGGCCCTA
TCAACGGCTCTGACTACGCCTATTGGGGCCAGGGCACCCAGGTGACAGTGAGCTCC

AS70950 (SEQ ID NO: 150)
CAGGTGCAGCTGGTGGAGTCTGGAGGAGGCTCTGCCCAGAGCGGAGGCTCCCTGCGGCTGTCTT
GCGCCATCAGCGAGTTCACCTACAAGAACACATGCGTGGGATGGTTTAGGCAGGCACCAGGCAA
GGAGAGAGAGGGAGTGGCAGCAATCGACAGCGATGGAAACACCAATTACGTGGACTCCGTGAA
GGGCAGGTTCACCATCTCTCAGGGCAACGCCAAGAATACAGTGTATCTGCAGATGAACTCCCTG
AAGCCTGAGGATACAGCCATGTACTATTGCGCAGCAGGAGCATATTGTGGCCGCCTGCTGCTGT
GGATCGGCAATTACGCCTATTGGGGCCAGGGCACCCAGGTGACAGTGAGCTCC

AS71402 (SEQ ID NO: 151)
CAGATGCAGCTGGTGGAGTCCGGAGGAGGCTCTGTGCAGGCAGGAGGCAGCCTGCGGCTGTCCT
GCGTGGTGTCTGGCTACACCTATAACAGGAATATGGCCTGGTTCAGGCAGGCACCAGGCAAGGA
GAGGGAGGGAGTGGCAGCAATGTACACAGGCAGCGGCACCACAGACTATGCCGATTCCGTGAA
GGGCAGGTTTACCATCTCTCACGACAACGCCAAGAATACACTGTACCTGCAGATGAACAGCCTG
AAGCCCGAGGACACCGCCACATACTATTGTGCAGCAGATACCGCAAGGAGAGGAGGCTCTTGG
AGCGGACCTTTCAAGTACGATTATTGGGGCCAGGGCACCCAGGTGACAGTGAGCTCC

AS71529 (SEQ ID NO: 152)
GAGGTGCAGCTGGTGGAGAGCGGAGGAGGCTCCGTGCAGGCAGGAGGCTCTCTGAGGCTGAGC
TGCGTGGTGTCCGAGTACCGGTATAGCTCCAGATACTGTATGGGCTGGTTCAGGCAGGCACCAG
GCAAGGAGAGGGAGGGAGTGGCAGCAATCGACTCCAACGGCTCTGCCGACTACGTGGATTCCG
TGAAGGGCCGGTTTACCATCTCTAAGGACAACGCCAAGAATACACTGTATCTGCAGATCAATTC
CGTGAGACCTGAGGATACCGCCATGTACTATTGCGCCGCCGACCACCTGGCCTACGATTGTTATT
CTGGCGCCACAAGCGTGTTCAGATATTGGGGCCAGGGCACCCAGGTGACAGTGTCTAGC

AS71661 (SEQ ID NO: 153)
CAGGTGCAGCTGGTGGAGAGCGGAGGAGGACTGGTGCAGGCAGGAGGCTCCCTGCGGCTGTCC
TGCTCTCCAAGCGGCACCACATTCGCCCACTACAACATGGTGGGCTGGTTTAGGCAGGCACCAG
GCAAGGACAGGGAGGGCGTGTCCTGTATCTCTAAGTACGGCGGCACCACATACTATGCCGACTC
TGTGAAGGGCCGGTTCACCATCTATAGAGATAACGCCAAGAATACACTGTTTCTGCAGATGAAC
AGCCTGAAGCCCGAGGATACCGCCATGTACTATTGCGCCATCGGCGTGCTGCCTAGCTCCACAG
CAATCTGTGCAGGAGCAGCAAATTATTGGGGACAGGGAACCCAGGTGACAGTGTCTAGC

-continued

SEQUENCE LISTING

AS72021 (SEQ ID NO: 154)
GAGGTGCAGCTGGCCGAGTCCGGAGGAGGCTCTGTGCAGGCAGGAGGCAGCCTGCGGCTGTCCT
GCGTGGTGTCTAGAAACACCTACAGCTCCTATTGTATGTCCTGGTTCAGGCAGGCACCAGGCAA
GGAGAGGGAGGGAGTGGCCGCCATCGACAATGTGAAGACAAGCTACGCCGATTCCGTGAAGGG
CCGGTTTACCATCTCTAAGGACAACGCCAAGAATACACTGTATCTGCAGATGAACAGCCTGAAG
CCCGAGGATACCGCCATGTACTATTGCGCCGCCCACCTGGAGCTGTGCTACTATACAGACCCTAT
GTACCAGTATGAGTACAATTATTGGGGCCAGGGCACCCAGGTGACAGTGTCTAGC

AS72052 (SEQ ID NO: 155)
CAGGTGCGGCTGGTGGAGTCTGGAGGAGGCAGCGTGCAGGCAGGAGGCTCCCTGCGGCTGTCTT
GCGCCGTGAGCGGCTTCAGGTACGCCTCTTATTGTATGGGATGGTTTAGGCAGGCACCAGGCAA
GGAGAGAGAGGGAGTGGCAGCAATCCACAGCGACGGAATCATCAGATACGCCGAGTCCGTGAA
GGGCCGCTTCACCATCTCTAAGGACAACGCCAAGAATACACTGTATCTGCAGCTGAACAGCCTG
AAGCCTGAGGATAATGCCATGTACTCCTGCGCAGCAGGAGCATATTGTGGAGCAGACGCCATCC
TGACCCTGTACGATTATGCCTTTTGGGGCCAGGGCACCCAGGTGACAGTGAGCTCC

AS72383 (SEQ ID NO: 156)
CAGGTGCGGCTGGTGGAGTCCGGAGGAGGACTGGTGCAGGCAGGAGGCTCTCAGAGGCTGAGC
TGCACCGCATCCGGACTGACATTCGACGATTCTGGAATGGGATGGTTTAGGCAGGCACCAGGCA
AGGGAAGGGAGGGCGTGAGCTGTATCACCTGGAACGGCCGGTCCACATACTATGCCGACTCTGT
GAAGGGCCGGTTCACCATCTCTAGAGATAACAGCAAGAATACACTGTATCTGCAGATGAACAGC
CTGAAGCCTGAGGACACCGCCATGTACTATTGCGCCGCCGCCTTTATCACCAAGACAGGCTGTA
GCTACGAGTATGATTACTCCGGCCAGGGCACCCAGGTGACAGTGAGCTCC

AS72479 (SEQ ID NO: 157)
CAGGTGAAGCTGGTGGAGAGCGGAGGAGGCTCCGTGCAGGCAGGAGGCTCTCTGCGGCTGAGC
TGCGCCGCCTCCGAGACCACAGACTGTAGATACGTGTGGAGGTGGTATCGCGAGGACCCCGGCA
TGGAGAGGGAGTTCGTGAGCTCCATCACCTCCGGCGGCTCTACATGGTACGCCGACTCTGTGAA
GGGCCGCTTTACCATCTCCCAGGATAACGCCAAGTCTACACTGTATCTGCAGATGAATAGCCTG
AAGCCCGAGGACTCCGGCATGTACTATTGCGAGTCTGATCCTGGATGGAGCGGATACCACGCAC
GGAGATGTGAGGTGTATCGGGGCCAGGGCATCCAGGTGACCGTGTCTAGC

AS72499 (SEQ ID NO: 158)
CAGGTGAGGCTGGTGGAGTCCGGAGGAGGCTCTGTGCAGGCAGGAGGCAGCCTGCGGCTGTCCT
GCGTGGTGTCTAGATTCACCTACAGCTCCTATTGTATGGGCTGGTTTAGGCAGGCACCAGGCAA
GGAGAGGGAGGGAGTGGCCGGCATCGAGAAGGACGATAGCACATACTATGCCGACTCCGTGAA
GGGCAGATTCACCATCTCTAAGGATAACGCCAAGAATACACTGTACCTGCAGATGAACAGCCTG
AAGCCCGAGGACACCGCCATGTACTATTGCGCCGCCAGAATCCCCGGAGGAAATTGTGGAGTGG
TGGCAAGAATGGCCTACTGGGATTATTGGGGCAAGGGCACCCTGGTGACAGTGTCTAGC

AS72531 (SEQ ID NO: 159)
CAGGTGCAGCTGGTGGAGTCTGGAGGAGGACTGGTGCAGGCAGGAGGCAGCCTGAGGCTGTCC
TGCACCGCATCTGGACTGACATTCGCCCACTACAACATGGTGGGCTGGTTTAGGCAGGCACCAG
GCAAGGACAGGGAGGGCGTGTCCTGTATCTCTAAGTATGGCGGCACCATCTACTATGCCGACAG
CGTGAAGGGCCGGTTCACCATCGATAGAAACAATGCCAAGAACACACTGTACCTGCAGATGAAC
AGCCTGAAGCCCGAGGATACCGCCATGTACTATTGCGCCATCGGCGTGCTGAGCTCCACAGCAA
GGGGACCTGGAGCAGCAAATTATTGGGGACAGGGCACCCAGGTGACAGTGTCTAGC

AS72669 (SEQ ID NO: 160)
GAGGTGCAGCTGGTGGAGTCCGGAGGAGGCTCTGTGCAGGCAGGAGGCAGCCTGAAGCTGTCC
TGCGCCGCCTCTCGGTTCACCTACAGCTCCTATTGTATGGGCTGGATCAGACAGGCACCAGGCA
AGGAGAGAGAGGGAGTGGCAATCTTCTACACCGGAGGAGGCAGGACATACTATGCCGACAGCG
TGAAGGGCCGCTTTACCATCTCCCAGGATACCGCCAAGAACACACTGTATCTGCAGATGAACAG
CCTGAAGCCTGAGGACACAGGCATCTACTATTGCGTGGCCGGCTTCTACTGTAGCGGCGGCTATT
GGGAGGGCGATTTTGGCTACTGGGGCCAGGGCACCCAGGTGACAGTGTCTAGC

AS72794 (SEQ ID NO: 161)
CAGGTGCAGCTGGTGGAGAGCGGAGGAGGACTGGTGCAGGCAGGAGGCAGCCTGCGGCTGTCC
TGCACAGCCTCTGGCTTCACCTTTGACGATTATGCAATGTCTTGGTTCAGGCAGGCACCAGGCAA
GGAGAGGGAGGGCGTGTCCTGTATCTCCGCCTCTGGCACCACAACCTACTATGGCGATAGCGTG
AAGGGCAGGTTTACAATCTCCCGCGACAACGCCAAGACAACCCTGATCCTGCAGATGAGCTCCC
TGAAGCCTGAGGATACCGCCATGTACTATTGCGCCGCCGACCGGTTCAGAGATTACTGTAGCGA
CTCCTGGTCTCACCTGTACAATTATGAGTACATGCACTGGGGCCAGGGCACACAGGTGACCGTG
TCTAGC

AS72805 (SEQ ID NO: 162)
CAGGTGCAGCTGGTGGAGTCCGGAGGCGACTCTGTGCAGGCAGGAGGCAGCCTGACCCTGTCCT
GCGTGGCATCTAGGCTGAGAGTGTCCAACAATTGTATGGGCTGGTTCAGGCAGGCACCAGGAAA
CGAGAGGGAGGGAGTGGCCACCCTGGGCTCTGACGGCCGGACAATCTATGCCGATTCTGTGAAG
GGCAGGTTTACCATCAGCAAGGACAACGTGGCCAATACACTGTACCTGCAGATGAACGGCCTGA
AGCTGGACGATACAGCCCTGTACTATTGCGCAGCAGCAGATTTCAGCTCCGGAGGATATTGTAA
TATCGCCAGCGTGTACCACTCCTATTTTCCTTACTGGGGCCAGGGCACCCAGGTGACAGTGTCTA
GC

-continued

SEQUENCE LISTING

AS72806 (SEQ ID NO: 163)
CAGGTGCAGCTGGTGGAGTCTGGAGGAGGCAGCGTGCAGGCAGGAGGCTCCCTGAGGCTGTCTT
GCGCAGCAAGCGGATACACCTATATGCCCCCTTGTATGGGATGGTTCAGGCAGGCACCAGGCAA
GGAGAGAGAGGGAGTGGCAACCATCTATGGAAGGGGAGGCAGCACATACTATGCCGACTCCGT
GAAGGGCCGCTTTACCATCTCTCAGGATAACGCCAAGAATACACTGTATCTGCAGATGAACAAT
CTGGAGCCCGAGGACACCGCCATGTACTATTGCGCCGCCGATAACCTGTGCTACGCCACAGGCA
TCCTGAGGTCCGCCTACGACTATTCTTACTGGGGCCAGGGCACCCAGGTGACAGTGAGCTCC

AS72835 (SEQ ID NO: 164)
CAGGTGCACCTGATGGAGTCTGGAGGAGGCAGCGTGCAGGCAGGAGGCTCCCTGCGGCTGTCTT
GCGCCGTGAGCGGCGGCTACACCTCTAGAACCGTGTGCATGGGCTGGTTCAGGCAGACCCCAGG
CAAGGAGAGGGAGGTGCTGGCAGCAATCTATAGGAGCGGCACCACATACTATCACGACTCCGT
GAAGGGCCGGTTTACCATCTCTAGAGACGGCGATAAGAACACAGTGTACCTGCAGATGGACAGC
CTGAAGCCCGAGGATACAGCCATGTACTATTGCGCAGCATCCCCAGGATATTCTGATGCAGCAT
GCGTGAGCGTGCCTCAGGCAAATAGATGGGGCCAGGGCACCCAGGTGACAGTGAGCTCC

AS77906 (SEQ ID NO: 165)
CAGGTGCGGCTGGTGGAGTCTGGAGGAGGCAGCGTGCAGGCAGGAGAGTCCCTGAGGCTGTCTT
GCGCACGCAGCGGAGTGGTGAAGTGTGACGTGGAGATGCGGTGGTACAGACAGTCTCCAGGCA
AGGAGAGGGAGTTCGTGGCCCTGATCGAGGCAGGAGGACACACCGAGTACGCAGACTCCGTGA
AGGGCCGCTTCACAATCTCTCAGGATAACGCCAAGATGCTGTTTTATCTGCAGATGAATAGCCTG
AAGCCCGAGGACACCGCCAAGTACTATTGCGTGGCCGCCCCCCGGTACTATACACTGTCCTGTC
CTAAGGATTTTTGGGGCAGAGGCACCCAGGTGACAGTGAGCTCC

AS77916 (SEQ ID NO: 166)
CAGGTGCACCTGATGGAGTCCGGAGGAGGCTCTGTGCAGGCAGGAGGCAGCCTGCGGCTGTCCT
GCGCCACCTCTGGCTACACAAGCTCCTGGAACTGTATGGGATGGTTCAGGCAGCCACCTGGCAA
GGAGAGAGAGGGAGTGGCCACCATCGCCAATAGGGGCCACAGCACATACTATGCCGACTCCGT
GAAGGGCCGCTTTACCATCTCTCAGGGCAACGCCAAGAATACAGTGTACCTGCAGATGAACAGC
CTGAAGCCCGAGGACACCGCCATGTACTATTGCGCCACCGATACATGGGCCTGCGTGGGCATCT
CCACAGATTTCGAGTATTGGGGCCAGGGCACCCAGGTGACAGTGTCTAGC

AS77932 (SEQ ID NO: 167)
CAGGTGCAGCTGAAGGAGTCTGGAGGAGGCAGCGTGCAGGCAGGAGGCTCCCTGCGGCTGTCTT
GCGCCGTGAGCGGCTACTGGTATTCTGTGGCCTGGATGGGCTGGTTCAGGCAGACCCCAGGCAA
GGAGCGCGAGGGAGTGGCAGCCGTGCTGAACGGAGGAGGCCGGAGATACTATGCCGACAGCGT
GAAGGGCAGGTTTACCATCTCCCAGGATAACTCTAAGAATACACTGTACCTGCAGATGAACAGC
CTGAAGCCCGAGGACACAGCCATGTACTATTGTGCAGCAGGAAACGGAGTGGGACACCCACTG
GGCCCTAGCGAGTACAATTATTGGGGCCAGGGCACCCAGGTGACAGTGAGCTCC

AS77934 (SEQ ID NO: 168)
GAGGTGCAGCTGGTGGAGTCCGGAGGAGGCTCTGTGCAGGCAGGAGGCAGCCTGAGGCTGTCC
TGCGCAGCATCTGGATACACCTATAGCTCCTACTCCATCGCATGGTTCAGGCAGGCACCAGGCA
AGGAGAGGGAGGGAGTGGCCGGCTTCTTTTACTCTGGCGGCCCTACATGTTATGCCGACAGCGT
GAAGGGCAGGTTTACCATCTCCCAGGATAACGCCAAGAATACACTGTATCTGCAGATGAACTCT
CTGAAGCCAGAGGACACCGCCATGTACTATTGCGCCGCCCGGAGAAGCAACACAAATGATTACT
GTTTCTATCCCACCTACACATATTGGGGCCAGGGCACCCAGGTGACAGTGTCTAGC

AS77978 (SEQ ID NO: 169)
CAGGTGCGGCTGGTGGAGAGCGGAGGAGGCTCCGTGCAGGCAGGAGGCTCTCTGCGGCTGAGC
TGCGCCGCCTCCGGCGCCACCTCTTGTCGGTGGAGAATGTCTTGGTACAGGCAGGCACCAGGCA
AGGAGAGAGAGTTCGTGAGCTCCATCGCCAACGGCGCCACAGAGTACGCCGATAGCGTGAAGG
GCAGGTTTACCATCTCCCAGGACAACGCCCGCAATACAATGTATCTGCAGATGAACAGCCTGTC
TCCCGAGGACACCGCCATGTACTATTGCGCCGCCGATCCTAGAGTGTACACCTCCAGGTGTGAC
CGCACATATCTGGGCCAGGGCACCCAGGTGACAGTGTCTAGC

AS77986 (SEQ ID NO: 170)
CAGGTGCAGCTGGTGGAGAGCGGAGGAGGCTCCGTGCAGGCAGGAGGCTCTCTGCGGCTGAGC
TGCGCAGCATCCGCCTCTGGATACACCTATAGCTCCGACAGCATGGCATGGTTCAGGCAGGCAC
CAGGCAAGGAGAGAGAGGGAGTGGCAGGAATCTCCACCGGAGGCAGGTCTACATACTATGCCG
ACAGCGTGAAGGGCCGCTTTACAATCTCCCAGGATAACGCCAAGACCACAGTGTACCTGCACAT
GAACAGCCTGAAGCCCGAGGACACCGCCATGTACTATTGTGCCGCCGATGGCCCTTCCATGACA
GCCATCCAGGCCCTGGGCGACCTGTATCCAGTGGATTTCGCATGGTGGGGACAGGGAACCCAGG
TGACAGTGTCTAGC

AS78117 (SEQ ID NO: 171)
CAGGTGAAGCTGGTGGAGTCCGGAGGAGGCTCTGTGCAGGCAGGAGGCGCCCTGCGGCTGTCTT
GCATCGTGCGGAGATACACCTATGCCACATACAGCATGGCCTGGTTCAGGCAGTCCCCAGGCAA
GGAGCGCGAGGGAGTGGCAGGACTGGACAGCGTGGGAGCCACCGGCTACGCCGAGTCTGTGAA
GGGCAGGTTTACAATCAGCAAGGATAACGCCAAGAATATCCTGTATCTGCAGATGAACTCCCTG
AAGCCCGAGGACACCGCCATGTACTATTGCGTGGTGGACCCCGCATCCGCCAAGGTGACCTATG
GCTCTTGGAGCACACCCTCTTACGCCTATTGGGGCCAGGGCACCCAGGTGACAGTGAGCTCC

AS78215 (SEQ ID NO: 172)
CAGGTGAAGCTGGTGGAGAGCGGAGGAGGCTCCGTGCAGGCAGGAGGCGCCCTGAGGCTGTCT
TGCGCCGCCAGCCGCTACACCTTCAGCTCCAACTGTATGGGATGGTTTAGGCAGGCACCAGGCA

-continued

SEQUENCE LISTING

```
AGGAGAGGGAGGGAGTGGCAACCATCGCATCCGCCTCTGGCTACACAGACTATCACGATTCCGT
GAAGGGCCGGTTCGCCATCTCTAGAGACAACGCCAAGAATACAGTGTATCTGCAGATGAACAGC
CTGAAGCCCGAGGATACCGCAACATACTATTGCGCAGCAAGGGCAGGACCTTGTTGGTCCTGGG
CCCAGGCCGACCTGTACAATTATTGGGGCCAGGGCACCCAGGTGACAGTGTCTAGC

AS78810 (SEQ ID NO: 173)
CAGGTGCACCTGGTGGAGAGCGGAGGAGGCTCCGTGCAGGCAGGAGGCTCTCTGAGGCTGAGC
TGCGCAGCATCCGGATATACCTACTATGACATGGGCTGGTTCAGGCTGGCACCAGGCAAGGAGA
GGGAGGGCATCGCCGCCATCAGCTCCTCTAGCTCCACATACTATGCCGACAGCGTGAAGGGCAG
GTTTACCATCTCCCGCGATTCTAACACACTGTACCTGCAGATGAACAGCCTGAAGCCTGAGGAC
ACCGCCATGTATTCCTGTGCAGCAGGCCGGTACGTGGGAAGAAAGCTGGAGGTGTACGATTATG
CCTACTGGGGCCAGGGCACCCAGGTGACAGTGTCTAGC

AS79101 (SEQ ID NO: 174)
CAGGTGCAGCTGGTGGAGTCCGGAGGAGGCTCTGTGCAGGCAGGAGGCAGCCTGAGGCTGTCCT
GCGCAGCATCTGGCGACACCTACTCTAACTATTGTATGGGCTGGTTCAGGCAGGCACCAGGCAA
GGAGAGGGAGGAGGTGGCAGCAATCGACTCTGATGGCAGCCGGAGATACCCCGACAGCGTGAA
GGGCAGATTCACAATCTCCAAGGATAACGCCAAGAAGATCCTGTACCTGCAGATGAATAGCCTG
AAGCCCGAGGACACCGCCATGTATTTTTGCGCCACAGATCCTAAGGTGGCCTGTGCAAGGGTGG
TGGAGTACGGAGGAGGATGGTATAGATGGGGACAGGGCACCCAGGTGACAGTGAGCTCC

AS79236 (SEQ ID NO: 175)
CAGGTGAAGCTGGTGGAGTCCGGAGGAGGCTCTGTGCAGGCAGGAGGCAGCCTGCGGCTGTCCT
GCGCCGTGTCTGGCTACACCTATAGCTCCTACTGTATGGCATGGTTCAGGCAGGCACCAGGAGA
GGAGAGGGAGGGAGTGGCCAGCATCGACGCAGGAGGAAGGACCACATACGTGGATTCCGTGAA
GGGCAGGTTTACCATCAGCAAGGACAACGCCAAGACATCCCTGTATCTGCAGATGAACAGCCTG
AAGCCCGAGGACACAGCCATGTACTATTGCGCCGTGGATGTGCGGACCAGATGTGGCGGCACAT
GGGATGGCGAGGCCGTGTACTTCCCTTATTGGGGCCAGGGCACCCAGGTGACAGTGTCTAGC

AS79274 (SEQ ID NO: 176)
CAGGTGCACCTGGTGGAGAGCGGAGGAGGCTCCGTGCAGGCAGGAGGCTCTCTGAGGCTGAGC
TGCGCAGCATCCAAGTACGCCTTCTGTACCTATGACATGTCCTGGTTTAGGCAGGCACCAGGCA
AGGAGAGGGAGGTGGTGAGCTCCATCGACTCTCGGGGCAACACAAATTACTCCGATTCTGTGAA
GGGCAGGTTCACCATCTCTCAGGACCACGCCAAGAACACACTGTACCTGCAGATGAATAGCCTG
AAGCCCGAGGATACCGCCATGTATACATGCGCAGCACAGATCGTGGGAGGCGCCCTGAGGTGTC
CTAGATTTGCCATGTATTGGGGCCAGGGCACCCAGGTGACAGTGTCTAGC

AS79285 (SEQ ID NO: 177)
CAGGTGCGGCTGGTGGAGTCCGGAGGAGGCTCTGTGCAGGCAGGAGGCAGCCTGGCCCTGTCCT
GCGAGACATCTAGGTACACCGTGTCTAACTATTGTATGGGCTGGTTCAGGCAGGTGAGCGGCAA
GGAGGTGGAGGGAGTGGCCCTGATCTCCACAGACGGCACCACAACCTACGCCGATAGCGTGAA
GGGCAGGTTCACAATCTCCAAGGACAACGCCAAGAATACCCTGTATCTGCAGATGAACAGCCTG
AAGAGCGAGGATACCGCCATGTACTTTTGCGCCGGCGTGTATGGCCTGATCTGGTACTATAAGC
CATGTCCTGCACAGAGGGAGTGGGCACTGCAGAGATACGGCTATTGGGGCCAGGGCACACAGG
TGACCGTGAGCTCC

AS79317 (SEQ ID NO: 178)
GAGGTGCAGCTGGCAGAGAGCGGAGGAGGCTCCGTGCAGCCAGGAGGCTCTCTGAGGCTGAGC
TGCGCAGCATCCGGATACAGCTCCTCTAGCGTGTGCATGGGATGGTTCAGGCAGGCACCAGGCA
AGGAGAGGGAGGGAGTGGCCATCATCTACGTGACCCTGGGCTCTATCGCCTATGCCGACAGCGT
GAAGGGCCGGTTTACCATCTCCAGAGACAACGCCAAGAATACACTGGATCTGGAGATGAACTCT
CTGAAGCCCGACGATACCGCCCTGTACTATTGCGCAGCAGGAGGATGTGGATACAGGGGAGTGG
CAGATGTGCCTGAGTTCACATATAGGGGCCAGGGCACCCAGGTGACAGTGTCCTCT
```

REFERENCES

1. Basta N O, Halliday G C, Makin G, Birch J, Feltbower R, Bown N, Elliott M, Moreno L, Barone G, Pearson A D J et al: Factors associated with recurrence and survival length following relapse in patients with neuroblastoma. British Journal Of Cancer 2016, 115:1048.
2. Matthay K K, Villablanca J G, Seeger R C, Stram D O, Harris R E, Ramsay N K, Swift P, Shimada H, Black C T, Brodeur G M et al: Treatment of High-Risk Neuroblastoma with Intensive Chemotherapy, Radiotherapy, Autologous Bone Marrow Transplantation, and 13-cis-Retinoic Acid. New England Journal of Medicine 1999, 341(16):1165-1173.
3. Heck J E, Ritz B, Hung R J, Hashibe M, Boffetta P: The epidemiology of neuroblastoma: a review. Paediatric and Perinatal Epidemiology 2009, 23(2):125-143.
4. Li N, Fu H, Hewitt S M, Dimitrov D S, Ho M: Therapeutically targeting glypican-2 via single-domain antibody-based chimeric antigen receptors and immunotoxins in neuroblastoma. Proceedings of the National Academy of Sciences 2017, 114(32):E6623-E6631.
5. Bosse K R, Raman P, Zhu Z, Lane M, Martinez D, Heitzeneder S, Rathi K S, Kendsersky N M, Randall M, Donovan L et al: Identification of GPC2 as an Oncoprotein and Candidate Immunotherapeutic Target in High-Risk Neuroblastoma. Cancer Cell 2017, 32(3):295-309.e212.
6. Stipp C, Litwack E, Lander A: Cerebroglycan: an integral membrane heparan sulfate proteoglycan that is unique to the developing nervous system and expressed specifically during neuronal differentiation. The Journal of Cell Biology 1994, 124(1):149-160.
7. Lugert S, Kremer T, Jagasia R, Herrmann A, Aigner S, Giachino C, Mendez-David I, Gardier A M, Carralot J P, Meistermann H et al: Glypican-2 levels in cerebrospinal fluid predict the status of adult hippocampal neurogenesis. Scientific Reports 2017, 7:46543.

8. Park J H, Rivière I, Gonen M, Wang X, Sénéchal B, Curran K J, Sauter C, Wang Y, Santomasso B, Mead E et al: Long-Term Follow-up of CD19 CAR Therapy in Acute Lymphoblastic Leukemia. New England Journal of Medicine 2018, 378(5):449-459.
9. Works M, Soni N, Hauskins C, Sierra C, Baturevych A, Jones J C, Curtis W, Carlson P, Johnstone T G, Kugler D et al: Anti-B-cell Maturation Antigen Chimeric Antigen Receptor T cell Function against Multiple Myeloma Is Enhanced in the Presence of Lenalidomide. *Molecular Cancer Therapeutics* 2019, 18(12):2246-2257.
10. Wang X, Walter M, Urak R, Weng L, Huynh C, Lim L, Wong C W, Chang W-C, Thomas S H, Sanchez J F et al: Lenalidomide Enhances the Function of CS1 Chimeric Antigen Receptor-Redirected T Cells Against Multiple Myeloma. *Clinical Cancer Research* 2018, 24(1):106-119.
11. Wang D, Aguilar B, Starr R, Alizadeh D, Brito A, Sarkissian A, Ostberg J R, Forman S J, Brown C E: Glioblastoma-targeted CD4+ CAR T cells mediate superior antitumor activity. *JCI Insight* 2018, 3(10)

The invention claimed is:

1. An antibody or antigen binding fragment thereof that specifically binds glypican-2 (GPC2), comprising a single variable domain on a heavy chain ($V_HH$) domain comprising a complementary determining region (CDR)1, a CDR2, and a CDR3, wherein:

the CDR1 comprises SEQ ID NO: 3, the CDR2 comprises SEQ ID NO: 33, and the CDR3 comprises SEQ ID NO: 64.

2. The antibody or antigen binding fragment thereof of claim 1, wherein (i) the $V_HH$ domain comprises an amino acid sequence having at least 90% sequence identity to an amino acid sequence selected from the group consisting of SEQ ID NOs: 95, 124, and 125; or (ii) the $V_HH$ domain comprises an amino acid sequence selected from the group consisting of SEQ ID NOs: 95, 124, and 125.

3. The antibody or antigen binding fragment thereof of claim 1, wherein the antibody or antigen binding fragment is a single-domain antibody (sdAb) or a heavy chain only antibody (HCAb).

4. The antibody or antigen binding fragment thereof of claim 1, comprising an Fc region.

5. An multispecific antibody comprising at least one $V_HH$ domain of the antibody or antigen binding fragment thereof of claim 1.

6. The multispecific antibody of claim 5, comprising, from N-terminus to C-terminus:

(i) a first $V_HH$ domain comprises SEQ ID NO: 124 and a second $V_HH$ domain comprises SEQ ID NO: 127, or (ii) a first $V_HH$ domain comprises SEQ ID NO: 127 and a second $V_HH$ domain comprises SEQ ID NO: 124, or (iii) a first $V_HH$ domain comprises SEQ ID NO: 124 and a second $V_HH$ domain comprises SEQ ID NO: 124.

7. The multispecific antibody of claim 6, wherein (i) the multispecific antibody comprises an amino acid sequence having at least 90% sequence identity to an amino acid sequence selected from the group consisting of SEQ ID NOs: 145-147; or (ii) the multispecific antibody comprises an amino acid sequence selected from the group consisting of SEQ ID NOs: 145-147.

8. A chimeric antigen receptor (CAR) that specifically binds to GPC2, comprising:

(a) an extracellular antigen binding domain comprising a $V_HH$ domain of the antibody or antigen binding fragment thereof of claim 1;

(b) a transmembrane domain; and (c) an intracellular signaling domain.

9. The CAR of claim 8, wherein the CAR comprises an amino acid sequence having at least 90% sequence identity to an amino acid sequence selected from the group consisting of SEQ ID NOs: 191, 220, 221, and 241-243.

10. The CAR of claim 8, wherein the CAR comprises an amino acid sequence selected from the group consisting of SEQ ID NOs: 191, 220, 221, and 241-243.

11. A method of treating a GPC2-positive cancer in a subject, comprising administering to the subject an effective amount of an engineered immune cell comprising the CAR of claim 8, wherein the engineered immune effector cell is a T cell, a NK cell, or a myeloid-derived phagocyte.

12. A nucleic acid molecule comprising one or more nucleic acid sequences encoding the antibody or antigen binding fragment of claim 1.

13. The nucleic acid molecule of claim 12, comprising the nucleic acid sequence of SEQ ID NO: 150.

14. A vector comprising the nucleic acid molecule of claim 12.

15. An engineered immune effector cell comprising the nucleic acid molecule of claim 12.

16. A pharmaceutical composition comprising an effective amount of the immune effector cell of claim 15 and a pharmaceutically acceptable carrier.

17. The pharmaceutical composition of claim 16, further comprising an immunomodulatory agent.

18. The pharmaceutical composition of claim 17, wherein the immunomodulatory agent is 3-(4-amino-1-oxo-1,3 dihydro-2H-isoindol-2-yl)piperidine-2,6-dione.

19. The immune effector cell of claim 15, wherein the engineered immune effector cell is a T cell selected from the group consisting of a cytotoxic T cell, a helper T cell, a natural killer T cell, and a γδ T cell.

* * * * *

SEQUENCE LISTING

```
<160> NUMBER OF SEQ ID NOS: 252

<210> SEQ ID NO 1
<211> LENGTH: 8
<212> TYPE: PRT
<213> ORGANISM: Artificial Sequence
<220> FEATURE:
<223> OTHER INFORMATION: AS70549 CDR1

<400> SEQUENCE: 1

Arg Tyr Thr Gly Arg Ser Ser Cys
1               5


<210> SEQ ID NO 2
<211> LENGTH: 5
<212> TYPE: PRT
<213> ORGANISM: Artificial Sequence
<220> FEATURE:
<223> OTHER INFORMATION: AS70771 CDR1

<400> SEQUENCE: 2

Gly Tyr Thr Gly Lys
1               5


<210> SEQ ID NO 3
<211> LENGTH: 8
<212> TYPE: PRT
<213> ORGANISM: Artificial Sequence
<220> FEATURE:
<223> OTHER INFORMATION: AS70950 CDR1

<400> SEQUENCE: 3

Glu Phe Thr Tyr Lys Asn Thr Cys
1               5


<210> SEQ ID NO 4
<211> LENGTH: 7
<212> TYPE: PRT
<213> ORGANISM: Artificial Sequence
<220> FEATURE:
<223> OTHER INFORMATION: AS71402 CDR1

<400> SEQUENCE: 4

Gly Tyr Thr Tyr Asn Arg Asn
1               5


<210> SEQ ID NO 5
<211> LENGTH: 9
<212> TYPE: PRT
<213> ORGANISM: Artificial Sequence
<220> FEATURE:
<223> OTHER INFORMATION: AS71529 CDR1

<400> SEQUENCE: 5

Glu Tyr Arg Tyr Ser Ser Arg Tyr Cys
```

```
1               5


<210> SEQ ID NO 6
<211> LENGTH: 9
<212> TYPE: PRT
<213> ORGANISM: Artificial Sequence
<220> FEATURE:
<223> OTHER INFORMATION: AS71661 CDR1

<400> SEQUENCE: 6

Gly Thr Thr Phe Ala His Tyr Asn Met
1               5


<210> SEQ ID NO 7
<211> LENGTH: 8
<212> TYPE: PRT
<213> ORGANISM: Artificial Sequence
<220> FEATURE:
<223> OTHER INFORMATION: AS72021 CDR1

<400> SEQUENCE: 7

Arg Asn Thr Tyr Ser Ser Tyr Cys
1               5


<210> SEQ ID NO 8
<211> LENGTH: 8
<212> TYPE: PRT
<213> ORGANISM: Artificial Sequence
<220> FEATURE:
<223> OTHER INFORMATION: AS72052 CDR1

<400> SEQUENCE: 8

Gly Phe Arg Tyr Ala Ser Tyr Cys
1               5


<210> SEQ ID NO 9
<211> LENGTH: 8
<212> TYPE: PRT
<213> ORGANISM: Artificial Sequence
<220> FEATURE:
<223> OTHER INFORMATION: AS72383 CDR1

<400> SEQUENCE: 9

Gly Leu Thr Phe Asp Asp Ser Gly
1               5


<210> SEQ ID NO 10
<211> LENGTH: 8
<212> TYPE: PRT
<213> ORGANISM: Artificial Sequence
<220> FEATURE:
<223> OTHER INFORMATION: AS72479 CDR1

<400> SEQUENCE: 10

Glu Thr Thr Asp Cys Arg Tyr Val
1               5


<210> SEQ ID NO 11
<211> LENGTH: 8
<212> TYPE: PRT
<213> ORGANISM: Artificial Sequence
<220> FEATURE:
<223> OTHER INFORMATION: AS72499 CDR1

<400> SEQUENCE: 11

Arg Phe Thr Tyr Ser Ser Tyr Cys
1               5
```

<210> SEQ ID NO 12
<211> LENGTH: 9
<212> TYPE: PRT
<213> ORGANISM: Artificial Sequence
<220> FEATURE:
<223> OTHER INFORMATION: AS72531 CDR1

<400> SEQUENCE: 12

Gly Leu Thr Phe Ala His Tyr Asn Met
1               5

<210> SEQ ID NO 13
<211> LENGTH: 8
<212> TYPE: PRT
<213> ORGANISM: Artificial Sequence
<220> FEATURE:
<223> OTHER INFORMATION: AS72794 CDR1

<400> SEQUENCE: 13

Gly Phe Thr Phe Asp Asp Tyr Ala
1               5

<210> SEQ ID NO 14
<211> LENGTH: 8
<212> TYPE: PRT
<213> ORGANISM: Artificial Sequence
<220> FEATURE:
<223> OTHER INFORMATION: AS72805 CDR1

<400> SEQUENCE: 14

Arg Leu Arg Val Ser Asn Asn Cys
1               5

<210> SEQ ID NO 15
<211> LENGTH: 8
<212> TYPE: PRT
<213> ORGANISM: Artificial Sequence
<220> FEATURE:
<223> OTHER INFORMATION: AS72806 CDR1

<400> SEQUENCE: 15

Gly Tyr Thr Tyr Met Pro Pro Cys
1               5

<210> SEQ ID NO 16
<211> LENGTH: 9
<212> TYPE: PRT
<213> ORGANISM: Artificial Sequence
<220> FEATURE:
<223> OTHER INFORMATION: AS72835 CDR1

<400> SEQUENCE: 16

Gly Gly Tyr Thr Ser Arg Thr Val Cys
1               5

<210> SEQ ID NO 17
<211> LENGTH: 8
<212> TYPE: PRT
<213> ORGANISM: Artificial Sequence
<220> FEATURE:
<223> OTHER INFORMATION: AS77906 CDR1

<400> SEQUENCE: 17

Gly Val Val Lys Cys Asp Val Glu
1               5

<210> SEQ ID NO 18
<211> LENGTH: 8
<212> TYPE: PRT
<213> ORGANISM: Artificial Sequence
<220> FEATURE:
<223> OTHER INFORMATION: AS77916 CDR1

<400> SEQUENCE: 18

Gly Tyr Thr Ser Ser Trp Asn Cys
1               5

<210> SEQ ID NO 19
<211> LENGTH: 8
<212> TYPE: PRT
<213> ORGANISM: Artificial Sequence
<220> FEATURE:
<223> OTHER INFORMATION: AS77932 CDR1

<400> SEQUENCE: 19

Gly Tyr Trp Tyr Ser Val Ala Trp
1               5

<210> SEQ ID NO 20
<211> LENGTH: 8
<212> TYPE: PRT
<213> ORGANISM: Artificial Sequence
<220> FEATURE:
<223> OTHER INFORMATION: AS77934 CDR1

<400> SEQUENCE: 20

Gly Tyr Thr Tyr Ser Ser Tyr Ser
1               5

<210> SEQ ID NO 21
<211> LENGTH: 8
<212> TYPE: PRT
<213> ORGANISM: Artificial Sequence
<220> FEATURE:
<223> OTHER INFORMATION: AS77978 CDR1

<400> SEQUENCE: 21

Gly Ala Thr Ser Cys Arg Trp Arg
1               5

<210> SEQ ID NO 22
<211> LENGTH: 10
<212> TYPE: PRT
<213> ORGANISM: Artificial Sequence
<220> FEATURE:
<223> OTHER INFORMATION: AS77986 CDR1

<400> SEQUENCE: 22

Ala Ser Gly Tyr Thr Tyr Ser Ser Asp Ser
1               5                   10

<210> SEQ ID NO 23
<211> LENGTH: 8
<212> TYPE: PRT
<213> ORGANISM: Artificial Sequence
<220> FEATURE:
<223> OTHER INFORMATION: AS78117 CDR1

<400> SEQUENCE: 23

Arg Tyr Thr Tyr Ala Thr Tyr Ser
1               5

<210> SEQ ID NO 24
<211> LENGTH: 8
<212> TYPE: PRT
<213> ORGANISM: Artificial Sequence
<220> FEATURE:
<223> OTHER INFORMATION: AS78215 CDR1

<400> SEQUENCE: 24

Arg Tyr Thr Phe Ser Ser Asn Cys
1 5

<210> SEQ ID NO 25
<211> LENGTH: 6
<212> TYPE: PRT
<213> ORGANISM: Artificial Sequence
<220> FEATURE:
<223> OTHER INFORMATION: AS78810 CDR1

<400> SEQUENCE: 25

Gly Tyr Thr Tyr Tyr Asp
1 5

<210> SEQ ID NO 26
<211> LENGTH: 8
<212> TYPE: PRT
<213> ORGANISM: Artificial Sequence
<220> FEATURE:
<223> OTHER INFORMATION: AS79101 CDR1

<400> SEQUENCE: 26

Gly Asp Thr Tyr Ser Asn Tyr Cys
1 5

<210> SEQ ID NO 27
<211> LENGTH: 8
<212> TYPE: PRT
<213> ORGANISM: Artificial Sequence
<220> FEATURE:
<223> OTHER INFORMATION: AS79236 CDR1

<400> SEQUENCE: 27

Gly Tyr Thr Tyr Ser Ser Tyr Cys
1 5

<210> SEQ ID NO 28
<211> LENGTH: 8
<212> TYPE: PRT
<213> ORGANISM: Artificial Sequence
<220> FEATURE:
<223> OTHER INFORMATION: AS79274 CDR1

<400> SEQUENCE: 28

Lys Tyr Ala Phe Cys Thr Tyr Asp
1 5

<210> SEQ ID NO 29
<211> LENGTH: 8
<212> TYPE: PRT
<213> ORGANISM: Artificial Sequence
<220> FEATURE:
<223> OTHER INFORMATION: AS79285 CDR1

<400> SEQUENCE: 29

Arg Tyr Thr Val Ser Asn Tyr Cys
1 5

<210> SEQ ID NO 30

<211> LENGTH: 8
<212> TYPE: PRT
<213> ORGANISM: Artificial Sequence
<220> FEATURE:
<223> OTHER INFORMATION: AS79317 CDR1

<400> SEQUENCE: 30

Gly Tyr Ser Ser Ser Ser Val Cys
1               5

<210> SEQ ID NO 31
<211> LENGTH: 8
<212> TYPE: PRT
<213> ORGANISM: Artificial Sequence
<220> FEATURE:
<223> OTHER INFORMATION: AS70549 CDR2

<400> SEQUENCE: 31

Ile Tyr Ser Asp Asp Gly Val Thr
1               5

<210> SEQ ID NO 32
<211> LENGTH: 7
<212> TYPE: PRT
<213> ORGANISM: Artificial Sequence
<220> FEATURE:
<223> OTHER INFORMATION: AS70771 CDR2

<400> SEQUENCE: 32

Ile Asp Asp Ala Gly Gly Thr
1               5

<210> SEQ ID NO 33
<211> LENGTH: 7
<212> TYPE: PRT
<213> ORGANISM: Artificial Sequence
<220> FEATURE:
<223> OTHER INFORMATION: AS70950 CDR2

<400> SEQUENCE: 33

Ile Asp Ser Asp Gly Asn Thr
1               5

<210> SEQ ID NO 34
<211> LENGTH: 8
<212> TYPE: PRT
<213> ORGANISM: Artificial Sequence
<220> FEATURE:
<223> OTHER INFORMATION: AS71402 CDR2

<400> SEQUENCE: 34

Met Tyr Thr Gly Ser Gly Thr Thr
1               5

<210> SEQ ID NO 35
<211> LENGTH: 7
<212> TYPE: PRT
<213> ORGANISM: Artificial Sequence
<220> FEATURE:
<223> OTHER INFORMATION: AS71529 CDR2

<400> SEQUENCE: 35

Ile Asp Ser Asn Gly Ser Ala
1               5

<210> SEQ ID NO 36
<211> LENGTH: 8

<212> TYPE: PRT
<213> ORGANISM: Artificial Sequence
<220> FEATURE:
<223> OTHER INFORMATION: AS71661 CDR2

<400> SEQUENCE: 36

Ile Ser Lys Tyr Gly Gly Thr Thr
1               5

<210> SEQ ID NO 37
<211> LENGTH: 6
<212> TYPE: PRT
<213> ORGANISM: Artificial Sequence
<220> FEATURE:
<223> OTHER INFORMATION: AS72021 CDR2

<400> SEQUENCE: 37

Ile Asp Asn Val Lys Thr
1               5

<210> SEQ ID NO 38
<211> LENGTH: 7
<212> TYPE: PRT
<213> ORGANISM: Artificial Sequence
<220> FEATURE:
<223> OTHER INFORMATION: AS72052 CDR2

<400> SEQUENCE: 38

Ile His Ser Asp Gly Ile Ile
1               5

<210> SEQ ID NO 39
<211> LENGTH: 8
<212> TYPE: PRT
<213> ORGANISM: Artificial Sequence
<220> FEATURE:
<223> OTHER INFORMATION: AS72383 CDR2

<400> SEQUENCE: 39

Ile Thr Trp Asn Gly Arg Ser Thr
1               5

<210> SEQ ID NO 40
<211> LENGTH: 7
<212> TYPE: PRT
<213> ORGANISM: Artificial Sequence
<220> FEATURE:
<223> OTHER INFORMATION: AS72479 CDR2

<400> SEQUENCE: 40

Ile Thr Ser Gly Gly Ser Thr
1               5

<210> SEQ ID NO 41
<211> LENGTH: 7
<212> TYPE: PRT
<213> ORGANISM: Artificial Sequence
<220> FEATURE:
<223> OTHER INFORMATION: AS72499 CDR2

<400> SEQUENCE: 41

Ile Glu Lys Asp Asp Ser Thr
1               5

<210> SEQ ID NO 42
<211> LENGTH: 7
<212> TYPE: PRT

<213> ORGANISM: Artificial Sequence
<220> FEATURE:
<223> OTHER INFORMATION: AS72531 CDR2

<400> SEQUENCE: 42

Ile Ser Lys Tyr Gly Gly Thr
1 5

<210> SEQ ID NO 43
<211> LENGTH: 8
<212> TYPE: PRT
<213> ORGANISM: Artificial Sequence
<220> FEATURE:
<223> OTHER INFORMATION: AS72669 CDR2

<400> SEQUENCE: 43

Phe Tyr Thr Gly Gly Gly Arg Thr
1 5

<210> SEQ ID NO 44
<211> LENGTH: 8
<212> TYPE: PRT
<213> ORGANISM: Artificial Sequence
<220> FEATURE:
<223> OTHER INFORMATION: AS72794 CDR2

<400> SEQUENCE: 44

Ile Ser Ala Ser Gly Thr Thr Thr
1 5

<210> SEQ ID NO 45
<211> LENGTH: 7
<212> TYPE: PRT
<213> ORGANISM: Artificial Sequence
<220> FEATURE:
<223> OTHER INFORMATION: AS72805 CDR2

<400> SEQUENCE: 45

Leu Gly Ser Asp Gly Arg Thr
1 5

<210> SEQ ID NO 46
<211> LENGTH: 8
<212> TYPE: PRT
<213> ORGANISM: Artificial Sequence
<220> FEATURE:
<223> OTHER INFORMATION: AS72806 CDR2

<400> SEQUENCE: 46

Ile Tyr Gly Arg Gly Gly Ser Thr
1 5

<210> SEQ ID NO 47
<211> LENGTH: 7
<212> TYPE: PRT
<213> ORGANISM: Artificial Sequence
<220> FEATURE:
<223> OTHER INFORMATION: AS72835 CDR2

<400> SEQUENCE: 47

Ile Tyr Arg Ser Gly Thr Thr
1 5

<210> SEQ ID NO 48
<211> LENGTH: 7
<212> TYPE: PRT
<213> ORGANISM: Artificial Sequence

<220> FEATURE:
<223> OTHER INFORMATION: AS77906 CDR2

<400> SEQUENCE: 48

Ile Glu Ala Gly Gly His Thr
1               5

<210> SEQ ID NO 49
<211> LENGTH: 8
<212> TYPE: PRT
<213> ORGANISM: Artificial Sequence
<220> FEATURE:
<223> OTHER INFORMATION: AS77916 CDR2

<400> SEQUENCE: 49

Ile Ala Asn Arg Gly His Ser Thr
1               5

<210> SEQ ID NO 50
<211> LENGTH: 8
<212> TYPE: PRT
<213> ORGANISM: Artificial Sequence
<220> FEATURE:
<223> OTHER INFORMATION: AS77932 CDR2

<400> SEQUENCE: 50

Val Leu Asn Gly Gly Gly Arg Arg
1               5

<210> SEQ ID NO 51
<211> LENGTH: 8
<212> TYPE: PRT
<213> ORGANISM: Artificial Sequence
<220> FEATURE:
<223> OTHER INFORMATION: AS77934 CDR2

<400> SEQUENCE: 51

Phe Phe Tyr Ser Gly Gly Pro Thr
1               5

<210> SEQ ID NO 52
<211> LENGTH: 6
<212> TYPE: PRT
<213> ORGANISM: Artificial Sequence
<220> FEATURE:
<223> OTHER INFORMATION: AS77978 CDR2

<400> SEQUENCE: 52

Ile Ala Asn Gly Ala Thr
1               5

<210> SEQ ID NO 53
<211> LENGTH: 8
<212> TYPE: PRT
<213> ORGANISM: Artificial Sequence
<220> FEATURE:
<223> OTHER INFORMATION: AS77986 CDR2

<400> SEQUENCE: 53

Ile Ser Thr Gly Gly Arg Ser Thr
1               5

<210> SEQ ID NO 54
<211> LENGTH: 7
<212> TYPE: PRT
<213> ORGANISM: Artificial Sequence
<220> FEATURE:

<223> OTHER INFORMATION: AS78117 CDR2

<400> SEQUENCE: 54

Leu Asp Ser Val Gly Ala Thr
1               5

<210> SEQ ID NO 55
<211> LENGTH: 8
<212> TYPE: PRT
<213> ORGANISM: Artificial Sequence
<220> FEATURE:
<223> OTHER INFORMATION: AS78215 CDR2

<400> SEQUENCE: 55

Ile Ala Ser Ala Ser Gly Tyr Thr
1               5

<210> SEQ ID NO 56
<211> LENGTH: 7
<212> TYPE: PRT
<213> ORGANISM: Artificial Sequence
<220> FEATURE:
<223> OTHER INFORMATION: AS78810 CDR2

<400> SEQUENCE: 56

Ile Ser Ser Ser Ser Ser Thr
1               5

<210> SEQ ID NO 57
<211> LENGTH: 7
<212> TYPE: PRT
<213> ORGANISM: Artificial Sequence
<220> FEATURE:
<223> OTHER INFORMATION: AS79101 CDR2

<400> SEQUENCE: 57

Ile Asp Ser Asp Gly Ser Arg
1               5

<210> SEQ ID NO 58
<211> LENGTH: 7
<212> TYPE: PRT
<213> ORGANISM: Artificial Sequence
<220> FEATURE:
<223> OTHER INFORMATION: AS79236 CDR2

<400> SEQUENCE: 58

Ile Asp Ala Gly Gly Arg Thr
1               5

<210> SEQ ID NO 59
<211> LENGTH: 7
<212> TYPE: PRT
<213> ORGANISM: Artificial Sequence
<220> FEATURE:
<223> OTHER INFORMATION: AS79274 CDR2

<400> SEQUENCE: 59

Ile Asp Ser Arg Gly Asn Thr
1               5

<210> SEQ ID NO 60
<211> LENGTH: 7
<212> TYPE: PRT
<213> ORGANISM: Artificial Sequence
<220> FEATURE:
<223> OTHER INFORMATION: AS79285 CDR2

<400> SEQUENCE: 60

Ile Ser Thr Asp Gly Thr Thr
1 5

<210> SEQ ID NO 61
<211> LENGTH: 8
<212> TYPE: PRT
<213> ORGANISM: Artificial Sequence
<220> FEATURE:
<223> OTHER INFORMATION: AS79317 CDR2

<400> SEQUENCE: 61

Ile Tyr Val Thr Leu Gly Ser Ile
1 5

<210> SEQ ID NO 62
<211> LENGTH: 19
<212> TYPE: PRT
<213> ORGANISM: Artificial Sequence
<220> FEATURE:
<223> OTHER INFORMATION: AS70549 CDR3

<400> SEQUENCE: 62

Ala Thr Arg Thr Thr Tyr Pro Gly Val Cys Pro Asp Asn Ala Ala Trp
1 5 10 15

Tyr Asp Tyr

<210> SEQ ID NO 63
<211> LENGTH: 22
<212> TYPE: PRT
<213> ORGANISM: Artificial Sequence
<220> FEATURE:
<223> OTHER INFORMATION: AS70771 CDR3

<400> SEQUENCE: 63

Ala Ala Asp Thr Phe Arg Trp Phe Met Arg Arg Ser Gly Pro Ile Asn
1 5 10 15

Gly Ser Asp Tyr Ala Tyr
20

<210> SEQ ID NO 64
<211> LENGTH: 18
<212> TYPE: PRT
<213> ORGANISM: Artificial Sequence
<220> FEATURE:
<223> OTHER INFORMATION: AS70950 CDR3

<400> SEQUENCE: 64

Ala Ala Gly Ala Tyr Cys Gly Arg Leu Leu Leu Trp Ile Gly Asn Tyr
1 5 10 15

Ala Tyr

<210> SEQ ID NO 65
<211> LENGTH: 19
<212> TYPE: PRT
<213> ORGANISM: Artificial Sequence
<220> FEATURE:
<223> OTHER INFORMATION: AS71402 CDR3

<400> SEQUENCE: 65

Ala Ala Asp Thr Ala Arg Arg Gly Gly Ser Trp Ser Gly Pro Phe Lys
1 5 10 15

Tyr Asp Tyr

<210> SEQ ID NO 66
<211> LENGTH: 19
<212> TYPE: PRT
<213> ORGANISM: Artificial Sequence
<220> FEATURE:
<223> OTHER INFORMATION: AS71529 CDR3

<400> SEQUENCE: 66

Ala Ala Asp His Leu Ala Tyr Asp Cys Tyr Ser Gly Ala Thr Ser Val
1 5 10 15

Phe Arg Tyr

<210> SEQ ID NO 67
<211> LENGTH: 18
<212> TYPE: PRT
<213> ORGANISM: Artificial Sequence
<220> FEATURE:
<223> OTHER INFORMATION: AS71661 CDR3

<400> SEQUENCE: 67

Ala Ile Gly Val Leu Pro Ser Ser Thr Ala Ile Cys Ala Gly Ala Ala
1 5 10 15

Asn Tyr

<210> SEQ ID NO 68
<211> LENGTH: 20
<212> TYPE: PRT
<213> ORGANISM: Artificial Sequence
<220> FEATURE:
<223> OTHER INFORMATION: AS72021 CDR3

<400> SEQUENCE: 68

Ala Ala His Leu Glu Leu Cys Tyr Tyr Thr Asp Pro Met Tyr Gln Tyr
1 5 10 15

Glu Tyr Asn Tyr
20

<210> SEQ ID NO 69
<211> LENGTH: 19
<212> TYPE: PRT
<213> ORGANISM: Artificial Sequence
<220> FEATURE:
<223> OTHER INFORMATION: AS72052 CDR3

<400> SEQUENCE: 69

Ala Ala Gly Ala Tyr Cys Gly Ala Asp Ala Ile Leu Thr Leu Tyr Asp
1 5 10 15

Tyr Ala Phe

<210> SEQ ID NO 70
<211> LENGTH: 13
<212> TYPE: PRT
<213> ORGANISM: Artificial Sequence
<220> FEATURE:
<223> OTHER INFORMATION: AS72383 CDR3

<400> SEQUENCE: 70

Ala Ala Ala Phe Ile Thr Lys Thr Gly Cys Ser Tyr Glu
1 5 10

<210> SEQ ID NO 71
<211> LENGTH: 14
<212> TYPE: PRT

<213> ORGANISM: Artificial Sequence
<220> FEATURE:
<223> OTHER INFORMATION: AS72479 CDR3

<400> SEQUENCE: 71

Glu Ser Asp Pro Gly Trp Ser Gly Tyr His Ala Arg Arg Cys
1 5 10

<210> SEQ ID NO 72
<211> LENGTH: 17
<212> TYPE: PRT
<213> ORGANISM: Artificial Sequence
<220> FEATURE:
<223> OTHER INFORMATION: AS72499 CDR3

<400> SEQUENCE: 72

Ala Ala Arg Ile Pro Gly Gly Asn Cys Gly Val Val Ala Arg Met Ala
1 5 10 15

Tyr

<210> SEQ ID NO 73
<211> LENGTH: 17
<212> TYPE: PRT
<213> ORGANISM: Artificial Sequence
<220> FEATURE:
<223> OTHER INFORMATION: AS72531 CDR3

<400> SEQUENCE: 73

Ala Ile Gly Val Leu Ser Ser Thr Ala Arg Gly Pro Gly Ala Ala Asn
1 5 10 15

Tyr

<210> SEQ ID NO 74
<211> LENGTH: 17
<212> TYPE: PRT
<213> ORGANISM: Artificial Sequence
<220> FEATURE:
<223> OTHER INFORMATION: AS72669 CDR3

<400> SEQUENCE: 74

Val Ala Gly Phe Tyr Cys Ser Gly Gly Tyr Trp Glu Gly Asp Phe Gly
1 5 10 15

Tyr

<210> SEQ ID NO 75
<211> LENGTH: 23
<212> TYPE: PRT
<213> ORGANISM: Artificial Sequence
<220> FEATURE:
<223> OTHER INFORMATION: AS72794 CDR3

<400> SEQUENCE: 75

Ala Ala Asp Arg Phe Arg Asp Tyr Cys Ser Asp Ser Trp Ser His Leu
1 5 10 15

Tyr Asn Tyr Glu Tyr Met His
20

<210> SEQ ID NO 76
<211> LENGTH: 23
<212> TYPE: PRT
<213> ORGANISM: Artificial Sequence
<220> FEATURE:
<223> OTHER INFORMATION: AS72805 CDR3

<400> SEQUENCE: 76

```
Ala Ala Ala Asp Phe Ser Ser Gly Gly Tyr Cys Asn Ile Ala Ser Val
1               5                   10                  15

Tyr His Ser Tyr Phe Pro Tyr
            20


<210> SEQ ID NO 77
<211> LENGTH: 20
<212> TYPE: PRT
<213> ORGANISM: Artificial Sequence
<220> FEATURE:
<223> OTHER INFORMATION: AS72806 CDR3

<400> SEQUENCE: 77

Ala Ala Asp Asn Leu Cys Tyr Ala Thr Gly Ile Leu Arg Ser Ala Tyr
1               5                   10                  15

Asp Tyr Ser Tyr
            20


<210> SEQ ID NO 78
<211> LENGTH: 19
<212> TYPE: PRT
<213> ORGANISM: Artificial Sequence
<220> FEATURE:
<223> OTHER INFORMATION: AS72835 CDR3

<400> SEQUENCE: 78

Ala Ala Ser Pro Gly Tyr Ser Asp Ala Ala Cys Val Ser Val Pro Gln
1               5                   10                  15

Ala Asn Arg


<210> SEQ ID NO 79
<211> LENGTH: 15
<212> TYPE: PRT
<213> ORGANISM: Artificial Sequence
<220> FEATURE:
<223> OTHER INFORMATION: AS77906 CDR3

<400> SEQUENCE: 79

Val Ala Ala Pro Arg Tyr Tyr Thr Leu Ser Cys Pro Lys Asp Phe
1               5                   10                  15


<210> SEQ ID NO 80
<211> LENGTH: 16
<212> TYPE: PRT
<213> ORGANISM: Artificial Sequence
<220> FEATURE:
<223> OTHER INFORMATION: AS77916 CDR3

<400> SEQUENCE: 80

Ala Thr Asp Thr Trp Ala Cys Val Gly Ile Ser Thr Asp Phe Glu Tyr
1               5                   10                  15


<210> SEQ ID NO 81
<211> LENGTH: 17
<212> TYPE: PRT
<213> ORGANISM: Artificial Sequence
<220> FEATURE:
<223> OTHER INFORMATION: AS77932 CDR3

<400> SEQUENCE: 81

Ala Ala Gly Asn Gly Val Gly His Pro Leu Gly Pro Ser Glu Tyr Asn
1               5                   10                  15

Tyr
```

<210> SEQ ID NO 82
<211> LENGTH: 18
<212> TYPE: PRT
<213> ORGANISM: Artificial Sequence
<220> FEATURE:
<223> OTHER INFORMATION: AS77934 CDR3

<400> SEQUENCE: 82

Ala Ala Arg Arg Ser Asn Thr Asn Asp Tyr Cys Phe Tyr Pro Thr Tyr
1 5 10 15

Thr Tyr

<210> SEQ ID NO 83
<211> LENGTH: 15
<212> TYPE: PRT
<213> ORGANISM: Artificial Sequence
<220> FEATURE:
<223> OTHER INFORMATION: AS77978 CDR3

<400> SEQUENCE: 83

Ala Ala Asp Pro Arg Val Tyr Thr Ser Arg Cys Asp Arg Thr Tyr
1 5 10 15

<210> SEQ ID NO 84
<211> LENGTH: 23
<212> TYPE: PRT
<213> ORGANISM: Artificial Sequence
<220> FEATURE:
<223> OTHER INFORMATION: AS77986 CDR3

<400> SEQUENCE: 84

Ala Ala Asp Gly Pro Ser Met Thr Ala Ile Gln Ala Leu Gly Asp Leu
1 5 10 15

Tyr Pro Val Asp Phe Ala Trp
20

<210> SEQ ID NO 85
<211> LENGTH: 21
<212> TYPE: PRT
<213> ORGANISM: Artificial Sequence
<220> FEATURE:
<223> OTHER INFORMATION: AS78117 CDR3

<400> SEQUENCE: 85

Val Val Asp Pro Ala Ser Ala Lys Val Thr Tyr Gly Ser Trp Ser Thr
1 5 10 15

Pro Ser Tyr Ala Tyr
20

<210> SEQ ID NO 86
<211> LENGTH: 18
<212> TYPE: PRT
<213> ORGANISM: Artificial Sequence
<220> FEATURE:
<223> OTHER INFORMATION: AS78215 CDR3

<400> SEQUENCE: 86

Ala Ala Arg Ala Gly Pro Cys Trp Ser Trp Ala Gln Ala Asp Leu Tyr
1 5 10 15

Asn Tyr

<210> SEQ ID NO 87
<211> LENGTH: 17
<212> TYPE: PRT

<213> ORGANISM: Artificial Sequence
<220> FEATURE:
<223> OTHER INFORMATION: AS78810 CDR3

<400> SEQUENCE: 87

Ala Ala Gly Arg Tyr Val Gly Arg Lys Leu Glu Val Tyr Asp Tyr Ala
1 5 10 15

Tyr

<210> SEQ ID NO 88
<211> LENGTH: 20
<212> TYPE: PRT
<213> ORGANISM: Artificial Sequence
<220> FEATURE:
<223> OTHER INFORMATION: AS79101 CDR3

<400> SEQUENCE: 88

Ala Thr Asp Pro Lys Val Ala Cys Ala Arg Val Val Glu Tyr Gly Gly
1 5 10 15

Gly Trp Tyr Arg
20

<210> SEQ ID NO 89
<211> LENGTH: 21
<212> TYPE: PRT
<213> ORGANISM: Artificial Sequence
<220> FEATURE:
<223> OTHER INFORMATION: AS79236 CDR3

<400> SEQUENCE: 89

Ala Val Asp Val Arg Thr Arg Cys Gly Gly Thr Trp Asp Gly Glu Ala
1 5 10 15

Val Tyr Phe Pro Tyr
20

<210> SEQ ID NO 90
<211> LENGTH: 17
<212> TYPE: PRT
<213> ORGANISM: Artificial Sequence
<220> FEATURE:
<223> OTHER INFORMATION: AS79274 CDR3

<400> SEQUENCE: 90

Ala Ala Gln Ile Val Gly Gly Ala Leu Arg Cys Pro Arg Phe Ala Met
1 5 10 15

Tyr

<210> SEQ ID NO 91
<211> LENGTH: 26
<212> TYPE: PRT
<213> ORGANISM: Artificial Sequence
<220> FEATURE:
<223> OTHER INFORMATION: AS79285 CDR3

<400> SEQUENCE: 91

Ala Gly Val Tyr Gly Leu Ile Trp Tyr Tyr Lys Pro Cys Pro Ala Gln
1 5 10 15

Arg Glu Trp Ala Leu Gln Arg Tyr Gly Tyr
20 25

<210> SEQ ID NO 92
<211> LENGTH: 18
<212> TYPE: PRT
<213> ORGANISM: Artificial Sequence

<220> FEATURE:
<223> OTHER INFORMATION: AS79317 CDR3

<400> SEQUENCE: 92

```
Ala Ala Gly Gly Cys Gly Tyr Arg Gly Val Ala Asp Val Pro Glu Phe
1               5                   10                  15

Thr Tyr
```

<210> SEQ ID NO 93
<211> LENGTH: 126
<212> TYPE: PRT
<213> ORGANISM: Artificial Sequence
<220> FEATURE:
<223> OTHER INFORMATION: AS70549

<400> SEQUENCE: 93

```
Gln Val Arg Leu Val Glu Ser Gly Gly Gly Ser Val Gln Ala Gly Gly
1               5                   10                  15

Ser Leu Thr Leu Ser Cys Ala Tyr Ser Arg Tyr Thr Gly Arg Ser Ser
            20                  25                  30

Cys Met Ala Trp Phe Arg Arg Pro Pro Gly Lys Lys Arg Glu Arg Val
        35                  40                  45

Ala Ser Ile Tyr Ser Asp Asp Gly Val Thr Val Tyr Ala Asp Ser Val
    50                  55                  60

Lys Gly Arg Phe Thr Ile Thr Gln Asp Ser Ala Gln Asn Thr Leu Tyr
65                  70                  75                  80

Leu Gln Met Asn Ser Leu Asp Pro Glu Asp Thr Ala Met Tyr Tyr Cys
                85                  90                  95

Ala Thr Arg Thr Thr Tyr Pro Gly Val Cys Pro Asp Asn Ala Ala Trp
            100                 105                 110

Tyr Asp Tyr Trp Gly Gln Gly Thr Gln Val Thr Val Ser Ser
        115                 120                 125
```

<210> SEQ ID NO 94
<211> LENGTH: 125
<212> TYPE: PRT
<213> ORGANISM: Artificial Sequence
<220> FEATURE:
<223> OTHER INFORMATION: AS70771

<400> SEQUENCE: 94

```
Gln Val Gln Leu Val Glu Ser Gly Gly Gly Ser Val Gln Ala Gly Gly
1               5                   10                  15

Ser Leu Arg Leu Ser Cys Ala Ala Ser Gly Tyr Thr Gly Lys Met Ala
            20                  25                  30

Trp Phe Arg Gln Ala Pro Gly Lys Glu Arg Glu Gly Val Ala Ala Ile
        35                  40                  45

Asp Asp Ala Gly Gly Thr Asn Tyr Ile Asp Ser Val Lys Gly Arg Phe
    50                  55                  60

Thr Ile Ser Lys Asp Asn Ala Glu Asn Thr Leu Tyr Leu Arg Met Asn
65                  70                  75                  80

Ser Leu Lys Pro Glu Asp Thr Ala Ile Tyr Tyr Cys Ala Ala Asp Thr
                85                  90                  95

Phe Arg Trp Phe Met Arg Arg Ser Gly Pro Ile Asn Gly Ser Asp Tyr
            100                 105                 110

Ala Tyr Trp Gly Gln Gly Thr Gln Val Thr Val Ser Ser
        115                 120                 125
```

<210> SEQ ID NO 95
<211> LENGTH: 124
<212> TYPE: PRT
<213> ORGANISM: Artificial Sequence
<220> FEATURE:
<223> OTHER INFORMATION: AS70950

<400> SEQUENCE: 95

```
Gln Val Gln Leu Val Glu Ser Gly Gly Gly Ser Ala Gln Ser Gly Gly
1               5                   10                  15

Ser Leu Arg Leu Ser Cys Ala Ile Ser Glu Phe Thr Tyr Lys Asn Thr
            20                  25                  30

Cys Val Gly Trp Phe Arg Gln Ala Pro Gly Lys Glu Arg Glu Gly Val
        35                  40                  45

Ala Ala Ile Asp Ser Asp Gly Asn Thr Asn Tyr Val Asp Ser Val Lys
    50                  55                  60

Gly Arg Phe Thr Ile Ser Gln Gly Asn Ala Lys Asn Thr Val Tyr Leu
65                  70                  75                  80

Gln Met Asn Ser Leu Lys Pro Glu Asp Thr Ala Met Tyr Tyr Cys Ala
                85                  90                  95

Ala Gly Ala Tyr Cys Gly Arg Leu Leu Leu Trp Ile Gly Asn Tyr Ala
            100                 105                 110

Tyr Trp Gly Gln Gly Thr Gln Val Thr Val Ser Ser
        115                 120
```

<210> SEQ ID NO 96
<211> LENGTH: 125
<212> TYPE: PRT
<213> ORGANISM: Artificial Sequence
<220> FEATURE:
<223> OTHER INFORMATION: AS71402

<400> SEQUENCE: 96

```
Gln Met Gln Leu Val Glu Ser Gly Gly Gly Ser Val Gln Ala Gly Gly
1               5                   10                  15

Ser Leu Arg Leu Ser Cys Val Val Ser Gly Tyr Thr Tyr Asn Arg Asn
            20                  25                  30

Met Ala Trp Phe Arg Gln Ala Pro Gly Lys Glu Arg Glu Gly Val Ala
        35                  40                  45

Ala Met Tyr Thr Gly Ser Gly Thr Thr Asp Tyr Ala Asp Ser Val Lys
    50                  55                  60

Gly Arg Phe Thr Ile Ser His Asp Asn Ala Lys Asn Thr Leu Tyr Leu
65                  70                  75                  80

Gln Met Asn Ser Leu Lys Pro Glu Asp Thr Ala Thr Tyr Tyr Cys Ala
                85                  90                  95

Ala Asp Thr Ala Arg Arg Gly Gly Ser Trp Ser Gly Pro Phe Lys Tyr
            100                 105                 110

Asp Tyr Trp Gly Gln Gly Thr Gln Val Thr Val Ser Ser
        115                 120                 125
```

<210> SEQ ID NO 97
<211> LENGTH: 126
<212> TYPE: PRT
<213> ORGANISM: Artificial Sequence
<220> FEATURE:
<223> OTHER INFORMATION: AS71529

<400> SEQUENCE: 97

```
Glu Val Gln Leu Val Glu Ser Gly Gly Gly Ser Val Gln Ala Gly Gly
1               5                   10                  15
```

```
Ser Leu Arg Leu Ser Cys Val Val Ser Glu Tyr Arg Tyr Ser Ser Arg
            20                  25                  30

Tyr Cys Met Gly Trp Phe Arg Gln Ala Pro Gly Lys Glu Arg Glu Gly
        35                  40                  45

Val Ala Ala Ile Asp Ser Asn Gly Ser Ala Asp Tyr Val Asp Ser Val
    50                  55                  60

Lys Gly Arg Phe Thr Ile Ser Lys Asp Asn Ala Lys Asn Thr Leu Tyr
65                  70                  75                  80

Leu Gln Ile Asn Ser Val Arg Pro Glu Asp Thr Ala Met Tyr Tyr Cys
                85                  90                  95

Ala Ala Asp His Leu Ala Tyr Asp Cys Tyr Ser Gly Ala Thr Ser Val
            100                 105                 110

Phe Arg Tyr Trp Gly Gln Gly Thr Gln Val Thr Val Ser Ser
        115                 120                 125


<210> SEQ ID NO 98
<211> LENGTH: 126
<212> TYPE: PRT
<213> ORGANISM: Artificial Sequence
<220> FEATURE:
<223> OTHER INFORMATION: AS71661

<400> SEQUENCE: 98

Gln Val Gln Leu Val Glu Ser Gly Gly Gly Leu Val Gln Ala Gly Gly
1               5                   10                  15

Ser Leu Arg Leu Ser Cys Ser Pro Ser Gly Thr Thr Phe Ala His Tyr
            20                  25                  30

Asn Met Val Gly Trp Phe Arg Gln Ala Pro Gly Lys Asp Arg Glu Gly
        35                  40                  45

Val Ser Cys Ile Ser Lys Tyr Gly Gly Thr Thr Tyr Tyr Ala Asp Ser
    50                  55                  60

Val Lys Gly Arg Phe Thr Ile Tyr Arg Asp Asn Ala Lys Asn Thr Leu
65                  70                  75                  80

Phe Leu Gln Met Asn Ser Leu Lys Pro Glu Asp Thr Ala Met Tyr Tyr
                85                  90                  95

Cys Ala Ile Gly Val Leu Pro Ser Ser Thr Ala Ile Cys Ala Gly Ala
            100                 105                 110

Ala Asn Tyr Trp Gly Gln Gly Thr Gln Val Thr Val Ser Ser
        115                 120                 125


<210> SEQ ID NO 99
<211> LENGTH: 125
<212> TYPE: PRT
<213> ORGANISM: Artificial Sequence
<220> FEATURE:
<223> OTHER INFORMATION: AS72021

<400> SEQUENCE: 99

Glu Val Gln Leu Ala Glu Ser Gly Gly Gly Ser Val Gln Ala Gly Gly
1               5                   10                  15

Ser Leu Arg Leu Ser Cys Val Val Ser Arg Asn Thr Tyr Ser Ser Tyr
            20                  25                  30

Cys Met Ser Trp Phe Arg Gln Ala Pro Gly Lys Glu Arg Glu Gly Val
        35                  40                  45

Ala Ala Ile Asp Asn Val Lys Thr Ser Tyr Ala Asp Ser Val Lys Gly
    50                  55                  60

Arg Phe Thr Ile Ser Lys Asp Asn Ala Lys Asn Thr Leu Tyr Leu Gln
```

```
65                  70                  75                  80

Met Asn Ser Leu Lys Pro Glu Asp Thr Ala Met Tyr Tyr Cys Ala Ala
                85                  90                  95

His Leu Glu Leu Cys Tyr Tyr Thr Asp Pro Met Tyr Gln Tyr Glu Tyr
            100                 105                 110

Asn Tyr Trp Gly Gln Gly Thr Gln Val Thr Val Ser Ser
        115                 120                 125


<210> SEQ ID NO 100
<211> LENGTH: 125
<212> TYPE: PRT
<213> ORGANISM: Artificial Sequence
<220> FEATURE:
<223> OTHER INFORMATION: AS72052

<400> SEQUENCE: 100

Gln Val Arg Leu Val Glu Ser Gly Gly Gly Ser Val Gln Ala Gly Gly
1               5                   10                  15

Ser Leu Arg Leu Ser Cys Ala Val Ser Gly Phe Arg Tyr Ala Ser Tyr
            20                  25                  30

Cys Met Gly Trp Phe Arg Gln Ala Pro Gly Lys Glu Arg Glu Gly Val
        35                  40                  45

Ala Ala Ile His Ser Asp Gly Ile Ile Arg Tyr Ala Glu Ser Val Lys
    50                  55                  60

Gly Arg Phe Thr Ile Ser Lys Asp Asn Ala Lys Asn Thr Leu Tyr Leu
65                  70                  75                  80

Gln Leu Asn Ser Leu Lys Pro Glu Asp Asn Ala Met Tyr Ser Cys Ala
                85                  90                  95

Ala Gly Ala Tyr Cys Gly Ala Asp Ala Ile Leu Thr Leu Tyr Asp Tyr
            100                 105                 110

Ala Phe Trp Gly Gln Gly Thr Gln Val Thr Val Ser Ser
        115                 120                 125


<210> SEQ ID NO 101
<211> LENGTH: 123
<212> TYPE: PRT
<213> ORGANISM: Artificial Sequence
<220> FEATURE:
<223> OTHER INFORMATION: AS72383

<400> SEQUENCE: 101

Gln Val Arg Leu Val Glu Ser Gly Gly Gly Leu Val Gln Ala Gly Gly
1               5                   10                  15

Ser Gln Arg Leu Ser Cys Thr Ala Ser Gly Leu Thr Phe Asp Asp Ser
            20                  25                  30

Gly Met Gly Trp Phe Arg Gln Ala Pro Gly Lys Gly Arg Glu Gly Val
        35                  40                  45

Ser Cys Ile Thr Trp Asn Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Ala Phe Ile Thr Lys Thr Gly Cys Ser Tyr Glu Tyr Asp Tyr
            100                 105                 110

Ser Gly Gln Gly Thr Gln Val Thr Val Ser Ser
        115                 120
```

-continued

<210> SEQ ID NO 102
<211> LENGTH: 123
<212> TYPE: PRT
<213> ORGANISM: Artificial Sequence
<220> FEATURE:
<223> OTHER INFORMATION: AS72479

<400> SEQUENCE: 102

```
Gln Val Lys Leu Val Glu Ser Gly Gly Gly Ser Val Gln Ala Gly Gly
1               5                   10                  15

Ser Leu Arg Leu Ser Cys Ala Ala Ser Glu Thr Thr Asp Cys Arg Tyr
            20                  25                  30

Val Trp Arg Trp Tyr Arg Glu Asp Pro Gly Met Glu Arg Glu Phe Val
        35                  40                  45

Ser Ser Ile Thr Ser Gly Gly Ser Thr Trp Tyr Ala Asp Ser Val Lys
    50                  55                  60

Gly Arg Phe Thr Ile Ser Gln Asp Asn Ala Lys Ser Thr Leu Tyr Leu
65                  70                  75                  80

Gln Met Asn Ser Leu Lys Pro Glu Asp Ser Gly Met Tyr Tyr Cys Glu
                85                  90                  95

Ser Asp Pro Gly Trp Ser Gly Tyr His Ala Arg Arg Cys Glu Val Tyr
            100                 105                 110

Arg Gly Gln Gly Ile Gln Val Thr Val Ser Ser
        115                 120
```

<210> SEQ ID NO 103
<211> LENGTH: 126
<212> TYPE: PRT
<213> ORGANISM: Artificial Sequence
<220> FEATURE:
<223> OTHER INFORMATION: AS72499

<400> SEQUENCE: 103

```
Gln Val Arg Leu Val Glu Ser Gly Gly Gly Ser Val Gln Ala Gly Gly
1               5                   10                  15

Ser Leu Arg Leu Ser Cys Val Val Ser Arg Phe Thr Tyr Ser Ser Tyr
            20                  25                  30

Cys Met Gly Trp Phe Arg Gln Ala Pro Gly Lys Glu Arg Glu Gly Val
        35                  40                  45

Ala Gly Ile Glu Lys Asp Asp Ser Thr Tyr Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Arg Ile Pro Gly Gly Asn Cys Gly Val Val Ala Arg Met Ala Tyr
            100                 105                 110

Trp Asp Tyr Trp Gly Lys Gly Thr Leu Val Thr Val Ser Ser
        115                 120                 125
```

<210> SEQ ID NO 104
<211> LENGTH: 125
<212> TYPE: PRT
<213> ORGANISM: Artificial Sequence
<220> FEATURE:
<223> OTHER INFORMATION: AS72531

<400> SEQUENCE: 104

```
Gln Val Gln Leu Val Glu Ser Gly Gly Gly Leu Val Gln Ala Gly Gly
```

```
1               5                   10                  15

Ser Leu Arg Leu Ser Cys Thr Ala Ser Gly Leu Thr Phe Ala His Tyr
            20                  25                  30

Asn Met Val Gly Trp Phe Arg Gln Ala Pro Gly Lys Asp Arg Glu Gly
        35                  40                  45

Val Ser Cys Ile Ser Lys Tyr Gly Gly Thr Ile Tyr Tyr Ala Asp Ser
    50                  55                  60

Val Lys Gly Arg Phe Thr Ile Asp Arg Asn Asn Ala Lys Asn Thr Leu
65                  70                  75                  80

Tyr Leu Gln Met Asn Ser Leu Lys Pro Glu Asp Thr Ala Met Tyr Tyr
                85                  90                  95

Cys Ala Ile Gly Val Leu Ser Ser Thr Ala Arg Gly Pro Gly Ala Ala
            100                 105                 110

Asn Tyr Trp Gly Gln Gly Thr Gln Val Thr Val Ser Ser
        115                 120                 125


<210> SEQ ID NO 105
<211> LENGTH: 124
<212> TYPE: PRT
<213> ORGANISM: Artificial Sequence
<220> FEATURE:
<223> OTHER INFORMATION: AS72669

<400> SEQUENCE: 105

Glu Val Gln Leu Val Glu Ser Gly Gly Gly Ser Val Gln Ala Gly Gly
1               5                   10                  15

Ser Leu Lys Leu Ser Cys Ala Ala Ser Arg Phe Thr Tyr Ser Ser Tyr
            20                  25                  30

Cys Met Gly Trp Ile Arg Gln Ala Pro Gly Lys Glu Arg Glu Gly Val
        35                  40                  45

Ala Ile Phe Tyr Thr Gly Gly Gly Arg Thr Tyr Tyr Ala Asp Ser Val
    50                  55                  60

Lys Gly Arg Phe Thr Ile Ser Gln Asp Thr Ala Lys Asn Thr Leu Tyr
65                  70                  75                  80

Leu Gln Met Asn Ser Leu Lys Pro Glu Asp Thr Gly Ile Tyr Tyr Cys
                85                  90                  95

Val Ala Gly Phe Tyr Cys Ser Gly Gly Tyr Trp Glu Gly Asp Phe Gly
            100                 105                 110

Tyr Trp Gly Gln Gly Thr Gln Val Thr Val Ser Ser
        115                 120


<210> SEQ ID NO 106
<211> LENGTH: 130
<212> TYPE: PRT
<213> ORGANISM: Artificial Sequence
<220> FEATURE:
<223> OTHER INFORMATION: AS72794

<400> SEQUENCE: 106

Gln Val Gln Leu Val Glu Ser Gly Gly Gly Leu Val Gln Ala Gly Gly
1               5                   10                  15

Ser Leu Arg Leu Ser Cys Thr Ala Ser Gly Phe Thr Phe Asp Asp Tyr
            20                  25                  30

Ala Met Ser Trp Phe Arg Gln Ala Pro Gly Lys Glu Arg Glu Gly Val
        35                  40                  45

Ser Cys Ile Ser Ala Ser Gly Thr Thr Thr Tyr Tyr Gly Asp Ser Val
    50                  55                  60
```

```
Lys Gly Arg Phe Thr Ile Ser Arg Asp Asn Ala Lys Thr Thr Leu Ile
65                  70                  75                  80

Leu Gln Met Ser Ser Leu Lys Pro Glu Asp Thr Ala Met Tyr Tyr Cys
                85                  90                  95

Ala Ala Asp Arg Phe Arg Asp Tyr Cys Ser Asp Ser Trp Ser His Leu
            100                 105                 110

Tyr Asn Tyr Glu Tyr Met His Trp Gly Gln Gly Thr Gln Val Thr Val
        115                 120                 125

Ser Ser
    130


<210> SEQ ID NO 107
<211> LENGTH: 129
<212> TYPE: PRT
<213> ORGANISM: Artificial Sequence
<220> FEATURE:
<223> OTHER INFORMATION: AS72805

<400> SEQUENCE: 107

Gln Val Gln Leu Val Glu Ser Gly Gly Asp Ser Val Gln Ala Gly Gly
1               5                   10                  15

Ser Leu Thr Leu Ser Cys Val Ala Ser Arg Leu Arg Val Ser Asn Asn
            20                  25                  30

Cys Met Gly Trp Phe Arg Gln Ala Pro Gly Asn Glu Arg Glu Gly Val
        35                  40                  45

Ala Thr Leu Gly Ser Asp Gly Arg Thr Ile Tyr Ala Asp Ser Val Lys
    50                  55                  60

Gly Arg Phe Thr Ile Ser Lys Asp Asn Val Ala Asn Thr Leu Tyr Leu
65                  70                  75                  80

Gln Met Asn Gly Leu Lys Leu Asp Asp Thr Ala Leu Tyr Tyr Cys Ala
                85                  90                  95

Ala Ala Asp Phe Ser Ser Gly Gly Tyr Cys Asn Ile Ala Ser Val Tyr
            100                 105                 110

His Ser Tyr Phe Pro Tyr Trp Gly Gln Gly Thr Gln Val Thr Val Ser
        115                 120                 125

Ser


<210> SEQ ID NO 108
<211> LENGTH: 127
<212> TYPE: PRT
<213> ORGANISM: Artificial Sequence
<220> FEATURE:
<223> OTHER INFORMATION: AS72806

<400> SEQUENCE: 108

Gln Val Gln Leu Val Glu Ser Gly Gly Gly Ser Val Gln Ala Gly Gly
1               5                   10                  15

Ser Leu Arg Leu Ser Cys Ala Ala Ser Gly Tyr Thr Tyr Met Pro Pro
            20                  25                  30

Cys Met Gly Trp Phe Arg Gln Ala Pro Gly Lys Glu Arg Glu Gly Val
        35                  40                  45

Ala Thr Ile Tyr Gly Arg Gly Gly Ser Thr Tyr Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Met Asn Asn Leu Glu Pro Glu Asp Thr Ala Met Tyr Tyr Cys
                85                  90                  95
```

```
Ala Ala Asp Asn Leu Cys Tyr Ala Thr Gly Ile Leu Arg Ser Ala Tyr
            100                 105                 110

Asp Tyr Ser Tyr Trp Gly Gln Gly Thr Gln Val Thr Val Ser Ser
        115                 120                 125


<210> SEQ ID NO 109
<211> LENGTH: 126
<212> TYPE: PRT
<213> ORGANISM: Artificial Sequence
<220> FEATURE:
<223> OTHER INFORMATION: AS72835

<400> SEQUENCE: 109

Gln Val His Leu Met Glu Ser Gly Gly Gly Ser Val Gln Ala Gly Gly
1               5                   10                  15

Ser Leu Arg Leu Ser Cys Ala Val Ser Gly Gly Tyr Thr Ser Arg Thr
            20                  25                  30

Val Cys Met Gly Trp Phe Arg Gln Thr Pro Gly Lys Glu Arg Glu Val
        35                  40                  45

Leu Ala Ala Ile Tyr Arg Ser Gly Thr Thr Tyr Tyr His Asp Ser Val
    50                  55                  60

Lys Gly Arg Phe Thr Ile Ser Arg Asp Gly Asp Lys Asn Thr Val Tyr
65                  70                  75                  80

Leu Gln Met Asp Ser Leu Lys Pro Glu Asp Thr Ala Met Tyr Tyr Cys
                85                  90                  95

Ala Ala Ser Pro Gly Tyr Ser Asp Ala Ala Cys Val Ser Val Pro Gln
            100                 105                 110

Ala Asn Arg Trp Gly Gln Gly Thr Gln Val Thr Val Ser Ser
        115                 120                 125


<210> SEQ ID NO 110
<211> LENGTH: 121
<212> TYPE: PRT
<213> ORGANISM: Artificial Sequence
<220> FEATURE:
<223> OTHER INFORMATION: AS77906

<400> SEQUENCE: 110

Gln Val Arg Leu Val Glu Ser Gly Gly Gly Ser Val Gln Ala Gly Glu
1               5                   10                  15

Ser Leu Arg Leu Ser Cys Ala Arg Ser Gly Val Val Lys Cys Asp Val
            20                  25                  30

Glu Met Arg Trp Tyr Arg Gln Ser Pro Gly Lys Glu Arg Glu Phe Val
        35                  40                  45

Ala Leu Ile Glu Ala Gly Gly His Thr Glu Tyr Ala Asp Ser Val Lys
    50                  55                  60

Gly Arg Phe Thr Ile Ser Gln Asp Asn Ala Lys Met Leu Phe Tyr Leu
65                  70                  75                  80

Gln Met Asn Ser Leu Lys Pro Glu Asp Thr Ala Lys Tyr Tyr Cys Val
                85                  90                  95

Ala Ala Pro Arg Tyr Tyr Thr Leu Ser Cys Pro Lys Asp Phe Trp Gly
            100                 105                 110

Arg Gly Thr Gln Val Thr Val Ser Ser
        115                 120


<210> SEQ ID NO 111
<211> LENGTH: 123
<212> TYPE: PRT
<213> ORGANISM: Artificial Sequence
```

<220> FEATURE:
<223> OTHER INFORMATION: AS77916

<400> SEQUENCE: 111

```
Gln Val His Leu Met Glu Ser Gly Gly Gly Ser Val Gln Ala Gly Gly
1               5                   10                  15

Ser Leu Arg Leu Ser Cys Ala Thr Ser Gly Tyr Thr Ser Ser Trp Asn
            20                  25                  30

Cys Met Gly Trp Phe Arg Gln Pro Pro Gly Lys Glu Arg Glu Gly Val
        35                  40                  45

Ala Thr Ile Ala Asn Arg Gly His Ser Thr Tyr Tyr Ala Asp Ser Val
    50                  55                  60

Lys Gly Arg Phe Thr Ile Ser Gln Gly Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Thr Asp Thr Trp Ala Cys Val Gly Ile Ser Thr Asp Phe Glu Tyr
            100                 105                 110

Trp Gly Gln Gly Thr Gln Val Thr Val Ser Ser
        115                 120
```

<210> SEQ ID NO 112
<211> LENGTH: 124
<212> TYPE: PRT
<213> ORGANISM: Artificial Sequence
<220> FEATURE:
<223> OTHER INFORMATION: AS77932

<400> SEQUENCE: 112

```
Gln Val Gln Leu Lys Glu Ser Gly Gly Gly Ser Val Gln Ala Gly Gly
1               5                   10                  15

Ser Leu Arg Leu Ser Cys Ala Val Ser Gly Tyr Trp Tyr Ser Val Ala
            20                  25                  30

Trp Met Gly Trp Phe Arg Gln Thr Pro Gly Lys Glu Arg Glu Gly Val
        35                  40                  45

Ala Ala Val Leu Asn Gly Gly Gly Arg Arg Tyr Tyr Ala Asp Ser Val
    50                  55                  60

Lys Gly Arg Phe Thr Ile Ser Gln Asp Asn Ser Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Gly Asn Gly Val Gly His Pro Leu Gly Pro Ser Glu Tyr Asn
            100                 105                 110

Tyr Trp Gly Gln Gly Thr Gln Val Thr Val Ser Ser
        115                 120
```

<210> SEQ ID NO 113
<211> LENGTH: 125
<212> TYPE: PRT
<213> ORGANISM: Artificial Sequence
<220> FEATURE:
<223> OTHER INFORMATION: AS77934

<400> SEQUENCE: 113

```
Glu Val Gln Leu Val Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Tyr
            20                  25                  30
```

```
Ser Ile Ala Trp Phe Arg Gln Ala Pro Gly Lys Glu Arg Glu Gly Val
        35                  40                  45

Ala Gly Phe Phe Tyr Ser Gly Gly Pro Thr Cys Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Arg Arg Ser Asn Thr Asn Asp Tyr Cys Phe Tyr Pro Thr Tyr
            100                 105                 110

Thr Tyr Trp Gly Gln Gly Thr Gln Val Thr Val Ser Ser
        115                 120                 125


<210> SEQ ID NO 114
<211> LENGTH: 120
<212> TYPE: PRT
<213> ORGANISM: Artificial Sequence
<220> FEATURE:
<223> OTHER INFORMATION: AS77978

<400> SEQUENCE: 114

Gln Val Arg Leu Val Glu Ser Gly Gly Gly Ser Val Gln Ala Gly Gly
1               5                   10                  15

Ser Leu Arg Leu Ser Cys Ala Ala Ser Gly Ala Thr Ser Cys Arg Trp
            20                  25                  30

Arg Met Ser Trp Tyr Arg Gln Ala Pro Gly Lys Glu Arg Glu Phe Val
        35                  40                  45

Ser Ser Ile Ala Asn Gly Ala Thr Glu Tyr Ala Asp Ser Val Lys Gly
    50                  55                  60

Arg Phe Thr Ile Ser Gln Asp Asn Ala Arg Asn Thr Met Tyr Leu Gln
65                  70                  75                  80

Met Asn Ser Leu Ser Pro Glu Asp Thr Ala Met Tyr Tyr Cys Ala Ala
                85                  90                  95

Asp Pro Arg Val Tyr Thr Ser Arg Cys Asp Arg Thr Tyr Leu Gly Gln
            100                 105                 110

Gly Thr Gln Val Thr Val Ser Ser
        115                 120


<210> SEQ ID NO 115
<211> LENGTH: 132
<212> TYPE: PRT
<213> ORGANISM: Artificial Sequence
<220> FEATURE:
<223> OTHER INFORMATION: [AS77986

<400> SEQUENCE: 115

Gln Val Gln Leu Val Glu Ser Gly Gly Gly Ser Val Gln Ala Gly Gly
1               5                   10                  15

Ser Leu Arg Leu Ser Cys Ala Ala Ser Ala Ser Gly Tyr Thr Tyr Ser
            20                  25                  30

Ser Asp Ser Met Ala Trp Phe Arg Gln Ala Pro Gly Lys Glu Arg Glu
        35                  40                  45

Gly Val Ala Gly Ile Ser Thr Gly Gly Arg Ser Thr Tyr Tyr Ala Asp
    50                  55                  60

Ser Val Lys Gly Arg Phe Thr Ile Ser Gln Asp Asn Ala Lys Thr Thr
65                  70                  75                  80

Val Tyr Leu His Met Asn Ser Leu Lys Pro Glu Asp Thr Ala Met Tyr
                85                  90                  95
```

```
Tyr Cys Ala Ala Asp Gly Pro Ser Met Thr Ala Ile Gln Ala Leu Gly
            100                 105                 110

Asp Leu Tyr Pro Val Asp Phe Ala Trp Trp Gly Gln Gly Thr Gln Val
        115                 120                 125

Thr Val Ser Ser
    130


<210> SEQ ID NO 116
<211> LENGTH: 127
<212> TYPE: PRT
<213> ORGANISM: Artificial Sequence
<220> FEATURE:
<223> OTHER INFORMATION: AS78117

<400> SEQUENCE: 116

Gln Val Lys Leu Val Glu Ser Gly Gly Gly Ser Val Gln Ala Gly Gly
1               5                   10                  15

Ala Leu Arg Leu Ser Cys Ile Val Arg Arg Tyr Thr Tyr Ala Thr Tyr
            20                  25                  30

Ser Met Ala Trp Phe Arg Gln Ser Pro Gly Lys Glu Arg Glu Gly Val
        35                  40                  45

Ala Gly Leu Asp Ser Val Gly Ala Thr Gly Tyr Ala Glu Ser Val Lys
    50                  55                  60

Gly Arg Phe Thr Ile Ser Lys Asp Asn Ala Lys Asn Ile Leu Tyr Leu
65                  70                  75                  80

Gln Met Asn Ser Leu Lys Pro Glu Asp Thr Ala Met Tyr Tyr Cys Val
                85                  90                  95

Val Asp Pro Ala Ser Ala Lys Val Thr Tyr Gly Ser Trp Ser Thr Pro
            100                 105                 110

Ser Tyr Ala Tyr Trp Gly Gln Gly Thr Gln Val Thr Val Ser Ser
        115                 120                 125


<210> SEQ ID NO 117
<211> LENGTH: 125
<212> TYPE: PRT
<213> ORGANISM: Artificial Sequence
<220> FEATURE:
<223> OTHER INFORMATION: AS78215

<400> SEQUENCE: 117

Gln Val Lys Leu Val Glu Ser Gly Gly Gly Ser Val Gln Ala Gly Gly
1               5                   10                  15

Ala Leu Arg Leu Ser Cys Ala Ala Ser Arg Tyr Thr Phe Ser Ser Asn
            20                  25                  30

Cys Met Gly Trp Phe Arg Gln Ala Pro Gly Lys Glu Arg Glu Gly Val
        35                  40                  45

Ala Thr Ile Ala Ser Ala Ser Gly Tyr Thr Asp Tyr His Asp Ser Val
    50                  55                  60

Lys Gly Arg Phe Ala Ile Ser Arg Asp Asn Ala Lys Asn Thr Val Tyr
65                  70                  75                  80

Leu Gln Met Asn Ser Leu Lys Pro Glu Asp Thr Ala Thr Tyr Tyr Cys
                85                  90                  95

Ala Ala Arg Ala Gly Pro Cys Trp Ser Trp Ala Gln Ala Asp Leu Tyr
            100                 105                 110

Asn Tyr Trp Gly Gln Gly Thr Gln Val Thr Val Ser Ser
        115                 120                 125
```

<210> SEQ ID NO 118
<211> LENGTH: 119
<212> TYPE: PRT
<213> ORGANISM: Artificial Sequence
<220> FEATURE:
<223> OTHER INFORMATION: AS78810

<400> SEQUENCE: 118

```
Gln Val His Leu Val Glu Ser Gly Gly Gly Ser Val Gln Ala Gly Gly
1               5                   10                  15

Ser Leu Arg Leu Ser Cys Ala Ala Ser Gly Tyr Thr Tyr Tyr Asp Met
            20                  25                  30

Gly Trp Phe Arg Leu Ala Pro Gly Lys Glu Arg Glu Gly Ile Ala Ala
        35                  40                  45

Ile Ser Ser Ser Ser Ser Thr Tyr Tyr Ala Asp Ser Val Lys Gly Arg
    50                  55                  60

Phe Thr Ile Ser Arg Asp Ser Asn Thr Leu Tyr Leu Gln Met Asn Ser
65                  70                  75                  80

Leu Lys Pro Glu Asp Thr Ala Met Tyr Ser Cys Ala Ala Gly Arg Tyr
                85                  90                  95

Val Gly Arg Lys Leu Glu Val Tyr Asp Tyr Ala Tyr Trp Gly Gln Gly
            100                 105                 110

Thr Gln Val Thr Val Ser Ser
        115
```

<210> SEQ ID NO 119
<211> LENGTH: 126
<212> TYPE: PRT
<213> ORGANISM: Artificial Sequence
<220> FEATURE:
<223> OTHER INFORMATION: AS79101

<400> SEQUENCE: 119

```
Gln Val Gln Leu Val Glu Ser Gly Gly Gly Ser Val Gln Ala Gly Gly
1               5                   10                  15

Ser Leu Arg Leu Ser Cys Ala Ala Ser Gly Asp Thr Tyr Ser Asn Tyr
            20                  25                  30

Cys Met Gly Trp Phe Arg Gln Ala Pro Gly Lys Glu Arg Glu Glu Val
        35                  40                  45

Ala Ala Ile Asp Ser Asp Gly Ser Arg Arg Tyr Pro Asp Ser Val Lys
    50                  55                  60

Gly Arg Phe Thr Ile Ser Lys Asp Asn Ala Lys Lys Ile Leu Tyr Leu
65                  70                  75                  80

Gln Met Asn Ser Leu Lys Pro Glu Asp Thr Ala Met Tyr Phe Cys Ala
                85                  90                  95

Thr Asp Pro Lys Val Ala Cys Ala Arg Val Val Glu Tyr Gly Gly Gly
            100                 105                 110

Trp Tyr Arg Trp Gly Gln Gly Thr Gln Val Thr Val Ser Ser
        115                 120                 125
```

<210> SEQ ID NO 120
<211> LENGTH: 127
<212> TYPE: PRT
<213> ORGANISM: Artificial Sequence
<220> FEATURE:
<223> OTHER INFORMATION: AS79236

<400> SEQUENCE: 120

```
Gln Val Lys Leu Val Glu Ser Gly Gly Gly Ser Val Gln Ala Gly Gly
1               5                   10                  15
```

```
Ser Leu Arg Leu Ser Cys Ala Val Ser Gly Tyr Thr Tyr Ser Ser Tyr
            20                  25                  30

Cys Met Ala Trp Phe Arg Gln Ala Pro Gly Glu Glu Arg Glu Gly Val
        35                  40                  45

Ala Ser Ile Asp Ala Gly Gly Arg Thr Thr Tyr Val Asp Ser Val Lys
    50                  55                  60

Gly Arg Phe Thr Ile Ser Lys Asp Asn Ala Lys Thr Ser Leu Tyr Leu
65                  70                  75                  80

Gln Met Asn Ser Leu Lys Pro Glu Asp Thr Ala Met Tyr Tyr Cys Ala
                85                  90                  95

Val Asp Val Arg Thr Arg Cys Gly Gly Thr Trp Asp Gly Glu Ala Val
            100                 105                 110

Tyr Phe Pro Tyr Trp Gly Gln Gly Thr Gln Val Thr Val Ser Ser
        115                 120                 125


<210> SEQ ID NO 121
<211> LENGTH: 123
<212> TYPE: PRT
<213> ORGANISM: Artificial Sequence
<220> FEATURE:
<223> OTHER INFORMATION: AS79274

<400> SEQUENCE: 121

Gln Val His Leu Val Glu Ser Gly Gly Gly Ser Val Gln Ala Gly Gly
1               5                   10                  15

Ser Leu Arg Leu Ser Cys Ala Ala Ser Lys Tyr Ala Phe Cys Thr Tyr
            20                  25                  30

Asp Met Ser Trp Phe Arg Gln Ala Pro Gly Lys Glu Arg Glu Val Val
        35                  40                  45

Ser Ser Ile Asp Ser Arg Gly Asn Thr Asn Tyr Ser Asp Ser Val Lys
    50                  55                  60

Gly Arg Phe Thr Ile Ser Gln Asp His Ala Lys Asn Thr Leu Tyr Leu
65                  70                  75                  80

Gln Met Asn Ser Leu Lys Pro Glu Asp Thr Ala Met Tyr Thr Cys Ala
                85                  90                  95

Ala Gln Ile Val Gly Gly Ala Leu Arg Cys Pro Arg Phe Ala Met Tyr
            100                 105                 110

Trp Gly Gln Gly Thr Gln Val Thr Val Ser Ser
        115                 120


<210> SEQ ID NO 122
<211> LENGTH: 132
<212> TYPE: PRT
<213> ORGANISM: Artificial Sequence
<220> FEATURE:
<223> OTHER INFORMATION: AS79285

<400> SEQUENCE: 122

Gln Val Arg Leu Val Glu Ser Gly Gly Gly Ser Val Gln Ala Gly Gly
1               5                   10                  15

Ser Leu Ala Leu Ser Cys Glu Thr Ser Arg Tyr Thr Val Ser Asn Tyr
            20                  25                  30

Cys Met Gly Trp Phe Arg Gln Val Ser Gly Lys Glu Val Glu Gly Val
        35                  40                  45

Ala Leu Ile Ser Thr Asp Gly Thr Thr Thr Tyr Ala Asp Ser Val Lys
    50                  55                  60

Gly Arg Phe Thr Ile Ser Lys Asp Asn Ala Lys Asn Thr Leu Tyr Leu
```

```
65                  70                  75                  80

Gln Met Asn Ser Leu Lys Ser Glu Asp Thr Ala Met Tyr Phe Cys Ala
                85                  90                  95

Gly Val Tyr Gly Leu Ile Trp Tyr Tyr Lys Pro Cys Pro Ala Gln Arg
            100                 105                 110

Glu Trp Ala Leu Gln Arg Tyr Gly Tyr Trp Gly Gln Gly Thr Gln Val
        115                 120                 125

Thr Val Ser Ser
    130


<210> SEQ ID NO 123
<211> LENGTH: 125
<212> TYPE: PRT
<213> ORGANISM: Artificial Sequence
<220> FEATURE:
<223> OTHER INFORMATION: AS79317

<400> SEQUENCE: 123

Glu Val Gln Leu Ala Glu Ser Gly Gly Gly Ser Val Gln Pro Gly Gly
1               5                   10                  15

Ser Leu Arg Leu Ser Cys Ala Ala Ser Gly Tyr Ser Ser Ser Ser Val
            20                  25                  30

Cys Met Gly Trp Phe Arg Gln Ala Pro Gly Lys Glu Arg Glu Gly Val
        35                  40                  45

Ala Ile Ile Tyr Val Thr Leu Gly Ser Ile Ala Tyr Ala Asp Ser Val
    50                  55                  60

Lys Gly Arg Phe Thr Ile Ser Arg Asp Asn Ala Lys Asn Thr Leu Asp
65                  70                  75                  80

Leu Glu Met Asn Ser Leu Lys Pro Asp Asp Thr Ala Leu Tyr Tyr Cys
                85                  90                  95

Ala Ala Gly Gly Cys Gly Tyr Arg Gly Val Ala Asp Val Pro Glu Phe
            100                 105                 110

Thr Tyr Arg Gly Gln Gly Thr Gln Val Thr Val Ser Ser
        115                 120                 125


<210> SEQ ID NO 124
<211> LENGTH: 124
<212> TYPE: PRT
<213> ORGANISM: Artificial Sequence
<220> FEATURE:
<223> OTHER INFORMATION: AS70950VH6

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ile Ser Glu Phe Thr Tyr Lys Asn Thr
            20                  25                  30

Cys Val Gly Trp Phe Arg Gln Ala Pro Gly Lys Gly Arg Glu Gly Val
        35                  40                  45

Ala Ala Ile Asp Ser Asp Gly Asn Thr Asn Tyr Val Asp Ser Val Lys
    50                  55                  60

Gly Arg Phe Thr Ile Ser Gln Asp Asn Ser Lys Asn Thr Val Tyr Leu
65                  70                  75                  80

Gln Met Asn Ser Leu Arg Ala Glu Asp Thr Ala Met Tyr Tyr Cys Ala
                85                  90                  95

Ala Gly Ala Tyr Cys Gly Arg Leu Leu Leu Trp Ile Gly Asn Tyr Ala
            100                 105                 110
```

```
Tyr Trp Gly Gln Gly Thr Leu Val Thr Val Ser Ser
        115                 120


<210> SEQ ID NO 125
<211> LENGTH: 124
<212> TYPE: PRT
<213> ORGANISM: Artificial Sequence
<220> FEATURE:
<223> OTHER INFORMATION: AS70950VH7

<400> SEQUENCE: 125

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Tyr Lys Asn Thr
            20                  25                  30

Cys Val Gly Trp Phe Arg Gln Ala Pro Gly Lys Gly Arg Glu Gly Val
        35                  40                  45

Ala Ala Ile Asp Ser Asp Gly Asn Thr Asn Tyr Val Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Met Tyr Tyr Cys Ala
                85                  90                  95

Ala Gly Ala Tyr Cys Gly Arg Leu Leu Leu Trp Ile Gly Asn Tyr Ala
            100                 105                 110

Tyr Trp Gly Gln Gly Thr Leu Val Thr Val Ser Ser
        115                 120


<210> SEQ ID NO 126
<211> LENGTH: 126
<212> TYPE: PRT
<213> ORGANISM: Artificial Sequence
<220> FEATURE:
<223> OTHER INFORMATION: AS71529VH5

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Val Ser Glu Tyr Arg Tyr Ser Ser Arg
            20                  25                  30

Tyr Cys Met Gly Trp Phe Arg Gln Ala Pro Gly Lys Gly Leu Glu Gly
        35                  40                  45

Val Ser Ala Ile Asp Ser Asn Gly Ser Ala Asp Tyr Val Asp Ser Val
    50                  55                  60

Lys Gly Arg Phe Thr Ile Ser Lys Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp His Leu Ala Tyr Asp Cys Tyr Ser Gly Ala Thr Ser Val
            100                 105                 110

Phe Arg Tyr Trp Gly Gln Gly Thr Leu Val Thr Val Ser Ser
        115                 120                 125


<210> SEQ ID NO 127
<211> LENGTH: 126
<212> TYPE: PRT
<213> ORGANISM: Artificial Sequence
<220> FEATURE:
<223> OTHER INFORMATION: AS71529VH6
```

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Val Ser Glu Tyr Arg Tyr Ser Ser Arg
            20                  25                  30

Tyr Cys Met Gly Trp Phe Arg Gln Ala Pro Gly Lys Gly Arg Glu Gly
        35                  40                  45

Val Ala Ala Ile Asp Ser Asn Gly Ser Ala Asp Tyr Val Asp Ser Val
    50                  55                  60

Lys Gly Arg Phe Thr Ile Ser Lys Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Ala Asp His Leu Ala Tyr Asp Cys Tyr Ser Gly Ala Thr Ser Val
            100                 105                 110

Phe Arg Tyr Trp Gly Gln Gly Thr Leu Val Thr Val Ser Ser
        115                 120                 125

<210> SEQ ID NO 128
<211> LENGTH: 125
<212> TYPE: PRT
<213> ORGANISM: Artificial Sequence
<220> FEATURE:
<223> OTHER INFORMATION: AS72052VH5

<400> SEQUENCE: 128

Gln Val Gln Leu Val Glu Ser Gly Gly Gly Val Val Gln Pro Gly Gly
1               5                   10                  15

Ser Leu Arg Leu Ser Cys Ala Val Ser Gly Phe Arg Tyr Ala Ser Tyr
            20                  25                  30

Cys Met Gly Trp Phe Arg Gln Ala Pro Gly Lys Gly Leu Glu Gly Val
        35                  40                  45

Ala Ala Ile His Ser Asp Gly Ile Ile Arg Tyr Ala Glu Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Gly Ala Tyr Cys Gly Ala Asp Ala Ile Leu Thr Leu Tyr Asp Tyr
            100                 105                 110

Ala Phe Trp Gly Gln Gly Thr Leu Val Thr Val Ser Ser
        115                 120                 125

<210> SEQ ID NO 129
<211> LENGTH: 125
<212> TYPE: PRT
<213> ORGANISM: Artificial Sequence
<220> FEATURE:
<223> OTHER INFORMATION: AS72052VH6

<400> SEQUENCE: 129

Gln Val Gln Leu Val Glu Ser Gly Gly Gly Val Val Gln Pro Gly Gly
1               5                   10                  15

Ser Leu Arg Leu Ser Cys Ala Val Ser Gly Phe Arg Tyr Ala Ser Tyr
            20                  25                  30

Cys Met Gly Trp Phe Arg Gln Ala Pro Gly Lys Gly Leu Glu Gly Val
        35                  40                  45

Ala Ala Ile His Ser Asp Gly Ile Ile Arg Tyr Ala Glu Ser Val Lys
50 55 60

Gly Arg Phe Thr Ile Ser Lys Asp Asn Ser Lys Asn Thr Leu Tyr Leu
65 70 75 80

Gln Met Asn Ser Leu Arg Ala Glu Asp Thr Ala Met Tyr Ser Cys Ala
85 90 95

Ala Gly Ala Tyr Cys Gly Ala Asp Ala Ile Leu Thr Leu Tyr Asp Tyr
100 105 110

Ala Phe Trp Gly Gln Gly Thr Leu Val Thr Val Ser Ser
115 120 125

<210> SEQ ID NO 130
<211> LENGTH: 124
<212> TYPE: PRT
<213> ORGANISM: Artificial Sequence
<220> FEATURE:
<223> OTHER INFORMATION: AS72669VH6

<400> SEQUENCE: 130

Gln Val Gln Leu Val Glu Ser Gly Gly Gly Val Val Gln Pro Gly Gly
1 5 10 15

Ser Leu Arg Leu Ser Cys Ala Ala Ser Arg Phe Thr Tyr Ser Ser Tyr
20 25 30

Cys Met Gly Trp Ile Arg Gln Ala Pro Gly Lys Gly Arg Glu Gly Val
35 40 45

Ala Ile Phe Tyr Thr Gly Gly Gly Arg Thr Tyr Tyr Ala Asp Ser Val
50 55 60

Lys Gly Arg Phe Thr Ile Ser Gln Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Val Ala Gly Phe Tyr Cys Ser Gly Gly Tyr Trp Glu Gly Asp Phe Gly
100 105 110

Tyr Trp Gly Gln Gly Thr Leu Val Thr Val Ser Ser
115 120

<210> SEQ ID NO 131
<211> LENGTH: 127
<212> TYPE: PRT
<213> ORGANISM: Artificial Sequence
<220> FEATURE:
<223> OTHER INFORMATION: AS78117VH4

<400> SEQUENCE: 131

Glu Val Gln Leu Val Glu Ser Gly Gly Gly Leu Val Gln Pro Gly Gly
1 5 10 15

Ser Leu Arg Leu Ser Cys Ile Val Ser Arg Tyr Thr Tyr Ala Thr Tyr
20 25 30

Ser Met Ala Trp Phe Arg Gln Ala Pro Gly Lys Gly Leu Glu Gly Val
35 40 45

Ser Gly Leu Asp Ser Val Gly Ala Thr Gly Tyr Ala Glu Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Val
85 90 95

Val Asp Pro Ala Ser Ala Lys Val Thr Tyr Gly Ser Trp Ser Thr Pro
100 105 110

```
Ser Tyr Ala Tyr Trp Gly Gln Gly Thr Leu Val Thr Val Ser Ser
        115                 120                 125
```

<210> SEQ ID NO 132
<211> LENGTH: 127
<212> TYPE: PRT
<213> ORGANISM: Artificial Sequence
<220> FEATURE:
<223> OTHER INFORMATION: AS78117VH5

<400> SEQUENCE: 132

```
Glu Val Gln Leu Val Glu Ser Gly Gly Gly Leu Val Gln Pro Gly Gly
1               5                   10                  15

Ser Leu Arg Leu Ser Cys Ile Val Ser Arg Tyr Thr Tyr Ala Thr Tyr
            20                  25                  30

Ser Met Ala Trp Phe Arg Gln Ala Pro Gly Lys Gly Leu Glu Gly Val
        35                  40                  45

Ser Gly Leu Asp Ser Val Gly Ala Thr Gly Tyr Ala Glu Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Val
                85                  90                  95

Val Asp Pro Ala Ser Ala Lys Val Thr Tyr Gly Ser Trp Ser Thr Pro
            100                 105                 110

Ser Tyr Ala Tyr Trp Gly Gln Gly Thr Leu Val Thr Val Ser Ser
        115                 120                 125
```

<210> SEQ ID NO 133
<211> LENGTH: 127
<212> TYPE: PRT
<213> ORGANISM: Artificial Sequence
<220> FEATURE:
<223> OTHER INFORMATION: AS78117VH6

<400> SEQUENCE: 133

```
Glu Val Gln Leu Val Glu Ser Gly Gly Gly Leu Val Gln Pro Gly Gly
1               5                   10                  15

Ser Leu Arg Leu Ser Cys Ile Val Ser Arg Tyr Thr Tyr Ala Thr Tyr
            20                  25                  30

Ser Met Ala Trp Phe Arg Gln Ala Pro Gly Lys Gly Leu Glu Gly Val
        35                  40                  45

Ser Gly Leu Asp Ser Val Gly Ala Thr Gly Tyr Ala Glu Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Met Tyr Tyr Cys Val
                85                  90                  95

Val Asp Pro Ala Ser Ala Lys Val Thr Tyr Gly Ser Trp Ser Thr Pro
            100                 105                 110

Ser Tyr Ala Tyr Trp Gly Gln Gly Thr Leu Val Thr Val Ser Ser
        115                 120                 125
```

<210> SEQ ID NO 134
<211> LENGTH: 127
<212> TYPE: PRT
<213> ORGANISM: Artificial Sequence
<220> FEATURE:
<223> OTHER INFORMATION: AS78117VH7

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ile Val Ser Arg Tyr Thr Tyr Ala Thr Tyr
            20                  25                  30

Ser Met Ala Trp Phe Arg Gln Ala Pro Gly Lys Gly Leu Glu Gly Val
        35                  40                  45

Ala Gly Leu Asp Ser Val Gly Ala Thr Gly Tyr Ala Glu Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Met Tyr Tyr Cys Val
                85                  90                  95

Val Asp Pro Ala Ser Ala Lys Val Thr Tyr Gly Ser Trp Ser Thr Pro
            100                 105                 110

Ser Tyr Ala Tyr Trp Gly Gln Gly Thr Leu Val Thr Val Ser Ser
        115                 120                 125

<210> SEQ ID NO 135
<211> LENGTH: 127
<212> TYPE: PRT
<213> ORGANISM: Artificial Sequence
<220> FEATURE:
<223> OTHER INFORMATION: AS79236VH4

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ser Ser Tyr
            20                  25                  30

Cys Met Ala Trp Phe Arg Gln Ala Pro Gly Lys Gly Leu Glu Gly Val
        35                  40                  45

Ala Ser Ile Asp Ala Gly Gly Arg Thr Thr Tyr Val Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Val Asp Val Arg Thr Arg Cys Gly Gly Thr Trp Asp Gly Glu Ala Val
            100                 105                 110

Tyr Phe Pro Tyr Trp Gly Gln Gly Thr Leu Val Thr Val Ser Ser
        115                 120                 125

<210> SEQ ID NO 136
<211> LENGTH: 127
<212> TYPE: PRT
<213> ORGANISM: Artificial Sequence
<220> FEATURE:
<223> OTHER INFORMATION: AS79236VH5

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Tyr Ser Ser Tyr
            20                  25                  30

Cys Met Ala Trp Phe Arg Gln Ala Pro Gly Lys Gly Leu Glu Gly Val
        35                  40                  45

```
Ala Ser Ile Asp Ala Gly Gly Arg Thr Thr Tyr Val Asp Ser Val Lys
    50                  55                  60

Gly Arg Phe Thr Ile Ser Lys Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Val Asp Val Arg Thr Arg Cys Gly Gly Thr Trp Asp Gly Glu Ala Val
            100                 105                 110

Tyr Phe Pro Tyr Trp Gly Gln Gly Thr Leu Val Thr Val Ser Ser
        115                 120                 125


<210> SEQ ID NO 137
<211> LENGTH: 127
<212> TYPE: PRT
<213> ORGANISM: Artificial Sequence
<220> FEATURE:
<223> OTHER INFORMATION: AS79236VH6

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Thr Tyr Ser Ser Tyr
            20                  25                  30

Cys Met Ala Trp Phe Arg Gln Ala Pro Gly Lys Gly Leu Glu Gly Val
        35                  40                  45

Ala Ser Ile Asp Ala Gly Gly Arg Thr Thr Tyr Val Asp Ser Val Lys
    50                  55                  60

Gly Arg Phe Thr Ile Ser Lys Asp Asn Ala Lys Asn Ser Leu Tyr Leu
65                  70                  75                  80

Gln Met Asn Ser Leu Arg Ala Glu Asp Thr Ala Met Tyr Tyr Cys Ala
                85                  90                  95

Val Asp Val Arg Thr Arg Cys Gly Gly Thr Trp Asp Gly Glu Ala Val
            100                 105                 110

Tyr Phe Pro Tyr Trp Gly Gln Gly Thr Leu Val Thr Val Ser Ser
        115                 120                 125


<210> SEQ ID NO 138
<211> LENGTH: 123
<212> TYPE: PRT
<213> ORGANISM: Artificial Sequence
<220> FEATURE:
<223> OTHER INFORMATION: AS77916VH6

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Thr Ser Gly Tyr Thr Ser Ser Trp Asn
            20                  25                  30

Cys Met Gly Trp Phe Arg Gln Ala Pro Gly Lys Gly Leu Glu Gly Val
        35                  40                  45

Ala Thr Ile Ala Asn Arg Gly His Ser Thr Tyr Tyr Ala Asp Ser Val
    50                  55                  60

Lys Gly Arg Phe Thr Ile Ser Gln Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asp Thr Trp Ala Cys Val Gly Ile Ser Thr Asp Phe Glu Tyr
```

100 105 110

Trp Gly Gln Gly Thr Leu Val Thr Val Ser Ser
115 120

<210> SEQ ID NO 139
<211> LENGTH: 123
<212> TYPE: PRT
<213> ORGANISM: Artificial Sequence
<220> FEATURE:
<223> OTHER INFORMATION: AS77916VH7

<400> SEQUENCE: 139

Glu Val Gln Leu Val Glu Ser Gly Gly Gly Leu Val Gln Pro Gly Gly
1 5 10 15

Ser Leu Arg Leu Ser Cys Ala Thr Ser Gly Tyr Thr Ser Ser Trp Asn
20 25 30

Cys Met Gly Trp Phe Arg Gln Ala Pro Gly Lys Gly Leu Glu Gly Val
35 40 45

Ala Thr Ile Ala Asn Arg Gly His Ser Thr Tyr Tyr Ala Asp Ser Val
50 55 60

Lys Gly Arg Phe Thr Ile Ser Gln Asp Asn Ser Lys Asn Thr Leu Tyr
65 70 75 80

Leu Gln Met Asn Ser Leu Arg Ala Glu Asp Thr Ala Met Tyr Tyr Cys
85 90 95

Ala Thr Asp Thr Trp Ala Cys Val Gly Ile Ser Thr Asp Phe Glu Tyr
100 105 110

Trp Gly Gln Gly Thr Leu Val Thr Val Ser Ser
115 120

<210> SEQ ID NO 140
<211> LENGTH: 123
<212> TYPE: PRT
<213> ORGANISM: Artificial Sequence
<220> FEATURE:
<223> OTHER INFORMATION: AS77916VH8

<400> SEQUENCE: 140

Glu Val Gln Leu Val Glu Ser Gly Gly Gly Leu Val Gln Pro Gly Gly
1 5 10 15

Ser Leu Arg Leu Ser Cys Ala Thr Ser Gly Tyr Thr Ser Ser Trp Asn
20 25 30

Cys Met Gly Trp Phe Arg Gln Ala Pro Gly Lys Gly Leu Glu Gly Val
35 40 45

Ala Thr Ile Ala Asn Arg Gly His Ser Thr Tyr Tyr Ala Asp Ser Val
50 55 60

Lys Gly Arg Phe Thr Ile Ser Gln Asp Asn Ser Lys Asn Thr Val Tyr
65 70 75 80

Leu Gln Met Asn Ser Leu Arg Ala Glu Asp Thr Ala Val Tyr Tyr Cys
85 90 95

Ala Thr Asp Thr Trp Ala Cys Val Gly Ile Ser Thr Asp Phe Glu Tyr
100 105 110

Trp Gly Gln Gly Thr Leu Val Thr Val Ser Ser
115 120

<210> SEQ ID NO 141
<211> LENGTH: 123
<212> TYPE: PRT
<213> ORGANISM: Artificial Sequence
<220> FEATURE:

<223> OTHER INFORMATION: AS77916VH9

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Thr Ser Gly Tyr Thr Ser Ser Trp Asn
            20                  25                  30

Cys Met Gly Trp Phe Arg Gln Ala Pro Gly Lys Gly Arg Glu Gly Val
        35                  40                  45

Ala Thr Ile Ala Asn Arg Gly His Ser Thr Tyr Tyr Ala Asp Ser Val
    50                  55                  60

Lys Gly Arg Phe Thr Ile Ser Gln Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asp Thr Trp Ala Cys Val Gly Ile Ser Thr Asp Phe Glu Tyr
            100                 105                 110

Trp Gly Gln Gly Thr Leu Val Thr Val Ser Ser
        115                 120

<210> SEQ ID NO 142
<211> LENGTH: 123
<212> TYPE: PRT
<213> ORGANISM: Artificial Sequence
<220> FEATURE:
<223> OTHER INFORMATION: AS77916VH10

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Thr Ser Gly Tyr Thr Ser Ser Trp Asn
            20                  25                  30

Cys Met Gly Trp Phe Arg Gln Ala Pro Gly Lys Gly Arg Glu Gly Val
        35                  40                  45

Ala Thr Ile Ala Asn Arg Gly His Ser Thr Tyr Tyr Ala Asp Ser Val
    50                  55                  60

Lys Gly Arg Phe Thr Ile Ser Gln Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Thr Asp Thr Trp Ala Cys Val Gly Ile Ser Thr Asp Phe Glu Tyr
            100                 105                 110

Trp Gly Gln Gly Thr Leu Val Thr Val Ser Ser
        115                 120

<210> SEQ ID NO 143
<211> LENGTH: 266
<212> TYPE: PRT
<213> ORGANISM: Artificial Sequence
<220> FEATURE:
<223> OTHER INFORMATION: AS71529VH5-AS72052VH5

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Val Ser Glu Tyr Arg Tyr Ser Ser Arg
            20                  25                  30

Tyr Cys Met Gly Trp Phe Arg Gln Ala Pro Gly Lys Gly Leu Glu Gly

```
        35                  40                  45

Val Ser Ala Ile Asp Ser Asn Gly Ser Ala Asp Tyr Val Asp Ser Val
    50                  55                  60

Lys Gly Arg Phe Thr Ile Ser Lys Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp His Leu Ala Tyr Asp Cys Tyr Ser Gly Ala Thr Ser Val
            100                 105                 110

Phe Arg Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Gln Val Gln
    130                 135                 140

Leu Val Glu Ser Gly Gly Gly Val Val Gln Pro Gly Gly Ser Leu Arg
145                 150                 155                 160

Leu Ser Cys Ala Val Ser Gly Phe Arg Tyr Ala Ser Tyr Cys Met Gly
                165                 170                 175

Trp Phe Arg Gln Ala Pro Gly Lys Gly Leu Glu Gly Val Ala Ala Ile
            180                 185                 190

His Ser Asp Gly Ile Ile Arg Tyr Ala Glu Ser Val Lys Gly Arg Phe
        195                 200                 205

Thr Ile Ser Lys Asp Asn Ser Lys Asn Thr Leu Tyr Leu Gln Met Asn
    210                 215                 220

Ser Leu Arg Ala Glu Asp Thr Ala Val Tyr Tyr Cys Ala Ala Gly Ala
225                 230                 235                 240

Tyr Cys Gly Ala Asp Ala Ile Leu Thr Leu Tyr Asp Tyr Ala Phe Trp
                245                 250                 255

Gly Gln Gly Thr Leu Val Thr Val Ser Ser
            260                 265


<210> SEQ ID NO 144
<211> LENGTH: 266
<212> TYPE: PRT
<213> ORGANISM: Artificial Sequence
<220> FEATURE:
<223> OTHER INFORMATION: AS72052VH5-AS71529VH5

<400> SEQUENCE: 144

Gln Val Gln Leu Val Glu Ser Gly Gly Gly Val Val Gln Pro Gly Gly
1               5                   10                  15

Ser Leu Arg Leu Ser Cys Ala Val Ser Gly Phe Arg Tyr Ala Ser Tyr
            20                  25                  30

Cys Met Gly Trp Phe Arg Gln Ala Pro Gly Lys Gly Leu Glu Gly Val
        35                  40                  45

Ala Ala Ile His Ser Asp Gly Ile Ile Arg Tyr Ala Glu Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Gly Ala Tyr Cys Gly Ala Asp Ala Ile Leu Thr Leu Tyr Asp Tyr
            100                 105                 110

Ala Phe Trp Gly Gln Gly Thr Leu Val Thr Val Ser Ser Gly Gly Gly
        115                 120                 125

Gly Ser Gly Gly Gly Gly Ser Gly Gly Gly Gly Ser Glu Val Gln Leu
```

-continued

```
    130                 135                 140

Val Glu Ser Gly Gly Gly Leu Val Gln Pro Gly Gly Ser Leu Arg Leu
145                 150                 155                 160

Ser Cys Ala Val Ser Glu Tyr Arg Tyr Ser Ser Arg Tyr Cys Met Gly
                165                 170                 175

Trp Phe Arg Gln Ala Pro Gly Lys Gly Leu Glu Gly Val Ser Ala Ile
            180                 185                 190

Asp Ser Asn Gly Ser Ala Asp Tyr Val Asp Ser Val Lys Gly Arg Phe
        195                 200                 205

Thr Ile Ser Lys Asp Asn Ser Lys Asn Thr Leu Tyr Leu Gln Met Asn
    210                 215                 220

Ser Leu Arg Ala Glu Asp Thr Ala Val Tyr Tyr Cys Ala Ala Asp His
225                 230                 235                 240

Leu Ala Tyr Asp Cys Tyr Ser Gly Ala Thr Ser Val Phe Arg Tyr Trp
                245                 250                 255

Gly Gln Gly Thr Leu Val Thr Val Ser Ser
            260                 265


<210> SEQ ID NO 145
<211> LENGTH: 265
<212> TYPE: PRT
<213> ORGANISM: Artificial Sequence
<220> FEATURE:
<223> OTHER INFORMATION: AS70950VH6-AS71529VH6

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ile Ser Glu Phe Thr Tyr Lys Asn Thr
            20                  25                  30

Cys Val Gly Trp Phe Arg Gln Ala Pro Gly Lys Gly Arg Glu Gly Val
        35                  40                  45

Ala Ala Ile Asp Ser Asp Gly Asn Thr Asn Tyr Val Asp Ser Val Lys
    50                  55                  60

Gly Arg Phe Thr Ile Ser Gln Asp Asn Ser Lys Asn Thr Val Tyr Leu
65                  70                  75                  80

Gln Met Asn Ser Leu Arg Ala Glu Asp Thr Ala Met Tyr Tyr Cys Ala
                85                  90                  95

Ala Gly Ala Tyr Cys Gly Arg Leu Leu Leu Trp Ile Gly Asn Tyr Ala
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Glu Val Gln Leu Val
    130                 135                 140

Glu Ser Gly Gly Gly Leu Val Gln Pro Gly Gly Ser Leu Arg Leu Ser
145                 150                 155                 160

Cys Ala Val Ser Glu Tyr Arg Tyr Ser Ser Arg Tyr Cys Met Gly Trp
                165                 170                 175

Phe Arg Gln Ala Pro Gly Lys Gly Arg Glu Gly Val Ala Ala Ile Asp
            180                 185                 190

Ser Asn Gly Ser Ala Asp Tyr Val Asp Ser Val Lys Gly Arg Phe Thr
        195                 200                 205

Ile Ser Lys Asp Asn Ser Lys Asn Thr Leu Tyr Leu Gln Met Asn Ser
    210                 215                 220

Leu Arg Ala Glu Asp Thr Ala Met Tyr Tyr Cys Ala Ala Asp His Leu
```

```
225                 230                 235                 240

Ala Tyr Asp Cys Tyr Ser Gly Ala Thr Ser Val Phe Arg Tyr Trp Gly
                245                 250                 255

Gln Gly Thr Leu Val Thr Val Ser Ser
            260                 265


<210> SEQ ID NO 146
<211> LENGTH: 265
<212> TYPE: PRT
<213> ORGANISM: Artificial Sequence
<220> FEATURE:
<223> OTHER INFORMATION: AS71529VH6-AS70950VH6

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Val Ser Glu Tyr Arg Tyr Ser Ser Arg
            20                  25                  30

Tyr Cys Met Gly Trp Phe Arg Gln Ala Pro Gly Lys Gly Arg Glu Gly
        35                  40                  45

Val Ala Ala Ile Asp Ser Asn Gly Ser Ala Asp Tyr Val Asp Ser Val
    50                  55                  60

Lys Gly Arg Phe Thr Ile Ser Lys Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Ala Asp His Leu Ala Tyr Asp Cys Tyr Ser Gly Ala Thr Ser Val
            100                 105                 110

Phe Arg Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ile Ser Glu Phe Thr Tyr Lys Asn Thr Cys Val Gly
                165                 170                 175

Trp Phe Arg Gln Ala Pro Gly Lys Gly Arg Glu Gly Val Ala Ala Ile
            180                 185                 190

Asp Ser Asp Gly Asn Thr Asn Tyr Val Asp Ser Val Lys Gly Arg Phe
        195                 200                 205

Thr Ile Ser Gln Asp Asn Ser Lys Asn Thr Val Tyr Leu Gln Met Asn
    210                 215                 220

Ser Leu Arg Ala Glu Asp Thr Ala Met Tyr Tyr Cys Ala Ala Gly Ala
225                 230                 235                 240

Tyr Cys Gly Arg Leu Leu Leu Trp Ile Gly Asn Tyr Ala Tyr Trp Gly
                245                 250                 255

Gln Gly Thr Leu Val Thr Val Ser Ser
            260                 265


<210> SEQ ID NO 147
<211> LENGTH: 263
<212> TYPE: PRT
<213> ORGANISM: Artificial Sequence
<220> FEATURE:
<223> OTHER INFORMATION: AS70950VH6-AS70950VH6

<400> SEQUENCE: 147
```

-continued

```
Glu Val Gln Leu Val Glu Ser Gly Gly Gly Leu Val Gln Pro Gly Gly
1               5                   10                  15

Ser Leu Arg Leu Ser Cys Ala Ile Ser Glu Phe Thr Tyr Lys Asn Thr
            20                  25                  30

Cys Val Gly Trp Phe Arg Gln Ala Pro Gly Lys Gly Arg Glu Gly Val
        35                  40                  45

Ala Ala Ile Asp Ser Asp Gly Asn Thr Asn Tyr Val Asp Ser Val Lys
    50                  55                  60

Gly Arg Phe Thr Ile Ser Gln Asp Asn Ser Lys Asn Thr Val Tyr Leu
65                  70                  75                  80

Gln Met Asn Ser Leu Arg Ala Glu Asp Thr Ala Met Tyr Tyr Cys Ala
                85                  90                  95

Ala Gly Ala Tyr Cys Gly Arg Leu Leu Leu Trp Ile Gly Asn Tyr Ala
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Glu Val Gln Leu Val
    130                 135                 140

Glu Ser Gly Gly Gly Leu Val Gln Pro Gly Gly Ser Leu Arg Leu Ser
145                 150                 155                 160

Cys Ala Ile Ser Glu Phe Thr Tyr Lys Asn Thr Cys Val Gly Trp Phe
                165                 170                 175

Arg Gln Ala Pro Gly Lys Gly Arg Glu Gly Val Ala Ala Ile Asp Ser
            180                 185                 190

Asp Gly Asn Thr Asn Tyr Val Asp Ser Val Lys Gly Arg Phe Thr Ile
        195                 200                 205

Ser Gln Asp Asn Ser Lys Asn Thr Val Tyr Leu Gln Met Asn Ser Leu
    210                 215                 220

Arg Ala Glu Asp Thr Ala Met Tyr Tyr Cys Ala Ala Gly Ala Tyr Cys
225                 230                 235                 240

Gly Arg Leu Leu Leu Trp Ile Gly Asn Tyr Ala Tyr Trp Gly Gln Gly
                245                 250                 255

Thr Leu Val Thr Val Ser Ser
            260
```

<210> SEQ ID NO 148
<211> LENGTH: 378
<212> TYPE: DNA
<213> ORGANISM: Artificial Sequence
<220> FEATURE:
<223> OTHER INFORMATION: AS70549

<400> SEQUENCE: 148

```
caggtgcggc tggtggagag cggaggaggc tccgtgcagg caggaggctc tctgaccctg      60

agctgcgcct actcccggta tacaggcaga agctcctgta tggcctggtt ccggagaccc     120

cctggcaaga agagggagag ggtggcatcc atctactctg acgatggcgt gaccgtgtat     180

gccgactctg tgaagggcag gtttaccatc acacaggata gcgcccagaa cacactgtac     240

ctgcagatga acagcctgga ccccgaggat accgccatgt actattgcgc cacacgcacc     300

acatatccag gcgtgtgccc agacaacgca gcatggtacg attattgggg ccagggcacc     360

caggtgacag tgtctagc                                                   378
```

<210> SEQ ID NO 149
<211> LENGTH: 375
<212> TYPE: DNA

<213> ORGANISM: Artificial Sequence
<220> FEATURE:
<223> OTHER INFORMATION: AS70771

<400> SEQUENCE: 149
caggtgcagc tggtggagtc tggaggaggc agcgtgcagg caggaggctc cctgaggctg 60
tcttgcgcag caagcggata caccggcaag atggcctggt tcaggcaggc accaggcaag 120
gagagggagg gagtggccgc catcgacgat gccggcggca caaactacat cgacagcgtg 180
aagggccggt ttaccatctc caaggataac gccgagaata cactgtatct gagaatgaac 240
agcctgaagc ccgaggacac cgccatctac tattgtgccg ccgatacatt cagatggttt 300
atgcggagat ccggccctat caacggctct gactacgcct attggggcca gggcacccag 360
gtgacagtga gctcc 375

<210> SEQ ID NO 150
<211> LENGTH: 372
<212> TYPE: DNA
<213> ORGANISM: Artificial Sequence
<220> FEATURE:
<223> OTHER INFORMATION: AS70950

<400> SEQUENCE: 150
caggtgcagc tggtggagtc tggaggaggc tctgcccaga gcggaggctc cctgcggctg 60
tcttgcgcca tcagcgagtt cacctacaag aacacatgcg tgggatggtt taggcaggca 120
ccaggcaagg agagagaggg agtggcagca atcgacagcg atggaaacac caattacgtg 180
gactccgtga agggcaggtt caccatctct cagggcaacg ccaagaatac agtgtatctg 240
cagatgaact ccctgaagcc tgaggataca gccatgtact attgcgcagc aggagcatat 300
tgtggccgcc tgctgctgtg gatcggcaat tacgcctatt ggggccaggg cacccaggtg 360
acagtgagct cc 372

<210> SEQ ID NO 151
<211> LENGTH: 375
<212> TYPE: DNA
<213> ORGANISM: Artificial Sequence
<220> FEATURE:
<223> OTHER INFORMATION: AS71402

<400> SEQUENCE: 151
cagatgcagc tggtggagtc cggaggaggc tctgtgcagg caggaggcag cctgcggctg 60
tcctgcgtgg tgtctggcta cacctataac aggaatatgg cctggttcag gcaggcacca 120
ggcaaggaga gggagggagt ggcagcaatg tacacaggca gcggcaccac agactatgcc 180
gattccgtga agggcaggtt taccatctct cacgacaacg ccaagaatac actgtacctg 240
cagatgaaca gcctgaagcc cgaggacacc gccacatact attgtgcagc agataccgca 300
aggagaggag gctcttggag cggacctttc aagtacgatt attggggcca gggcacccag 360
gtgacagtga gctcc 375

<210> SEQ ID NO 152
<211> LENGTH: 378
<212> TYPE: DNA
<213> ORGANISM: Artificial Sequence
<220> FEATURE:
<223> OTHER INFORMATION: AS71529

<400> SEQUENCE: 152
gaggtgcagc tggtggagag cggaggaggc tccgtgcagg caggaggctc tctgaggctg 60

-continued

```
agctgcgtgg tgtccgagta ccggtatagc tccagatact gtatgggctg gttcaggcag    120

gcaccaggca aggagaggga gggagtggca gcaatcgact ccaacggctc tgccgactac    180

gtggattccg tgaagggccg gtttaccatc tctaaggaca acgccaagaa tacactgtat    240

ctgcagatca attccgtgag acctgaggat accgccatgt actattgcgc cgccgaccac    300

ctggcctacg attgttattc tggcgccaca agcgtgttca gatattgggg ccagggcacc    360

caggtgacag tgtctagc                                                  378
```

```
<210> SEQ ID NO 153
<211> LENGTH: 378
<212> TYPE: DNA
<213> ORGANISM: Artificial Sequence
<220> FEATURE:
<223> OTHER INFORMATION: AS71661

<400> SEQUENCE: 153

caggtgcagc tggtggagag cggaggagga ctggtgcagg caggaggctc cctgcggctg     60

tcctgctctc caagcggcac cacattcgcc cactacaaca tggtgggctg gtttaggcag    120

gcaccaggca aggacaggga gggcgtgtcc tgtatctcta agtacggcgg caccacatac    180

tatgccgact ctgtgaaggg ccggttcacc atctatagag ataacgccaa gaatacactg    240

tttctgcaga tgaacagcct gaagcccgag gataccgcca tgtactattg cgccatcggc    300

gtgctgccta gctccacagc aatctgtgca ggagcagcaa attattgggg acagggaacc    360

caggtgacag tgtctagc                                                  378
```

```
<210> SEQ ID NO 154
<211> LENGTH: 375
<212> TYPE: DNA
<213> ORGANISM: Artificial Sequence
<220> FEATURE:
<223> OTHER INFORMATION: AS72021

<400> SEQUENCE: 154

gaggtgcagc tggccgagtc cggaggaggc tctgtgcagg caggaggcag cctgcggctg     60

tcctgcgtgg tgtctagaaa cacctacagc tcctattgta tgtcctggtt caggcaggca    120

ccaggcaagg agagggaggg agtggccgcc atcgacaatg tgaagacaag ctacgccgat    180

tccgtgaagg gccggtttac catctctaag gacaacgcca agaatacact gtatctgcag    240

atgaacagcc tgaagcccga ggataccgcc atgtactatt gcgccgccca cctggagctg    300

tgctactata cagaccctat gtaccagtat gagtacaatt attggggcca gggcacccag    360

gtgacagtgt ctagc                                                     375
```

```
<210> SEQ ID NO 155
<211> LENGTH: 375
<212> TYPE: DNA
<213> ORGANISM: Artificial Sequence
<220> FEATURE:
<223> OTHER INFORMATION: AS72052

<400> SEQUENCE: 155

caggtgcggc tggtggagtc tggaggaggc agcgtgcagg caggaggctc cctgcggctg     60

tcttgcgccg tgagcggctt caggtacgcc tcttattgta tgggatggtt taggcaggca    120

ccaggcaagg agagagaggg agtggcagca atccacagcg acggaatcat cagatacgcc    180

gagtccgtga agggccgctt caccatctct aaggacaacg ccaagaatac actgtatctg    240
```

```
cagctgaaca gcctgaagcc tgaggataat gccatgtact cctgcgcagc aggagcatat    300

tgtggagcag acgccatcct gaccctgtac gattatgcct tttggggcca gggcacccag    360

gtgacagtga gctcc                                                     375


<210> SEQ ID NO 156
<211> LENGTH: 369
<212> TYPE: DNA
<213> ORGANISM: Artificial Sequence
<220> FEATURE:
<223> OTHER INFORMATION: AS72383

<400> SEQUENCE: 156

caggtgcggc tggtggagtc cggaggagga ctggtgcagg caggaggctc tcagaggctg     60

agctgcaccg catccggact gacattcgac gattctggaa tgggatggtt taggcaggca    120

ccaggcaagg gaagggaggg cgtgagctgt atcacctgga acggccggtc cacatactat    180

gccgactctg tgaagggccg gttcaccatc tctagagata acagcaagaa tacactgtat    240

ctgcagatga acagcctgaa gcctgaggac accgccatgt actattgcgc cgccgccttt    300

atcaccaaga caggctgtag ctacgagtat gattactccg gccagggcac ccaggtgaca    360

gtgagctcc                                                            369


<210> SEQ ID NO 157
<211> LENGTH: 369
<212> TYPE: DNA
<213> ORGANISM: Artificial Sequence
<220> FEATURE:
<223> OTHER INFORMATION: AS72479

<400> SEQUENCE: 157

caggtgaagc tggtggagag cggaggaggc tccgtgcagg caggaggctc tctgcggctg     60

agctgcgccg cctccgagac cacagactgt agatacgtgt ggaggtggta tcgcgaggac    120

cccggcatgg agagggagtt cgtgagctcc atcacctccg gcggctctac atggtacgcc    180

gactctgtga agggccgctt taccatctcc caggataacg ccaagtctac actgtatctg    240

cagatgaata gcctgaagcc cgaggactcc ggcatgtact attgcgagtc tgatcctgga    300

tggagcggat accacgcacg gagatgtgag gtgtatcggg gccagggcat ccaggtgacc    360

gtgtctagc                                                            369


<210> SEQ ID NO 158
<211> LENGTH: 378
<212> TYPE: DNA
<213> ORGANISM: Artificial Sequence
<220> FEATURE:
<223> OTHER INFORMATION: AS72499

<400> SEQUENCE: 158

caggtgaggc tggtggagtc cggaggaggc tctgtgcagg caggaggcag cctgcggctg     60

tcctgcgtgg tgtctagatt cacctacagc tcctattgta tgggctggtt taggcaggca    120

ccaggcaagg agagggaggg agtggccggc atcgagaagg acgatagcac atactatgcc    180

gactccgtga agggcagatt caccatctct aaggataacg ccaagaatac actgtacctg    240

cagatgaaca gcctgaagcc cgaggacacc gccatgtact attgcgccgc cagaatcccc    300

ggaggaaatt gtggagtggt ggcaagaatg gcctactggg attattgggg caagggcacc    360

ctggtgacag tgtctagc                                                  378
```

<210> SEQ ID NO 159
<211> LENGTH: 375
<212> TYPE: DNA
<213> ORGANISM: Artificial Sequence
<220> FEATURE:
<223> OTHER INFORMATION: AS72531

<400> SEQUENCE: 159
caggtgcagc tggtggagtc tggaggagga ctggtgcagg caggaggcag cctgaggctg 60
tcctgcaccg catctggact gacattcgcc cactacaaca tggtgggctg gtttaggcag 120
gcaccaggca aggacaggga gggcgtgtcc tgtatctcta agtatggcgg caccatctac 180
tatgccgaca gcgtgaaggg ccggttcacc atcgatagaa acaatgccaa gaacacactg 240
tacctgcaga tgaacagcct gaagcccgag gataccgcca tgtactattg cgccatcggc 300
gtgctgagct ccacagcaag gggacctgga gcagcaaatt attggggaca gggcacccag 360
gtgacagtgt ctagc 375

<210> SEQ ID NO 160
<211> LENGTH: 372
<212> TYPE: DNA
<213> ORGANISM: Artificial Sequence
<220> FEATURE:
<223> OTHER INFORMATION: AS72669

<400> SEQUENCE: 160
gaggtgcagc tggtggagtc cggaggaggc tctgtgcagg caggaggcag cctgaagctg 60
tcctgcgccg cctctcggtt cacctacagc tcctattgta tgggctggat cagacaggca 120
ccaggcaagg agagagaggg agtggcaatc ttctacaccg gaggaggcag gacatactat 180
gccgacagcg tgaagggccg ctttaccatc tcccaggata ccgccaagaa cacactgtat 240
ctgcagatga acagcctgaa gcctgaggac acaggcatct actattgcgt ggccggcttc 300
tactgtagcg gcggctattg ggagggcgat tttggctact ggggccaggg cacccaggtg 360
acagtgtcta gc 372

<210> SEQ ID NO 161
<211> LENGTH: 390
<212> TYPE: DNA
<213> ORGANISM: Artificial Sequence
<220> FEATURE:
<223> OTHER INFORMATION: AS72794

<400> SEQUENCE: 161
caggtgcagc tggtggagag cggaggagga ctggtgcagg caggaggcag cctgcggctg 60
tcctgcacag cctctggctt cacctttgac gattatgcaa tgtcttggtt caggcaggca 120
ccaggcaagg agagggaggg cgtgtcctgt atctccgcct ctggcaccac aacctactat 180
ggcgatagcg tgaagggcag gtttacaatc tcccgcgaca acgccaagac aaccctgatc 240
ctgcagatga gctccctgaa gcctgaggat accgccatgt actattgcgc cgccgaccgg 300
ttcagagatt actgtagcga ctcctggtct cacctgtaca attatgagta catgcactgg 360
ggccagggca cacaggtgac cgtgtctagc 390

<210> SEQ ID NO 162
<211> LENGTH: 387
<212> TYPE: DNA
<213> ORGANISM: Artificial Sequence
<220> FEATURE:
<223> OTHER INFORMATION: AS72805

<400> SEQUENCE: 162
caggtgcagc tggtggagtc cggaggcgac tctgtgcagg caggaggcag cctgaccctg 60
tcctgcgtgg catctaggct gagagtgtcc aacaattgta tgggctggtt caggcaggca 120
ccaggaaacg agagggaggg agtggccacc ctgggctctg acggccggac aatctatgcc 180
gattctgtga agggcaggtt taccatcagc aaggacaacg tggccaatac actgtacctg 240
cagatgaacg gcctgaagct ggacgataca gccctgtact attgcgcagc agcagatttc 300
agctccggag gatattgtaa tatcgccagc gtgtaccact cctattttcc ttactggggc 360
cagggcaccc aggtgacagt gtctagc 387

<210> SEQ ID NO 163
<211> LENGTH: 381
<212> TYPE: DNA
<213> ORGANISM: Artificial Sequence
<220> FEATURE:
<223> OTHER INFORMATION: AS72806

<400> SEQUENCE: 163
caggtgcagc tggtggagtc tggaggaggc agcgtgcagg caggaggctc cctgaggctg 60
tcttgcgcag caagcggata cacctatatg ccccccttgta tgggatggtt caggcaggca 120
ccaggcaagg agagagaggg agtggcaacc atctatggaa ggggaggcag cacatactat 180
gccgactccg tgaagggccg ctttaccatc tctcaggata acgccaagaa tacactgtat 240
ctgcagatga acaatctgga gcccgaggac accgccatgt actattgcgc cgccgataac 300
ctgtgctacg ccacaggcat cctgaggtcc gcctacgact attcttactg gggccagggc 360
acccaggtga cagtgagctc c 381

<210> SEQ ID NO 164
<211> LENGTH: 378
<212> TYPE: DNA
<213> ORGANISM: Artificial Sequence
<220> FEATURE:
<223> OTHER INFORMATION: AS72835

<400> SEQUENCE: 164
caggtgcacc tgatggagtc tggaggaggc agcgtgcagg caggaggctc cctgcggctg 60
tcttgcgccg tgagcggcgg ctacacctct agaaccgtgt gcatgggctg gttcaggcag 120
accccaggca aggagaggga ggtgctggca gcaatctata ggagcggcac cacatactat 180
cacgactccg tgaagggccg gtttaccatc tctagagacg gcgataagaa cacagtgtac 240
ctgcagatgg acagcctgaa gcccgaggat acagccatgt actattgcgc agcatcccca 300
ggatattctg atgcagcatg cgtgagcgtg cctcaggcaa atagatgggg ccagggcacc 360
caggtgacag tgagctcc 378

<210> SEQ ID NO 165
<211> LENGTH: 363
<212> TYPE: DNA
<213> ORGANISM: Artificial Sequence
<220> FEATURE:
<223> OTHER INFORMATION: AS77906

<400> SEQUENCE: 165
caggtgcggc tggtggagtc tggaggaggc agcgtgcagg caggagagtc cctgaggctg 60
tcttgcgcac gcagcggagt ggtgaagtgt gacgtggaga tgcggtggta cagacagtct 120
ccaggcaagg agagggagtt cgtggccctg atcgaggcag gaggacacac cgagtacgca 180
gactccgtga agggccgctt cacaatctct caggataacg ccaagatgct gttttatctg 240
cagatgaata gcctgaagcc cgaggacacc gccaagtact attgcgtggc cgccccccgg 300
tactatacac tgtcctgtcc taaggatttt tggggcagag gcacccaggt gacagtgagc 360
tcc 363

<210> SEQ ID NO 166
<211> LENGTH: 369
<212> TYPE: DNA
<213> ORGANISM: Artificial Sequence
<220> FEATURE:
<223> OTHER INFORMATION: AS77916

<400> SEQUENCE: 166
caggtgcacc tgatggagtc cggaggaggc tctgtgcagg caggaggcag cctgcggctg 60
tcctgcgcca cctctggcta cacaagctcc tggaactgta tgggatggtt caggcagcca 120
cctggcaagg agagagaggg agtggccacc atcgccaata ggggccacag cacatactat 180
gccgactccg tgaagggccg ctttaccatc tctcagggca acgccaagaa tacagtgtac 240
ctgcagatga acagcctgaa gcccgaggac accgccatgt actattgcgc caccgataca 300
tgggcctgcg tgggcatctc cacagatttc gagtattggg gccagggcac ccaggtgaca 360
gtgtctagc 369

<210> SEQ ID NO 167
<211> LENGTH: 372
<212> TYPE: DNA
<213> ORGANISM: Artificial Sequence
<220> FEATURE:
<223> OTHER INFORMATION: AS77932

<400> SEQUENCE: 167
caggtgcagc tgaaggagtc tggaggaggc agcgtgcagg caggaggctc cctgcggctg 60
tcttgcgccg tgagcggcta ctggtattct gtggcctgga tgggctggtt caggcagacc 120
ccaggcaagg agcgcgaggg agtggcagcc gtgctgaacg gaggaggccg gagatactat 180
gccgacagcg tgaagggcag gtttaccatc tcccaggata actctaagaa tacactgtac 240
ctgcagatga acagcctgaa gcccgaggac acagccatgt actattgtgc agcaggaaac 300
ggagtgggac acccactggg ccctagcgag tacaattatt ggggccaggg cacccaggtg 360
acagtgagct cc 372

<210> SEQ ID NO 168
<211> LENGTH: 375
<212> TYPE: DNA
<213> ORGANISM: Artificial Sequence
<220> FEATURE:
<223> OTHER INFORMATION: AS77934

<400> SEQUENCE: 168
gaggtgcagc tggtggagtc cggaggaggc tctgtgcagg caggaggcag cctgaggctg 60
tcctgcgcag catctggata cacctatagc tcctactcca tcgcatggtt caggcaggca 120
ccaggcaagg agagggaggg agtggccggc ttcttttact ctggcggccc tacatgttat 180
gccgacagcg tgaagggcag gtttaccatc tcccaggata acgccaagaa tacactgtat 240
ctgcagatga actctctgaa gccagaggac accgccatgt actattgcgc cgcccggaga 300
agcaacacaa atgattactg tttctatccc acctacacat attggggcca gggcacccag 360

```
gtgacagtgt ctagc                                                   375


<210> SEQ ID NO 169
<211> LENGTH: 360
<212> TYPE: DNA
<213> ORGANISM: Artificial Sequence
<220> FEATURE:
<223> OTHER INFORMATION: AS77978

<400> SEQUENCE: 169

caggtgcggc tggtggagag cggaggaggc tccgtgcagg caggaggctc tctgcggctg    60

agctgcgccg cctccggcgc cacctcttgt cggtggagaa tgtcttggta caggcaggca   120

ccaggcaagg agagagagtt cgtgagctcc atcgccaacg gcgccacaga gtacgccgat   180

agcgtgaagg gcaggtttac catctcccag gacaacgccc gcaatacaat gtatctgcag   240

atgaacagcc tgtctcccga ggacaccgcc atgtactatt gcgccgccga tcctagagtg   300

tacacctcca ggtgtgaccg cacatatctg ggccagggca cccaggtgac agtgtctagc   360


<210> SEQ ID NO 170
<211> LENGTH: 396
<212> TYPE: DNA
<213> ORGANISM: Artificial Sequence
<220> FEATURE:
<223> OTHER INFORMATION: AS77986

<400> SEQUENCE: 170

caggtgcagc tggtggagag cggaggaggc tccgtgcagg caggaggctc tctgcggctg    60

agctgcgcag catccgcctc tggatacacc tatagctccg acagcatggc atggttcagg   120

caggcaccag gcaaggagag agagggagtg gcaggaatct ccaccggagg caggtctaca   180

tactatgccg acagcgtgaa gggccgcttt acaatctccc aggataacgc caagaccaca   240

gtgtacctgc acatgaacag cctgaagccc gaggacaccg ccatgtacta ttgtgccgcc   300

gatggccctt ccatgacagc catccaggcc ctgggcgacc tgtatccagt ggatttcgca   360

tggtggggac agggaaccca ggtgacagtg tctagc                            396


<210> SEQ ID NO 171
<211> LENGTH: 381
<212> TYPE: DNA
<213> ORGANISM: Artificial Sequence
<220> FEATURE:
<223> OTHER INFORMATION: AS78117

<400> SEQUENCE: 171

caggtgaagc tggtggagtc cggaggaggc tctgtgcagg caggaggcgc cctgcggctg    60

tcttgcatcg tgcggagata cacctatgcc acatacagca tggcctggtt caggcagtcc   120

ccaggcaagg agcgcgaggg agtggcagga ctggacagcg tgggagccac cggctacgcc   180

gagtctgtga agggcaggtt tacaatcagc aaggataacg ccaagaatat cctgtatctg   240

cagatgaact ccctgaagcc cgaggacacc gccatgtact attgcgtggt ggaccccgca   300

tccgccaagg tgacctatgg ctcttggagc acaccctctt acgcctattg gggccagggc   360

acccaggtga cagtgagctc c                                            381


<210> SEQ ID NO 172
<211> LENGTH: 375
<212> TYPE: DNA
<213> ORGANISM: Artificial Sequence
<220> FEATURE:
<223> OTHER INFORMATION: AS78215
```

<400> SEQUENCE: 172
caggtgaagc tggtggagag cggaggaggc tccgtgcagg caggaggcgc cctgaggctg 60
tcttgcgccg ccagccgcta caccttcagc tccaactgta tgggatggtt taggcaggca 120
ccaggcaagg agagggaggg agtggcaacc atcgcatccg cctctggcta cacagactat 180
cacgattccg tgaagggccg gttcgccatc tctagagaca acgccaagaa tacagtgtat 240
ctgcagatga acagcctgaa gcccgaggat accgcaacat actattgcgc agcaagggca 300
ggaccttgtt ggtcctgggc ccaggccgac ctgtacaatt attggggcca gggcacccag 360
gtgacagtgt ctagc 375

<210> SEQ ID NO 173
<211> LENGTH: 357
<212> TYPE: DNA
<213> ORGANISM: Artificial Sequence
<220> FEATURE:
<223> OTHER INFORMATION: AS78810

<400> SEQUENCE: 173
caggtgcacc tggtggagag cggaggaggc tccgtgcagg caggaggctc tctgaggctg 60
agctgcgcag catccggata tacctactat gacatgggct ggttcaggct ggcaccaggc 120
aaggagaggg agggcatcgc cgccatcagc tcctctagct ccacatacta tgccgacagc 180
gtgaagggca ggtttaccat ctcccgcgat tctaacacac tgtacctgca gatgaacagc 240
ctgaagcctg aggacaccgc catgtattcc tgtgcagcag gccggtacgt gggaagaaag 300
ctggaggtgt acgattatgc ctactggggc cagggcaccc aggtgacagt gtctagc 357

<210> SEQ ID NO 174
<211> LENGTH: 378
<212> TYPE: DNA
<213> ORGANISM: Artificial Sequence
<220> FEATURE:
<223> OTHER INFORMATION: AS79101

<400> SEQUENCE: 174
caggtgcagc tggtggagtc cggaggaggc tctgtgcagg caggaggcag cctgaggctg 60
tcctgcgcag catctggcga cacctactct aactattgta tgggctggtt caggcaggca 120
ccaggcaagg agagggagga ggtggcagca atcgactctg atggcagccg gagatacccc 180
gacagcgtga agggcagatt cacaatctcc aaggataacg ccaagaagat cctgtacctg 240
cagatgaata gcctgaagcc cgaggacacc gccatgtatt tttgcgccac agatcctaag 300
gtggcctgtg caagggtggt ggagtacgga ggaggatggt atagatgggg acagggcacc 360
caggtgacag tgagctcc 378

<210> SEQ ID NO 175
<211> LENGTH: 381
<212> TYPE: DNA
<213> ORGANISM: Artificial Sequence
<220> FEATURE:
<223> OTHER INFORMATION: AS79236

<400> SEQUENCE: 175
caggtgaagc tggtggagtc cggaggaggc tctgtgcagg caggaggcag cctgcggctg 60
tcctgcgccg tgtctggcta cacctatagc tcctactgta tggcatggtt caggcaggca 120
ccaggagagg agagggaggg agtggccagc atcgacgcag gaggaaggac cacatacgtg 180

-continued

```
gattccgtga agggcaggtt taccatcagc aaggacaacg ccaagacatc cctgtatctg    240

cagatgaaca gcctgaagcc cgaggacaca gccatgtact attgcgccgt ggatgtgcgg    300

accagatgtg gcggcacatg ggatggcgag gccgtgtact tcccttattg gggccagggc    360

acccaggtga cagtgtctag c                                              381
```

<210> SEQ ID NO 176
<211> LENGTH: 369
<212> TYPE: DNA
<213> ORGANISM: Artificial Sequence
<220> FEATURE:
<223> OTHER INFORMATION: AS79274

<400> SEQUENCE: 176

```
caggtgcacc tggtggagag cggaggaggc tccgtgcagg caggaggctc tctgaggctg     60

agctgcgcag catccaagta cgccttctgt acctatgaca tgtcctggtt taggcaggca    120

ccaggcaagg agagggaggt ggtgagctcc atcgactctc ggggcaacac aaattactcc    180

gattctgtga agggcaggtt caccatctct caggaccacg ccaagaacac actgtacctg    240

cagatgaata gcctgaagcc cgaggatacc gccatgtata catgcgcagc acagatcgtg    300

ggaggcgccc tgaggtgtcc tagatttgcc atgtattggg gccagggcac ccaggtgaca    360

gtgtctagc                                                            369
```

<210> SEQ ID NO 177
<211> LENGTH: 396
<212> TYPE: DNA
<213> ORGANISM: Artificial Sequence
<220> FEATURE:
<223> OTHER INFORMATION: AS79285

<400> SEQUENCE: 177

```
caggtgcggc tggtggagtc cggaggaggc tctgtgcagg caggaggcag cctggccctg     60

tcctgcgaga catctaggta caccgtgtct aactattgta tgggctggtt caggcaggtg    120

agcggcaagg aggtggaggg agtggccctg atctccacag acggcaccac aacctacgcc    180

gatagcgtga agggcaggtt cacaatctcc aaggacaacg ccaagaatac cctgtatctg    240

cagatgaaca gcctgaagag cgaggatacc gccatgtact tttgcgccgg cgtgtatggc    300

ctgatctggt actataagcc atgtcctgca cagagggagt gggcactgca gagatacggc    360

tattggggcc agggcacaca ggtgaccgtg agctcc                             396
```

<210> SEQ ID NO 178
<211> LENGTH: 375
<212> TYPE: DNA
<213> ORGANISM: Artificial Sequence
<220> FEATURE:
<223> OTHER INFORMATION: AS79317

<400> SEQUENCE: 178

```
gaggtgcagc tggcagagag cggaggaggc tccgtgcagc caggaggctc tctgaggctg     60

agctgcgcag catccggata cagctcctct agcgtgtgca tgggatggtt caggcaggca    120

ccaggcaagg agagggaggg agtggccatc atctacgtga ccctgggctc tatcgcctat    180

gccgacagcg tgaagggccg gtttaccatc tccagagaca acgccaagaa tacactggat    240

ctggagatga actctctgaa gcccgacgat accgccctgt actattgcgc agcaggagga    300

tgtggataca ggggagtggc agatgtgcct gagttcacat ataggggcca gggcacccag    360

gtgacagtgt cctct                                                     375
```

<210> SEQ ID NO 179
<211> LENGTH: 19
<212> TYPE: PRT
<213> ORGANISM: Artificial Sequence
<220> FEATURE:
<223> OTHER INFORMATION: mouse Ig heavy chain signal peptide

<400> SEQUENCE: 179

Met Gly Trp Ser Trp Ile Leu Leu Phe Leu Leu Ser Val Thr Ala Gly
1 5 10 15

Val His Ser

<210> SEQ ID NO 180
<211> LENGTH: 6
<212> TYPE: PRT
<213> ORGANISM: Artificial Sequence
<220> FEATURE:
<223> OTHER INFORMATION: 6XHis-tag

<400> SEQUENCE: 180

His His His His His His
1 5

<210> SEQ ID NO 181
<211> LENGTH: 15
<212> TYPE: PRT
<213> ORGANISM: Artificial Sequence
<220> FEATURE:
<223> OTHER INFORMATION: glycine-serine linker

<400> SEQUENCE: 181

Gly Gly Gly Gly Ser Gly Gly Gly Gly Ser Gly Gly Gly Gly Ser
1 5 10 15

<210> SEQ ID NO 182
<211> LENGTH: 21
<212> TYPE: PRT
<213> ORGANISM: Artificial Sequence
<220> FEATURE:
<223> OTHER INFORMATION: CD8alpha signal peptide

<400> SEQUENCE: 182

Met Ala Leu Pro Val Thr Ala Leu Leu Leu Pro Leu Ala Leu Leu Leu
1 5 10 15

His Ala Ala Arg Pro
20

<210> SEQ ID NO 183
<211> LENGTH: 45
<212> TYPE: PRT
<213> ORGANISM: Artificial Sequence
<220> FEATURE:
<223> OTHER INFORMATION: CD8alpha hinge

<400> SEQUENCE: 183

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 184

-continued

<211> LENGTH: 24
<212> TYPE: PRT
<213> ORGANISM: Artificial Sequence
<220> FEATURE:
<223> OTHER INFORMATION: CD8alpha transmembrane domain

<400> SEQUENCE: 184

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 185
<211> LENGTH: 42
<212> TYPE: PRT
<213> ORGANISM: Artificial Sequence
<220> FEATURE:
<223> OTHER INFORMATION: 4-1BB intracellular domain

<400> SEQUENCE: 185

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 186
<211> LENGTH: 41
<212> TYPE: PRT
<213> ORGANISM: Artificial Sequence
<220> FEATURE:
<223> OTHER INFORMATION: CD28 intracellular domain

<400> SEQUENCE: 186

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 187
<211> LENGTH: 112
<212> TYPE: PRT
<213> ORGANISM: Artificial Sequence
<220> FEATURE:
<223> OTHER INFORMATION: CD3zeta intracellular domain

<400> SEQUENCE: 187

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

```
Thr Lys Asp Thr Tyr Asp Ala Leu His Met Gln Ala Leu Pro Pro Arg
            100                 105                 110


<210> SEQ ID NO 188
<211> LENGTH: 22
<212> TYPE: PRT
<213> ORGANISM: Artificial Sequence
<220> FEATURE:
<223> OTHER INFORMATION: P2A element

<400> SEQUENCE: 188

Gly Ser Gly Ala Thr Asn Phe Ser Leu Leu Lys Gln Ala Gly Asp Val
1               5                   10                  15

Glu Glu Asn Pro Gly Pro
            20


<210> SEQ ID NO 189
<211> LENGTH: 370
<212> TYPE: PRT
<213> ORGANISM: Artificial Sequence
<220> FEATURE:
<223> OTHER INFORMATION: CAS70549-BBz

<400> SEQUENCE: 189

Met Ala Leu Pro Val Thr Ala Leu Leu Leu Pro Leu Ala Leu Leu Leu
1               5                   10                  15

His Ala Ala Arg Pro Gln Val Arg Leu Val Glu Ser Gly Gly Gly Ser
            20                  25                  30

Val Gln Ala Gly Gly Ser Leu Thr Leu Ser Cys Ala Tyr Ser Arg Tyr
        35                  40                  45

Thr Gly Arg Ser Ser Cys Met Ala Trp Phe Arg Arg Pro Pro Gly Lys
    50                  55                  60

Lys Arg Glu Arg Val Ala Ser Ile Tyr Ser Asp Asp Gly Val Thr Val
65                  70                  75                  80

Tyr Ala Asp Ser Val Lys Gly Arg Phe Thr Ile Thr Gln Asp Ser Ala
                85                  90                  95

Gln Asn Thr Leu Tyr Leu Gln Met Asn Ser Leu Asp Pro Glu Asp Thr
            100                 105                 110

Ala Met Tyr Tyr Cys Ala Thr Arg Thr Thr Tyr Pro Gly Val Cys Pro
        115                 120                 125

Asp Asn Ala Ala Trp Tyr Asp Tyr Trp Gly Gln Gly Thr Gln Val Thr
    130                 135                 140

Val Ser Ser Thr Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
                165                 170                 175

Ala Ala Gly Gly Ala Val His Thr Arg Gly Leu Asp Phe Ala Cys Asp
            180                 185                 190

Ile Tyr Ile Trp Ala Pro Leu Ala Gly Thr Cys Gly Val Leu Leu Leu
        195                 200                 205

Ser Leu Val Ile Thr Leu Tyr Cys Lys Arg Gly Arg Lys Lys Leu Leu
    210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255

Glu Leu Arg Val Lys Phe Ser Arg Ser Ala Asp Ala Pro Ala Tyr Lys
```

```
            260                 265                 270

Gln Gly Gln Asn Gln Leu Tyr Asn Glu Leu Asn Leu Gly Arg Arg Glu
        275                 280                 285

Glu Tyr Asp Val Leu Asp Lys Arg Arg Gly Arg Asp Pro Glu Met Gly
    290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
            340                 345                 350

Thr Ala Thr Lys Asp Thr Tyr Asp Ala Leu His Met Gln Ala Leu Pro
        355                 360                 365

Pro Arg
    370


<210> SEQ ID NO 190
<211> LENGTH: 369
<212> TYPE: PRT
<213> ORGANISM: Artificial Sequence
<220> FEATURE:
<223> OTHER INFORMATION: CAS70771-BBz

<400> SEQUENCE: 190

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Ser
            20                  25                  30

Val Gln Ala Gly Gly Ser Leu Arg Leu Ser Cys Ala Ala Ser Gly Tyr
        35                  40                  45

Thr Gly Lys Met Ala Trp Phe Arg Gln Ala Pro Gly Lys Glu Arg Glu
    50                  55                  60

Gly Val Ala Ala Ile Asp Asp Ala Gly Gly Thr Asn Tyr Ile Asp Ser
65                  70                  75                  80

Val Lys Gly Arg Phe Thr Ile Ser Lys Asp Asn Ala Glu Asn Thr Leu
                85                  90                  95

Tyr Leu Arg Met Asn Ser Leu Lys Pro Glu Asp Thr Ala Ile Tyr Tyr
            100                 105                 110

Cys Ala Ala Asp Thr Phe Arg Trp Phe Met Arg Arg Ser Gly Pro Ile
        115                 120                 125

Asn Gly Ser Asp Tyr Ala Tyr Trp Gly Gln Gly Thr Gln Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
```

```
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
    290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg


<210> SEQ ID NO 191
<211> LENGTH: 368
<212> TYPE: PRT
<213> ORGANISM: Artificial Sequence
<220> FEATURE:
<223> OTHER INFORMATION: [CAS70950-BBz

<400> SEQUENCE: 191

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Ser
            20                  25                  30

Ala Gln Ser Gly Gly Ser Leu Arg Leu Ser Cys Ala Ile Ser Glu Phe
        35                  40                  45

Thr Tyr Lys Asn Thr Cys Val Gly Trp Phe Arg Gln Ala Pro Gly Lys
    50                  55                  60

Glu Arg Glu Gly Val Ala Ala Ile Asp Ser Asp Gly Asn Thr Asn Tyr
65                  70                  75                  80

Val Asp Ser Val Lys Gly Arg Phe Thr Ile Ser Gln Gly Asn Ala Lys
                85                  90                  95

Asn Thr Val Tyr Leu Gln Met Asn Ser Leu Lys Pro Glu Asp Thr Ala
            100                 105                 110

Met Tyr Tyr Cys Ala Ala Gly Ala Tyr Cys Gly Arg Leu Leu Leu Trp
        115                 120                 125

Ile Gly Asn Tyr Ala Tyr Trp Gly Gln Gly Thr Gln Val Thr Val Ser
    130                 135                 140

Ser Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

Gly Gly Ala Val His Thr Arg Gly Leu Asp Phe Ala Cys Asp Ile Tyr
            180                 185                 190

Ile Trp Ala Pro Leu Ala Gly Thr Cys Gly Val Leu Leu Leu Ser Leu
        195                 200                 205

Val Ile Thr Leu Tyr Cys Lys Arg Gly Arg Lys Lys Leu Leu Tyr Ile
    210                 215                 220

Phe Lys Gln Pro Phe Met Arg Pro Val Gln Thr Thr Gln Glu Glu Asp
225                 230                 235                 240
```

-continued

```
Gly Cys Ser Cys Arg Phe Pro Glu Glu Glu Glu Gly Gly Cys Glu Leu
                245                 250                 255

Arg Val Lys Phe Ser Arg Ser Ala Asp Ala Pro Ala Tyr Lys Gln Gly
            260                 265                 270

Gln Asn Gln Leu Tyr Asn Glu Leu Asn Leu Gly Arg Arg Glu Glu Tyr
        275                 280                 285

Asp Val Leu Asp Lys Arg Arg Gly Arg Asp Pro Glu Met Gly Gly Lys
    290                 295                 300

Pro Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
                325                 330                 335

Arg Arg Gly Lys Gly His Asp Gly Leu Tyr Gln Gly Leu Ser Thr Ala
            340                 345                 350

Thr Lys Asp Thr Tyr Asp Ala Leu His Met Gln Ala Leu Pro Pro Arg
        355                 360                 365


<210> SEQ ID NO 192
<211> LENGTH: 369
<212> TYPE: PRT
<213> ORGANISM: Artificial Sequence
<220> FEATURE:
<223> OTHER INFORMATION: CAS71402-BBz

<400> SEQUENCE: 192

Met Ala Leu Pro Val Thr Ala Leu Leu Leu Pro Leu Ala Leu Leu Leu
1               5                   10                  15

His Ala Ala Arg Pro Gln Met Gln Leu Val Glu Ser Gly Gly Gly Ser
            20                  25                  30

Val Gln Ala Gly Gly Ser Leu Arg Leu Ser Cys Val Val Ser Gly Tyr
        35                  40                  45

Thr Tyr Asn Arg Asn Met Ala Trp Phe Arg Gln Ala Pro Gly Lys Glu
    50                  55                  60

Arg Glu Gly Val Ala Ala Met Tyr Thr Gly Ser Gly Thr Thr Asp Tyr
65                  70                  75                  80

Ala Asp Ser Val Lys Gly Arg Phe Thr Ile Ser His Asp Asn Ala Lys
                85                  90                  95

Asn Thr Leu Tyr Leu Gln Met Asn Ser Leu Lys Pro Glu Asp Thr Ala
            100                 105                 110

Thr Tyr Tyr Cys Ala Ala Asp Thr Ala Arg Arg Gly Gly Ser Trp Ser
        115                 120                 125

Gly Pro Phe Lys Tyr Asp Tyr Trp Gly Gln Gly Thr Gln Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240
```

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
    290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg

<210> SEQ ID NO 193
<211> LENGTH: 370
<212> TYPE: PRT
<213> ORGANISM: Artificial Sequence
<220> FEATURE:
<223> OTHER INFORMATION: CAS71529-BBz

<400> SEQUENCE: 193

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Ser
            20                  25                  30

Val Gln Ala Gly Gly Ser Leu Arg Leu Ser Cys Val Val Ser Glu Tyr
        35                  40                  45

Arg Tyr Ser Ser Arg Tyr Cys Met Gly Trp Phe Arg Gln Ala Pro Gly
    50                  55                  60

Lys Glu Arg Glu Gly Val Ala Ala Ile Asp Ser Asn Gly Ser Ala Asp
65                  70                  75                  80

Tyr Val Asp Ser Val Lys Gly Arg Phe Thr Ile Ser Lys Asp Asn Ala
                85                  90                  95

Lys Asn Thr Leu Tyr Leu Gln Ile Asn Ser Val Arg Pro Glu Asp Thr
            100                 105                 110

Ala Met Tyr Tyr Cys Ala Ala Asp His Leu Ala Tyr Asp Cys Tyr Ser
        115                 120                 125

Gly Ala Thr Ser Val Phe Arg Tyr Trp Gly Gln Gly Thr Gln Val Thr
    130                 135                 140

Val Ser Ser Thr Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
                165                 170                 175

Ala Ala Gly Gly Ala Val His Thr Arg Gly Leu Asp Phe Ala Cys Asp
            180                 185                 190

Ile Tyr Ile Trp Ala Pro Leu Ala Gly Thr Cys Gly Val Leu Leu Leu
        195                 200                 205

Ser Leu Val Ile Thr Leu Tyr Cys Lys Arg Gly Arg Lys Lys Leu Leu
    210                 215                 220

-continued

```
Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255

Glu Leu Arg Val Lys Phe Ser Arg Ser Ala Asp Ala Pro Ala Tyr Lys
            260                 265                 270

Gln Gly Gln Asn Gln Leu Tyr Asn Glu Leu Asn Leu Gly Arg Arg Glu
        275                 280                 285

Glu Tyr Asp Val Leu Asp Lys Arg Arg Gly Arg Asp Pro Glu Met Gly
    290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
            340                 345                 350

Thr Ala Thr Lys Asp Thr Tyr Asp Ala Leu His Met Gln Ala Leu Pro
        355                 360                 365

Pro Arg
    370


<210> SEQ ID NO 194
<211> LENGTH: 370
<212> TYPE: PRT
<213> ORGANISM: Artificial Sequence
<220> FEATURE:
<223> OTHER INFORMATION: CAS71661-BBz

<400> SEQUENCE: 194

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ser Pro Ser Gly Thr
        35                  40                  45

Thr Phe Ala His Tyr Asn Met Val Gly Trp Phe Arg Gln Ala Pro Gly
    50                  55                  60

Lys Asp Arg Glu Gly Val Ser Cys Ile Ser Lys Tyr Gly Gly Thr Thr
65                  70                  75                  80

Tyr Tyr Ala Asp Ser Val Lys Gly Arg Phe Thr Ile Tyr Arg Asp Asn
                85                  90                  95

Ala Lys Asn Thr Leu Phe Leu Gln Met Asn Ser Leu Lys Pro Glu Asp
            100                 105                 110

Thr Ala Met Tyr Tyr Cys Ala Ile Gly Val Leu Pro Ser Ser Thr Ala
        115                 120                 125

Ile Cys Ala Gly Ala Ala Asn Tyr Trp Gly Gln Gly Thr Gln Val Thr
    130                 135                 140

Val Ser Ser Thr Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
                165                 170                 175

Ala Ala Gly Gly Ala Val His Thr Arg Gly Leu Asp Phe Ala Cys Asp
            180                 185                 190

Ile Tyr Ile Trp Ala Pro Leu Ala Gly Thr Cys Gly Val Leu Leu Leu
        195                 200                 205
```

-continued

Ser Leu Val Ile Thr Leu Tyr Cys Lys Arg Gly Arg Lys Lys Leu Leu
    210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255

Glu Leu Arg Val Lys Phe Ser Arg Ser Ala Asp Ala Pro Ala Tyr Lys
            260                 265                 270

Gln Gly Gln Asn Gln Leu Tyr Asn Glu Leu Asn Leu Gly Arg Arg Glu
        275                 280                 285

Glu Tyr Asp Val Leu Asp Lys Arg Arg Gly Arg Asp Pro Glu Met Gly
    290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
            340                 345                 350

Thr Ala Thr Lys Asp Thr Tyr Asp Ala Leu His Met Gln Ala Leu Pro
        355                 360                 365

Pro Arg
    370

<210> SEQ ID NO 195
<211> LENGTH: 369
<212> TYPE: PRT
<213> ORGANISM: Artificial Sequence
<220> FEATURE:
<223> OTHER INFORMATION: CAS72021-BBz

<400> SEQUENCE: 195

Met Ala Leu Pro Val Thr Ala Leu Leu Leu Pro Leu Ala Leu Leu Leu
1               5                   10                  15

His Ala Ala Arg Pro Glu Val Gln Leu Ala Glu Ser Gly Gly Gly Ser
            20                  25                  30

Val Gln Ala Gly Gly Ser Leu Arg Leu Ser Cys Val Val Ser Arg Asn
        35                  40                  45

Thr Tyr Ser Ser Tyr Cys Met Ser Trp Phe Arg Gln Ala Pro Gly Lys
    50                  55                  60

Glu Arg Glu Gly Val Ala Ala Ile Asp Asn Val Lys Thr Ser Tyr Ala
65                  70                  75                  80

Asp Ser Val Lys Gly Arg Phe Thr Ile Ser Lys Asp Asn Ala Lys Asn
                85                  90                  95

Thr Leu Tyr Leu Gln Met Asn Ser Leu Lys Pro Glu Asp Thr Ala Met
            100                 105                 110

Tyr Tyr Cys Ala Ala His Leu Glu Leu Cys Tyr Tyr Thr Asp Pro Met
        115                 120                 125

Tyr Gln Tyr Glu Tyr Asn Tyr Trp Gly Gln Gly Thr Gln Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

```
Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
    290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg


<210> SEQ ID NO 196
<211> LENGTH: 369
<212> TYPE: PRT
<213> ORGANISM: Artificial Sequence
<220> FEATURE:
<223> OTHER INFORMATION: CAS72052-BBz

<400> SEQUENCE: 196

Met Ala Leu Pro Val Thr Ala Leu Leu Leu Pro Leu Ala Leu Leu Leu
1               5                   10                  15

His Ala Ala Arg Pro Gln Val Arg Leu Val Glu Ser Gly Gly Gly Ser
            20                  25                  30

Val Gln Ala Gly Gly Ser Leu Arg Leu Ser Cys Ala Val Ser Gly Phe
        35                  40                  45

Arg Tyr Ala Ser Tyr Cys Met Gly Trp Phe Arg Gln Ala Pro Gly Lys
    50                  55                  60

Glu Arg Glu Gly Val Ala Ala Ile His Ser Asp Gly Ile Ile Arg Tyr
65                  70                  75                  80

Ala Glu Ser Val Lys Gly Arg Phe Thr Ile Ser Lys Asp Asn Ala Lys
                85                  90                  95

Asn Thr Leu Tyr Leu Gln Leu Asn Ser Leu Lys Pro Glu Asp Asn Ala
            100                 105                 110

Met Tyr Ser Cys Ala Ala Gly Ala Tyr Cys Gly Ala Asp Ala Ile Leu
        115                 120                 125

Thr Leu Tyr Asp Tyr Ala Phe Trp Gly Gln Gly Thr Gln Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
```

```
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
    290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg
```

<210> SEQ ID NO 197
<211> LENGTH: 367
<212> TYPE: PRT
<213> ORGANISM: Artificial Sequence
<220> FEATURE:
<223> OTHER INFORMATION: CAS72383-BBz

<400> SEQUENCE: 197

```
Met Ala Leu Pro Val Thr Ala Leu Leu Leu Pro Leu Ala Leu Leu Leu
1               5                   10                  15

His Ala Ala Arg Pro Gln Val Arg Leu Val Glu Ser Gly Gly Gly Leu
            20                  25                  30

Val Gln Ala Gly Gly Ser Gln Arg Leu Ser Cys Thr Ala Ser Gly Leu
        35                  40                  45

Thr Phe Asp Asp Ser Gly Met Gly Trp Phe Arg Gln Ala Pro Gly Lys
    50                  55                  60

Gly Arg Glu Gly Val Ser Cys Ile Thr Trp Asn Gly Arg Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Lys Pro Glu Asp Thr
            100                 105                 110

Ala Met Tyr Tyr Cys Ala Ala Ala Phe Ile Thr Lys Thr Gly Cys Ser
        115                 120                 125

Tyr Glu Tyr Asp Tyr Ser Gly Gln Gly Thr Gln Val Thr Val Ser Ser
    130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175
```

```
Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Lys Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
    290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365


<210> SEQ ID NO 198
<211> LENGTH: 367
<212> TYPE: PRT
<213> ORGANISM: Artificial Sequence
<220> FEATURE:
<223> OTHER INFORMATION: CAS72479-BBz

<400> SEQUENCE: 198

Met Ala Leu Pro Val Thr Ala Leu Leu Leu Pro Leu Ala Leu Leu Leu
1               5                   10                  15

His Ala Ala Arg Pro Gln Val Lys Leu Val Glu Ser Gly Gly Gly Ser
            20                  25                  30

Val Gln Ala Gly Gly Ser Leu Arg Leu Ser Cys Ala Ala Ser Glu Thr
        35                  40                  45

Thr Asp Cys Arg Tyr Val Trp Arg Trp Tyr Arg Glu Asp Pro Gly Met
    50                  55                  60

Glu Arg Glu Phe Val Ser Ser Ile Thr Ser Gly Gly Ser Thr Trp Tyr
65                  70                  75                  80

Ala Asp Ser Val Lys Gly Arg Phe Thr Ile Ser Gln Asp Asn Ala Lys
                85                  90                  95

Ser Thr Leu Tyr Leu Gln Met Asn Ser Leu Lys Pro Glu Asp Ser Gly
            100                 105                 110

Met Tyr Tyr Cys Glu Ser Asp Pro Gly Trp Ser Gly Tyr His Ala Arg
        115                 120                 125

Arg Cys Glu Val Tyr Arg Gly Gln Gly Ile Gln Val Thr Val Ser Ser
    130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175
```

```
Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Lys Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
    290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365


<210> SEQ ID NO 199
<211> LENGTH: 370
<212> TYPE: PRT
<213> ORGANISM: Artificial Sequence
<220> FEATURE:
<223> OTHER INFORMATION: CAS72499-BBz

<400> SEQUENCE: 199

Met Ala Leu Pro Val Thr Ala Leu Leu Leu Pro Leu Ala Leu Leu Leu
1               5                   10                  15

His Ala Ala Arg Pro Gln Val Arg Leu Val Glu Ser Gly Gly Gly Ser
            20                  25                  30

Val Gln Ala Gly Gly Ser Leu Arg Leu Ser Cys Val Val Ser Arg Phe
        35                  40                  45

Thr Tyr Ser Ser Tyr Cys Met Gly Trp Phe Arg Gln Ala Pro Gly Lys
    50                  55                  60

Glu Arg Glu Gly Val Ala Gly Ile Glu Lys Asp Asp Ser Thr Tyr Tyr
65                  70                  75                  80

Ala Asp Ser Val Lys Gly Arg Phe Thr Ile Ser Lys Asp Asn Ala Lys
                85                  90                  95

Asn Thr Leu Tyr Leu Gln Met Asn Ser Leu Lys Pro Glu Asp Thr Ala
            100                 105                 110

Met Tyr Tyr Cys Ala Ala Arg Ile Pro Gly Gly Asn Cys Gly Val Val
        115                 120                 125

Ala Arg Met Ala Tyr Trp Asp Tyr Trp Gly Lys Gly Thr Leu Val Thr
    130                 135                 140

Val Ser Ser Thr Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
                165                 170                 175
```

```
Ala Ala Gly Gly Ala Val His Thr Arg Gly Leu Asp Phe Ala Cys Asp
            180                 185                 190

Ile Tyr Ile Trp Ala Pro Leu Ala Gly Thr Cys Gly Val Leu Leu Leu
        195                 200                 205

Ser Leu Val Ile Thr Leu Tyr Cys Lys Arg Gly Arg Lys Lys Leu Leu
    210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255

Glu Leu Arg Val Lys Phe Ser Arg Ser Ala Asp Ala Pro Ala Tyr Lys
            260                 265                 270

Gln Gly Gln Asn Gln Leu Tyr Asn Glu Leu Asn Leu Gly Arg Arg Glu
        275                 280                 285

Glu Tyr Asp Val Leu Asp Lys Arg Arg Gly Arg Asp Pro Glu Met Gly
    290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
            340                 345                 350

Thr Ala Thr Lys Asp Thr Tyr Asp Ala Leu His Met Gln Ala Leu Pro
        355                 360                 365

Pro Arg
    370


<210> SEQ ID NO 200
<211> LENGTH: 369
<212> TYPE: PRT
<213> ORGANISM: Artificial Sequence
<220> FEATURE:
<223> OTHER INFORMATION: CAS72531-BBz

<400> SEQUENCE: 200

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Thr Ala Ser Gly Leu
        35                  40                  45

Thr Phe Ala His Tyr Asn Met Val Gly Trp Phe Arg Gln Ala Pro Gly
    50                  55                  60

Lys Asp Arg Glu Gly Val Ser Cys Ile Ser Lys Tyr Gly Gly Thr Ile
65                  70                  75                  80

Tyr Tyr Ala Asp Ser Val Lys Gly Arg Phe Thr Ile Asp Arg Asn Asn
                85                  90                  95

Ala Lys Asn Thr Leu Tyr Leu Gln Met Asn Ser Leu Lys Pro Glu Asp
            100                 105                 110

Thr Ala Met Tyr Tyr Cys Ala Ile Gly Val Leu Ser Ser Thr Ala Arg
        115                 120                 125

Gly Pro Gly Ala Ala Asn Tyr Trp Gly Gln Gly Thr Gln Val Thr Val
    130                 135                 140

Ser Ser Thr Thr Thr Pro Ala Pro Arg Pro Pro Thr Pro Ala Pro Thr
145                 150                 155                 160
```

Ile Ala Ser Gln Pro Leu Ser Leu Arg Pro Glu Ala Cys Arg Pro Ala
165 170 175

Ala Gly Gly Ala Val His Thr Arg Gly Leu Asp Phe Ala Cys Asp Ile
180 185 190

Tyr Ile Trp Ala Pro Leu Ala Gly Thr Cys Gly Val Leu Leu Leu Ser
195 200 205

Leu Val Ile Thr Leu Tyr Cys Lys Arg Gly Arg Lys Lys Leu Leu Tyr
210 215 220

Ile Phe Lys Gln Pro Phe Met Arg Pro Val Gln Thr Thr Gln Glu Glu
225 230 235 240

Asp Gly Cys Ser Cys Arg Phe Pro Glu Glu Glu Glu Gly Gly Cys Glu
245 250 255

Leu Arg Val Lys Phe Ser Arg Ser Ala Asp Ala Pro Ala Tyr Lys Gln
260 265 270

Gly Gln Asn Gln Leu Tyr Asn Glu Leu Asn Leu Gly Arg Arg Glu Glu
275 280 285

Tyr Asp Val Leu Asp Lys Arg Arg Gly Arg Asp Pro Glu Met Gly Gly
290 295 300

Lys Pro Arg Arg Lys Asn Pro Gln Glu Gly Leu Tyr Asn Glu Leu Gln
305 310 315 320

Lys Asp Lys Met Ala Glu Ala Tyr Ser Glu Ile Gly Met Lys Gly Glu
325 330 335

Arg Arg Arg Gly Lys Gly His Asp Gly Leu Tyr Gln Gly Leu Ser Thr
340 345 350

Ala Thr Lys Asp Thr Tyr Asp Ala Leu His Met Gln Ala Leu Pro Pro
355 360 365

Arg

<210> SEQ ID NO 201
<211> LENGTH: 368
<212> TYPE: PRT
<213> ORGANISM: Artificial Sequence
<220> FEATURE:
<223> OTHER INFORMATION: CAS72669-BBz

<400> SEQUENCE: 201

Met Ala Leu Pro Val Thr Ala Leu Leu Leu Pro Leu Ala Leu Leu Leu
1 5 10 15

His Ala Ala Arg Pro Glu Val Gln Leu Val Glu Ser Gly Gly Gly Ser
20 25 30

Val Gln Ala Gly Gly Ser Leu Lys Leu Ser Cys Ala Ala Ser Arg Phe
35 40 45

Thr Tyr Ser Ser Tyr Cys Met Gly Trp Ile Arg Gln Ala Pro Gly Lys
50 55 60

Glu Arg Glu Gly Val Ala Ile Phe Tyr Thr Gly Gly Gly Arg Thr Tyr
65 70 75 80

Tyr Ala Asp Ser Val Lys Gly Arg Phe Thr Ile Ser Gln Asp Thr Ala
85 90 95

Lys Asn Thr Leu Tyr Leu Gln Met Asn Ser Leu Lys Pro Glu Asp Thr
100 105 110

Gly Ile Tyr Tyr Cys Val Ala Gly Phe Tyr Cys Ser Gly Gly Tyr Trp
115 120 125

Glu Gly Asp Phe Gly Tyr Trp Gly Gln Gly Thr Gln Val Thr Val Ser
130 135 140

Ser Thr Thr Thr Pro Ala Pro Arg Pro Pro Thr Pro Ala Pro Thr Ile
145 150 155 160

Ala Ser Gln Pro Leu Ser Leu Arg Pro Glu Ala Cys Arg Pro Ala Ala
165 170 175

Gly Gly Ala Val His Thr Arg Gly Leu Asp Phe Ala Cys Asp Ile Tyr
180 185 190

Ile Trp Ala Pro Leu Ala Gly Thr Cys Gly Val Leu Leu Leu Ser Leu
195 200 205

Val Ile Thr Leu Tyr Cys Lys Arg Gly Arg Lys Lys Leu Leu Tyr Ile
210 215 220

Phe Lys Gln Pro Phe Met Arg Pro Val Gln Thr Thr Gln Glu Glu Asp
225 230 235 240

Gly Cys Ser Cys Arg Phe Pro Glu Glu Glu Glu Gly Gly Cys Glu Leu
245 250 255

Arg Val Lys Phe Ser Arg Ser Ala Asp Ala Pro Ala Tyr Lys Gln Gly
260 265 270

Gln Asn Gln Leu Tyr Asn Glu Leu Asn Leu Gly Arg Arg Glu Glu Tyr
275 280 285

Asp Val Leu Asp Lys Arg Arg Gly Arg Asp Pro Glu Met Gly Gly Lys
290 295 300

Pro Arg Arg Lys Asn Pro Gln Glu Gly Leu Tyr Asn Glu Leu Gln Lys
305 310 315 320

Asp Lys Met Ala Glu Ala Tyr Ser Glu Ile Gly Met Lys Gly Glu Arg
325 330 335

Arg Arg Gly Lys Gly His Asp Gly Leu Tyr Gln Gly Leu Ser Thr Ala
340 345 350

Thr Lys Asp Thr Tyr Asp Ala Leu His Met Gln Ala Leu Pro Pro Arg
355 360 365

<210> SEQ ID NO 202
<211> LENGTH: 374
<212> TYPE: PRT
<213> ORGANISM: Artificial Sequence
<220> FEATURE:
<223> OTHER INFORMATION: CAS72794-BBz

<400> SEQUENCE: 202

Met Ala Leu Pro Val Thr Ala Leu Leu Leu Pro Leu Ala Leu Leu Leu
1 5 10 15

His Ala Ala Arg Pro Gln Val Gln Leu Val Glu Ser Gly Gly Gly Leu
20 25 30

Val Gln Ala Gly Gly Ser Leu Arg Leu Ser Cys Thr Ala Ser Gly Phe
35 40 45

Thr Phe Asp Asp Tyr Ala Met Ser Trp Phe Arg Gln Ala Pro Gly Lys
50 55 60

Glu Arg Glu Gly Val Ser Cys Ile Ser Ala Ser Gly Thr Thr Thr Tyr
65 70 75 80

Tyr Gly Asp Ser Val Lys Gly Arg Phe Thr Ile Ser Arg Asp Asn Ala
85 90 95

Lys Thr Thr Leu Ile Leu Gln Met Ser Ser Leu Lys Pro Glu Asp Thr
100 105 110

Ala Met Tyr Tyr Cys Ala Ala Asp Arg Phe Arg Asp Tyr Cys Ser Asp
115 120 125

Ser Trp Ser His Leu Tyr Asn Tyr Glu Tyr Met His Trp Gly Gln Gly
130 135 140

Thr Gln Val Thr Val Ser Ser Thr Thr Thr Pro Ala Pro Arg Pro Pro
145 150 155 160

Thr Pro Ala Pro Thr Ile Ala Ser Gln Pro Leu Ser Leu Arg Pro Glu
165 170 175

Ala Cys Arg Pro Ala Ala Gly Gly Ala Val His Thr Arg Gly Leu Asp
180 185 190

Phe Ala Cys Asp Ile Tyr Ile Trp Ala Pro Leu Ala Gly Thr Cys Gly
195 200 205

Val Leu Leu Leu Ser Leu Val Ile Thr Leu Tyr Cys Lys Arg Gly Arg
210 215 220

Lys Lys Leu Leu Tyr Ile Phe Lys Gln Pro Phe Met Arg Pro Val Gln
225 230 235 240

Thr Thr Gln Glu Glu Asp Gly Cys Ser Cys Arg Phe Pro Glu Glu Glu
245 250 255

Glu Gly Gly Cys Glu Leu Arg Val Lys Phe Ser Arg Ser Ala Asp Ala
260 265 270

Pro Ala Tyr Lys Gln Gly Gln Asn Gln Leu Tyr Asn Glu Leu Asn Leu
275 280 285

Gly Arg Arg Glu Glu Tyr Asp Val Leu Asp Lys Arg Arg Gly Arg Asp
290 295 300

Pro Glu Met Gly Gly Lys Pro Arg Arg Lys Asn Pro Gln Glu Gly Leu
305 310 315 320

Tyr Asn Glu Leu Gln Lys Asp Lys Met Ala Glu Ala Tyr Ser Glu Ile
325 330 335

Gly Met Lys Gly Glu Arg Arg Arg Gly Lys Gly His Asp Gly Leu Tyr
340 345 350

Gln Gly Leu Ser Thr Ala Thr Lys Asp Thr Tyr Asp Ala Leu His Met
355 360 365

Gln Ala Leu Pro Pro Arg
370

<210> SEQ ID NO 203
<211> LENGTH: 373
<212> TYPE: PRT
<213> ORGANISM: Artificial Sequence
<220> FEATURE:
<223> OTHER INFORMATION: CAS72805-BBz

<400> SEQUENCE: 203

Met Ala Leu Pro Val Thr Ala Leu Leu Leu Pro Leu Ala Leu Leu Leu
1 5 10 15

His Ala Ala Arg Pro Gln Val Gln Leu Val Glu Ser Gly Gly Asp Ser
20 25 30

Val Gln Ala Gly Gly Ser Leu Thr Leu Ser Cys Val Ala Ser Arg Leu
35 40 45

Arg Val Ser Asn Asn Cys Met Gly Trp Phe Arg Gln Ala Pro Gly Asn
50 55 60

Glu Arg Glu Gly Val Ala Thr Leu Gly Ser Asp Gly Arg Thr Ile Tyr
65 70 75 80

Ala Asp Ser Val Lys Gly Arg Phe Thr Ile Ser Lys Asp Asn Val Ala
85 90 95

Asn Thr Leu Tyr Leu Gln Met Asn Gly Leu Lys Leu Asp Asp Thr Ala
100 105 110

Leu Tyr Tyr Cys Ala Ala Ala Asp Phe Ser Ser Gly Gly Tyr Cys Asn
115 120 125

-continued

```
Ile Ala Ser Val Tyr His Ser Tyr Phe Pro Tyr Trp Gly Gln Gly Thr
    130                 135                 140

Gln Val Thr Val Ser Ser Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255

Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285

Arg Arg Glu Glu Tyr Asp Val Leu Asp Lys Arg Arg Gly Arg Asp Pro
    290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
    370


<210> SEQ ID NO 204
<211> LENGTH: 371
<212> TYPE: PRT
<213> ORGANISM: Artificial Sequence
<220> FEATURE:
<223> OTHER INFORMATION: CAS72806-BBz

<400> SEQUENCE: 204

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Ser
            20                  25                  30

Val Gln Ala Gly Gly Ser Leu Arg Leu Ser Cys Ala Ala Ser Gly Tyr
        35                  40                  45

Thr Tyr Met Pro Pro Cys Met Gly Trp Phe Arg Gln Ala Pro Gly Lys
    50                  55                  60

Glu Arg Glu Gly Val Ala Thr Ile Tyr Gly Arg Gly Gly Ser Thr Tyr
65                  70                  75                  80

Tyr Ala Asp Ser Val Lys Gly Arg Phe Thr Ile Ser Gln Asp Asn Ala
                85                  90                  95

Lys Asn Thr Leu Tyr Leu Gln Met Asn Asn Leu Glu Pro Glu Asp Thr
            100                 105                 110
```

```
Ala Met Tyr Tyr Cys Ala Ala Asp Asn Leu Cys Tyr Ala Thr Gly Ile
        115                 120                 125

Leu Arg Ser Ala Tyr Asp Tyr Ser Tyr Trp Gly Gln Gly Thr Gln Val
    130                 135                 140

Thr Val Ser Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
                245                 250                 255

Cys Glu Leu Arg Val Lys Phe Ser Arg Ser Ala Asp Ala Pro Ala Tyr
            260                 265                 270

Lys Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
    370
```

<210> SEQ ID NO 205
<211> LENGTH: 370
<212> TYPE: PRT
<213> ORGANISM: Artificial Sequence
<220> FEATURE:
<223> OTHER INFORMATION: CAS72835-BBz

<400> SEQUENCE: 205

```
Met Ala Leu Pro Val Thr Ala Leu Leu Leu Pro Leu Ala Leu Leu Leu
1               5                   10                  15

His Ala Ala Arg Pro Gln Val His Leu Met Glu Ser Gly Gly Gly Ser
            20                  25                  30

Val Gln Ala Gly Gly Ser Leu Arg Leu Ser Cys Ala Val Ser Gly Gly
        35                  40                  45

Tyr Thr Ser Arg Thr Val Cys Met Gly Trp Phe Arg Gln Thr Pro Gly
    50                  55                  60

Lys Glu Arg Glu Val Leu Ala Ala Ile Tyr Arg Ser Gly Thr Thr Tyr
65                  70                  75                  80

Tyr His Asp Ser Val Lys Gly Arg Phe Thr Ile Ser Arg Asp Gly Asp
                85                  90                  95
```

-continued

```
Lys Asn Thr Val Tyr Leu Gln Met Asp Ser Leu Lys Pro Glu Asp Thr
            100                 105                 110

Ala Met Tyr Tyr Cys Ala Ala Ser Pro Gly Tyr Ser Asp Ala Ala Cys
        115                 120                 125

Val Ser Val Pro Gln Ala Asn Arg Trp Gly Gln Gly Thr Gln Val Thr
    130                 135                 140

Val Ser Ser Thr Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
                165                 170                 175

Ala Ala Gly Gly Ala Val His Thr Arg Gly Leu Asp Phe Ala Cys Asp
            180                 185                 190

Ile Tyr Ile Trp Ala Pro Leu Ala Gly Thr Cys Gly Val Leu Leu Leu
        195                 200                 205

Ser Leu Val Ile Thr Leu Tyr Cys Lys Arg Gly Arg Lys Lys Leu Leu
    210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255

Glu Leu Arg Val Lys Phe Ser Arg Ser Ala Asp Ala Pro Ala Tyr Lys
            260                 265                 270

Gln Gly Gln Asn Gln Leu Tyr Asn Glu Leu Asn Leu Gly Arg Arg Glu
        275                 280                 285

Glu Tyr Asp Val Leu Asp Lys Arg Arg Gly Arg Asp Pro Glu Met Gly
    290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
            340                 345                 350

Thr Ala Thr Lys Asp Thr Tyr Asp Ala Leu His Met Gln Ala Leu Pro
        355                 360                 365

Pro Arg
    370
```

<210> SEQ ID NO 206
<211> LENGTH: 365
<212> TYPE: PRT
<213> ORGANISM: Artificial Sequence
<220> FEATURE:
<223> OTHER INFORMATION: CAS77906-BBz

<400> SEQUENCE: 206

```
Met Ala Leu Pro Val Thr Ala Leu Leu Leu Pro Leu Ala Leu Leu Leu
1               5                   10                  15

His Ala Ala Arg Pro Gln Val Arg Leu Val Glu Ser Gly Gly Gly Ser
            20                  25                  30

Val Gln Ala Gly Glu Ser Leu Arg Leu Ser Cys Ala Arg Ser Gly Val
        35                  40                  45

Val Lys Cys Asp Val Glu Met Arg Trp Tyr Arg Gln Ser Pro Gly Lys
    50                  55                  60

Glu Arg Glu Phe Val Ala Leu Ile Glu Ala Gly Gly His Thr Glu Tyr
65                  70                  75                  80
```

```
Ala Asp Ser Val Lys Gly Arg Phe Thr Ile Ser Gln Asp Asn Ala Lys
                85                  90                  95

Met Leu Phe Tyr Leu Gln Met Asn Ser Leu Lys Pro Glu Asp Thr Ala
            100                 105                 110

Lys Tyr Tyr Cys Val Ala Ala Pro Arg Tyr Tyr Thr Leu Ser Cys Pro
        115                 120                 125

Lys Asp Phe Trp Gly Arg Gly Thr Gln Val Thr Val Ser Ser Thr Thr
    130                 135                 140

Thr Pro Ala Pro Arg Pro Pro Thr Pro Ala Pro Thr Ile Ala Ser Gln
145                 150                 155                 160

Pro Leu Ser Leu Arg Pro Glu Ala Cys Arg Pro Ala Ala Gly Gly Ala
                165                 170                 175

Val His Thr Arg Gly Leu Asp Phe Ala Cys Asp Ile Tyr Ile Trp Ala
            180                 185                 190

Pro Leu Ala Gly Thr Cys Gly Val Leu Leu Leu Ser Leu Val Ile Thr
        195                 200                 205

Leu Tyr Cys Lys Arg Gly Arg Lys Lys Leu Leu Tyr Ile Phe Lys Gln
    210                 215                 220

Pro Phe Met Arg Pro Val Gln Thr Thr Gln Glu Glu Asp Gly Cys Ser
225                 230                 235                 240

Cys Arg Phe Pro Glu Glu Glu Glu Gly Gly Cys Glu Leu Arg Val Lys
                245                 250                 255

Phe Ser Arg Ser Ala Asp Ala Pro Ala Tyr Lys Gln Gly Gln Asn Gln
            260                 265                 270

Leu Tyr Asn Glu Leu Asn Leu Gly Arg Arg Glu Glu Tyr Asp Val Leu
        275                 280                 285

Asp Lys Arg Arg Gly Arg Asp Pro Glu Met Gly Gly Lys Pro Arg Arg
    290                 295                 300

Lys Asn Pro Gln Glu Gly Leu Tyr Asn Glu Leu Gln Lys Asp Lys Met
305                 310                 315                 320

Ala Glu Ala Tyr Ser Glu Ile Gly Met Lys Gly Glu Arg Arg Arg Gly
                325                 330                 335

Lys Gly His Asp Gly Leu Tyr Gln Gly Leu Ser Thr Ala Thr Lys Asp
            340                 345                 350

Thr Tyr Asp Ala Leu His Met Gln Ala Leu Pro Pro Arg
        355                 360                 365


<210> SEQ ID NO 207
<211> LENGTH: 367
<212> TYPE: PRT
<213> ORGANISM: Artificial Sequence
<220> FEATURE:
<223> OTHER INFORMATION: CAS77916-BBz

<400> SEQUENCE: 207

Met Ala Leu Pro Val Thr Ala Leu Leu Leu Pro Leu Ala Leu Leu Leu
1               5                   10                  15

His Ala Ala Arg Pro Gln Val His Leu Met Glu Ser Gly Gly Gly Ser
            20                  25                  30

Val Gln Ala Gly Gly Ser Leu Arg Leu Ser Cys Ala Thr Ser Gly Tyr
        35                  40                  45

Thr Ser Ser Trp Asn Cys Met Gly Trp Phe Arg Gln Pro Pro Gly Lys
    50                  55                  60

Glu Arg Glu Gly Val Ala Thr Ile Ala Asn Arg Gly His Ser Thr Tyr
65                  70                  75                  80
```

```
Tyr Ala Asp Ser Val Lys Gly Arg Phe Thr Ile Ser Gln Gly Asn Ala
                85                  90                  95

Lys Asn Thr Val Tyr Leu Gln Met Asn Ser Leu Lys Pro Glu Asp Thr
            100                 105                 110

Ala Met Tyr Tyr Cys Ala Thr Asp Thr Trp Ala Cys Val Gly Ile Ser
        115                 120                 125

Thr Asp Phe Glu Tyr Trp Gly Gln Gly Thr Gln Val Thr Val Ser Ser
    130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Lys Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
    290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365
```

<210> SEQ ID NO 208
<211> LENGTH: 368
<212> TYPE: PRT
<213> ORGANISM: Artificial Sequence
<220> FEATURE:
<223> OTHER INFORMATION: CAS77932-BBz

<400> SEQUENCE: 208

```
Met Ala Leu Pro Val Thr Ala Leu Leu Leu Pro Leu Ala Leu Leu Leu
1               5                   10                  15

His Ala Ala Arg Pro Gln Val Gln Leu Lys Glu Ser Gly Gly Gly Ser
            20                  25                  30

Val Gln Ala Gly Gly Ser Leu Arg Leu Ser Cys Ala Val Ser Gly Tyr
        35                  40                  45

Trp Tyr Ser Val Ala Trp Met Gly Trp Phe Arg Gln Thr Pro Gly Lys
    50                  55                  60

Glu Arg Glu Gly Val Ala Ala Val Leu Asn Gly Gly Gly Arg Arg Tyr
65                  70                  75                  80
```

-continued

```
Tyr Ala Asp Ser Val Lys Gly Arg Phe Thr Ile Ser Gln Asp Asn Ser
                85                  90                  95

Lys Asn Thr Leu Tyr Leu Gln Met Asn Ser Leu Lys Pro Glu Asp Thr
            100                 105                 110

Ala Met Tyr Tyr Cys Ala Ala Gly Asn Gly Val Gly His Pro Leu Gly
        115                 120                 125

Pro Ser Glu Tyr Asn Tyr Trp Gly Gln Gly Thr Gln Val Thr Val Ser
    130                 135                 140

Ser Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

Gly Gly Ala Val His Thr Arg Gly Leu Asp Phe Ala Cys Asp Ile Tyr
            180                 185                 190

Ile Trp Ala Pro Leu Ala Gly Thr Cys Gly Val Leu Leu Leu Ser Leu
        195                 200                 205

Val Ile Thr Leu Tyr Cys Lys Arg Gly Arg Lys Lys Leu Leu Tyr Ile
    210                 215                 220

Phe Lys Gln Pro Phe Met Arg Pro Val Gln Thr Thr Gln Glu Glu Asp
225                 230                 235                 240

Gly Cys Ser Cys Arg Phe Pro Glu Glu Glu Glu Gly Gly Cys Glu Leu
                245                 250                 255

Arg Val Lys Phe Ser Arg Ser Ala Asp Ala Pro Ala Tyr Lys Gln Gly
            260                 265                 270

Gln Asn Gln Leu Tyr Asn Glu Leu Asn Leu Gly Arg Arg Glu Glu Tyr
        275                 280                 285

Asp Val Leu Asp Lys Arg Arg Gly Arg Asp Pro Glu Met Gly Gly Lys
    290                 295                 300

Pro Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
                325                 330                 335

Arg Arg Gly Lys Gly His Asp Gly Leu Tyr Gln Gly Leu Ser Thr Ala
            340                 345                 350

Thr Lys Asp Thr Tyr Asp Ala Leu His Met Gln Ala Leu Pro Pro Arg
        355                 360                 365
```

<210> SEQ ID NO 209
<211> LENGTH: 369
<212> TYPE: PRT
<213> ORGANISM: Artificial Sequence
<220> FEATURE:
<223> OTHER INFORMATION: CAS77934-BBz

<400> SEQUENCE: 209

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Ser
            20                  25                  30

Val Gln Ala Gly Gly Ser Leu Arg Leu Ser Cys Ala Ala Ser Gly Tyr
        35                  40                  45

Thr Tyr Ser Ser Tyr Ser Ile Ala Trp Phe Arg Gln Ala Pro Gly Lys
    50                  55                  60

Glu Arg Glu Gly Val Ala Gly Phe Phe Tyr Ser Gly Gly Pro Thr Cys
65                  70                  75                  80
```

```
Tyr Ala Asp Ser Val Lys Gly Arg Phe Thr Ile Ser Gln Asp Asn Ala
                85                  90                  95

Lys Asn Thr Leu Tyr Leu Gln Met Asn Ser Leu Lys Pro Glu Asp Thr
            100                 105                 110

Ala Met Tyr Tyr Cys Ala Ala Arg Arg Ser Asn Thr Asn Asp Tyr Cys
        115                 120                 125

Phe Tyr Pro Thr Tyr Thr Tyr Trp Gly Gln Gly Thr Gln Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
    290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg
```

<210> SEQ ID NO 210
<211> LENGTH: 364
<212> TYPE: PRT
<213> ORGANISM: Artificial Sequence
<220> FEATURE:
<223> OTHER INFORMATION: CAS77978-BBz

<400> SEQUENCE: 210

```
Met Ala Leu Pro Val Thr Ala Leu Leu Leu Pro Leu Ala Leu Leu Leu
1               5                   10                  15

His Ala Ala Arg Pro Gln Val Arg Leu Val Glu Ser Gly Gly Gly Ser
            20                  25                  30

Val Gln Ala Gly Gly Ser Leu Arg Leu Ser Cys Ala Ala Ser Gly Ala
        35                  40                  45

Thr Ser Cys Arg Trp Arg Met Ser Trp Tyr Arg Gln Ala Pro Gly Lys
    50                  55                  60

Glu Arg Glu Phe Val Ser Ser Ile Ala Asn Gly Ala Thr Glu Tyr Ala
```

65 70 75 80

Asp Ser Val Lys Gly Arg Phe Thr Ile Ser Gln Asp Asn Ala Arg Asn
85 90 95

Thr Met Tyr Leu Gln Met Asn Ser Leu Ser Pro Glu Asp Thr Ala Met
100 105 110

Tyr Tyr Cys Ala Ala Asp Pro Arg Val Tyr Thr Ser Arg Cys Asp Arg
115 120 125

Thr Tyr Leu Gly Gln Gly Thr Gln Val Thr Val Ser Ser Thr Thr Thr
130 135 140

Pro Ala Pro Arg Pro Pro Thr Pro Ala Pro Thr Ile Ala Ser Gln Pro
145 150 155 160

Leu Ser Leu Arg Pro Glu Ala Cys Arg Pro Ala Ala Gly Gly Ala Val
165 170 175

His Thr Arg Gly Leu Asp Phe Ala Cys Asp Ile Tyr Ile Trp Ala Pro
180 185 190

Leu Ala Gly Thr Cys Gly Val Leu Leu Leu Ser Leu Val Ile Thr Leu
195 200 205

Tyr Cys Lys Arg Gly Arg Lys Lys Leu Leu Tyr Ile Phe Lys Gln Pro
210 215 220

Phe Met Arg Pro Val Gln Thr Thr Gln Glu Glu Asp Gly Cys Ser Cys
225 230 235 240

Arg Phe Pro Glu Glu Glu Glu Gly Gly Cys Glu Leu Arg Val Lys Phe
245 250 255

Ser Arg Ser Ala Asp Ala Pro Ala Tyr Lys Gln Gly Gln Asn Gln Leu
260 265 270

Tyr Asn Glu Leu Asn Leu Gly Arg Arg Glu Glu Tyr Asp Val Leu Asp
275 280 285

Lys Arg Arg Gly Arg Asp Pro Glu Met Gly Gly Lys Pro Arg Arg Lys
290 295 300

Asn Pro Gln Glu Gly Leu Tyr Asn Glu Leu Gln Lys Asp Lys Met Ala
305 310 315 320

Glu Ala Tyr Ser Glu Ile Gly Met Lys Gly Glu Arg Arg Arg Gly Lys
325 330 335

Gly His Asp Gly Leu Tyr Gln Gly Leu Ser Thr Ala Thr Lys Asp Thr
340 345 350

Tyr Asp Ala Leu His Met Gln Ala Leu Pro Pro Arg
355 360

<210> SEQ ID NO 211
<211> LENGTH: 376
<212> TYPE: PRT
<213> ORGANISM: Artificial Sequence
<220> FEATURE:
<223> OTHER INFORMATION: CAS77986-BBz

<400> SEQUENCE: 211

Met Ala Leu Pro Val Thr Ala Leu Leu Leu Pro Leu Ala Leu Leu Leu
1 5 10 15

His Ala Ala Arg Pro Gln Val Gln Leu Val Glu Ser Gly Gly Gly Ser
20 25 30

Val Gln Ala Gly Gly Ser Leu Arg Leu Ser Cys Ala Ala Ser Ala Ser
35 40 45

Gly Tyr Thr Tyr Ser Ser Asp Ser Met Ala Trp Phe Arg Gln Ala Pro
50 55 60

Gly Lys Glu Arg Glu Gly Val Ala Gly Ile Ser Thr Gly Gly Arg Ser

```
65                  70                  75                  80

Thr Tyr Tyr Ala Asp Ser Val Lys Gly Arg Phe Thr Ile Ser Gln Asp
                85                  90                  95

Asn Ala Lys Thr Thr Val Tyr Leu His Met Asn Ser Leu Lys Pro Glu
            100                 105                 110

Asp Thr Ala Met Tyr Tyr Cys Ala Ala Asp Gly Pro Ser Met Thr Ala
        115                 120                 125

Ile Gln Ala Leu Gly Asp Leu Tyr Pro Val Asp Phe Ala Trp Trp Gly
    130                 135                 140

Gln Gly Thr Gln Val Thr Val Ser Ser Thr Thr Thr Pro Ala Pro Arg
145                 150                 155                 160

Pro Pro Thr Pro Ala Pro Thr Ile Ala Ser Gln Pro Leu Ser Leu Arg
                165                 170                 175

Pro Glu Ala Cys Arg Pro Ala Ala Gly Gly Ala Val His Thr Arg Gly
            180                 185                 190

Leu Asp Phe Ala Cys Asp Ile Tyr Ile Trp Ala Pro Leu Ala Gly Thr
        195                 200                 205

Cys Gly Val Leu Leu Leu Ser Leu Val Ile Thr Leu Tyr Cys Lys Arg
    210                 215                 220

Gly Arg Lys Lys Leu Leu Tyr Ile Phe Lys Gln Pro Phe Met Arg Pro
225                 230                 235                 240

Val Gln Thr Thr Gln Glu Glu Asp Gly Cys Ser Cys Arg Phe Pro Glu
                245                 250                 255

Glu Glu Glu Gly Gly Cys Glu Leu Arg Val Lys Phe Ser Arg Ser Ala
            260                 265                 270

Asp Ala Pro Ala Tyr Lys Gln Gly Gln Asn Gln Leu Tyr Asn Glu Leu
        275                 280                 285

Asn Leu Gly Arg Arg Glu Glu Tyr Asp Val Leu Asp Lys Arg Arg Gly
    290                 295                 300

Arg Asp Pro Glu Met Gly Gly Lys Pro Arg Arg Lys Asn Pro Gln Glu
305                 310                 315                 320

Gly Leu Tyr Asn Glu Leu Gln Lys Asp Lys Met Ala Glu Ala Tyr Ser
                325                 330                 335

Glu Ile Gly Met Lys Gly Glu Arg Arg Arg Gly Lys Gly His Asp Gly
            340                 345                 350

Leu Tyr Gln Gly Leu Ser Thr Ala Thr Lys Asp Thr Tyr Asp Ala Leu
        355                 360                 365

His Met Gln Ala Leu Pro Pro Arg
    370                 375


<210> SEQ ID NO 212
<211> LENGTH: 371
<212> TYPE: PRT
<213> ORGANISM: Artificial Sequence
<220> FEATURE:
<223> OTHER INFORMATION: CAS78117-BBz

<400> SEQUENCE: 212

Met Ala Leu Pro Val Thr Ala Leu Leu Leu Pro Leu Ala Leu Leu Leu
1               5                   10                  15

His Ala Ala Arg Pro Gln Val Lys Leu Val Glu Ser Gly Gly Gly Ser
            20                  25                  30

Val Gln Ala Gly Gly Ala Leu Arg Leu Ser Cys Ile Val Arg Arg Tyr
        35                  40                  45

Thr Tyr Ala Thr Tyr Ser Met Ala Trp Phe Arg Gln Ser Pro Gly Lys
```

```
    50                  55                  60

Glu Arg Glu Gly Val Ala Gly Leu Asp Ser Val Gly Ala Thr Gly Tyr
65                  70                  75                  80

Ala Glu Ser Val Lys Gly Arg Phe Thr Ile Ser Lys Asp Asn Ala Lys
                85                  90                  95

Asn Ile Leu Tyr Leu Gln Met Asn Ser Leu Lys Pro Glu Asp Thr Ala
            100                 105                 110

Met Tyr Tyr Cys Val Val Asp Pro Ala Ser Ala Lys Val Thr Tyr Gly
        115                 120                 125

Ser Trp Ser Thr Pro Ser Tyr Ala Tyr Trp Gly Gln Gly Thr Gln Val
    130                 135                 140

Thr Val Ser Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
                245                 250                 255

Cys Glu Leu Arg Val Lys Phe Ser Arg Ser Ala Asp Ala Pro Ala Tyr
            260                 265                 270

Lys Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
    370


<210> SEQ ID NO 213
<211> LENGTH: 369
<212> TYPE: PRT
<213> ORGANISM: Artificial Sequence
<220> FEATURE:
<223> OTHER INFORMATION: CAS78215-BBz

<400> SEQUENCE: 213

Met Ala Leu Pro Val Thr Ala Leu Leu Leu Pro Leu Ala Leu Leu Leu
1               5                   10                  15

His Ala Ala Arg Pro Gln Val Lys Leu Val Glu Ser Gly Gly Gly Ser
            20                  25                  30

Val Gln Ala Gly Gly Ala Leu Arg Leu Ser Cys Ala Ala Ser Arg Tyr
```

```
        35                  40                  45

Thr Phe Ser Ser Asn Cys Met Gly Trp Phe Arg Gln Ala Pro Gly Lys
    50                  55                  60

Glu Arg Glu Gly Val Ala Thr Ile Ala Ser Ala Ser Gly Tyr Thr Asp
65                  70                  75                  80

Tyr His Asp Ser Val Lys Gly Arg Phe Ala Ile Ser Arg Asp Asn Ala
                85                  90                  95

Lys Asn Thr Val Tyr Leu Gln Met Asn Ser Leu Lys Pro Glu Asp Thr
            100                 105                 110

Ala Thr Tyr Tyr Cys Ala Ala Arg Ala Gly Pro Cys Trp Ser Trp Ala
        115                 120                 125

Gln Ala Asp Leu Tyr Asn Tyr Trp Gly Gln Gly Thr Gln Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
    290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg
```

<210> SEQ ID NO 214
<211> LENGTH: 363
<212> TYPE: PRT
<213> ORGANISM: Artificial Sequence
<220> FEATURE:
<223> OTHER INFORMATION: CAS78810-BBz

<400> SEQUENCE: 214

```
Met Ala Leu Pro Val Thr Ala Leu Leu Leu Pro Leu Ala Leu Leu Leu
1               5                   10                  15

His Ala Ala Arg Pro Gln Val His Leu Val Glu Ser Gly Gly Gly Ser
            20                  25                  30
```

```
Val Gln Ala Gly Gly Ser Leu Arg Leu Ser Cys Ala Ala Ser Gly Tyr
        35                  40                  45

Thr Tyr Tyr Asp Met Gly Trp Phe Arg Leu Ala Pro Gly Lys Glu Arg
    50                  55                  60

Glu Gly Ile Ala Ala Ile Ser Ser Ser Ser Ser Thr Tyr Tyr Ala Asp
65                  70                  75                  80

Ser Val Lys Gly Arg Phe Thr Ile Ser Arg Asp Ser Asn Thr Leu Tyr
                85                  90                  95

Leu Gln Met Asn Ser Leu Lys Pro Glu Asp Thr Ala Met Tyr Ser Cys
            100                 105                 110

Ala Ala Gly Arg Tyr Val Gly Arg Lys Leu Glu Val Tyr Asp Tyr Ala
        115                 120                 125

Tyr Trp Gly Gln Gly Thr Gln Val Thr Val Ser Ser Thr Thr Thr Pro
    130                 135                 140

Ala Pro Arg Pro Pro Thr Pro Ala Pro Thr Ile Ala Ser Gln Pro Leu
145                 150                 155                 160

Ser Leu Arg Pro Glu Ala Cys Arg Pro Ala Ala Gly Gly Ala Val His
                165                 170                 175

Thr Arg Gly Leu Asp Phe Ala Cys Asp Ile Tyr Ile Trp Ala Pro Leu
            180                 185                 190

Ala Gly Thr Cys Gly Val Leu Leu Leu Ser Leu Val Ile Thr Leu Tyr
        195                 200                 205

Cys Lys Arg Gly Arg Lys Lys Leu Leu Tyr Ile Phe Lys Gln Pro Phe
    210                 215                 220

Met Arg Pro Val Gln Thr Thr Gln Glu Glu Asp Gly Cys Ser Cys Arg
225                 230                 235                 240

Phe Pro Glu Glu Glu Glu Gly Gly Cys Glu Leu Arg Val Lys Phe Ser
                245                 250                 255

Arg Ser Ala Asp Ala Pro Ala Tyr Lys Gln Gly Gln Asn Gln Leu Tyr
            260                 265                 270

Asn Glu Leu Asn Leu Gly Arg Arg Glu Glu Tyr Asp Val Leu Asp Lys
        275                 280                 285

Arg Arg Gly Arg Asp Pro Glu Met Gly Gly Lys Pro Arg Arg Lys Asn
    290                 295                 300

Pro Gln Glu Gly Leu Tyr Asn Glu Leu Gln Lys Asp Lys Met Ala Glu
305                 310                 315                 320

Ala Tyr Ser Glu Ile Gly Met Lys Gly Glu Arg Arg Arg Gly Lys Gly
                325                 330                 335

His Asp Gly Leu Tyr Gln Gly Leu Ser Thr Ala Thr Lys Asp Thr Tyr
            340                 345                 350

Asp Ala Leu His Met Gln Ala Leu Pro Pro Arg
        355                 360
```

<210> SEQ ID NO 215
<211> LENGTH: 370
<212> TYPE: PRT
<213> ORGANISM: Artificial Sequence
<220> FEATURE:
<223> OTHER INFORMATION: CAS79101-BBz

<400> SEQUENCE: 215

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Ser
            20                  25                  30
```

```
Val Gln Ala Gly Gly Ser Leu Arg Leu Ser Cys Ala Ala Ser Gly Asp
        35                  40                  45

Thr Tyr Ser Asn Tyr Cys Met Gly Trp Phe Arg Gln Ala Pro Gly Lys
    50                  55                  60

Glu Arg Glu Glu Val Ala Ala Ile Asp Ser Asp Gly Ser Arg Arg Tyr
65                  70                  75                  80

Pro Asp Ser Val Lys Gly Arg Phe Thr Ile Ser Lys Asp Asn Ala Lys
                85                  90                  95

Lys Ile Leu Tyr Leu Gln Met Asn Ser Leu Lys Pro Glu Asp Thr Ala
            100                 105                 110

Met Tyr Phe Cys Ala Thr Asp Pro Lys Val Ala Cys Ala Arg Val Val
        115                 120                 125

Glu Tyr Gly Gly Gly Trp Tyr Arg Trp Gly Gln Gly Thr Gln Val Thr
    130                 135                 140

Val Ser Ser Thr Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
                165                 170                 175

Ala Ala Gly Gly Ala Val His Thr Arg Gly Leu Asp Phe Ala Cys Asp
            180                 185                 190

Ile Tyr Ile Trp Ala Pro Leu Ala Gly Thr Cys Gly Val Leu Leu Leu
        195                 200                 205

Ser Leu Val Ile Thr Leu Tyr Cys Lys Arg Gly Arg Lys Lys Leu Leu
    210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255

Glu Leu Arg Val Lys Phe Ser Arg Ser Ala Asp Ala Pro Ala Tyr Lys
            260                 265                 270

Gln Gly Gln Asn Gln Leu Tyr Asn Glu Leu Asn Leu Gly Arg Arg Glu
        275                 280                 285

Glu Tyr Asp Val Leu Asp Lys Arg Arg Gly Arg Asp Pro Glu Met Gly
    290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
            340                 345                 350

Thr Ala Thr Lys Asp Thr Tyr Asp Ala Leu His Met Gln Ala Leu Pro
        355                 360                 365

Pro Arg
    370


<210> SEQ ID NO 216
<211> LENGTH: 371
<212> TYPE: PRT
<213> ORGANISM: Artificial Sequence
<220> FEATURE:
<223> OTHER INFORMATION: CAS79236-BBz

<400> SEQUENCE: 216

Met Ala Leu Pro Val Thr Ala Leu Leu Leu Pro Leu Ala Leu Leu Leu
1               5                   10                  15
```

-continued

```
His Ala Ala Arg Pro Gln Val Lys Leu Val Glu Ser Gly Gly Gly Ser
            20                  25                  30

Val Gln Ala Gly Gly Ser Leu Arg Leu Ser Cys Ala Val Ser Gly Tyr
        35                  40                  45

Thr Tyr Ser Ser Tyr Cys Met Ala Trp Phe Arg Gln Ala Pro Gly Glu
    50                  55                  60

Glu Arg Glu Gly Val Ala Ser Ile Asp Ala Gly Gly Arg Thr Thr Tyr
65                  70                  75                  80

Val Asp Ser Val Lys Gly Arg Phe Thr Ile Ser Lys Asp Asn Ala Lys
                85                  90                  95

Thr Ser Leu Tyr Leu Gln Met Asn Ser Leu Lys Pro Glu Asp Thr Ala
            100                 105                 110

Met Tyr Tyr Cys Ala Val Asp Val Arg Thr Arg Cys Gly Gly Thr Trp
        115                 120                 125

Asp Gly Glu Ala Val Tyr Phe Pro Tyr Trp Gly Gln Gly Thr Gln Val
    130                 135                 140

Thr Val Ser Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
                245                 250                 255

Cys Glu Leu Arg Val Lys Phe Ser Arg Ser Ala Asp Ala Pro Ala Tyr
            260                 265                 270

Lys Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
    370
```

<210> SEQ ID NO 217
<211> LENGTH: 367
<212> TYPE: PRT
<213> ORGANISM: Artificial Sequence
<220> FEATURE:
<223> OTHER INFORMATION: CAS79274-BBz

<400> SEQUENCE: 217

```
Met Ala Leu Pro Val Thr Ala Leu Leu Leu Pro Leu Ala Leu Leu Leu
1               5                   10                  15

His Ala Ala Arg Pro Gln Val His Leu Val Glu Ser Gly Gly Gly Ser
            20                  25                  30

Val Gln Ala Gly Gly Ser Leu Arg Leu Ser Cys Ala Ala Ser Lys Tyr
        35                  40                  45

Ala Phe Cys Thr Tyr Asp Met Ser Trp Phe Arg Gln Ala Pro Gly Lys
    50                  55                  60

Glu Arg Glu Val Val Ser Ser Ile Asp Ser Arg Gly Asn Thr Asn Tyr
65                  70                  75                  80

Ser Asp Ser Val Lys Gly Arg Phe Thr Ile Ser Gln Asp His Ala Lys
                85                  90                  95

Asn Thr Leu Tyr Leu Gln Met Asn Ser Leu Lys Pro Glu Asp Thr Ala
            100                 105                 110

Met Tyr Thr Cys Ala Ala Gln Ile Val Gly Gly Ala Leu Arg Cys Pro
        115                 120                 125

Arg Phe Ala Met Tyr Trp Gly Gln Gly Thr Gln Val Thr Val Ser Ser
    130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Lys Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
    290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365
```

<210> SEQ ID NO 218
<211> LENGTH: 376
<212> TYPE: PRT
<213> ORGANISM: Artificial Sequence
<220> FEATURE:
<223> OTHER INFORMATION: CAS79285-BBz

<400> SEQUENCE: 218

```
Met Ala Leu Pro Val Thr Ala Leu Leu Leu Pro Leu Ala Leu Leu Leu
1               5                   10                  15

His Ala Ala Arg Pro Gln Val Arg Leu Val Glu Ser Gly Gly Gly Ser
            20                  25                  30

Val Gln Ala Gly Gly Ser Leu Ala Leu Ser Cys Glu Thr Ser Arg Tyr
        35                  40                  45

Thr Val Ser Asn Tyr Cys Met Gly Trp Phe Arg Gln Val Ser Gly Lys
    50                  55                  60

Glu Val Glu Gly Val Ala Leu Ile Ser Thr Asp Gly Thr Thr Thr Tyr
65                  70                  75                  80

Ala Asp Ser Val Lys Gly Arg Phe Thr Ile Ser Lys Asp Asn Ala Lys
                85                  90                  95

Asn Thr Leu Tyr Leu Gln Met Asn Ser Leu Lys Ser Glu Asp Thr Ala
            100                 105                 110

Met Tyr Phe Cys Ala Gly Val Tyr Gly Leu Ile Trp Tyr Tyr Lys Pro
        115                 120                 125

Cys Pro Ala Gln Arg Glu Trp Ala Leu Gln Arg Tyr Gly Tyr Trp Gly
    130                 135                 140

Gln Gly Thr Gln Val Thr Val Ser Ser Thr Thr Thr Pro Ala Pro Arg
145                 150                 155                 160

Pro Pro Thr Pro Ala Pro Thr Ile Ala Ser Gln Pro Leu Ser Leu Arg
                165                 170                 175

Pro Glu Ala Cys Arg Pro Ala Ala Gly Gly Ala Val His Thr Arg Gly
            180                 185                 190

Leu Asp Phe Ala Cys Asp Ile Tyr Ile Trp Ala Pro Leu Ala Gly Thr
        195                 200                 205

Cys Gly Val Leu Leu Leu Ser Leu Val Ile Thr Leu Tyr Cys Lys Arg
    210                 215                 220

Gly Arg Lys Lys Leu Leu Tyr Ile Phe Lys Gln Pro Phe Met Arg Pro
225                 230                 235                 240

Val Gln Thr Thr Gln Glu Glu Asp Gly Cys Ser Cys Arg Phe Pro Glu
                245                 250                 255

Glu Glu Glu Gly Gly Cys Glu Leu Arg Val Lys Phe Ser Arg Ser Ala
            260                 265                 270

Asp Ala Pro Ala Tyr Lys Gln Gly Gln Asn Gln Leu Tyr Asn Glu Leu
        275                 280                 285

Asn Leu Gly Arg Arg Glu Glu Tyr Asp Val Leu Asp Lys Arg Arg Gly
    290                 295                 300

Arg Asp Pro Glu Met Gly Gly Lys Pro Arg Arg Lys Asn Pro Gln Glu
305                 310                 315                 320

Gly Leu Tyr Asn Glu Leu Gln Lys Asp Lys Met Ala Glu Ala Tyr Ser
                325                 330                 335

Glu Ile Gly Met Lys Gly Glu Arg Arg Arg Gly Lys Gly His Asp Gly
            340                 345                 350

Leu Tyr Gln Gly Leu Ser Thr Ala Thr Lys Asp Thr Tyr Asp Ala Leu
        355                 360                 365

His Met Gln Ala Leu Pro Pro Arg
    370                 375
```

<210> SEQ ID NO 219
<211> LENGTH: 369
<212> TYPE: PRT
<213> ORGANISM: Artificial Sequence
<220> FEATURE:

<223> OTHER INFORMATION: CAS79317-BBz

<400> SEQUENCE: 219

Met Ala Leu Pro Val Thr Ala Leu Leu Leu Pro Leu Ala Leu Leu Leu
1 5 10 15

His Ala Ala Arg Pro Glu Val Gln Leu Ala Glu Ser Gly Gly Gly Ser
20 25 30

Val Gln Pro Gly Gly Ser Leu Arg Leu Ser Cys Ala Ala Ser Gly Tyr
35 40 45

Ser Ser Ser Ser Val Cys Met Gly Trp Phe Arg Gln Ala Pro Gly Lys
50 55 60

Glu Arg Glu Gly Val Ala Ile Ile Tyr Val Thr Leu Gly Ser Ile Ala
65 70 75 80

Tyr Ala Asp Ser Val Lys Gly Arg Phe Thr Ile Ser Arg Asp Asn Ala
85 90 95

Lys Asn Thr Leu Asp Leu Glu Met Asn Ser Leu Lys Pro Asp Asp Thr
100 105 110

Ala Leu Tyr Tyr Cys Ala Ala Gly Gly Cys Gly Tyr Arg Gly Val Ala
115 120 125

Asp Val Pro Glu Phe Thr Tyr Arg Gly Gln Gly Thr Gln Val Thr Val
130 135 140

Ser Ser Thr Thr Thr Pro Ala Pro Arg Pro Pro Thr Pro Ala Pro Thr
145 150 155 160

Ile Ala Ser Gln Pro Leu Ser Leu Arg Pro Glu Ala Cys Arg Pro Ala
165 170 175

Ala Gly Gly Ala Val His Thr Arg Gly Leu Asp Phe Ala Cys Asp Ile
180 185 190

Tyr Ile Trp Ala Pro Leu Ala Gly Thr Cys Gly Val Leu Leu Leu Ser
195 200 205

Leu Val Ile Thr Leu Tyr Cys Lys Arg Gly Arg Lys Lys Leu Leu Tyr
210 215 220

Ile Phe Lys Gln Pro Phe Met Arg Pro Val Gln Thr Thr Gln Glu Glu
225 230 235 240

Asp Gly Cys Ser Cys Arg Phe Pro Glu Glu Glu Glu Gly Gly Cys Glu
245 250 255

Leu Arg Val Lys Phe Ser Arg Ser Ala Asp Ala Pro Ala Tyr Lys Gln
260 265 270

Gly Gln Asn Gln Leu Tyr Asn Glu Leu Asn Leu Gly Arg Arg Glu Glu
275 280 285

Tyr Asp Val Leu Asp Lys Arg Arg Gly Arg Asp Pro Glu Met Gly Gly
290 295 300

Lys Pro Arg Arg Lys Asn Pro Gln Glu Gly Leu Tyr Asn Glu Leu Gln
305 310 315 320

Lys Asp Lys Met Ala Glu Ala Tyr Ser Glu Ile Gly Met Lys Gly Glu
325 330 335

Arg Arg Arg Gly Lys Gly His Asp Gly Leu Tyr Gln Gly Leu Ser Thr
340 345 350

Ala Thr Lys Asp Thr Tyr Asp Ala Leu His Met Gln Ala Leu Pro Pro
355 360 365

Arg

<210> SEQ ID NO 220
<211> LENGTH: 368
<212> TYPE: PRT

<213> ORGANISM: Artificial Sequence
<220> FEATURE:
<223> OTHER INFORMATION: CAS70950VH6-BBz

<400> SEQUENCE: 220

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ile Ser Glu Phe
        35                  40                  45

Thr Tyr Lys Asn Thr Cys Val Gly Trp Phe Arg Gln Ala Pro Gly Lys
    50                  55                  60

Gly Arg Glu Gly Val Ala Ala Ile Asp Ser Asp Gly Asn Thr Asn Tyr
65                  70                  75                  80

Val Asp Ser Val Lys Gly Arg Phe Thr Ile Ser Gln Asp Asn Ser Lys
                85                  90                  95

Asn Thr Val Tyr Leu Gln Met Asn Ser Leu Arg Ala Glu Asp Thr Ala
            100                 105                 110

Met Tyr Tyr Cys Ala Ala Gly Ala Tyr Cys Gly Arg Leu Leu Leu Trp
        115                 120                 125

Ile Gly Asn Tyr Ala Tyr Trp Gly Gln Gly Thr Leu Val Thr Val Ser
    130                 135                 140

Ser Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

Gly Gly Ala Val His Thr Arg Gly Leu Asp Phe Ala Cys Asp Ile Tyr
            180                 185                 190

Ile Trp Ala Pro Leu Ala Gly Thr Cys Gly Val Leu Leu Leu Ser Leu
        195                 200                 205

Val Ile Thr Leu Tyr Cys Lys Arg Gly Arg Lys Lys Leu Leu Tyr Ile
    210                 215                 220

Phe Lys Gln Pro Phe Met Arg Pro Val Gln Thr Thr Gln Glu Glu Asp
225                 230                 235                 240

Gly Cys Ser Cys Arg Phe Pro Glu Glu Glu Glu Gly Gly Cys Glu Leu
                245                 250                 255

Arg Val Lys Phe Ser Arg Ser Ala Asp Ala Pro Ala Tyr Lys Gln Gly
            260                 265                 270

Gln Asn Gln Leu Tyr Asn Glu Leu Asn Leu Gly Arg Arg Glu Glu Tyr
        275                 280                 285

Asp Val Leu Asp Lys Arg Arg Gly Arg Asp Pro Glu Met Gly Gly Lys
    290                 295                 300

Pro Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
                325                 330                 335

Arg Arg Gly Lys Gly His Asp Gly Leu Tyr Gln Gly Leu Ser Thr Ala
            340                 345                 350

Thr Lys Asp Thr Tyr Asp Ala Leu His Met Gln Ala Leu Pro Pro Arg
        355                 360                 365
```

<210> SEQ ID NO 221
<211> LENGTH: 368
<212> TYPE: PRT

-continued

<213> ORGANISM: Artificial Sequence
<220> FEATURE:
<223> OTHER INFORMATION: CAS70950VH7-BBz

<400> SEQUENCE: 221

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Glu Phe
        35                  40                  45

Thr Tyr Lys Asn Thr Cys Val Gly Trp Phe Arg Gln Ala Pro Gly Lys
    50                  55                  60

Gly Arg Glu Gly Val Ala Ala Ile Asp Ser Asp Gly Asn Thr Asn Tyr
65                  70                  75                  80

Val Asp Ser Val Lys Gly Arg Phe Thr Ile Ser Arg Asp Asn Ser Lys
                85                  90                  95

Asn Thr Val Tyr Leu Gln Met Asn Ser Leu Arg Ala Glu Asp Thr Ala
            100                 105                 110

Met Tyr Tyr Cys Ala Ala Gly Ala Tyr Cys Gly Arg Leu Leu Leu Trp
        115                 120                 125

Ile Gly Asn Tyr Ala Tyr Trp Gly Gln Gly Thr Leu Val Thr Val Ser
    130                 135                 140

Ser Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

Gly Gly Ala Val His Thr Arg Gly Leu Asp Phe Ala Cys Asp Ile Tyr
            180                 185                 190

Ile Trp Ala Pro Leu Ala Gly Thr Cys Gly Val Leu Leu Leu Ser Leu
        195                 200                 205

Val Ile Thr Leu Tyr Cys Lys Arg Gly Arg Lys Lys Leu Leu Tyr Ile
    210                 215                 220

Phe Lys Gln Pro Phe Met Arg Pro Val Gln Thr Thr Gln Glu Glu Asp
225                 230                 235                 240

Gly Cys Ser Cys Arg Phe Pro Glu Glu Glu Glu Gly Gly Cys Glu Leu
                245                 250                 255

Arg Val Lys Phe Ser Arg Ser Ala Asp Ala Pro Ala Tyr Lys Gln Gly
            260                 265                 270

Gln Asn Gln Leu Tyr Asn Glu Leu Asn Leu Gly Arg Arg Glu Glu Tyr
        275                 280                 285

Asp Val Leu Asp Lys Arg Arg Gly Arg Asp Pro Glu Met Gly Gly Lys
    290                 295                 300

Pro Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
                325                 330                 335

Arg Arg Gly Lys Gly His Asp Gly Leu Tyr Gln Gly Leu Ser Thr Ala
            340                 345                 350

Thr Lys Asp Thr Tyr Asp Ala Leu His Met Gln Ala Leu Pro Pro Arg
        355                 360                 365
```

<210> SEQ ID NO 222
<211> LENGTH: 370
<212> TYPE: PRT

```
<213> ORGANISM: Artificial Sequence
<220> FEATURE:
<223> OTHER INFORMATION: CAS71529VH5-BBz

<400> SEQUENCE: 222

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Val Ser Glu Tyr
        35                  40                  45

Arg Tyr Ser Ser Arg Tyr Cys Met Gly Trp Phe Arg Gln Ala Pro Gly
    50                  55                  60

Lys Gly Leu Glu Gly Val Ser Ala Ile Asp Ser Asn Gly Ser Ala Asp
65                  70                  75                  80

Tyr Val Asp Ser Val Lys Gly Arg Phe Thr Ile Ser Lys Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Ala Asp His Leu Ala Tyr Asp Cys Tyr Ser
        115                 120                 125

Gly Ala Thr Ser Val Phe Arg Tyr Trp Gly Gln Gly Thr Leu Val Thr
    130                 135                 140

Val Ser Ser Thr Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
                165                 170                 175

Ala Ala Gly Gly Ala Val His Thr Arg Gly Leu Asp Phe Ala Cys Asp
            180                 185                 190

Ile Tyr Ile Trp Ala Pro Leu Ala Gly Thr Cys Gly Val Leu Leu Leu
        195                 200                 205

Ser Leu Val Ile Thr Leu Tyr Cys Lys Arg Gly Arg Lys Lys Leu Leu
    210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255

Glu Leu Arg Val Lys Phe Ser Arg Ser Ala Asp Ala Pro Ala Tyr Lys
            260                 265                 270

Gln Gly Gln Asn Gln Leu Tyr Asn Glu Leu Asn Leu Gly Arg Arg Glu
        275                 280                 285

Glu Tyr Asp Val Leu Asp Lys Arg Arg Gly Arg Asp Pro Glu Met Gly
    290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
            340                 345                 350

Thr Ala Thr Lys Asp Thr Tyr Asp Ala Leu His Met Gln Ala Leu Pro
        355                 360                 365

Pro Arg
    370
```

```
<210> SEQ ID NO 223
<211> LENGTH: 370
<212> TYPE: PRT
<213> ORGANISM: Artificial Sequence
<220> FEATURE:
<223> OTHER INFORMATION: CAS71529VH6-BBz

<400> SEQUENCE: 223

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Val Ser Glu Tyr
        35                  40                  45

Arg Tyr Ser Ser Arg Tyr Cys Met Gly Trp Phe Arg Gln Ala Pro Gly
    50                  55                  60

Lys Gly Arg Glu Gly Val Ala Ala Ile Asp Ser Asn Gly Ser Ala Asp
65                  70                  75                  80

Tyr Val Asp Ser Val Lys Gly Arg Phe Thr Ile Ser Lys Asp Asn Ser
                85                  90                  95

Lys Asn Thr Leu Tyr Leu Gln Met Asn Ser Leu Arg Ala Glu Asp Thr
            100                 105                 110

Ala Met Tyr Tyr Cys Ala Ala Asp His Leu Ala Tyr Asp Cys Tyr Ser
        115                 120                 125

Gly Ala Thr Ser Val Phe Arg Tyr Trp Gly Gln Gly Thr Leu Val Thr
    130                 135                 140

Val Ser Ser Thr Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
                165                 170                 175

Ala Ala Gly Gly Ala Val His Thr Arg Gly Leu Asp Phe Ala Cys Asp
            180                 185                 190

Ile Tyr Ile Trp Ala Pro Leu Ala Gly Thr Cys Gly Val Leu Leu Leu
        195                 200                 205

Ser Leu Val Ile Thr Leu Tyr Cys Lys Arg Gly Arg Lys Lys Leu Leu
    210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255

Glu Leu Arg Val Lys Phe Ser Arg Ser Ala Asp Ala Pro Ala Tyr Lys
            260                 265                 270

Gln Gly Gln Asn Gln Leu Tyr Asn Glu Leu Asn Leu Gly Arg Arg Glu
        275                 280                 285

Glu Tyr Asp Val Leu Asp Lys Arg Arg Gly Arg Asp Pro Glu Met Gly
    290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
            340                 345                 350

Thr Ala Thr Lys Asp Thr Tyr Asp Ala Leu His Met Gln Ala Leu Pro
        355                 360                 365

Pro Arg
```

370

<210> SEQ ID NO 224
<211> LENGTH: 369
<212> TYPE: PRT
<213> ORGANISM: Artificial Sequence
<220> FEATURE:
<223> OTHER INFORMATION: CAS72052VH5-BBz

<400> SEQUENCE: 224

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Gly Ser Leu Arg Leu Ser Cys Ala Val Ser Gly Phe
        35                  40                  45

Arg Tyr Ala Ser Tyr Cys Met Gly Trp Phe Arg Gln Ala Pro Gly Lys
    50                  55                  60

Gly Leu Glu Gly Val Ala Ala Ile His Ser Asp Gly Ile Ile Arg Tyr
65                  70                  75                  80

Ala Glu Ser Val Lys Gly Arg Phe Thr Ile Ser Lys Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Ala Gly Ala Tyr Cys Gly Ala Asp Ala Ile Leu
        115                 120                 125

Thr Leu Tyr Asp Tyr Ala Phe Trp Gly Gln Gly Thr Leu Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
    290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro

```
        355                 360                 365

Arg


<210> SEQ ID NO 225
<211> LENGTH: 369
<212> TYPE: PRT
<213> ORGANISM: Artificial Sequence
<220> FEATURE:
<223> OTHER INFORMATION: CAS72052VH6-BBz

<400> SEQUENCE: 225

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Gly Ser Leu Arg Leu Ser Cys Ala Val Ser Gly Phe
        35                  40                  45

Arg Tyr Ala Ser Tyr Cys Met Gly Trp Phe Arg Gln Ala Pro Gly Lys
    50                  55                  60

Gly Leu Glu Gly Val Ala Ala Ile His Ser Asp Gly Ile Ile Arg Tyr
65                  70                  75                  80

Ala Glu Ser Val Lys Gly Arg Phe Thr Ile Ser Lys Asp Asn Ser Lys
                85                  90                  95

Asn Thr Leu Tyr Leu Gln Met Asn Ser Leu Arg Ala Glu Asp Thr Ala
            100                 105                 110

Met Tyr Ser Cys Ala Ala Gly Ala Tyr Cys Gly Ala Asp Ala Ile Leu
        115                 120                 125

Thr Leu Tyr Asp Tyr Ala Phe Trp Gly Gln Gly Thr Leu Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
    290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350
```

Ala Thr Lys Asp Thr Tyr Asp Ala Leu His Met Gln Ala Leu Pro Pro
355 360 365

Arg

<210> SEQ ID NO 226
<211> LENGTH: 368
<212> TYPE: PRT
<213> ORGANISM: Artificial Sequence
<220> FEATURE:
<223> OTHER INFORMATION: CAS72669VH6-BBz

<400> SEQUENCE: 226

Met Ala Leu Pro Val Thr Ala Leu Leu Leu Pro Leu Ala Leu Leu Leu
1 5 10 15

His Ala Ala Arg Pro Gln Val Gln Leu Val Glu Ser Gly Gly Gly Val
20 25 30

Val Gln Pro Gly Gly Ser Leu Arg Leu Ser Cys Ala Ala Ser Arg Phe
35 40 45

Thr Tyr Ser Ser Tyr Cys Met Gly Trp Ile Arg Gln Ala Pro Gly Lys
50 55 60

Gly Arg Glu Gly Val Ala Ile Phe Tyr Thr Gly Gly Gly Arg Thr Tyr
65 70 75 80

Tyr Ala Asp Ser Val Lys Gly Arg Phe Thr Ile Ser Gln Asp Asn Ser
85 90 95

Lys Asn Thr Leu Tyr Leu Gln Met Asn Ser Leu Arg Ala Glu Asp Thr
100 105 110

Ala Val Tyr Tyr Cys Val Ala Gly Phe Tyr Cys Ser Gly Gly Tyr Trp
115 120 125

Glu Gly Asp Phe Gly Tyr Trp Gly Gln Gly Thr Leu Val Thr Val Ser
130 135 140

Ser Thr Thr Thr Pro Ala Pro Arg Pro Pro Thr Pro Ala Pro Thr Ile
145 150 155 160

Ala Ser Gln Pro Leu Ser Leu Arg Pro Glu Ala Cys Arg Pro Ala Ala
165 170 175

Gly Gly Ala Val His Thr Arg Gly Leu Asp Phe Ala Cys Asp Ile Tyr
180 185 190

Ile Trp Ala Pro Leu Ala Gly Thr Cys Gly Val Leu Leu Leu Ser Leu
195 200 205

Val Ile Thr Leu Tyr Cys Lys Arg Gly Arg Lys Lys Leu Leu Tyr Ile
210 215 220

Phe Lys Gln Pro Phe Met Arg Pro Val Gln Thr Thr Gln Glu Glu Asp
225 230 235 240

Gly Cys Ser Cys Arg Phe Pro Glu Glu Glu Glu Gly Gly Cys Glu Leu
245 250 255

Arg Val Lys Phe Ser Arg Ser Ala Asp Ala Pro Ala Tyr Lys Gln Gly
260 265 270

Gln Asn Gln Leu Tyr Asn Glu Leu Asn Leu Gly Arg Arg Glu Glu Tyr
275 280 285

Asp Val Leu Asp Lys Arg Arg Gly Arg Asp Pro Glu Met Gly Gly Lys
290 295 300

Pro Arg Arg Lys Asn Pro Gln Glu Gly Leu Tyr Asn Glu Leu Gln Lys
305 310 315 320

Asp Lys Met Ala Glu Ala Tyr Ser Glu Ile Gly Met Lys Gly Glu Arg
325 330 335

```
Arg Arg Gly Lys Gly His Asp Gly Leu Tyr Gln Gly Leu Ser Thr Ala
            340                 345                 350

Thr Lys Asp Thr Tyr Asp Ala Leu His Met Gln Ala Leu Pro Pro Arg
        355                 360                 365


<210> SEQ ID NO 227
<211> LENGTH: 371
<212> TYPE: PRT
<213> ORGANISM: Artificial Sequence
<220> FEATURE:
<223> OTHER INFORMATION: CAS78117VH4-BBz

<400> SEQUENCE: 227

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ile Val Ser Arg Tyr
        35                  40                  45

Thr Tyr Ala Thr Tyr Ser Met Ala Trp Phe Arg Gln Ala Pro Gly Lys
    50                  55                  60

Gly Leu Glu Gly Val Ser Gly Leu Asp Ser Val Gly Ala Thr Gly Tyr
65                  70                  75                  80

Ala Glu Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Val Val Asp Pro Ala Ser Ala Lys Val Thr Tyr Gly
        115                 120                 125

Ser Trp Ser Thr Pro Ser Tyr Ala Tyr Trp Gly Gln Gly Thr Leu Val
    130                 135                 140

Thr Val Ser Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
                245                 250                 255

Cys Glu Leu Arg Val Lys Phe Ser Arg Ser Ala Asp Ala Pro Ala Tyr
            260                 265                 270

Lys Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335
```

-continued

```
Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
    370


<210> SEQ ID NO 228
<211> LENGTH: 371
<212> TYPE: PRT
<213> ORGANISM: Artificial Sequence
<220> FEATURE:
<223> OTHER INFORMATION: CAS78117VH5-BBz

<400> SEQUENCE: 228

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ile Val Ser Arg Tyr
        35                  40                  45

Thr Tyr Ala Thr Tyr Ser Met Ala Trp Phe Arg Gln Ala Pro Gly Lys
    50                  55                  60

Gly Leu Glu Gly Val Ser Gly Leu Asp Ser Val Gly Ala Thr Gly Tyr
65                  70                  75                  80

Ala Glu Ser Val Lys Gly Arg Phe Thr Ile Ser Lys Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Val Val Asp Pro Ala Ser Ala Lys Val Thr Tyr Gly
        115                 120                 125

Ser Trp Ser Thr Pro Ser Tyr Ala Tyr Trp Gly Gln Gly Thr Leu Val
    130                 135                 140

Thr Val Ser Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
                245                 250                 255

Cys Glu Leu Arg Val Lys Phe Ser Arg Ser Ala Asp Ala Pro Ala Tyr
            260                 265                 270

Lys Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320
```

```
Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
    370


<210> SEQ ID NO 229
<211> LENGTH: 371
<212> TYPE: PRT
<213> ORGANISM: Artificial Sequence
<220> FEATURE:
<223> OTHER INFORMATION: CAS78117VH6-BBz

<400> SEQUENCE: 229

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ile Val Ser Arg Tyr
        35                  40                  45

Thr Tyr Ala Thr Tyr Ser Met Ala Trp Phe Arg Gln Ala Pro Gly Lys
    50                  55                  60

Gly Leu Glu Gly Val Ser Gly Leu Asp Ser Val Gly Ala Thr Gly Tyr
65                  70                  75                  80

Ala Glu Ser Val Lys Gly Arg Phe Thr Ile Ser Lys Asp Asn Ser Lys
                85                  90                  95

Asn Thr Leu Tyr Leu Gln Met Asn Ser Leu Arg Ala Glu Asp Thr Ala
            100                 105                 110

Met Tyr Tyr Cys Val Val Asp Pro Ala Ser Ala Lys Val Thr Tyr Gly
        115                 120                 125

Ser Trp Ser Thr Pro Ser Tyr Ala Tyr Trp Gly Gln Gly Thr Leu Val
    130                 135                 140

Thr Val Ser Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
                245                 250                 255

Cys Glu Leu Arg Val Lys Phe Ser Arg Ser Ala Asp Ala Pro Ala Tyr
            260                 265                 270

Lys Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300
```

-continued

```
Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
    370


<210> SEQ ID NO 230
<211> LENGTH: 371
<212> TYPE: PRT
<213> ORGANISM: Artificial Sequence
<220> FEATURE:
<223> OTHER INFORMATION: CAS78117VH7-BBz

<400> SEQUENCE: 230

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ile Val Ser Arg Tyr
        35                  40                  45

Thr Tyr Ala Thr Tyr Ser Met Ala Trp Phe Arg Gln Ala Pro Gly Lys
    50                  55                  60

Gly Leu Glu Gly Val Ala Gly Leu Asp Ser Val Gly Ala Thr Gly Tyr
65                  70                  75                  80

Ala Glu Ser Val Lys Gly Arg Phe Thr Ile Ser Lys Asp Asn Ser Lys
                85                  90                  95

Asn Thr Leu Tyr Leu Gln Met Asn Ser Leu Arg Ala Glu Asp Thr Ala
            100                 105                 110

Met Tyr Tyr Cys Val Val Asp Pro Ala Ser Ala Lys Val Thr Tyr Gly
        115                 120                 125

Ser Trp Ser Thr Pro Ser Tyr Ala Tyr Trp Gly Gln Gly Thr Leu Val
    130                 135                 140

Thr Val Ser Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
                245                 250                 255

Cys Glu Leu Arg Val Lys Phe Ser Arg Ser Ala Asp Ala Pro Ala Tyr
            260                 265                 270

Lys Gln Gly Gln Asn Gln Leu Tyr Asn Glu Leu Asn Leu Gly Arg Arg
        275                 280                 285
```

-continued

Glu Glu Tyr Asp Val Leu Asp Lys Arg Arg Gly Arg Asp Pro Glu Met
290 295 300

Gly Gly Lys Pro Arg Arg Lys Asn Pro Gln Glu Gly Leu Tyr Asn Glu
305 310 315 320

Leu Gln Lys Asp Lys Met Ala Glu Ala Tyr Ser Glu Ile Gly Met Lys
325 330 335

Gly Glu Arg Arg Arg Gly Lys Gly His Asp Gly Leu Tyr Gln Gly Leu
340 345 350

Ser Thr Ala Thr Lys Asp Thr Tyr Asp Ala Leu His Met Gln Ala Leu
355 360 365

Pro Pro Arg
370

<210> SEQ ID NO 231
<211> LENGTH: 371
<212> TYPE: PRT
<213> ORGANISM: Artificial Sequence
<220> FEATURE:
<223> OTHER INFORMATION: CAS79236VH4-BBz

<400> SEQUENCE: 231

Met Ala Leu Pro Val Thr Ala Leu Leu Leu Pro Leu Ala Leu Leu Leu
1 5 10 15

His Ala Ala Arg Pro Glu Val Gln Leu Val Glu Ser Gly Gly Gly Leu
20 25 30

Val Gln Pro Gly Gly Ser Leu Arg Leu Ser Cys Ala Ala Ser Gly Tyr
35 40 45

Thr Tyr Ser Ser Tyr Cys Met Ala Trp Phe Arg Gln Ala Pro Gly Lys
50 55 60

Gly Leu Glu Gly Val Ala Ser Ile Asp Ala Gly Gly Arg Thr Thr Tyr
65 70 75 80

Val Asp Ser Val Lys Gly Arg Phe Thr Ile Ser Arg Asp Asn Ala Lys
85 90 95

Asn Ser Leu Tyr Leu Gln Met Asn Ser Leu Arg Ala Glu Asp Thr Ala
100 105 110

Val Tyr Tyr Cys Ala Val Asp Val Arg Thr Arg Cys Gly Gly Thr Trp
115 120 125

Asp Gly Glu Ala Val Tyr Phe Pro Tyr Trp Gly Gln Gly Thr Leu Val
130 135 140

Thr Val Ser Ser Thr Thr Thr Pro Ala Pro Arg Pro Pro Thr Pro Ala
145 150 155 160

Pro Thr Ile Ala Ser Gln Pro Leu Ser Leu Arg Pro Glu Ala Cys Arg
165 170 175

Pro Ala Ala Gly Gly Ala Val His Thr Arg Gly Leu Asp Phe Ala Cys
180 185 190

Asp Ile Tyr Ile Trp Ala Pro Leu Ala Gly Thr Cys Gly Val Leu Leu
195 200 205

Leu Ser Leu Val Ile Thr Leu Tyr Cys Lys Arg Gly Arg Lys Lys Leu
210 215 220

Leu Tyr Ile Phe Lys Gln Pro Phe Met Arg Pro Val Gln Thr Thr Gln
225 230 235 240

Glu Glu Asp Gly Cys Ser Cys Arg Phe Pro Glu Glu Glu Glu Gly Gly
245 250 255

Cys Glu Leu Arg Val Lys Phe Ser Arg Ser Ala Asp Ala Pro Ala Tyr
260 265 270

```
Lys Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
    370


<210> SEQ ID NO 232
<211> LENGTH: 371
<212> TYPE: PRT
<213> ORGANISM: Artificial Sequence
<220> FEATURE:
<223> OTHER INFORMATION: CAS79236VH5-BBz

<400> SEQUENCE: 232

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Val Ser Gly Tyr
        35                  40                  45

Thr Tyr Ser Ser Tyr Cys Met Ala Trp Phe Arg Gln Ala Pro Gly Lys
    50                  55                  60

Gly Leu Glu Gly Val Ala Ser Ile Asp Ala Gly Gly Arg Thr Thr Tyr
65                  70                  75                  80

Val Asp Ser Val Lys Gly Arg Phe Thr Ile Ser Lys Asp Asn Ala Lys
                85                  90                  95

Asn Ser Leu Tyr Leu Gln Met Asn Ser Leu Arg Ala Glu Asp Thr Ala
            100                 105                 110

Val Tyr Tyr Cys Ala Val Asp Val Arg Thr Arg Cys Gly Gly Thr Trp
        115                 120                 125

Asp Gly Glu Ala Val Tyr Phe Pro Tyr Trp Gly Gln Gly Thr Leu Val
    130                 135                 140

Thr Val Ser Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
                245                 250                 255
```

```
Cys Glu Leu Arg Val Lys Phe Ser Arg Ser Ala Asp Ala Pro Ala Tyr
            260                 265                 270

Lys Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
    370


<210> SEQ ID NO 233
<211> LENGTH: 371
<212> TYPE: PRT
<213> ORGANISM: Artificial Sequence
<220> FEATURE:
<223> OTHER INFORMATION: CAS79236VH6-BBz

<400> SEQUENCE: 233

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Val Ser Gly Tyr
        35                  40                  45

Thr Tyr Ser Ser Tyr Cys Met Ala Trp Phe Arg Gln Ala Pro Gly Lys
    50                  55                  60

Gly Leu Glu Gly Val Ala Ser Ile Asp Ala Gly Gly Arg Thr Thr Tyr
65                  70                  75                  80

Val Asp Ser Val Lys Gly Arg Phe Thr Ile Ser Lys Asp Asn Ala Lys
                85                  90                  95

Asn Ser Leu Tyr Leu Gln Met Asn Ser Leu Arg Ala Glu Asp Thr Ala
            100                 105                 110

Met Tyr Tyr Cys Ala Val Asp Val Arg Thr Arg Cys Gly Gly Thr Trp
        115                 120                 125

Asp Gly Glu Ala Val Tyr Phe Pro Tyr Trp Gly Gln Gly Thr Leu Val
    130                 135                 140

Thr Val Ser Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240
```

```
Glu Glu Asp Gly Cys Ser Cys Arg Phe Pro Glu Glu Glu Glu Gly Gly
                245                 250                 255

Cys Glu Leu Arg Val Lys Phe Ser Arg Ser Ala Asp Ala Pro Ala Tyr
            260                 265                 270

Lys Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
    370


<210> SEQ ID NO 234
<211> LENGTH: 367
<212> TYPE: PRT
<213> ORGANISM: Artificial Sequence
<220> FEATURE:
<223> OTHER INFORMATION: CAS77916VH6-BBz

<400> SEQUENCE: 234

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Thr Ser Gly Tyr
        35                  40                  45

Thr Ser Ser Trp Asn Cys Met Gly Trp Phe Arg Gln Ala Pro Gly Lys
    50                  55                  60

Gly Leu Glu Gly Val Ala Thr Ile Ala Asn Arg Gly His Ser Thr Tyr
65                  70                  75                  80

Tyr Ala Asp Ser Val Lys Gly Arg Phe Thr Ile Ser Gln Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Thr Asp Thr Trp Ala Cys Val Gly Ile Ser
        115                 120                 125

Thr Asp Phe Glu Tyr Trp Gly Gln Gly Thr Leu Val Thr Val Ser Ser
    130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
    210                 215                 220
```

-continued

```
Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Lys Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
    290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365


<210> SEQ ID NO 235
<211> LENGTH: 367
<212> TYPE: PRT
<213> ORGANISM: Artificial Sequence
<220> FEATURE:
<223> OTHER INFORMATION: CAS77916VH7-BBz

<400> SEQUENCE: 235

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Thr Ser Gly Tyr
        35                  40                  45

Thr Ser Ser Trp Asn Cys Met Gly Trp Phe Arg Gln Ala Pro Gly Lys
    50                  55                  60

Gly Leu Glu Gly Val Ala Thr Ile Ala Asn Arg Gly His Ser Thr Tyr
65                  70                  75                  80

Tyr Ala Asp Ser Val Lys Gly Arg Phe Thr Ile Ser Gln Asp Asn Ser
                85                  90                  95

Lys Asn Thr Leu Tyr Leu Gln Met Asn Ser Leu Arg Ala Glu Asp Thr
            100                 105                 110

Ala Met Tyr Tyr Cys Ala Thr Asp Thr Trp Ala Cys Val Gly Ile Ser
        115                 120                 125

Thr Asp Phe Glu Tyr Trp Gly Gln Gly Thr Leu Val Thr Val Ser Ser
    130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
    210                 215                 220
```

```
Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Lys Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
    290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365


<210> SEQ ID NO 236
<211> LENGTH: 367
<212> TYPE: PRT
<213> ORGANISM: Artificial Sequence
<220> FEATURE:
<223> OTHER INFORMATION: CAS77916VH8-BBz

<400> SEQUENCE: 236

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Thr Ser Gly Tyr
        35                  40                  45

Thr Ser Ser Trp Asn Cys Met Gly Trp Phe Arg Gln Ala Pro Gly Lys
    50                  55                  60

Gly Leu Glu Gly Val Ala Thr Ile Ala Asn Arg Gly His Ser Thr Tyr
65                  70                  75                  80

Tyr Ala Asp Ser Val Lys Gly Arg Phe Thr Ile Ser Gln Asp Asn Ser
                85                  90                  95

Lys Asn Thr Val Tyr Leu Gln Met Asn Ser Leu Arg Ala Glu Asp Thr
            100                 105                 110

Ala Val Tyr Tyr Cys Ala Thr Asp Thr Trp Ala Cys Val Gly Ile Ser
        115                 120                 125

Thr Asp Phe Glu Tyr Trp Gly Gln Gly Thr Leu Val Thr Val Ser Ser
    130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
    210                 215                 220
```

```
Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Lys Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
    290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365


<210> SEQ ID NO 237
<211> LENGTH: 367
<212> TYPE: PRT
<213> ORGANISM: Artificial Sequence
<220> FEATURE:
<223> OTHER INFORMATION: CAS77916VH9-BBz

<400> SEQUENCE: 237

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Thr Ser Gly Tyr
        35                  40                  45

Thr Ser Ser Trp Asn Cys Met Gly Trp Phe Arg Gln Ala Pro Gly Lys
    50                  55                  60

Gly Arg Glu Gly Val Ala Thr Ile Ala Asn Arg Gly His Ser Thr Tyr
65                  70                  75                  80

Tyr Ala Asp Ser Val Lys Gly Arg Phe Thr Ile Ser Gln Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Thr Asp Thr Trp Ala Cys Val Gly Ile Ser
        115                 120                 125

Thr Asp Phe Glu Tyr Trp Gly Gln Gly Thr Leu Val Thr Val Ser Ser
    130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
    210                 215                 220
```

-continued

```
Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Lys Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
    290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365


<210> SEQ ID NO 238
<211> LENGTH: 367
<212> TYPE: PRT
<213> ORGANISM: Artificial Sequence
<220> FEATURE:
<223> OTHER INFORMATION: CAS77916VH10-BBz

<400> SEQUENCE: 238

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Thr Ser Gly Tyr
        35                  40                  45

Thr Ser Ser Trp Asn Cys Met Gly Trp Phe Arg Gln Ala Pro Gly Lys
    50                  55                  60

Gly Arg Glu Gly Val Ala Thr Ile Ala Asn Arg Gly His Ser Thr Tyr
65                  70                  75                  80

Tyr Ala Asp Ser Val Lys Gly Arg Phe Thr Ile Ser Gln Asp Asn Ser
                85                  90                  95

Lys Asn Thr Val Tyr Leu Gln Met Asn Ser Leu Arg Ala Glu Asp Thr
            100                 105                 110

Ala Val Tyr Tyr Cys Ala Thr Asp Thr Trp Ala Cys Val Gly Ile Ser
        115                 120                 125

Thr Asp Phe Glu Tyr Trp Gly Gln Gly Thr Leu Val Thr Val Ser Ser
    130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
    210                 215                 220
```

-continued

```
Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Lys Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
    290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365
```

<210> SEQ ID NO 239
<211> LENGTH: 510
<212> TYPE: PRT
<213> ORGANISM: Artificial Sequence
<220> FEATURE:
<223> OTHER INFORMATION: CAS71529VH5-AS72052VH5-BBz

<400> SEQUENCE: 239

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Val Ser Glu Tyr
        35                  40                  45

Arg Tyr Ser Ser Arg Tyr Cys Met Gly Trp Phe Arg Gln Ala Pro Gly
    50                  55                  60

Lys Gly Leu Glu Gly Val Ser Ala Ile Asp Ser Asn Gly Ser Ala Asp
65                  70                  75                  80

Tyr Val Asp Ser Val Lys Gly Arg Phe Thr Ile Ser Lys Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Ala Asp His Leu Ala Tyr Asp Cys Tyr Ser
        115                 120                 125

Gly Ala Thr Ser Val Phe Arg Tyr Trp Gly Gln Gly Thr Leu Val Thr
    130                 135                 140

Val Ser Ser Gly Gly Gly Gly Ser Gly Gly Gly Gly Ser Gly Gly Gly
145                 150                 155                 160

Gly Ser Gln Val Gln Leu Val Glu Ser Gly Gly Gly Val Val Gln Pro
                165                 170                 175

Gly Gly Ser Leu Arg Leu Ser Cys Ala Val Ser Gly Phe Arg Tyr Ala
            180                 185                 190

Ser Tyr Cys Met Gly Trp Phe Arg Gln Ala Pro Gly Lys Gly Leu Glu
        195                 200                 205

Gly Val Ala Ala Ile His Ser Asp Gly Ile Ile Arg Tyr Ala Glu Ser
    210                 215                 220
```

Val Lys Gly Arg Phe Thr Ile Ser Lys Asp Asn Ser Lys Asn Thr Leu
225 230 235 240

Tyr Leu Gln Met Asn Ser Leu Arg Ala Glu Asp Thr Ala Val Tyr Tyr
245 250 255

Cys Ala Ala Gly Ala Tyr Cys Gly Ala Asp Ala Ile Leu Thr Leu Tyr
260 265 270

Asp Tyr Ala Phe Trp Gly Gln Gly Thr Leu Val Thr Val Ser Ser Thr
275 280 285

Thr Thr Pro Ala Pro Arg Pro Pro Thr Pro Ala Pro Thr Ile Ala Ser
290 295 300

Gln Pro Leu Ser Leu Arg Pro Glu Ala Cys Arg Pro Ala Ala Gly Gly
305 310 315 320

Ala Val His Thr Arg Gly Leu Asp Phe Ala Cys Asp Ile Tyr Ile Trp
325 330 335

Ala Pro Leu Ala Gly Thr Cys Gly Val Leu Leu Leu Ser Leu Val Ile
340 345 350

Thr Leu Tyr Cys Lys Arg Gly Arg Lys Lys Leu Leu Tyr Ile Phe Lys
355 360 365

Gln Pro Phe Met Arg Pro Val Gln Thr Thr Gln Glu Glu Asp Gly Cys
370 375 380

Ser Cys Arg Phe Pro Glu Glu Glu Glu Gly Gly Cys Glu Leu Arg Val
385 390 395 400

Lys Phe Ser Arg Ser Ala Asp Ala Pro Ala Tyr Lys Gln Gly Gln Asn
405 410 415

Gln Leu Tyr Asn Glu Leu Asn Leu Gly Arg Arg Glu Glu Tyr Asp Val
420 425 430

Leu Asp Lys Arg Arg Gly Arg Asp Pro Glu Met Gly Gly Lys Pro Arg
435 440 445

Arg Lys Asn Pro Gln Glu Gly Leu Tyr Asn Glu Leu Gln Lys Asp Lys
450 455 460

Met Ala Glu Ala Tyr Ser Glu Ile Gly Met Lys Gly Glu Arg Arg Arg
465 470 475 480

Gly Lys Gly His Asp Gly Leu Tyr Gln Gly Leu Ser Thr Ala Thr Lys
485 490 495

Asp Thr Tyr Asp Ala Leu His Met Gln Ala Leu Pro Pro Arg
500 505 510

<210> SEQ ID NO 240
<211> LENGTH: 510
<212> TYPE: PRT
<213> ORGANISM: Artificial Sequence
<220> FEATURE:
<223> OTHER INFORMATION: CAS72052VH5-AS71529VH5-BBz

<400> SEQUENCE: 240

Met Ala Leu Pro Val Thr Ala Leu Leu Leu Pro Leu Ala Leu Leu Leu
1 5 10 15

His Ala Ala Arg Pro Gln Val Gln Leu Val Glu Ser Gly Gly Gly Val
20 25 30

Val Gln Pro Gly Gly Ser Leu Arg Leu Ser Cys Ala Val Ser Gly Phe
35 40 45

Arg Tyr Ala Ser Tyr Cys Met Gly Trp Phe Arg Gln Ala Pro Gly Lys
50 55 60

Gly Leu Glu Gly Val Ala Ala Ile His Ser Asp Gly Ile Ile Arg Tyr
65 70 75 80

```
Ala Glu Ser Val Lys Gly Arg Phe Thr Ile Ser Lys Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Ala Gly Ala Tyr Cys Gly Ala Asp Ala Ile Leu
        115                 120                 125

Thr Leu Tyr Asp Tyr Ala Phe Trp Gly Gln Gly Thr Leu Val Thr Val
    130                 135                 140

Ser Ser Gly Gly Gly Gly Ser Gly Gly Gly Gly Ser Gly Gly Gly Gly
145                 150                 155                 160

Ser Glu Val Gln Leu Val Glu Ser Gly Gly Gly Leu Val Gln Pro Gly
                165                 170                 175

Gly Ser Leu Arg Leu Ser Cys Ala Val Ser Glu Tyr Arg Tyr Ser Ser
            180                 185                 190

Arg Tyr Cys Met Gly Trp Phe Arg Gln Ala Pro Gly Lys Gly Leu Glu
        195                 200                 205

Gly Val Ser Ala Ile Asp Ser Asn Gly Ser Ala Asp Tyr Val Asp Ser
    210                 215                 220

Val Lys Gly Arg Phe Thr Ile Ser Lys Asp Asn Ser Lys Asn Thr Leu
225                 230                 235                 240

Tyr Leu Gln Met Asn Ser Leu Arg Ala Glu Asp Thr Ala Val Tyr Tyr
                245                 250                 255

Cys Ala Ala Asp His Leu Ala Tyr Asp Cys Tyr Ser Gly Ala Thr Ser
            260                 265                 270

Val Phe Arg Tyr Trp Gly Gln Gly Thr Leu Val Thr Val Ser Ser Thr
        275                 280                 285

Thr Thr Pro Ala Pro Arg Pro Pro Thr Pro Ala Pro Thr Ile Ala Ser
    290                 295                 300

Gln Pro Leu Ser Leu Arg Pro Glu Ala Cys Arg Pro Ala Ala Gly Gly
305                 310                 315                 320

Ala Val His Thr Arg Gly Leu Asp Phe Ala Cys Asp Ile Tyr Ile Trp
                325                 330                 335

Ala Pro Leu Ala Gly Thr Cys Gly Val Leu Leu Leu Ser Leu Val Ile
            340                 345                 350

Thr Leu Tyr Cys Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Lys Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
```

500 505 510

<210> SEQ ID NO 241
<211> LENGTH: 509
<212> TYPE: PRT
<213> ORGANISM: Artificial Sequence
<220> FEATURE:
<223> OTHER INFORMATION: CAS70950VH6-AS71529VH6-BBz

<400> SEQUENCE: 241

Met Ala Leu Pro Val Thr Ala Leu Leu Leu Pro Leu Ala Leu Leu Leu
1 5 10 15

His Ala Ala Arg Pro Glu Val Gln Leu Val Glu Ser Gly Gly Gly Leu
20 25 30

Val Gln Pro Gly Gly Ser Leu Arg Leu Ser Cys Ala Ile Ser Glu Phe
35 40 45

Thr Tyr Lys Asn Thr Cys Val Gly Trp Phe Arg Gln Ala Pro Gly Lys
50 55 60

Gly Arg Glu Gly Val Ala Ala Ile Asp Ser Asp Gly Asn Thr Asn Tyr
65 70 75 80

Val Asp Ser Val Lys Gly Arg Phe Thr Ile Ser Gln Asp Asn Ser Lys
85 90 95

Asn Thr Val Tyr Leu Gln Met Asn Ser Leu Arg Ala Glu Asp Thr Ala
100 105 110

Met Tyr Tyr Cys Ala Ala Gly Ala Tyr Cys Gly Arg Leu Leu Leu Trp
115 120 125

Ile Gly Asn Tyr Ala Tyr Trp Gly Gln Gly Thr Leu Val Thr Val Ser
130 135 140

Ser Gly Gly Gly Gly Ser Gly Gly Gly Gly Ser Gly Gly Gly Gly Ser
145 150 155 160

Glu Val Gln Leu Val Glu Ser Gly Gly Gly Leu Val Gln Pro Gly Gly
165 170 175

Ser Leu Arg Leu Ser Cys Ala Val Ser Glu Tyr Arg Tyr Ser Ser Arg
180 185 190

Tyr Cys Met Gly Trp Phe Arg Gln Ala Pro Gly Lys Gly Arg Glu Gly
195 200 205

Val Ala Ala Ile Asp Ser Asn Gly Ser Ala Asp Tyr Val Asp Ser Val
210 215 220

Lys Gly Arg Phe Thr Ile Ser Lys Asp Asn Ser Lys Asn Thr Leu Tyr
225 230 235 240

Leu Gln Met Asn Ser Leu Arg Ala Glu Asp Thr Ala Met Tyr Tyr Cys
245 250 255

Ala Ala Asp His Leu Ala Tyr Asp Cys Tyr Ser Gly Ala Thr Ser Val
260 265 270

Phe Arg Tyr Trp Gly Gln Gly Thr Leu Val Thr Val Ser Ser Thr Thr
275 280 285

Thr Pro Ala Pro Arg Pro Pro Thr Pro Ala Pro Thr Ile Ala Ser Gln
290 295 300

Pro Leu Ser Leu Arg Pro Glu Ala Cys Arg Pro Ala Ala Gly Gly Ala
305 310 315 320

Val His Thr Arg Gly Leu Asp Phe Ala Cys Asp Ile Tyr Ile Trp Ala
325 330 335

Pro Leu Ala Gly Thr Cys Gly Val Leu Leu Leu Ser Leu Val Ile Thr
340 345 350

Leu Tyr Cys Lys Arg Gly Arg Lys Lys Leu Leu Tyr Ile Phe Lys Gln

-continued

```
        355                 360                 365

Pro Phe Met Arg Pro Val Gln Thr Thr Gln Glu Glu Asp Gly Cys Ser
    370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Lys Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505


<210> SEQ ID NO 242
<211> LENGTH: 509
<212> TYPE: PRT
<213> ORGANISM: Artificial Sequence
<220> FEATURE:
<223> OTHER INFORMATION: CAS71529VH6-AS70950VH6-BBz

<400> SEQUENCE: 242

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Val Ser Glu Tyr
        35                  40                  45

Arg Tyr Ser Ser Arg Tyr Cys Met Gly Trp Phe Arg Gln Ala Pro Gly
    50                  55                  60

Lys Gly Arg Glu Gly Val Ala Ala Ile Asp Ser Asn Gly Ser Ala Asp
65                  70                  75                  80

Tyr Val Asp Ser Val Lys Gly Arg Phe Thr Ile Ser Lys Asp Asn Ser
                85                  90                  95

Lys Asn Thr Leu Tyr Leu Gln Met Asn Ser Leu Arg Ala Glu Asp Thr
            100                 105                 110

Ala Met Tyr Tyr Cys Ala Ala Asp His Leu Ala Tyr Asp Cys Tyr Ser
        115                 120                 125

Gly Ala Thr Ser Val Phe Arg Tyr Trp Gly Gln Gly Thr Leu Val Thr
    130                 135                 140

Val Ser Ser Gly Gly Gly Gly Ser Gly Gly Gly Gly Ser Gly Gly Gly
145                 150                 155                 160

Gly Ser Glu Val Gln Leu Val Glu Ser Gly Gly Gly Leu Val Gln Pro
                165                 170                 175

Gly Gly Ser Leu Arg Leu Ser Cys Ala Ile Ser Glu Phe Thr Tyr Lys
            180                 185                 190

Asn Thr Cys Val Gly Trp Phe Arg Gln Ala Pro Gly Lys Gly Arg Glu
        195                 200                 205

Gly Val Ala Ala Ile Asp Ser Asp Gly Asn Thr Asn Tyr Val Asp Ser
```

-continued

```
    210                 215                 220

Val Lys Gly Arg Phe Thr Ile Ser Gln Asp Asn Ser Lys Asn Thr Val
225                 230                 235                 240

Tyr Leu Gln Met Asn Ser Leu Arg Ala Glu Asp Thr Ala Met Tyr Tyr
                245                 250                 255

Cys Ala Ala Gly Ala Tyr Cys Gly Arg Leu Leu Leu Trp Ile Gly Asn
            260                 265                 270

Tyr Ala Tyr Trp Gly Gln Gly Thr Leu Val Thr Val Ser Ser Thr Thr
        275                 280                 285

Thr Pro Ala Pro Arg Pro Pro Thr Pro Ala Pro Thr Ile Ala Ser Gln
    290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
            340                 345                 350

Leu Tyr Cys Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
    370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Lys Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505


<210> SEQ ID NO 243
<211> LENGTH: 507
<212> TYPE: PRT
<213> ORGANISM: Artificial Sequence
<220> FEATURE:
<223> OTHER INFORMATION: CAS70950VH6-AS70950VH6-BBz

<400> SEQUENCE: 243

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ile Ser Glu Phe
        35                  40                  45

Thr Tyr Lys Asn Thr Cys Val Gly Trp Phe Arg Gln Ala Pro Gly Lys
    50                  55                  60

Gly Arg Glu Gly Val Ala Ala Ile Asp Ser Asp Gly Asn Thr Asn Tyr
```

-continued

```
65                  70                  75                  80

Val Asp Ser Val Lys Gly Arg Phe Thr Ile Ser Gln Asp Asn Ser Lys
                85                  90                  95

Asn Thr Val Tyr Leu Gln Met Asn Ser Leu Arg Ala Glu Asp Thr Ala
            100                 105                 110

Met Tyr Tyr Cys Ala Ala Gly Ala Tyr Cys Gly Arg Leu Leu Leu Trp
        115                 120                 125

Ile Gly Asn Tyr Ala Tyr Trp Gly Gln Gly Thr Leu Val Thr Val Ser
    130                 135                 140

Ser Gly Gly Gly Gly Ser Gly Gly Gly Gly Ser Gly Gly Gly Gly Ser
145                 150                 155                 160

Glu Val Gln Leu Val Glu Ser Gly Gly Gly Leu Val Gln Pro Gly Gly
                165                 170                 175

Ser Leu Arg Leu Ser Cys Ala Ile Ser Glu Phe Thr Tyr Lys Asn Thr
            180                 185                 190

Cys Val Gly Trp Phe Arg Gln Ala Pro Gly Lys Gly Arg Glu Gly Val
        195                 200                 205

Ala Ala Ile Asp Ser Asp Gly Asn Thr Asn Tyr Val Asp Ser Val Lys
    210                 215                 220

Gly Arg Phe Thr Ile Ser Gln Asp Asn Ser Lys Asn Thr Val Tyr Leu
225                 230                 235                 240

Gln Met Asn Ser Leu Arg Ala Glu Asp Thr Ala Met Tyr Tyr Cys Ala
                245                 250                 255

Ala Gly Ala Tyr Cys Gly Arg Leu Leu Leu Trp Ile Gly Asn Tyr Ala
            260                 265                 270

Tyr Trp Gly Gln Gly Thr Leu Val Thr Val Ser Ser Thr Thr Thr Pro
        275                 280                 285

Ala Pro Arg Pro Pro Thr Pro Ala Pro Thr Ile Ala Ser Gln Pro Leu
    290                 295                 300

Ser Leu Arg Pro Glu Ala Cys Arg Pro Ala Ala Gly Gly Ala Val His
305                 310                 315                 320

Thr Arg Gly Leu Asp Phe Ala Cys Asp Ile Tyr Ile Trp Ala Pro Leu
                325                 330                 335

Ala Gly Thr Cys Gly Val Leu Leu Leu Ser Leu Val Ile Thr Leu Tyr
            340                 345                 350

Cys Lys Arg Gly Arg Lys Lys Leu Leu Tyr Ile Phe Lys Gln Pro Phe
        355                 360                 365

Met Arg Pro Val Gln Thr Thr Gln Glu Glu Asp Gly Cys Ser Cys Arg
    370                 375                 380

Phe Pro Glu Glu Glu Glu Gly Gly Cys Glu Leu Arg Val Lys Phe Ser
385                 390                 395                 400

Arg Ser Ala Asp Ala Pro Ala Tyr Lys Gln Gly Gln Asn Gln Leu Tyr
                405                 410                 415

Asn Glu Leu Asn Leu Gly Arg Arg Glu Glu Tyr Asp Val Leu Asp Lys
            420                 425                 430

Arg Arg Gly Arg Asp Pro Glu Met Gly Gly Lys Pro Arg Arg Lys Asn
        435                 440                 445

Pro Gln Glu Gly Leu Tyr Asn Glu Leu Gln Lys Asp Lys Met Ala Glu
    450                 455                 460

Ala Tyr Ser Glu Ile Gly Met Lys Gly Glu Arg Arg Arg Gly Lys Gly
465                 470                 475                 480

His Asp Gly Leu Tyr Gln Gly Leu Ser Thr Ala Thr Lys Asp Thr Tyr
                485                 490                 495
```

```
Asp Ala Leu His Met Gln Ala Leu Pro Pro Arg
            500                 505


<210> SEQ ID NO 244
<211> LENGTH: 268
<212> TYPE: PRT
<213> ORGANISM: Artificial Sequence
<220> FEATURE:
<223> OTHER INFORMATION: AS78117VH4-AS71529VH6

<400> SEQUENCE: 244

Glu Val Gln Leu Val Glu Ser Gly Gly Gly Leu Val Gln Pro Gly Gly
1               5                   10                  15

Ser Leu Arg Leu Ser Cys Ile Val Ser Arg Tyr Thr Tyr Ala Thr Tyr
            20                  25                  30

Ser Met Ala Trp Phe Arg Gln Ala Pro Gly Lys Gly Leu Glu Gly Val
        35                  40                  45

Ser Gly Leu Asp Ser Val Gly Ala Thr Gly Tyr Ala Glu Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Val
                85                  90                  95

Val Asp Pro Ala Ser Ala Lys Val Thr Tyr Gly Ser Trp Ser Thr Pro
            100                 105                 110

Ser Tyr Ala Tyr Trp Gly Gln Gly Thr Leu Val Thr Val Ser Ser Gly
        115                 120                 125

Gly Gly Gly Ser Gly Gly Gly Gly Ser Gly Gly Gly Gly Ser Glu Val
    130                 135                 140

Gln Leu Val Glu Ser Gly Gly Gly Leu Val Gln Pro Gly Gly Ser Leu
145                 150                 155                 160

Arg Leu Ser Cys Ala Val Ser Glu Tyr Arg Tyr Ser Ser Arg Tyr Cys
                165                 170                 175

Met Gly Trp Phe Arg Gln Ala Pro Gly Lys Gly Arg Glu Gly Val Ala
            180                 185                 190

Ala Ile Asp Ser Asn Gly Ser Ala Asp Tyr Val Asp Ser Val Lys Gly
        195                 200                 205

Arg Phe Thr Ile Ser Lys Asp Asn Ser Lys Asn Thr Leu Tyr Leu Gln
    210                 215                 220

Met Asn Ser Leu Arg Ala Glu Asp Thr Ala Met Tyr Tyr Cys Ala Ala
225                 230                 235                 240

Asp His Leu Ala Tyr Asp Cys Tyr Ser Gly Ala Thr Ser Val Phe Arg
                245                 250                 255

Tyr Trp Gly Gln Gly Thr Leu Val Thr Val Ser Ser
            260                 265


<210> SEQ ID NO 245
<211> LENGTH: 268
<212> TYPE: PRT
<213> ORGANISM: Artificial Sequence
<220> FEATURE:
<223> OTHER INFORMATION: AS71529VH6-AS78117VH4

<400> SEQUENCE: 245

Glu Val Gln Leu Val Glu Ser Gly Gly Gly Leu Val Gln Pro Gly Gly
1               5                   10                  15

Ser Leu Arg Leu Ser Cys Ala Val Ser Glu Tyr Arg Tyr Ser Ser Arg
```

```
            20                  25                  30

Tyr Cys Met Gly Trp Phe Arg Gln Ala Pro Gly Lys Gly Arg Glu Gly
        35                  40                  45

Val Ala Ala Ile Asp Ser Asn Gly Ser Ala Asp Tyr Val Asp Ser Val
    50                  55                  60

Lys Gly Arg Phe Thr Ile Ser Lys Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Ala Asp His Leu Ala Tyr Asp Cys Tyr Ser Gly Ala Thr Ser Val
            100                 105                 110

Phe Arg Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ile Val Ser Arg Tyr Thr Tyr Ala Thr Tyr Ser Met Ala
                165                 170                 175

Trp Phe Arg Gln Ala Pro Gly Lys Gly Leu Glu Gly Val Ser Gly Leu
            180                 185                 190

Asp Ser Val Gly Ala Thr Gly Tyr Ala Glu Ser Val Lys Gly Arg Phe
        195                 200                 205

Thr Ile Ser Arg Asp Asn Ser Lys Asn Thr Leu Tyr Leu Gln Met Asn
    210                 215                 220

Ser Leu Arg Ala Glu Asp Thr Ala Val Tyr Tyr Cys Val Val Asp Pro
225                 230                 235                 240

Ala Ser Ala Lys Val Thr Tyr Gly Ser Trp Ser Thr Pro Ser Tyr Ala
                245                 250                 255

Tyr Trp Gly Gln Gly Thr Leu Val Thr Val Ser Ser
            260                 265


<210> SEQ ID NO 246
<211> LENGTH: 512
<212> TYPE: PRT
<213> ORGANISM: Artificial Sequence
<220> FEATURE:
<223> OTHER INFORMATION: CAS78117VH4-AS71529VH6-BBz

<400> SEQUENCE: 246

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ile Val Ser Arg Tyr
        35                  40                  45

Thr Tyr Ala Thr Tyr Ser Met Ala Trp Phe Arg Gln Ala Pro Gly Lys
    50                  55                  60

Gly Leu Glu Gly Val Ser Gly Leu Asp Ser Val Gly Ala Thr Gly Tyr
65                  70                  75                  80

Ala Glu Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Val Val Asp Pro Ala Ser Ala Lys Val Thr Tyr Gly
```

-continued

```
        115                 120                 125

Ser Trp Ser Thr Pro Ser Tyr Ala Tyr Trp Gly Gln Gly Thr Leu Val
    130                 135                 140

Thr Val Ser Ser Gly Gly Gly Gly Ser Gly Gly Gly Gly Ser Gly Gly
145                 150                 155                 160

Gly Gly Ser Glu Val Gln Leu Val Glu Ser Gly Gly Gly Leu Val Gln
                165                 170                 175

Pro Gly Gly Ser Leu Arg Leu Ser Cys Ala Val Ser Glu Tyr Arg Tyr
            180                 185                 190

Ser Ser Arg Tyr Cys Met Gly Trp Phe Arg Gln Ala Pro Gly Lys Gly
        195                 200                 205

Arg Glu Gly Val Ala Ala Ile Asp Ser Asn Gly Ser Ala Asp Tyr Val
    210                 215                 220

Asp Ser Val Lys Gly Arg Phe Thr Ile Ser Lys Asp Asn Ser Lys Asn
225                 230                 235                 240

Thr Leu Tyr Leu Gln Met Asn Ser Leu Arg Ala Glu Asp Thr Ala Met
                245                 250                 255

Tyr Tyr Cys Ala Ala Asp His Leu Ala Tyr Asp Cys Tyr Ser Gly Ala
            260                 265                 270

Thr Ser Val Phe Arg Tyr Trp Gly Gln Gly Thr Leu Val Thr Val Ser
        275                 280                 285

Ser Thr Thr Thr Pro Ala Pro Arg Pro Pro Thr Pro Ala Pro Thr Ile
    290                 295                 300

Ala Ser Gln Pro Leu Ser Leu Arg Pro Glu Ala Cys Arg Pro Ala Ala
305                 310                 315                 320

Gly Gly Ala Val His Thr Arg Gly Leu Asp Phe Ala Cys Asp Ile Tyr
                325                 330                 335

Ile Trp Ala Pro Leu Ala Gly Thr Cys Gly Val Leu Leu Leu Ser Leu
            340                 345                 350

Val Ile Thr Leu Tyr Cys Lys Arg Gly Arg Lys Lys Leu Leu Tyr Ile
        355                 360                 365

Phe Lys Gln Pro Phe Met Arg Pro Val Gln Thr Thr Gln Glu Glu Asp
    370                 375                 380

Gly Cys Ser Cys Arg Phe Pro Glu Glu Glu Glu Gly Gly Cys Glu Leu
385                 390                 395                 400

Arg Val Lys Phe Ser Arg Ser Ala Asp Ala Pro Ala Tyr Lys Gln Gly
                405                 410                 415

Gln Asn Gln Leu Tyr Asn Glu Leu Asn Leu Gly Arg Arg Glu Glu Tyr
            420                 425                 430

Asp Val Leu Asp Lys Arg Arg Gly Arg Asp Pro Glu Met Gly Gly Lys
        435                 440                 445

Pro Arg Arg Lys Asn Pro Gln Glu Gly Leu Tyr Asn Glu Leu Gln Lys
    450                 455                 460

Asp Lys Met Ala Glu Ala Tyr Ser Glu Ile Gly Met Lys Gly Glu Arg
465                 470                 475                 480

Arg Arg Gly Lys Gly His Asp Gly Leu Tyr Gln Gly Leu Ser Thr Ala
                485                 490                 495

Thr Lys Asp Thr Tyr Asp Ala Leu His Met Gln Ala Leu Pro Pro Arg
            500                 505                 510
```

<210> SEQ ID NO 247
<211> LENGTH: 512
<212> TYPE: PRT
<213> ORGANISM: Artificial Sequence
<220> FEATURE:
<223> OTHER INFORMATION: CAS71529VH6-AS78117VH4-BBz

<400> SEQUENCE: 247

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Val Ser Glu Tyr
        35                  40                  45

Arg Tyr Ser Ser Arg Tyr Cys Met Gly Trp Phe Arg Gln Ala Pro Gly
    50                  55                  60

Lys Gly Arg Glu Gly Val Ala Ala Ile Asp Ser Asn Gly Ser Ala Asp
65                  70                  75                  80

Tyr Val Asp Ser Val Lys Gly Arg Phe Thr Ile Ser Lys Asp Asn Ser
                85                  90                  95

Lys Asn Thr Leu Tyr Leu Gln Met Asn Ser Leu Arg Ala Glu Asp Thr
            100                 105                 110

Ala Met Tyr Tyr Cys Ala Ala Asp His Leu Ala Tyr Asp Cys Tyr Ser
        115                 120                 125

Gly Ala Thr Ser Val Phe Arg Tyr Trp Gly Gln Gly Thr Leu Val Thr
    130                 135                 140

Val Ser Ser Gly Gly Gly Gly Ser Gly Gly Gly Gly Ser Gly Gly Gly
145                 150                 155                 160

Gly Ser Glu Val Gln Leu Val Glu Ser Gly Gly Gly Leu Val Gln Pro
                165                 170                 175

Gly Gly Ser Leu Arg Leu Ser Cys Ile Val Ser Arg Tyr Thr Tyr Ala
            180                 185                 190

Thr Tyr Ser Met Ala Trp Phe Arg Gln Ala Pro Gly Lys Gly Leu Glu
        195                 200                 205

Gly Val Ser Gly Leu Asp Ser Val Gly Ala Thr Gly Tyr Ala Glu Ser
    210                 215                 220

Val Lys Gly Arg Phe Thr Ile Ser Arg Asp Asn Ser Lys Asn Thr Leu
225                 230                 235                 240

Tyr Leu Gln Met Asn Ser Leu Arg Ala Glu Asp Thr Ala Val Tyr Tyr
                245                 250                 255

Cys Val Val Asp Pro Ala Ser Ala Lys Val Thr Tyr Gly Ser Trp Ser
            260                 265                 270

Thr Pro Ser Tyr Ala Tyr Trp Gly Gln Gly Thr Leu Val Thr Val Ser
        275                 280                 285

Ser Thr Thr Thr Pro Ala Pro Arg Pro Pro Thr Pro Ala Pro Thr Ile
    290                 295                 300

Ala Ser Gln Pro Leu Ser Leu Arg Pro Glu Ala Cys Arg Pro Ala Ala
305                 310                 315                 320

Gly Gly Ala Val His Thr Arg Gly Leu Asp Phe Ala Cys Asp Ile Tyr
                325                 330                 335

Ile Trp Ala Pro Leu Ala Gly Thr Cys Gly Val Leu Leu Leu Ser Leu
            340                 345                 350

Val Ile Thr Leu Tyr Cys Lys Arg Gly Arg Lys Lys Leu Leu Tyr Ile
        355                 360                 365

Phe Lys Gln Pro Phe Met Arg Pro Val Gln Thr Thr Gln Glu Glu Asp
    370                 375                 380

Gly Cys Ser Cys Arg Phe Pro Glu Glu Glu Glu Gly Gly Cys Glu Leu
385                 390                 395                 400
```

```
Arg Val Lys Phe Ser Arg Ser Ala Asp Ala Pro Ala Tyr Lys Gln Gly
                405                 410                 415

Gln Asn Gln Leu Tyr Asn Glu Leu Asn Leu Gly Arg Arg Glu Glu Tyr
            420                 425                 430

Asp Val Leu Asp Lys Arg Arg Gly Arg Asp Pro Glu Met Gly Gly Lys
        435                 440                 445

Pro Arg Arg Lys Asn Pro Gln Glu Gly Leu Tyr Asn Glu Leu Gln Lys
    450                 455                 460

Asp Lys Met Ala Glu Ala Tyr Ser Glu Ile Gly Met Lys Gly Glu Arg
465                 470                 475                 480

Arg Arg Gly Lys Gly His Asp Gly Leu Tyr Gln Gly Leu Ser Thr Ala
                485                 490                 495

Thr Lys Asp Thr Tyr Asp Ala Leu His Met Gln Ala Leu Pro Pro Arg
            500                 505                 510


<210> SEQ ID NO 248
<211> LENGTH: 364
<212> TYPE: PRT
<213> ORGANISM: Artificial Sequence
<220> FEATURE:
<223> OTHER INFORMATION: GPC2-CD28z

<400> SEQUENCE: 248

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ile Ser Glu Phe
        35                  40                  45

Thr Tyr Lys Asn Thr Cys Val Gly Trp Phe Arg Gln Ala Pro Gly Lys
    50                  55                  60

Gly Arg Glu Gly Val Ala Ala Ile Asp Ser Asp Gly Asn Thr Asn Tyr
65                  70                  75                  80

Val Asp Ser Val Lys Gly Arg Phe Thr Ile Ser Gln Asp Asn Ser Lys
                85                  90                  95

Asn Thr Val Tyr Leu Gln Met Asn Ser Leu Arg Ala Glu Asp Thr Ala
            100                 105                 110

Met Tyr Tyr Cys Ala Ala Gly Ala Tyr Cys Gly Arg Leu Leu Leu Trp
        115                 120                 125

Ile Gly Asn Tyr Ala Tyr Trp Gly Gln Gly Thr Leu Val Thr Val Ser
    130                 135                 140

Ser Ile Glu Val Met Tyr Pro Pro Pro Tyr Leu Asp Asn Glu Lys Ser
145                 150                 155                 160

Asn Gly Thr Ile Ile His Val Lys Gly Lys His Leu Cys Pro Ser Pro
                165                 170                 175

Leu Phe Pro Gly Pro Ser Lys Pro Phe Trp Val Leu Val Val Val Gly
            180                 185                 190

Gly Val Leu Ala Cys Tyr Ser Leu Leu Val Thr Val Ala Phe Ile Ile
        195                 200                 205

Phe Trp Val Arg Ser Lys Arg Ser Arg Leu Leu His Ser Asp Tyr Met
    210                 215                 220

Asn Met Thr Pro Arg Arg Pro Gly Pro Thr Arg Lys His Tyr Gln Pro
225                 230                 235                 240

Tyr Ala Pro Pro Arg Asp Phe Ala Ala Tyr Arg Ser Arg Val Lys Phe
                245                 250                 255
```

```
Ser Arg Ser Ala Asp Ala Pro Ala Tyr Lys Gln Gly Gln Asn Gln Leu
            260                 265                 270

Tyr Asn Glu Leu Asn Leu Gly Arg Arg Glu Glu Tyr Asp Val Leu Asp
        275                 280                 285

Lys Arg Arg Gly Arg Asp Pro Glu Met Gly Gly Lys Pro Arg Arg Lys
    290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
                325                 330                 335

Gly His Asp Gly Leu Tyr Gln Gly Leu Ser Thr Ala Thr Lys Asp Thr
            340                 345                 350

Tyr Asp Ala Leu His Met Gln Ala Leu Pro Pro Arg
        355                 360


<210> SEQ ID NO 249
<211> LENGTH: 371
<212> TYPE: PRT
<213> ORGANISM: Artificial Sequence
<220> FEATURE:
<223> OTHER INFORMATION: GPC2-CD27z

<400> SEQUENCE: 249

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ile Ser Glu Phe
        35                  40                  45

Thr Tyr Lys Asn Thr Cys Val Gly Trp Phe Arg Gln Ala Pro Gly Lys
    50                  55                  60

Gly Arg Glu Gly Val Ala Ala Ile Asp Ser Asp Gly Asn Thr Asn Tyr
65                  70                  75                  80

Val Asp Ser Val Lys Gly Arg Phe Thr Ile Ser Gln Asp Asn Ser Lys
                85                  90                  95

Asn Thr Val Tyr Leu Gln Met Asn Ser Leu Arg Ala Glu Asp Thr Ala
            100                 105                 110

Met Tyr Tyr Cys Ala Ala Gly Ala Tyr Cys Gly Arg Leu Leu Leu Trp
        115                 120                 125

Ile Gly Asn Tyr Ala Tyr Trp Gly Gln Gly Thr Leu Val Thr Val Ser
    130                 135                 140

Ser Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

Gly Gly Ala Val His Thr Arg Gly Leu Asp Phe Ala Cys Asp Ile Leu
            180                 185                 190

Val Ile Phe Ser Gly Met Phe Leu Val Phe Thr Leu Ala Gly Ala Leu
        195                 200                 205

Phe Leu His Gln Arg Arg Lys Tyr Arg Ser Asn Lys Gly Glu Ser Pro
    210                 215                 220

Val Glu Pro Ala Glu Pro Cys His Tyr Ser Cys Pro Arg Glu Glu Glu
225                 230                 235                 240

Gly Ser Thr Ile Pro Ile Gln Glu Asp Tyr Arg Lys Pro Glu Pro Ala
                245                 250                 255
```

Cys Ser Pro Arg Val Lys Phe Ser Arg Ser Ala Asp Ala Pro Ala Tyr
260 265 270

Lys Gln Gly Gln Asn Gln Leu Tyr Asn Glu Leu Asn Leu Gly Arg Arg
275 280 285

Glu Glu Tyr Asp Val Leu Asp Lys Arg Arg Gly Arg Asp Pro Glu Met
290 295 300

Gly Gly Lys Pro Arg Arg Lys Asn Pro Gln Glu Gly Leu Tyr Asn Glu
305 310 315 320

Leu Gln Lys Asp Lys Met Ala Glu Ala Tyr Ser Glu Ile Gly Met Lys
325 330 335

Gly Glu Arg Arg Arg Gly Lys Gly His Asp Gly Leu Tyr Gln Gly Leu
340 345 350

Ser Thr Ala Thr Lys Asp Thr Tyr Asp Ala Leu His Met Gln Ala Leu
355 360 365

Pro Pro Arg
370

<210> SEQ ID NO 250
<211> LENGTH: 361
<212> TYPE: PRT
<213> ORGANISM: Artificial Sequence
<220> FEATURE:
<223> OTHER INFORMATION: GPC2-ICOSz

<400> SEQUENCE: 250

Met Ala Leu Pro Val Thr Ala Leu Leu Leu Pro Leu Ala Leu Leu Leu
1 5 10 15

His Ala Ala Arg Pro Glu Val Gln Leu Val Glu Ser Gly Gly Gly Leu
20 25 30

Val Gln Pro Gly Gly Ser Leu Arg Leu Ser Cys Ala Ile Ser Glu Phe
35 40 45

Thr Tyr Lys Asn Thr Cys Val Gly Trp Phe Arg Gln Ala Pro Gly Lys
50 55 60

Gly Arg Glu Gly Val Ala Ala Ile Asp Ser Asp Gly Asn Thr Asn Tyr
65 70 75 80

Val Asp Ser Val Lys Gly Arg Phe Thr Ile Ser Gln Asp Asn Ser Lys
85 90 95

Asn Thr Val Tyr Leu Gln Met Asn Ser Leu Arg Ala Glu Asp Thr Ala
100 105 110

Met Tyr Tyr Cys Ala Ala Gly Ala Tyr Cys Gly Arg Leu Leu Leu Trp
115 120 125

Ile Gly Asn Tyr Ala Tyr Trp Gly Gln Gly Thr Leu Val Thr Val Ser
130 135 140

Ser Thr Thr Thr Pro Ala Pro Arg Pro Pro Thr Pro Ala Pro Thr Ile
145 150 155 160

Ala Ser Gln Pro Leu Ser Leu Arg Pro Glu Ala Cys Arg Pro Ala Ala
165 170 175

Gly Gly Ala Val His Thr Arg Gly Leu Asp Phe Ala Cys Asp Phe Trp
180 185 190

Leu Pro Ile Gly Cys Ala Ala Phe Val Val Val Cys Ile Leu Gly Cys
195 200 205

Ile Leu Ile Cys Trp Leu Thr Lys Lys Lys Tyr Ser Ser Ser Val His
210 215 220

Asp Pro Asn Gly Glu Tyr Met Phe Met Arg Ala Val Asn Thr Ala Lys
225 230 235 240

Lys Ser Arg Leu Thr Asp Val Thr Leu Arg Val Lys Phe Ser Arg Ser
245 250 255

Ala Asp Ala Pro Ala Tyr Lys Gln Gly Gln Asn Gln Leu Tyr Asn Glu
260 265 270

Leu Asn Leu Gly Arg Arg Glu Glu Tyr Asp Val Leu Asp Lys Arg Arg
275 280 285

Gly Arg Asp Pro Glu Met Gly Gly Lys Pro Arg Arg Lys Asn Pro Gln
290 295 300

Glu Gly Leu Tyr Asn Glu Leu Gln Lys Asp Lys Met Ala Glu Ala Tyr
305 310 315 320

Ser Glu Ile Gly Met Lys Gly Glu Arg Arg Arg Gly Lys Gly His Asp
325 330 335

Gly Leu Tyr Gln Gly Leu Ser Thr Ala Thr Lys Asp Thr Tyr Asp Ala
340 345 350

Leu His Met Gln Ala Leu Pro Pro Arg
355 360

<210> SEQ ID NO 251
<211> LENGTH: 444
<212> TYPE: PRT
<213> ORGANISM: Artificial Sequence
<220> FEATURE:
<223> OTHER INFORMATION: GPC2-CD2z

<400> SEQUENCE: 251

Met Ala Leu Pro Val Thr Ala Leu Leu Leu Pro Leu Ala Leu Leu Leu
1 5 10 15

His Ala Ala Arg Pro Glu Val Gln Leu Val Glu Ser Gly Gly Gly Leu
20 25 30

Val Gln Pro Gly Gly Ser Leu Arg Leu Ser Cys Ala Ile Ser Glu Phe
35 40 45

Thr Tyr Lys Asn Thr Cys Val Gly Trp Phe Arg Gln Ala Pro Gly Lys
50 55 60

Gly Arg Glu Gly Val Ala Ala Ile Asp Ser Asp Gly Asn Thr Asn Tyr
65 70 75 80

Val Asp Ser Val Lys Gly Arg Phe Thr Ile Ser Gln Asp Asn Ser Lys
85 90 95

Asn Thr Val Tyr Leu Gln Met Asn Ser Leu Arg Ala Glu Asp Thr Ala
100 105 110

Met Tyr Tyr Cys Ala Ala Gly Ala Tyr Cys Gly Arg Leu Leu Leu Trp
115 120 125

Ile Gly Asn Tyr Ala Tyr Trp Gly Gln Gly Thr Leu Val Thr Val Ser
130 135 140

Ser Thr Thr Thr Pro Ala Pro Arg Pro Pro Thr Pro Ala Pro Thr Ile
145 150 155 160

Ala Ser Gln Pro Leu Ser Leu Arg Pro Glu Ala Cys Arg Pro Ala Ala
165 170 175

Gly Gly Ala Val His Thr Arg Gly Leu Asp Phe Ala Cys Asp Ile Tyr
180 185 190

Leu Ile Ile Gly Ile Cys Gly Gly Gly Ser Leu Leu Met Val Phe Val
195 200 205

Ala Leu Leu Val Phe Tyr Ile Thr Lys Arg Lys Lys Gln Arg Ser Arg
210 215 220

Arg Asn Asp Glu Glu Leu Glu Thr Arg Ala His Arg Val Ala Thr Glu
225 230 235 240

Glu Arg Gly Arg Lys Pro His Gln Ile Pro Ala Ser Thr Pro Gln Asn
245 250 255

Pro Ala Thr Ser Gln His Pro Pro Pro Pro Pro Gly His Arg Ser Gln
260 265 270

Ala Pro Ser His Arg Pro Pro Pro Pro Gly His Arg Val Gln His Gln
275 280 285

Pro Gln Lys Arg Pro Pro Ala Pro Ser Gly Thr Gln Val His Gln Gln
290 295 300

Lys Gly Pro Pro Leu Pro Arg Pro Arg Val Gln Pro Lys Pro Pro His
305 310 315 320

Gly Ala Ala Glu Asn Ser Leu Ser Pro Ser Ser Asn Arg Val Lys Phe
325 330 335

Ser Arg Ser Ala Asp Ala Pro Ala Tyr Lys Gln Gly Gln Asn Gln Leu
340 345 350

Tyr Asn Glu Leu Asn Leu Gly Arg Arg Glu Glu Tyr Asp Val Leu Asp
355 360 365

Lys Arg Arg Gly Arg Asp Pro Glu Met Gly Gly Lys Pro Arg Arg Lys
370 375 380

Asn Pro Gln Glu Gly Leu Tyr Asn Glu Leu Gln Lys Asp Lys Met Ala
385 390 395 400

Glu Ala Tyr Ser Glu Ile Gly Met Lys Gly Glu Arg Arg Arg Gly Lys
405 410 415

Gly His Asp Gly Leu Tyr Gln Gly Leu Ser Thr Ala Thr Lys Asp Thr
420 425 430

Tyr Asp Ala Leu His Met Gln Ala Leu Pro Pro Arg
435 440

<210> SEQ ID NO 252
<211> LENGTH: 365
<212> TYPE: PRT
<213> ORGANISM: Artificial Sequence
<220> FEATURE:
<223> OTHER INFORMATION: GPC2-OX40z

<400> SEQUENCE: 252

Met Ala Leu Pro Val Thr Ala Leu Leu Leu Pro Leu Ala Leu Leu Leu
1 5 10 15

His Ala Ala Arg Pro Glu Val Gln Leu Val Glu Ser Gly Gly Gly Leu
20 25 30

Val Gln Pro Gly Gly Ser Leu Arg Leu Ser Cys Ala Ile Ser Glu Phe
35 40 45

Thr Tyr Lys Asn Thr Cys Val Gly Trp Phe Arg Gln Ala Pro Gly Lys
50 55 60

Gly Arg Glu Gly Val Ala Ala Ile Asp Ser Asp Gly Asn Thr Asn Tyr
65 70 75 80

Val Asp Ser Val Lys Gly Arg Phe Thr Ile Ser Gln Asp Asn Ser Lys
85 90 95

Asn Thr Val Tyr Leu Gln Met Asn Ser Leu Arg Ala Glu Asp Thr Ala
100 105 110

Met Tyr Tyr Cys Ala Ala Gly Ala Tyr Cys Gly Arg Leu Leu Leu Trp
115 120 125

Ile Gly Asn Tyr Ala Tyr Trp Gly Gln Gly Thr Leu Val Thr Val Ser
130 135 140

Ser Thr Thr Thr Pro Ala Pro Arg Pro Pro Thr Pro Ala Pro Thr Ile
145 150 155 160

-continued

```
Ala Ser Gln Pro Leu Ser Leu Arg Pro Glu Ala Cys Arg Pro Ala Ala
                165                 170                 175

Gly Gly Ala Val His Thr Arg Gly Leu Asp Phe Ala Cys Asp Val Ala
            180                 185                 190

Ala Ile Leu Gly Leu Gly Leu Val Leu Gly Leu Leu Gly Pro Leu Ala
        195                 200                 205

Ile Leu Leu Ala Leu Tyr Leu Leu Arg Arg Asp Gln Arg Leu Pro Pro
    210                 215                 220

Asp Ala His Lys Pro Pro Gly Gly Gly Ser Phe Arg Thr Pro Ile Gln
225                 230                 235                 240

Glu Glu Gln Ala Asp Ala His Ser Thr Leu Ala Lys Ile Arg Val Lys
                245                 250                 255

Phe Ser Arg Ser Ala Asp Ala Pro Ala Tyr Lys Gln Gly Gln Asn Gln
            260                 265                 270

Leu Tyr Asn Glu Leu Asn Leu Gly Arg Arg Glu Glu Tyr Asp Val Leu
        275                 280                 285

Asp Lys Arg Arg Gly Arg Asp Pro Glu Met Gly Gly Lys Pro Arg Arg
    290                 295                 300

Lys Asn Pro Gln Glu Gly Leu Tyr Asn Glu Leu Gln Lys Asp Lys Met
305                 310                 315                 320

Ala Glu Ala Tyr Ser Glu Ile Gly Met Lys Gly Glu Arg Arg Arg Gly
                325                 330                 335

Lys Gly His Asp Gly Leu Tyr Gln Gly Leu Ser Thr Ala Thr Lys Asp
            340                 345                 350

Thr Tyr Asp Ala Leu His Met Gln Ala Leu Pro Pro Arg
        355                 360                 365
```